US008053439B2

(12) United States Patent
Choi et al.

(10) Patent No.: US 8,053,439 B2
(45) Date of Patent: Nov. 8, 2011

(54) BENZOPHENONE DERIVATIVES USEFUL FOR INHIBITING FORMATION OF MICROTUBULE

(75) Inventors: Nam-Song Choi, Cheonan-si (KR); Young-Mi Kim, Cheonan-si (KR); Young-Hoon Kim, Yongin-si (KR); Jae-Kwang Lee, Cheonan-si (KR); In-Taek Lim, Cheonan-si (KR); Ho-Jin Choi, Hwaseong-si (KR); Hyun-Mo Yang, Cheonan-si (KR); Seung-Kee Moon, Cheonan-si (KR); Soo-Jin Kim, Cheonan-si (KR); Hyun-Jung Yu, Cheonan-si (KR); Jae-Su Shin, Seoul (KR); Young-Min Kwon, Goyang-si (KR); Sung-Sook Lee, Cheonan-si (KR); Soon-Kil Ahn, Seoul (KR); Sun-Ju Kong, Cheonan-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 12/441,601

(22) PCT Filed: Sep. 21, 2007

(86) PCT No.: PCT/KR2007/004625
§ 371 (c)(1),
(2), (4) Date: Mar. 17, 2009

(87) PCT Pub. No.: WO2008/038955
PCT Pub. Date: Apr. 3, 2008

(65) Prior Publication Data
US 2009/0275575 A1 Nov. 5, 2009

(30) Foreign Application Priority Data
Sep. 27, 2006 (KR) .................. 10-2006-0094019

(51) Int. Cl.
| | |
|---|---|
| *A61K 31/341* | (2006.01) |
| *A61K 31/381* | (2006.01) |
| *A61K 31/40* | (2006.01) |
| *A61K 31/415* | (2006.01) |
| *A61K 31/4164* | (2006.01) |
| *A61K 31/4196* | (2006.01) |
| *A61K 31/421* | (2006.01) |
| *A61K 31/426* | (2006.01) |
| *A61K 31/4418* | (2006.01) |
| *A61K 31/454* | (2006.01) |
| *A61K 31/505* | (2006.01) |
| *A61K 31/12* | (2006.01) |
| *C07C 49/786* | (2006.01) |
| *C07D 307/46* | (2006.01) |
| *C07D 333/22* | (2006.01) |
| *C07D 207/333* | (2006.01) |
| *C07D 231/12* | (2006.01) |
| *C07D 233/64* | (2006.01) |
| *C07D 277/24* | (2006.01) |
| *C07D 263/32* | (2006.01) |
| *C07D 231/46* | (2006.01) |
| *C07D 239/26* | (2006.01) |

(52) U.S. Cl. ........ 514/256; 514/438; 514/461; 514/423; 514/427; 514/383; 514/399; 514/400; 514/365; 514/374; 514/340; 514/357; 514/686; 549/506; 549/77; 548/531; 548/204; 548/235; 548/265.8; 548/340.1; 548/375.1; 546/337; 546/269.7; 544/335

(58) Field of Classification Search .................. None
See application file for complete search history.

(56) References Cited

U.S. PATENT DOCUMENTS

| | | | |
|---|---|---|---|
| 3,900,501 A | 8/1975 | Ning et al. | |
| 4,579,679 A * | 4/1986 | Papir | 252/500 |
| 4,641,160 A * | 2/1987 | Kondo et al. | 503/220 |
| 6,720,331 B2 | 4/2004 | Yeh et al. | |
| 6,962,929 B2 | 11/2005 | Flygare et al. | |

FOREIGN PATENT DOCUMENTS

| | | |
|---|---|---|
| DE | 2051013 A1 | 12/1971 |
| DE | 2163522 A1 | 7/1972 |
| WO | 98/05315 A1 | 2/1998 |
| WO | 99/34788 A1 | 7/1999 |
| WO | 00/50398 A3 | 8/2000 |
| WO | 2004/002965 A1 | 1/2004 |
| WO | 2004/054498 A2 | 7/2004 |
| WO | 2004/078144 A2 | 9/2004 |
| WO | 2005/009940 A1 | 2/2005 |
| WO | 2005/100301 A1 | 10/2005 |
| WO | 2006/063585 A1 | 6/2006 |

OTHER PUBLICATIONS

Tsuruda, et al. Yakugaku Zasshi, 109:33 (1989) [pp. 33, 37, and 42 only].*
Byrn, et al. Solid State Chemistry of Drugs, 2d, Ch. 11:Hydrates and Solvates, pp. 233-247 (1999).*
Morrissette, et al. Adv. Drug Delivery Rev. 56:275 (2004).*
Rouhi, Chem. & Eng. News, Feb. 24, 2003, 81(8), 32-35.*
Wyatt, et al., Benzophenone derivatives: a novel series of potent and selective inhibitors of human immunodeficiency virus type 1 reverse transcriptase, Journal of Medicinal Chemistry, 1995, 38(10):1657-65.

(Continued)

*Primary Examiner* — Yong Chu
*Assistant Examiner* — Michael Barker
(74) *Attorney, Agent, or Firm* — Lucas & Mercanti, LLP

(57) ABSTRACT

Disclosed herein are novel benzophenone derivatives represented by formula I, a pharmaceutically acceptable salt thereof, a hydrate thereof or a solvate thereof, a pharmacological composition containing the same, and a use of the composition as therapeutic drugs. The benzophenone derivatives have an inhibition activity of microtubule formation and can be used to treat a normal proliferative state of a malignant tumor by killing the actively proliferating cells.

18 Claims, No Drawings

OTHER PUBLICATIONS

Kim, et al., Synthesis of nitrile and benzoyl substituted poly(biphenylene oxide)s via nitro displacement reaction, Polymer, 2006, 47(13):4549-4565.

Jarikov, et al., Photochemistry and photophysics of triarylmethane dye leuconitriles, Journal of Organic Chemistry, 2001, 66(3):659-671.

Yamamoto, et al., Influence of methyl group in the fries rearrangement of 4-biphenylyl-4'-methyl benzoate and 4-byphenylyl-4'-methyl acetate, Nihon Yukagakkaishi, 2000, 49(5):73-77.

Isoda, et al., The fries rearrangement of 4-biphenylyI-4'-methyl benzoate and 4-byphenylyl-4'-methyl acetate, Nihon Kagakukaishi, 1999, 6:421-423.

Allen, et al., Synthesis and thermal and photo-oxidative behaviour of novel aminated 2-hydroxybenzophenone stabilizers in polyolefin films, European Polymer Journal, 1991, 27(8):789-794.

Bruns, et al., Structure-activity relationships for enhancement of adenosine A1 receptor binding by 2-amino-3-benzoylthiophenes, Molecular Pharmacology, 1990, 38(6):950-958.

Kulkarni, et al., Substituted benzophenones as possiele anticonvulsants, Biological Memoirs, 1985, 11(2):192-196.

Giovannini, et al., Photolyse des 3-Phenyl-2, 1-benzisoxazols und einiger seiner Derivate in Salzsäure bzw. Schwefelsäure, Helvetica Chimica Acta, 1979, 62(26):185-197.

Giovannini, et al., Photolyse des 3-Phenyl-2, 1-benzisoxazols und einiger seiner Derivate in Bromwasserstoffsäure, Helvetica Chimica Acta, 1979, 62(27):198-204.

Xiao, et al., The sulindac derivatives OSI-461, OSIP486823, and OSIP487703 arrest colon cancer cells in mitosis by causing microtubule depolymerization, Molecular Cancer Therapeutics, 2006, 5(1):60-67.

Nguyen, et al., A common pharmacophore for a diverse set of colchicine site inhibitors using a structure-based approach, J. Med. Chem., 2005, 48(19):6107-6116.

Molodtsov, et al., Force production by depolymerizing microtubules: A theoretical study, PNAS, 2005, 102(12): 4353-4358.

Hsieh, et al., Pharmaceutical design of antimitotic agents based on combretastatins, Current Pharmaceutical Design, 2005, 11(13):1655-1677.

Honore, et al., Understanding microtubule dynamics for improved cancer therapy, Cellular Molecular Life Sciences, 2005, 62:3039-3056.

Jordan, et al., Microtubules as a target for anticancer drugs, Nature Reviews Cancer, 2004, 4(4):253-265.

Liou, et al., Synthesis and structure-activity relationship of 2-aminobenzophenone derivatives as antimitotic agents, Journal of Medicinal Chemistry, 2002, 45(12):2556-2562.

Liou, et al., Synthesis and structure-activity relationships of 3-aminobenzophenones as antimitotic agents, Journal of Medicinal Chemistry, 2004, 47(11):2897-2905.

Pettit, et al., Antineoplastic agents. 443. Synthesis of the cancer cell growth inhibitor hydroxyphenstatin and its sodium diphosphate prodrug, Journal of Medicinal Chemistry, 2000, 43(14):2731-2737.

Welch, et al., Atropisomeric quinazolin-4-one derivatives are potent noncompetitive alpha-amino-3-hydroxy-5-methyl-4-isoxazolepropionic acid (AMPA) receptor antagonists, Bioorganic & Medicinal Chemistry Letters, 2001, 11(2):177-181.

Jang, et al., Highly selective catalytic Friedel—Crafts acylation and sulfonylation of activated aromatic compounds using indium metal, Tetrahedron Letters, 2006, 47(34):6063-6066.

Waite, et al., A Scalable synthesis of the thromboxane receptor antagonist 3-{3-[2-(4-chlorobenzenesulfonamido) ethyl]-5-(4-fluorobenzyl)phenyl}propionic acid via a regioselective heck cross-coupling strategy, Organic Process Research Development, 1998, 2(2):116-120.

Morris, et al., A general route to pyridine-modified salicylaldehydes via Suzuki coupling, Tetrahedron Letters, 2001, 42(11):2093-2096.

Reeder, et al., An improved method for the palladium cross-coupling reaction of oxazol-2-ylzinc derivatives with aryl bromides, Organic Process Research & Development, 2003, 7(5):696-699.

Bellamy, et al., (Benzoylphenyl)piperidines: a new class of immunomodulators, Journal of Medicinal Chemistry, 1991, 34(5):1545-1552.

* cited by examiner

BENZOPHENONE DERIVATIVES USEFUL FOR INHIBITING FORMATION OF MICROTUBULE

CROSS-REFERENCE TO RELATED APPLICATIONS

This application is a 371 of PCT/KR2007/004625 filed on Sep. 21, 2006, which claims the benefit of Korean Patent Application No. 10-2006-0094019 filed on Sep. 27, 2006, the contents of each of which are incorporated herein by reference.

TECHNICAL FIELD

The present invention relates to novel benzophenone derivatives, a pharmaceutically acceptable salt thereof, a hydrate thereof or a solvate thereof, a pharmacological composition including the benzophenone derivatives, and a use of the composition as therapeutic drugs. The benzophenone derivative has an inhibition activity of microtubule formation and can be used to treat a normal proliferative state of a malignant tumor by killing the actively proliferating cells.

BACKGROUND ART

Tumor diseases characterized in abnormally controlled cell proliferation are a leading cause of death for humans and other mammals. Cancer chemotherapy has provided novel and effective drugs to treat such diseases, and as a result, it was proved that the medicine for inhibiting formation of microtubules is also effective in inhibiting proliferation of tumor cells (see *Mol Cancer Ther.* 5, 60-67, 2006; *J. Med. Chem.*, 48, 6107-6116, 2005; *PNAS*, 102, 4353-4358, 2005; *Curr Pharm Des.* 11, 1655-77, 2005; *Cell. Mol. Life. Sci.* 62, 3039-3056, 2005; and *Nature Cancer Reviews* 4, 253-265, 2005). Microtubules serve a very important role in regulation of cell architecture, division and metabolism. The microtubule system of eukaryotic cells includes a dynamic state of assembly and disassembly that forms microtubules in both tumor cells and normal cells by polymerization of different kinds of tubulin dimers. In tumor cells, tubulins are polymerized into microtubules to form a mitotic spindle. Subsequently, when the use of the mitotic spindle is terminated, it is depolymerized. Inhibition of the microtubule formation inhibits normal dynamic reorganization of the microtubule network that is essential for vital interphase and mitotic cellular functions. In addition, drugs for inhibiting cell proliferation in the tumor cells by discontinuing polymerization or depolymerization of microtubules occupy a part of the most effective chemotherapeutic drugs used for cancers (U.S. Pat. No. 6,962,929; WO 04/002965; WO 04/054498; WO 99/34788; and U.S. Pat. No. 6,720,331). Cell toxicity and antitumor characteristics included in the benzophenone derivatives of the present invention are derived from the ability to promote cell death (programmed cell suicide) by inhibiting microtubule assembly from tubulin dimers so as to prevent microtubule polymerization.

Psoriasis, a common chronic skin disease characterized by the presence of dry scales and plaques, is regarded as a result of abnormal cell proliferation. The disease results from hyperproliferation of the epidermis and incomplete differentiation of keratinocyte. Psoriasis is often generated in the scalp, elbows, knees, back, hips, nails, eyebrows, and genitals, and may range in severity from mild to extremely debilitating. In the end, psoriasis is progressed to psoriatic arthritis, pustular psoriasis, or exfoliative psoriatic dermatitis. Treatments for psoriasis have yet to be established. Milder cases are often treated with topical corticosteroids. However, more sever cases may be treated with antiproliferative agents, such as the antimetabolite (methotrexate), a DNA synthesis inhibitor (hydroxyurea), and a microtubule disrupter (colchicines).

Other diseases associated with an abnormally high level of cell proliferation include restenosis, where vascular smooth muscle cells are involved, inflammatory disease such as glomerulonephritis, transplant rejection, where endothelial cells are involved, infectious disease such as HIV infection and malaria, where specific immune cells and other infected cells are involved, and the like. Infectious and parasitic pathogens per se (e.g., bacteria, trypanosomes, fungi, etc.) are also subjected to selective proliferative control using the compositions and compounds of the present invention (see WO 98/05315).

The present inventors have earnestly and intensively conducted research to treat the above-mentioned diseases. As a result, the present inventors have developed a novel derivative different from the well-known compounds, and completed the present invention.

DISCLOSURE

Technical Problem

Therefore, the present invention has been made in view of the above problems, and it is an object of the present invention to provide compounds which directly or indirectly are toxic to actively dividing cells, and are useful in the treatment of malignant tumors, viral or bacterial infections, vascular restenosis, inflammatory diseases, autoimmune diseases, or psoriasis.

It is another object of the present invention to provide a novel benzophenone derivative as an inhibitor of a microtubule formation, an isomer thereof, a pharmaceutically acceptable salt thereof, a hydrate thereof or a solvate thereof.

It is yet another object of the present invention to provide a pharmacological composition including a benzophenone derivative, an isomer thereof, a pharmaceutically acceptable salt thereof, a hydrate thereof, or a solvate thereof as an effective component.

Technical Solution

In accordance with an aspect of the present invention, the above and other objects can be accomplished by the provision of a compound represented by the following formula I, an isomer thereof a pharmaceutically acceptable salt thereof, a hydrate thereof or a solvate thereof.

In accordance with another aspect of the present invention, there is provided a pharmacological composition having inhibiting function of a microtubule formation including a compound represented by the following formula I, an isomer thereof, a pharmaceutically acceptable salt thereof, a hydrate thereof or a solvate thereof.

[Formula 1]

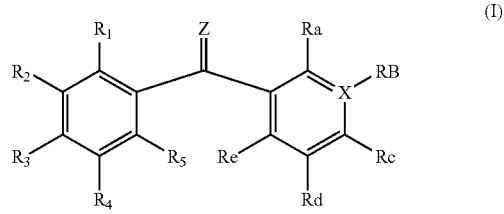

wherein, $R_1$, $R_2$, $R_3$, $R_4$, and $R_5$ may be identical to or different from each other, may form a dioxane or dioxolane ring by connecting with adjacent carbons, and are each independently hydrogen, hydroxyl, hydroxyalkyl, fluoro, bromo, chloro, substituted or unsubstituted $C_{1-6}$ alkyl, $C_{1-3}$ alkoxy, formyl, [1,3]dioxane, or a functional group represented by the following structural formula 1,

[Structural Formula 1]

wherein, q is 1 or 2, and $R_6$ and $R_7$ are each independently hydrogen or $C_{1-3}$ alkyl;

Z is O, S, $CH_2$, or a functional group represented by the following structural formula 2,

[Structural Formula 2]

wherein, $R_8$ is hydrogen or $C_{1-3}$ alkyl;

X is C or N, provided that when X is C, Rb is hydrogen, $C_{1-3}$ alkoxy, substituted or unsubstituted $C_{1-6}$ alkyl, or a functional group represented by the structural formula 1, and when X is N, Rb does not exist;

Ra is hydrogen, fluoro, —$CONH_2$, —COOH, nitro, —O—$R_9$ (wherein, $R_9$ is hydrogen, substituted or unsubstituted $C_{1-6}$ alkyl, phenyl, —$SO_2$—$R_{10}$, or —$CO_2R_{10}$, wherein $R_{10}$ is substituted or unsubstituted $C_{1-6}$ alkyl, or substituted or unsubstituted phenyl), —CO—$R_{10}$ or —COO—$R_{10}$ (wherein, $R_{10}$ is the same as defined above), or a functional group represented by the following structural formula 3,

[Structural formula 3]

wherein, $R_{11}$ and $R_{12}$ are each independently hydrogen, formyl, $C_{1-3}$ alkoxy, pyridine, pyrimidine, substituted or unsubstituted $C_{1-6}$ alkyl, hydroxyalkyl, —CO—$R_{10}$, —COO—$R_{10}$, or —$SO_2$—$R_{10}$, wherein $R_{10}$ is the same as defined above, or a $C_5$ or $C_6$ heterocyclic ring arbitrarily containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, thiol, amino, nitro, thiomethyl, carboxylic acid, methylcarboxylate, —$CF_3$, or —$NR_{13}R_{14}$, wherein $R_{13}$ and $R_{14}$ are each independently hydrogen, substituted or unsubstituted $C_{1-6}$ alkyl, hydroxyalkyl, CO—$R_{10}$), —COO—$R_{10}$, or —$SO_2$—$R_{10}$, wherein $R_{10}$ is the same as defined above);

Rc and Rd are each independently hydrogen, a $C_5$ or $C_6$ heterocyclic ring arbitrarily containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, or —$NR_{13}R_{14}$, wherein $R_{13}$ and $R_{14}$ are the same as defined above), or a $R_{15}$-substituted phenyl (wherein, $R_{15}$ is hydrogen, hydroxyl, nitro, substituted or unsubstituted $C_{1-6}$ alkyl, $C_{1-3}$ alkoxy, fluoro, nitrile, —$NR_{11}R_{12}$, —COO—$R_{10}$, or —$SO_2$—$R_{10}$, wherein $R_{10}$, $R_{11}$, and $R_{12}$ are the same as defined above), provided that Rc and Rd may not be hydrogen simultaneously; and Re is hydrogen or halogen (preferably, fluorine or bromine).

BEST MODE

As the compound of the present invention, a compound represented by the following formula I, an isomer thereof, a pharmaceutically acceptable salt thereof, a hydrate thereof, or a solvate thereof is preferable.

[Formula I]

(I)

wherein, $R_1$, $R_2$, $R_3$, $R_4$, and $R_5$ may be identical to or different from each other, and are each independently hydroxyl, hydroxyalkyl, fluoro, bromo, substituted or unsubstituted $C_{1-6}$ alkyl, $C_{1-3}$ alkoxy, formyl, or a functional group represented by the following structural formula 1,

[Structural Formula 1]

wherein, q is 1 or 2, and $R_6$ and $R_7$ are each independently hydrogen or $C_{1-3}$ alkyl;

Z is O, S, $CH_2$, or a functional group represented by the following structural formula 2,

[Structural Formula 2]

wherein, $R_8$ is hydrogen or $C_{1-3}$ alkyl;

X is C or N, provided that when X is C, Rb is hydrogen, $C_{1-3}$ alkoxy, substituted or unsubstituted $C_{1-6}$ alkyl, or a functional group represented by the structural formula 1, and when X is N, Rb does not exist;

Ra is hydrogen, fluoro, —$CONH_2$, —COOH, nitro, —O—$R_9$ (wherein, $R_9$ is hydrogen, substituted or unsubstituted $C_{1-6}$ alkyl, —$SO_2$—$R_{10}$, or —$CO_2R_{10}$, wherein $R_{10}$ is substituted or unsubstituted $C_{1-6}$ alkyl, or substituted or unsubstituted phenyl), or a functional group represented by the following structural formula 3,

[Structural formula 3]

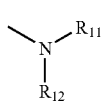

wherein, $R_{11}$ and $R_{12}$ are each independently hydrogen, formyl, $C_{1-3}$ alkoxy, pyridine, pyrimidine, substituted or unsubstituted $C_{1-6}$ alkyl, hydroxyalkyl, —CO—$R_{10}$, —COO—$R_{10}$, or —SO$_2$—$R_{10}$, wherein $R_{10}$ is the same as defined above, or a $C_5$ or $C_6$ heterocyclic ring arbitrarily containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, amino, nitro, thiomethyl, carboxylic acid, methylcarboxylate, —CF$_3$, or —NR$_{13}$R$_{14}$, wherein $R_{13}$ and $R_{14}$ are each independently hydrogen, substituted or unsubstituted $C_{1-6}$ alkyl);

Rc and Rd are each independently hydrogen, a $C_5$ or $C_6$ heterocyclic ring arbitrarily containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, or —NR$_{13}$R$_{14}$, wherein $R_{13}$ and $R_{14}$ are the same as defined above), or a $R_{15}$-substituted phenyl (wherein, $R_{15}$ is hydroxyl, nitro, substituted or unsubstituted $C_{1-6}$ alkyl, $C_{1-3}$ alkoxy, fluoro, nitrile, —NR$_{11}$R$_{12}$, —COO—$R_{10}$, or —SO$_2$—$R_{10}$, wherein $R_{10}$, $R_{11}$, and $R_{12}$ are the same as defined above), provided that Rc and Rd may not be hydrogen simultaneously; and Re is hydrogen.

As the compound of the present invention, particularly, a compound represented by the formula I, in which Rc or Rd is a functional group selected from the group consisting of the following structural formulas, an isomer thereof, a pharmaceutically acceptable salt thereof, a hydrate thereof, or a solvate thereof is more preferable.

[Structural Formula 4]

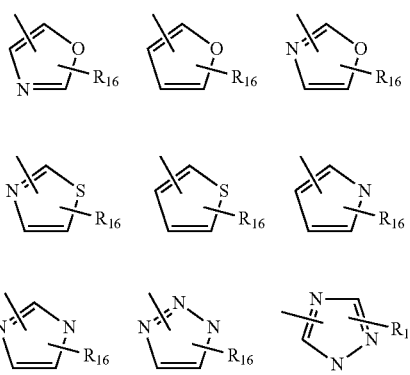

wherein, $R_{16}$ is hydrogen, amino, aminoacyl, or $C_{1-3}$ alkyl.

Another preferable compound of the present invention is a compound represented by the formula I, in which Rc or Rd is a functional group selected from the group consisting of the following structural formula, an isomer thereof, a pharmaceutically acceptable salt thereof, a hydrate thereof, or a solvate thereof.

[Structure Formula 5]

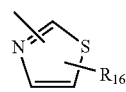

wherein, $R_{16}$ is the same as defined above.

Yet another preferable compound of the present invention is a compound represented by the formula I, in which Re or Rd is a functional group selected from the group consisting of the following structural formulas, an isomer thereof, a pharmaceutically acceptable salt thereof, a hydrate thereof, or a solvate thereof.

[Structural Formula 6]

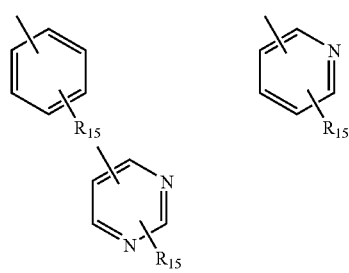

wherein, $R_{15}$ is the same as defined above.

Yet another preferable compound of the present invention is a compound represented by the formula I, in which Ra is a functional group selected from the group consisting of the following structural formulas, an isomer thereof, a pharmaceutically acceptable salt thereof, a hydrate thereof, or a solvate thereof.

[Structural Formula 7]

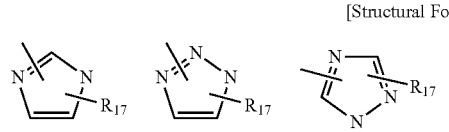

wherein, $R_{17}$ is substituted or unsubstituted $C_{1-6}$ alkyl, $C_{1-3}$ alkoxy, thiol, amino, nitro, thiomethyl, carboxylic acid, methylcarboxylate, or CF$_3$.

Yet another preferable compound of the present invention is a compound represented by the formula I, an isomer thereof, a pharmaceutically acceptable salt thereof, a hydrate thereof, or a solvate thereof, in which Ra is a functional group selected from the group consisting of the following structural formulas,

[Structural Formula 7]

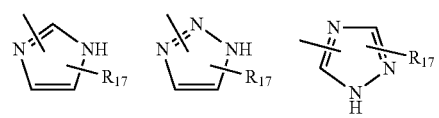

wherein, $R_{17}$ is methyl, amino, nitro, thiomethyl, carboxylic acid, methylcarboxylate, or CF$_3$, in which Rc or Rd is a functional group selected from the group consisting of the following structural formulas.

[Structural Formula 8]

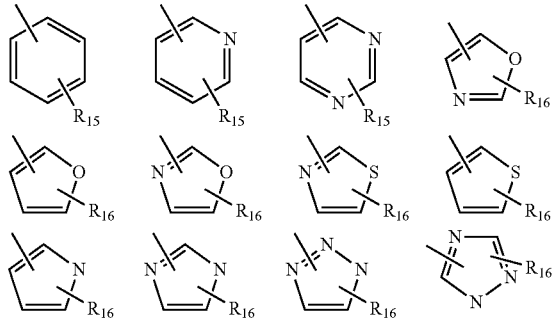

wherein, $R_{15}$ is hydrogen, hydroxyl, nitro, substituted or unsubstituted $C_{1-6}$ alkyl, $C_{1-3}$ alkoxy, fluoro, nitrile, —$NR_{11}R_{12}$, —COO—$R_{10}$, or —$SO_2$—$R_{10}$, wherein $R_{10}$, $R_{11}$, and $R_{12}$ are each independently the same as defined above; and $R_{16}$ is hydrogen, amino, aminoacyl, or $C_{1-3}$ alkyl.

Particularly preferable compounds of the present invention is a compound represented by the formula I, an isomer thereof, a pharmaceutically acceptable salt thereof, a hydrate thereof, or a solvate thereof, in which Ra is a functional group selected from the group consisting of the following structural formula,

[Structural formula 3]

wherein, $R_{11}$ and $R_{12}$ are each independently the same as defined above, in which Rc or Rd is a functional group selected from the group consisting of the following structural formulas.

[Structural Formula 8]

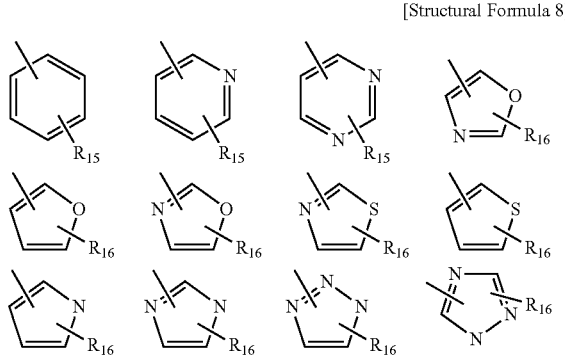

wherein, $R_{15}$ and $R_{16}$ are each independently the same as defined above.

A Still more preferable compound of the present invention is a compound represented by the formula I, in which Ra is a functional group selected from the group consisting of the following structural formula, an isomer thereof, a pharmaceutically acceptable salt thereof, a hydrate thereof, or a solvate thereof.

[Structural Formula 9]

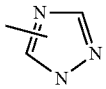

Particularly, a compound of the present invention represented by the formula I, in which Ra is $NH_2$, an isomer thereof, a pharmaceutically acceptable salt thereof, a hydrate thereof, or a solvate thereof is preferable.

Moreover, a compound of the present invention represented by the formula I, in which $R_1$, $R_2$, $R_3$, $R_4$ and $R_5$ are fluorine, an isomer thereof, a pharmaceutically acceptable salt thereof, a hydrate thereof, or a solvate thereof is particularly preferable.

Especially, a compound of the present invention represented by the formula I, in which $R_2$, $R_3$ and $R_4$ are methoxy, an isomer thereof, a pharmaceutically acceptable salt thereof, a hydrate thereof, or a solvate thereof is preferable.

The compound represented by the formula I may contain at least one asymmetric carbon atom, thus the compound may exist as at least two or more of stereoisomers. Such steroisomers, for example, a stereoisomer mixture of the compound represented by the formula I, or an appropriate salt or derivative thereof can be separated by a conventional technique such as fractional crystallization, column chromatography, or HPLC. Each enantiomer of the compound represented by the formula I can be separated by HPLC separation of a corresponding racemate using a chiral support. On the other hand, the corresponding racemate is reacted with an appropriate photoactive acid or base to form a mixture, and the mixture is separated by fractional crystallization or column chromatography. All isomers are included in the scope of the present invention.

Examples of the pharmaceutically acceptable salt of a compound represented by the formula I include inorganic salts (e.g., sulfite, hydrochloride, phosphate, hydrobromide, etc.), organic salts (maleate, succinate, acetate, toluenesulfonate, mesylate, benzenesulfonate, tartrate, citrate, etc.), alkaline metal salts such as lithium, sodium or potassium, or alkali earth metal salts such as calcium or magnesium.

Preferable specific examples of the compound of the present invention include compounds listed in Tables 1 to 10, pharmaceutically acceptable salts thereof, hydrates thereof, or solvates thereof.

TABLE 1

| Compound Structure |
| --- |
| Compound 200 |

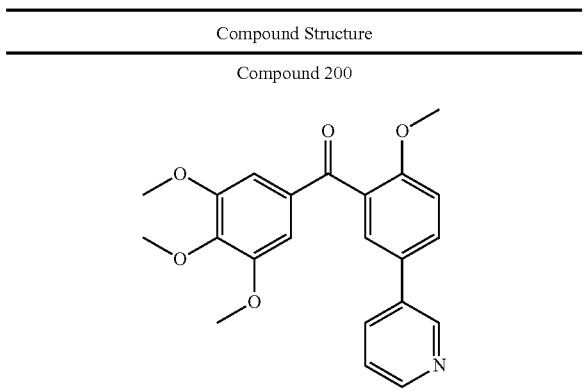

TABLE 1-continued
Compound Structure
Compound 203
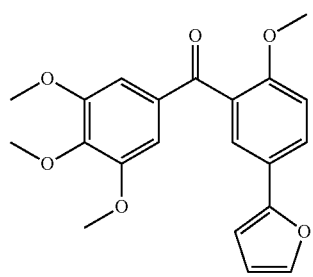
Compound 206
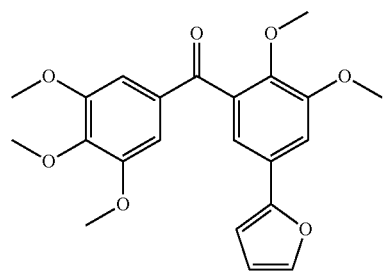
Compound 207
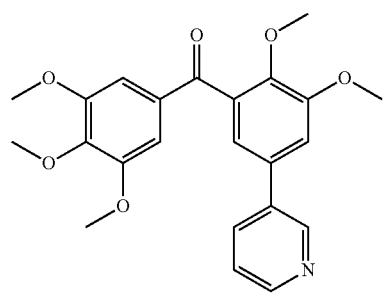
Compound 211
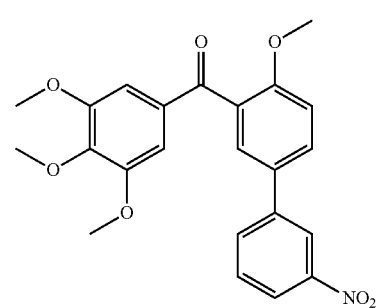
Compound 212
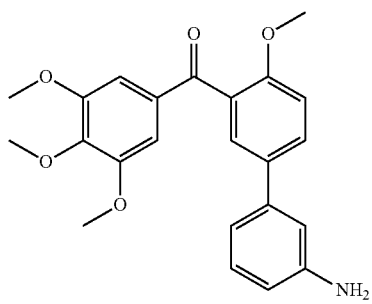
Compound 213
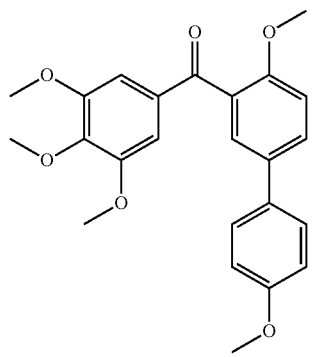
Compound 214
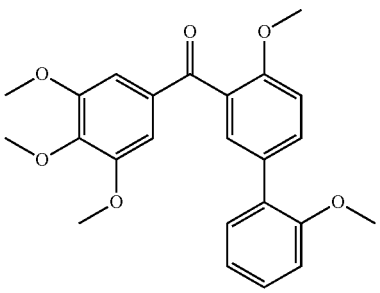
Compound 216
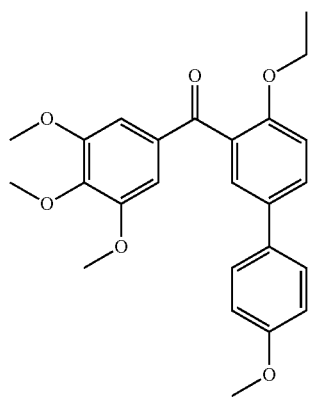

TABLE 1-continued
Compound Structure
Compound 218
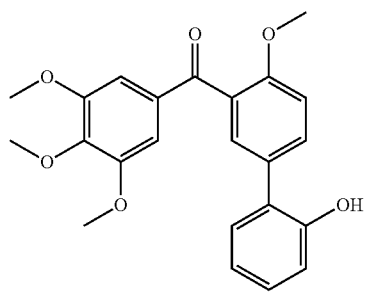
Compound 220
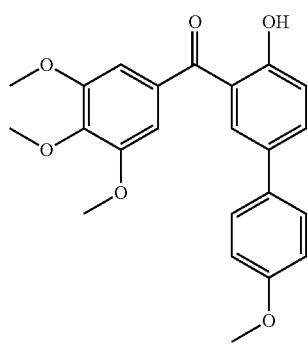
Compound 223
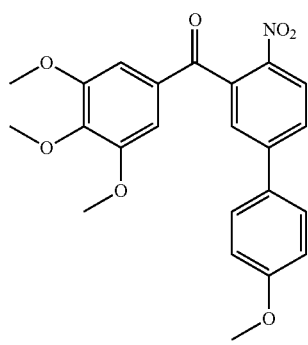
Compound 224
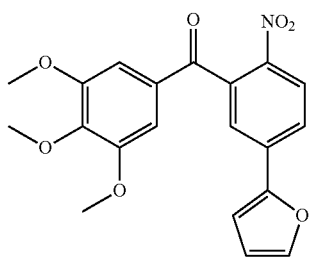
TABLE 1-continued
Compound Structure
Compound 225
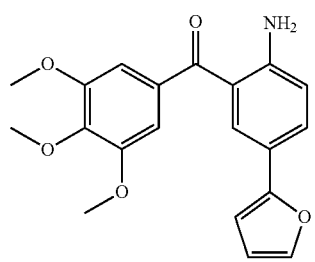
Compound 226
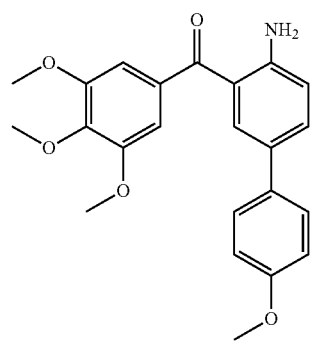
Compound 227
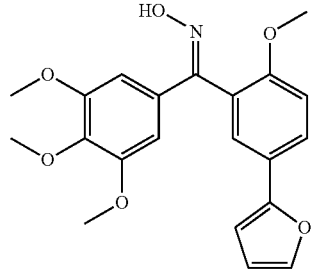
Compound 228
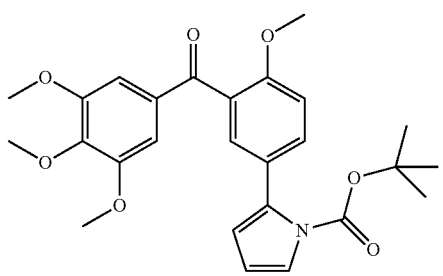

TABLE 1-continued
Compound Structure
Compound 229
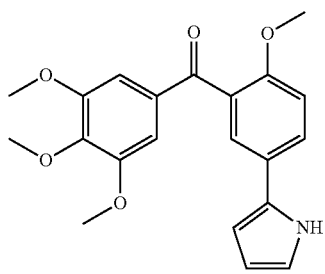
Compound 231
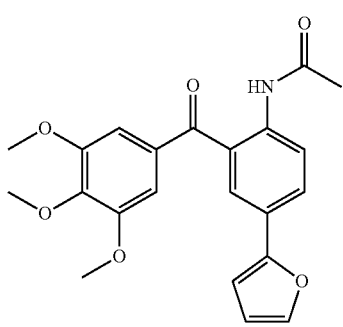
Compound 232
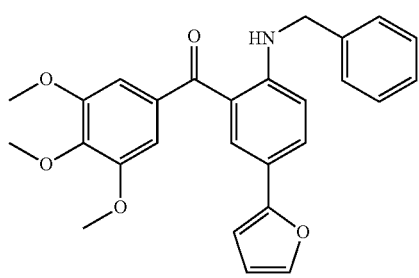
Compound 233
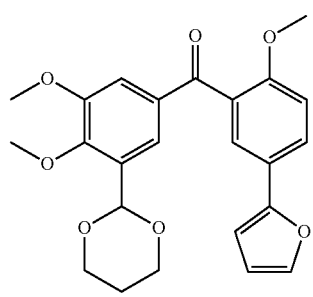
TABLE 1-continued
Compound Structure
Compound 234
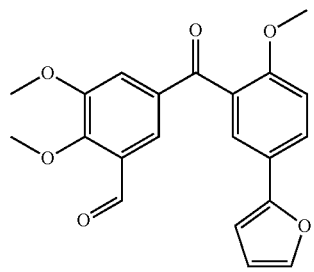
Compound 235
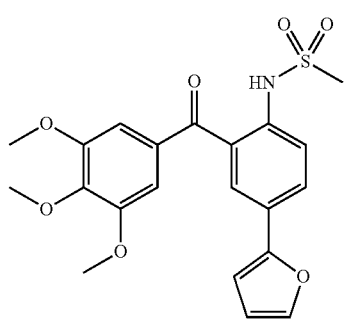
Compound 236
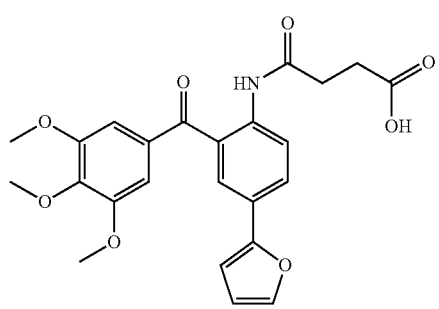
Compound 237
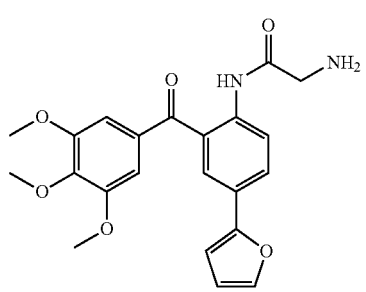

TABLE 1-continued
| Compound Structure |
|---|
| Compound 238 |
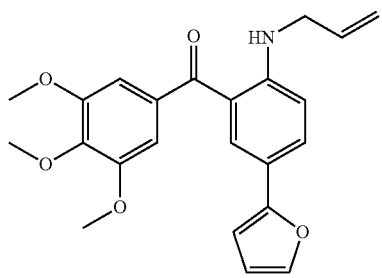
Compound 239
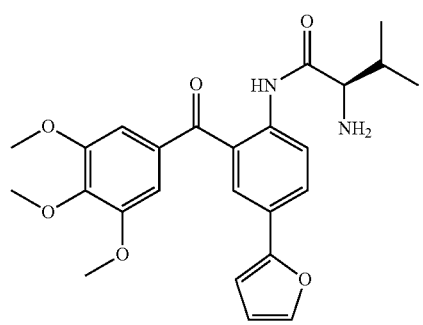
Compound 240
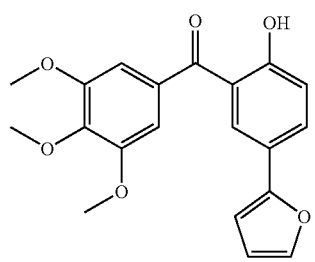
Compound 241
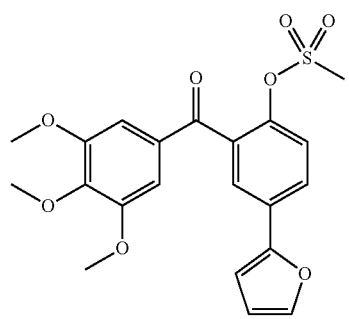
TABLE 1-continued
| Compound Structure |
|---|
| Compound 242 |
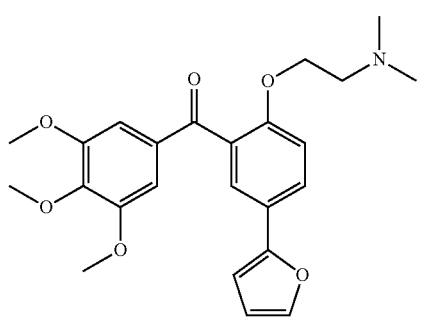
TABLE 2
| Compound Structure |
|---|
| Compound 243 |
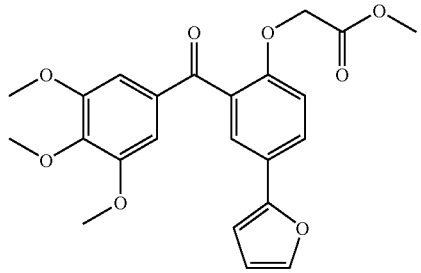
Compound 244
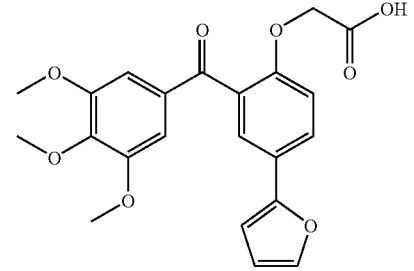
Compound 245
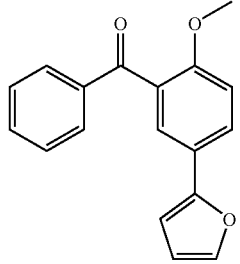

TABLE 2-continued
Compound Structure
Compound 246
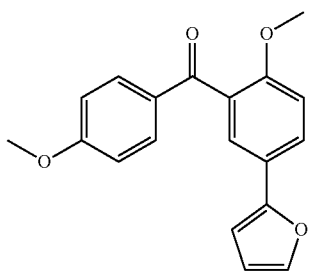
Compound 247
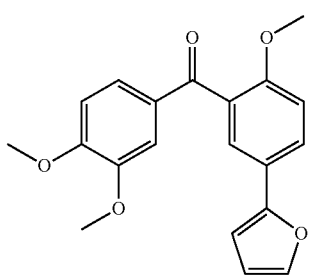
Compound 248
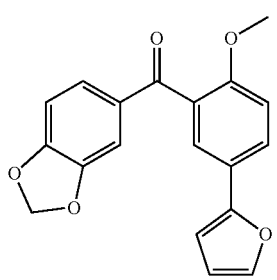
Compound 249
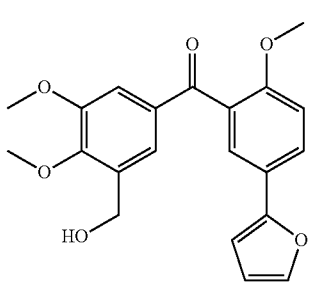
Compound 253
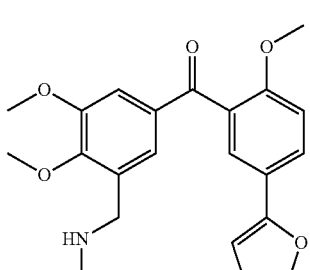
TABLE 2-continued
Compound Structure
Compound 255
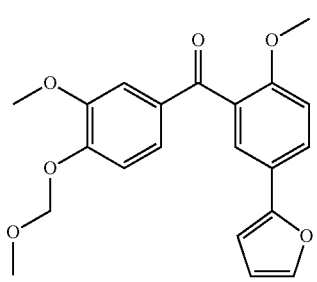
Compound 256
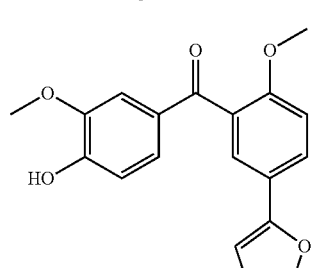
Compound 257
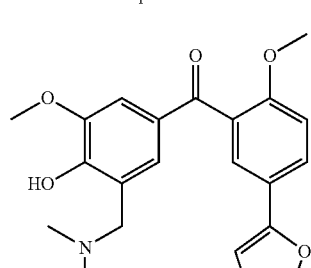
Compound 260
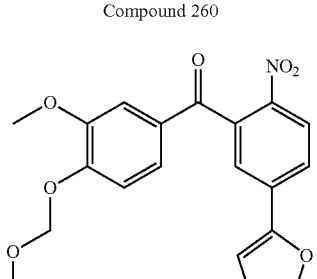
Compound 261
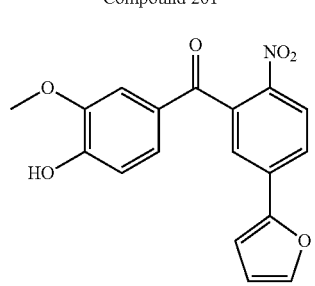

TABLE 2-continued
| Compound Structure |
|---|
| Compound 262 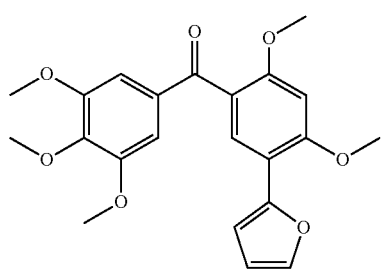 |
| Compound 263 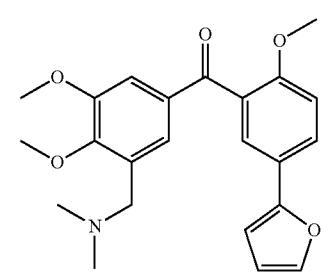 |
| Compound 264 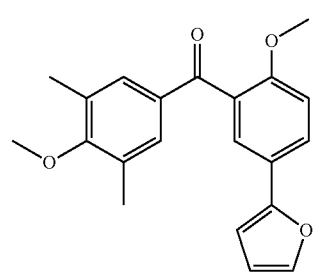 |
| Compound 265 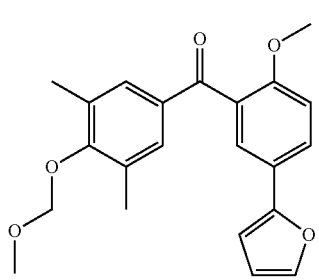 |
| Compound 266 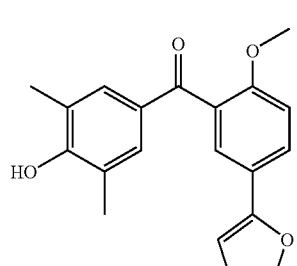 |
| Compound 267 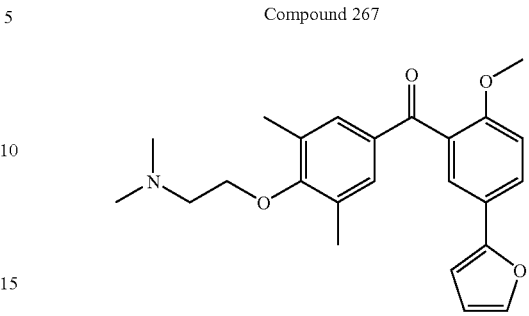 |
| Compound 268 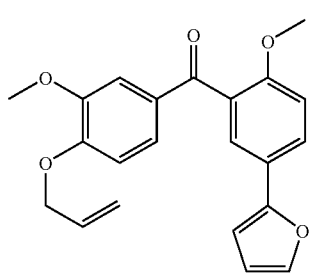 |
| Compound 269 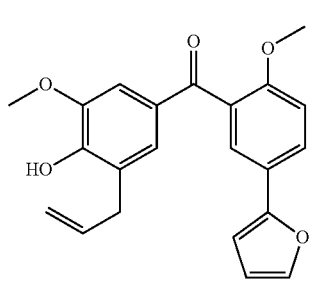 |
| Compound 271 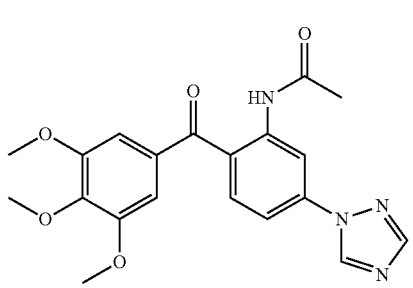 |
| Compound 272 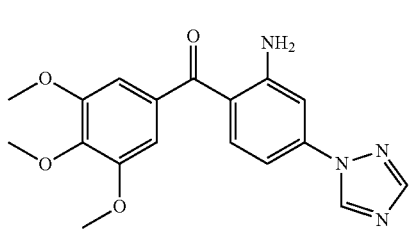 |

TABLE 2-continued
Compound Structure
Compound 273
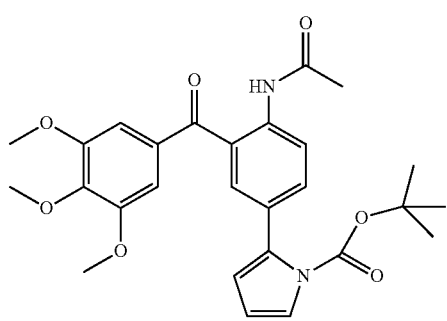
Compound 274
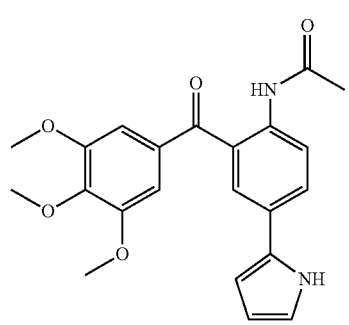
Compound 275
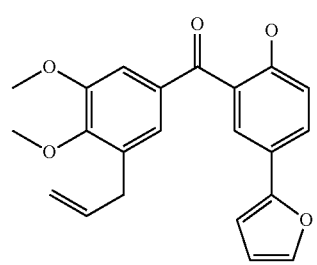
Compound 276
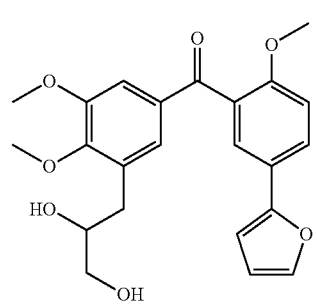
TABLE 2-continued
Compound Structure
Compound 277
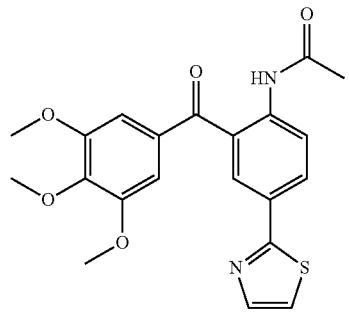
Compound 278
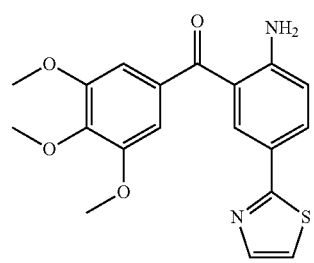
Compound 279
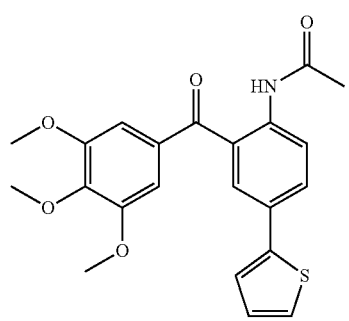
TABLE 3
Compound Structure
Compound 281
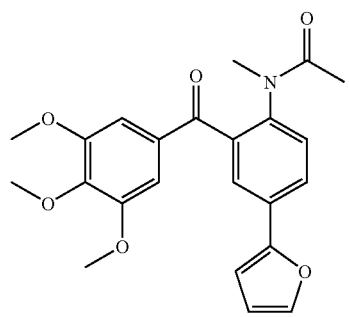

TABLE 3-continued
| Compound Structure |
|---|
| Compound 282 |
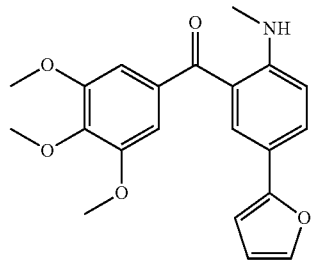
Compound 283
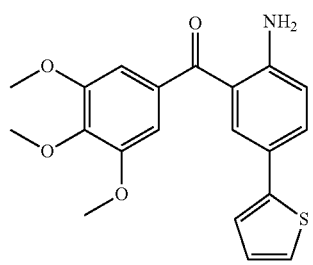
Compound 284
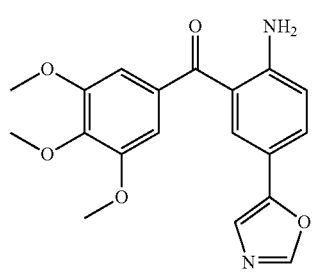
Compound 285
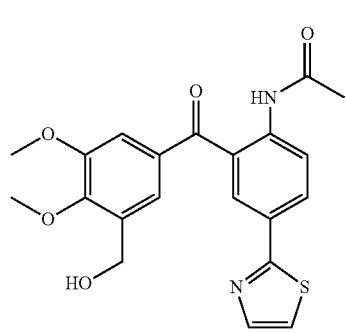
Compound 286
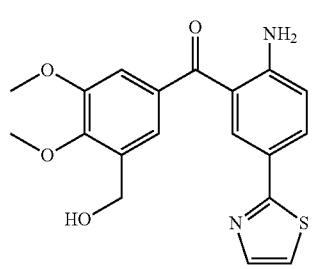
TABLE 3-continued
| Compound Structure |
|---|
| Compound 288 |
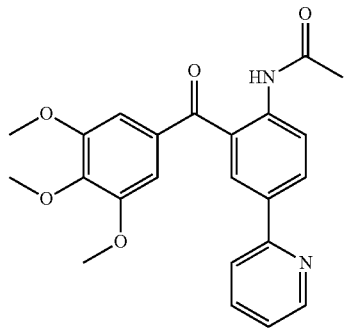
Compound 289
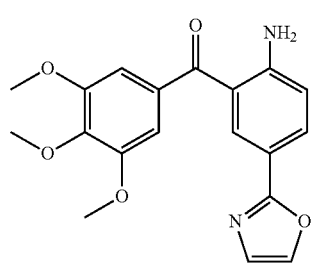
Compound 290
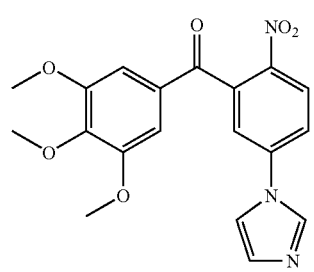
Compound 291
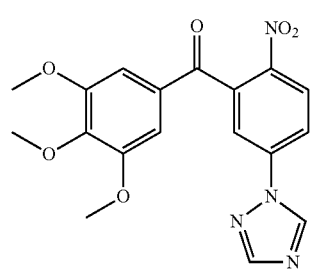
Compound 293
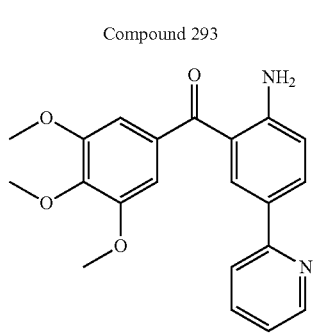

TABLE 3-continued
Compound Structure
Compound 294
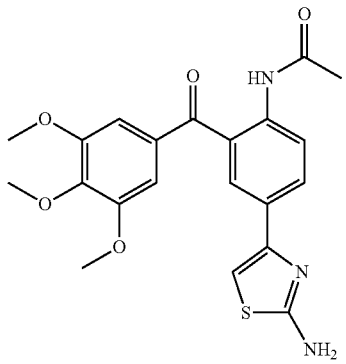
Compound 295
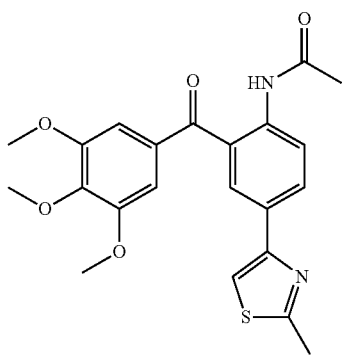
Compound 296
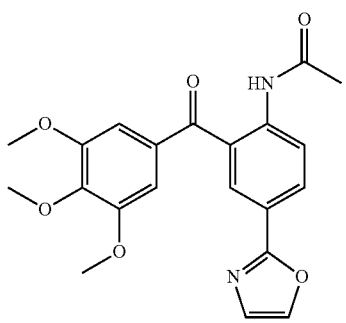
Compound 297
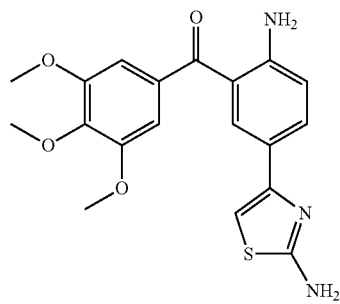
TABLE 3-continued
Compound Structure
Compound 298
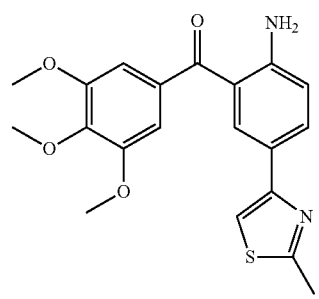
Compound 300
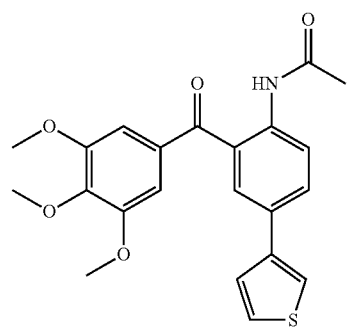
Compound 301
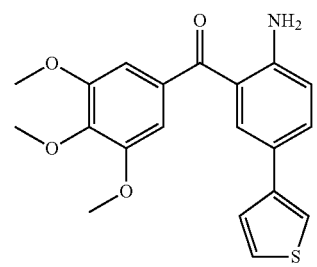
Compound 302
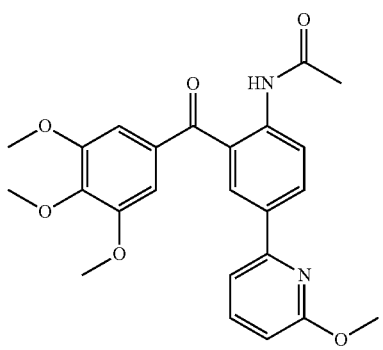

TABLE 3-continued
Compound Structure
Compound 303
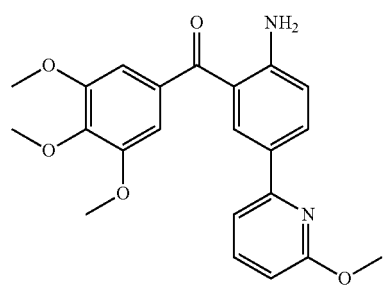
Compound 306
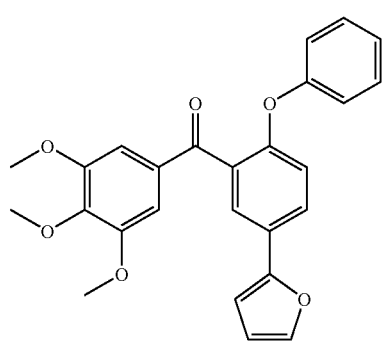
Compound 307
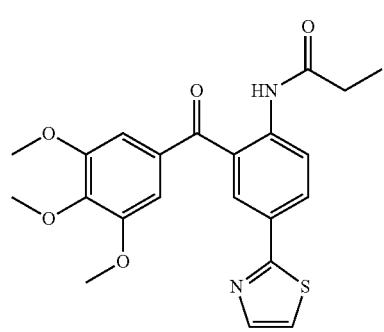
Compound 308
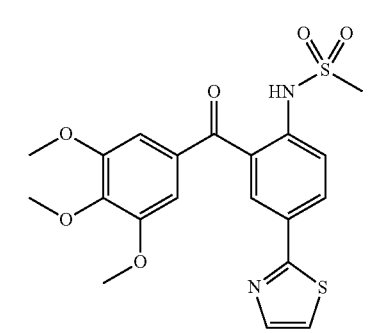
TABLE 3-continued
Compound Structure
Compound 309
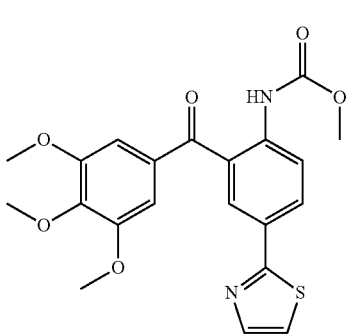
Compound 311
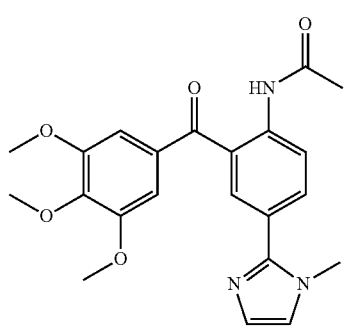
Compound 312
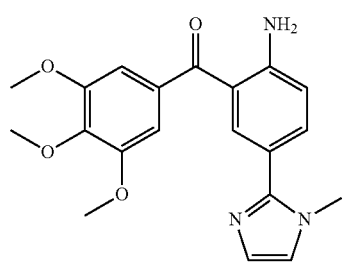
Compound 313
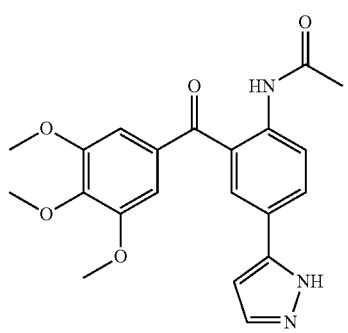

TABLE 3-continued
| Compound Structure |
|---|
| Compound 314 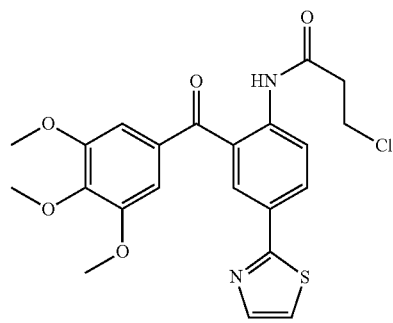 |
| Compound 315 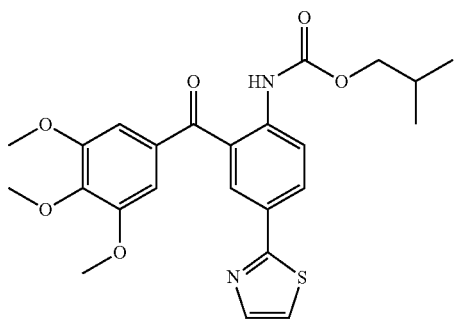 |
| Compound 316 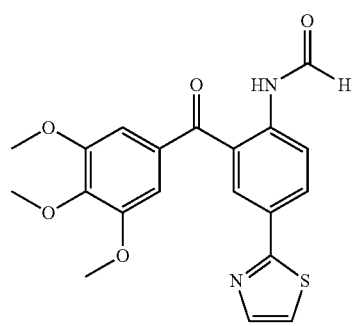 |
TABLE 4
| Compound Structure |
|---|
| Compound 317 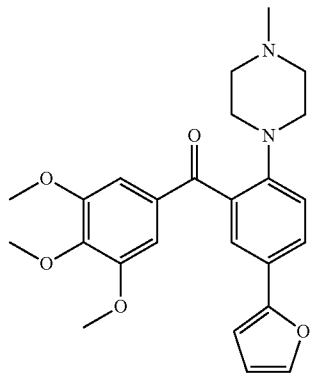 |
| Compound 318 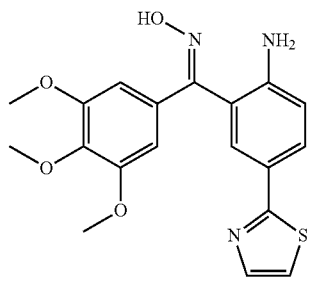 |
| Compound 320 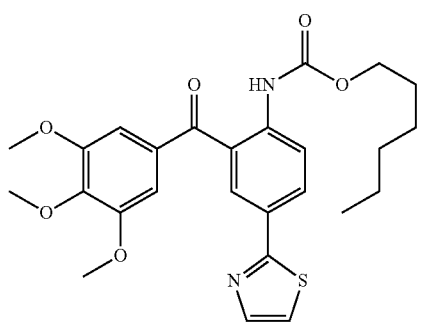 |
| Compound 321 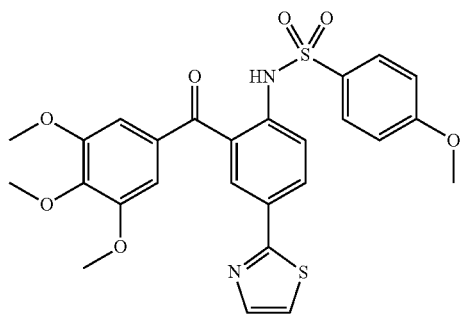 |

TABLE 4-continued
Compound Structure
Compound 322
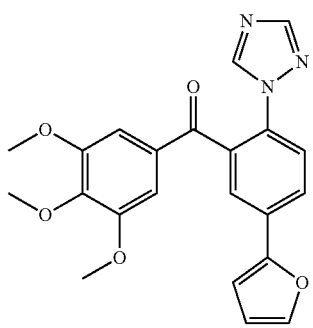
Compound 323
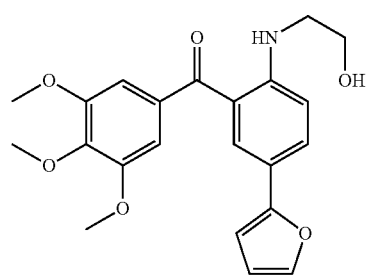
Compound 324
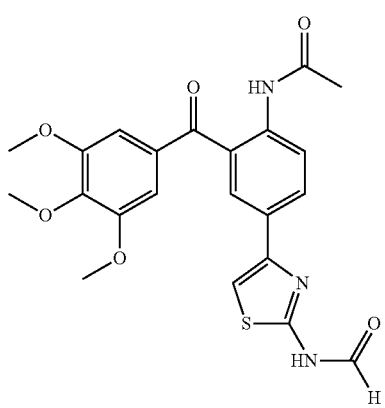
Compound 326
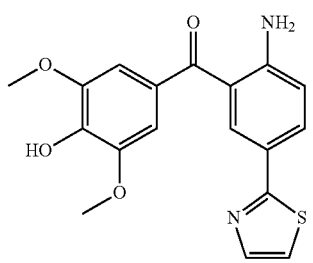
TABLE 4-continued
Compound Structure
Compound 327
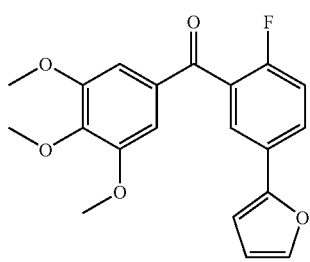
Compound 328
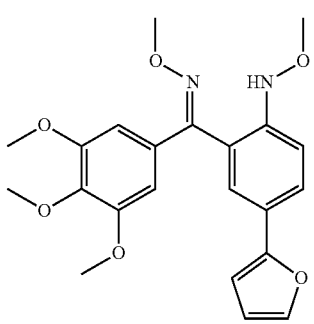
Compound 329
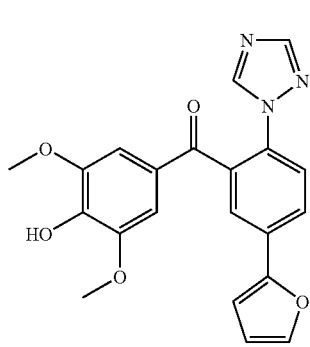
Compound 330
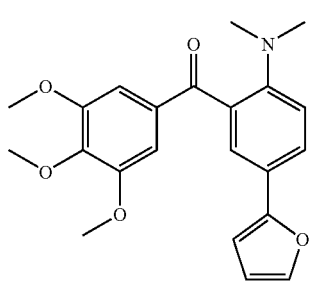

TABLE 4-continued
Compound Structure
Compound 331
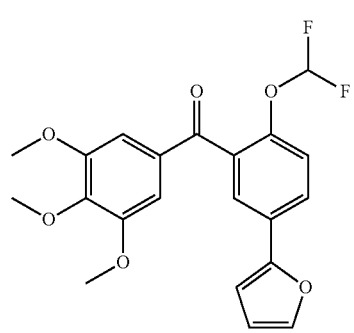
Compound 332
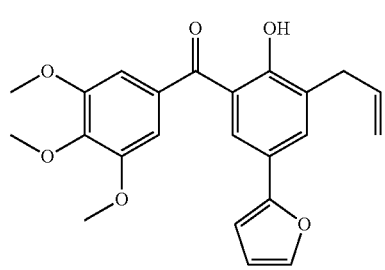
Compound 333
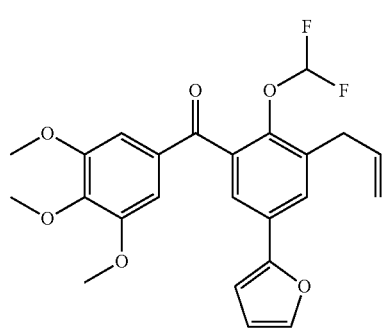
Compound 334
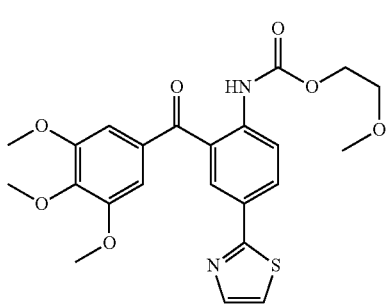
TABLE 4-continued
Compound Structure
Compound 335
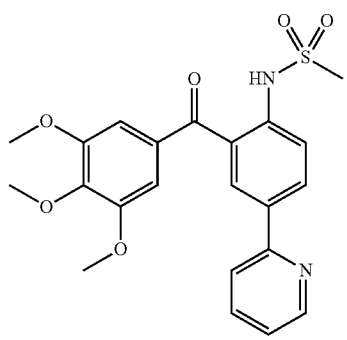
Compound 336
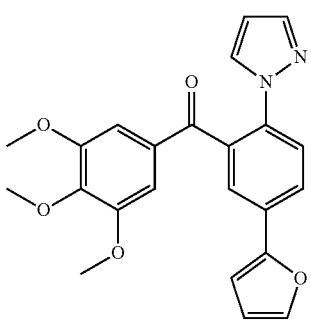
Compound 337
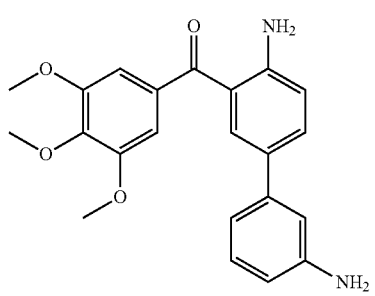
Compound 338
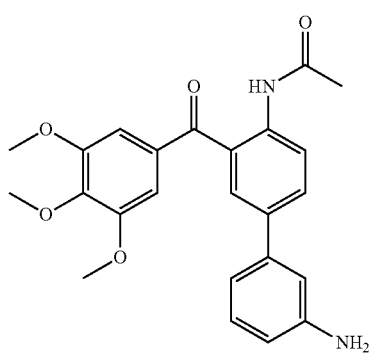

TABLE 4-continued
Compound Structure
Compound 339
Compound 340
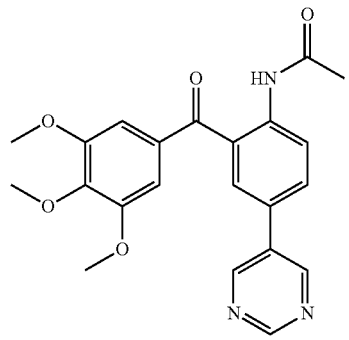
Compound 341
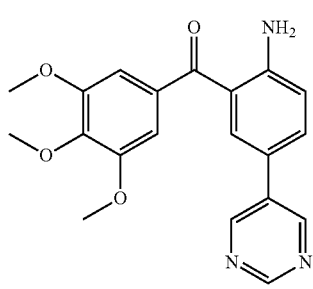
Compound 342
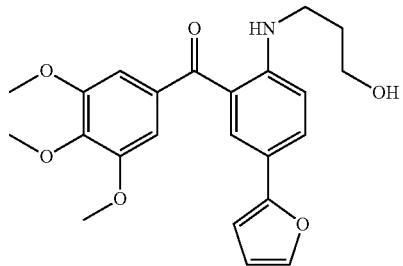
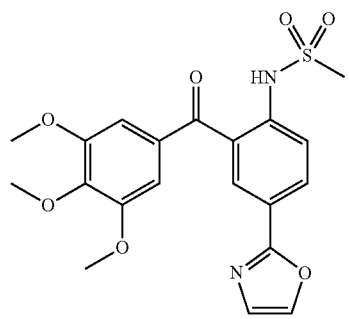
TABLE 4-continued
Compound Structure
Compound 346
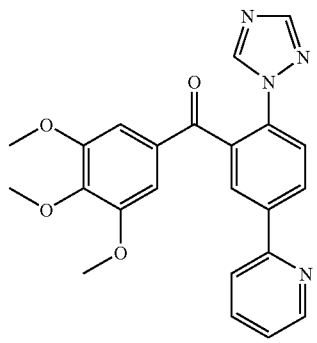
Compound 347
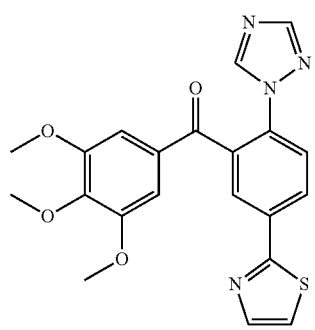
Compound 348
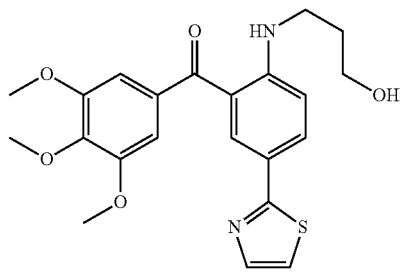
Compound 350
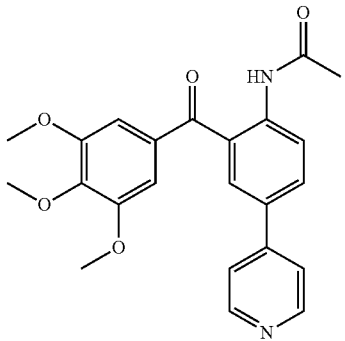

TABLE 4-continued
| Compound Structure |
|---|
| Compound 352 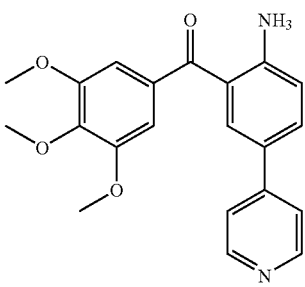 |
| Compound 354 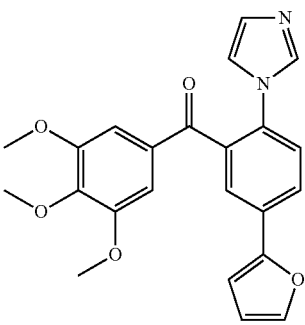 |
TABLE 5
| Compound Structure |
|---|
| Compound 357 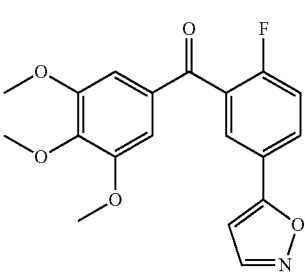 |
| Compound 359 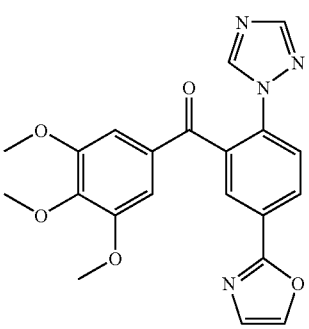 |
TABLE 5-continued
| Compound Structure |
|---|
| Compound 360 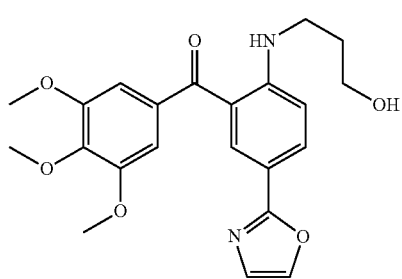 |
| Compound 363 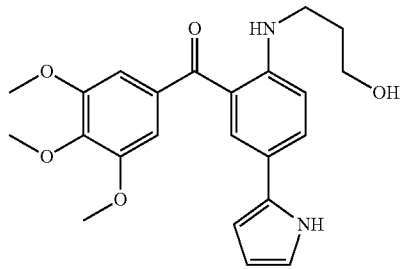 |
| Compound 364 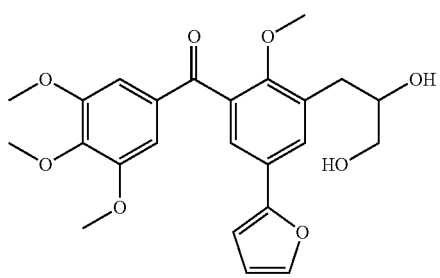 |
| Compound 365 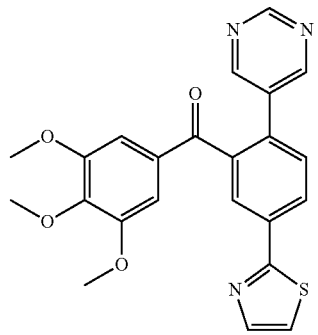 |

TABLE 5-continued
Compound Structure
Compound 366
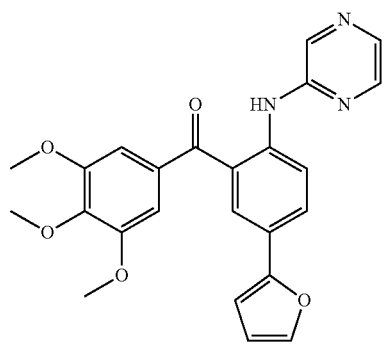
Compound 367
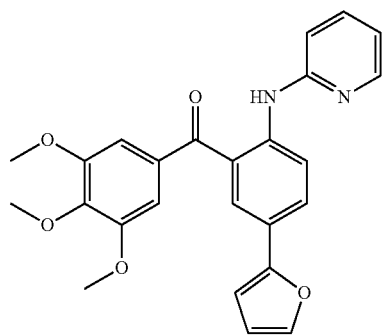
Compound 368
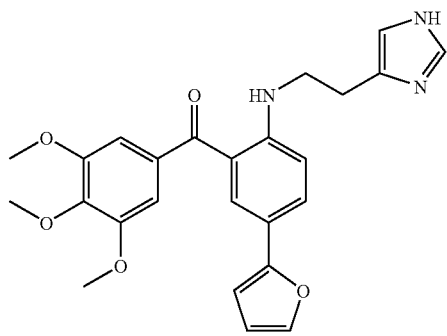
Compound 369
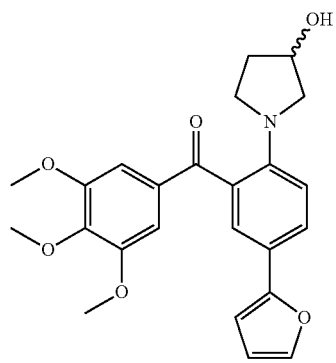
TABLE 5-continued
Compound Structure
Compound 370
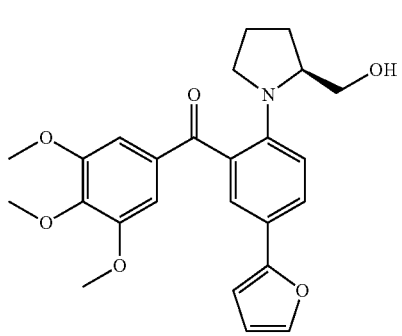
Compound 371
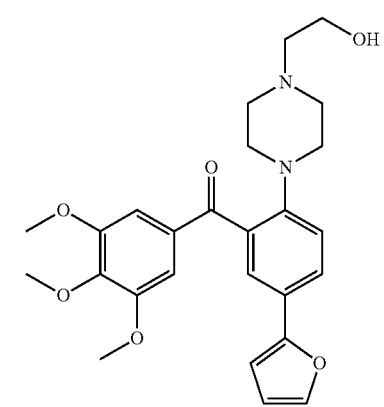
Compound 372
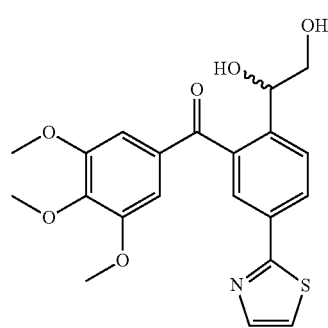
Compound 373
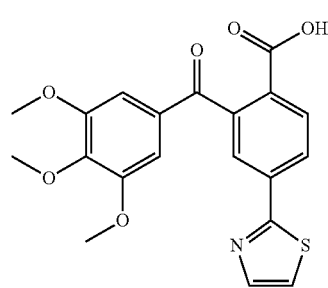

TABLE 5-continued
Compound Structure
Compound 374
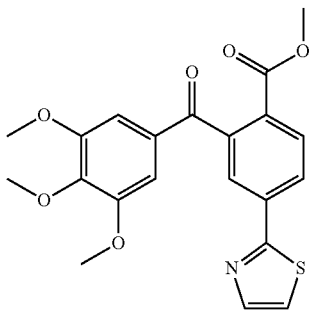
Compound 375
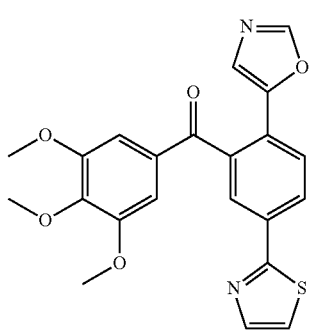
Compound 376
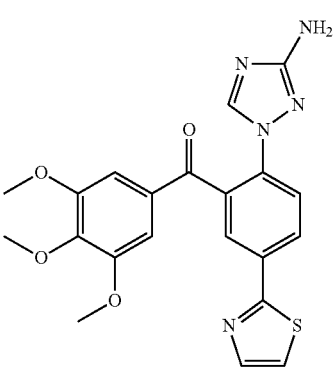
Compound 377
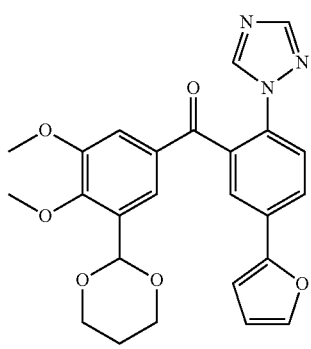
TABLE 5-continued
Compound Structure
Compound 378
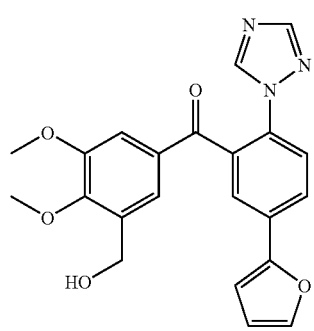
Compound 379
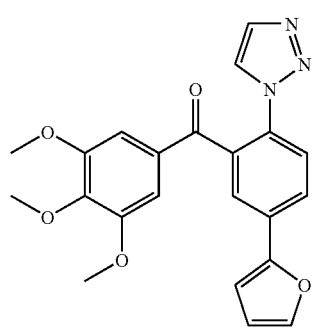
Compound 380
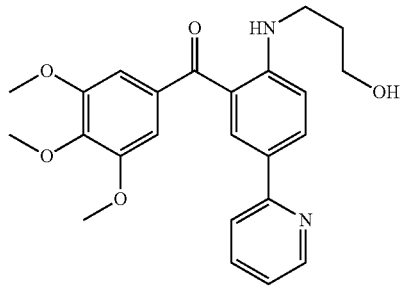
Compound 381
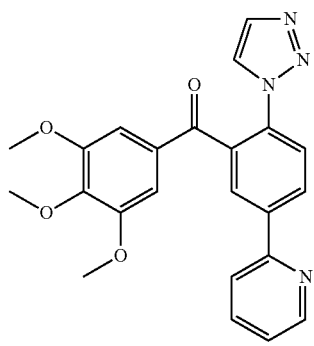

TABLE 5-continued
Compound Structure
Compound 382
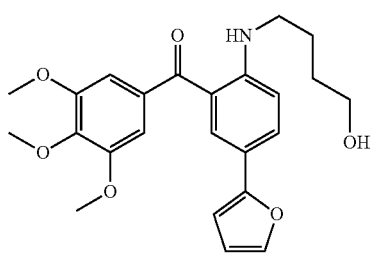
Compound 383
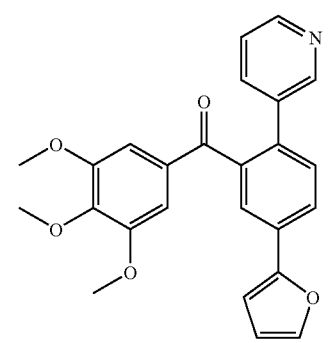
Compound 384
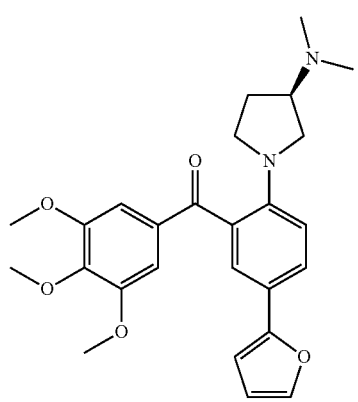
Compound 385
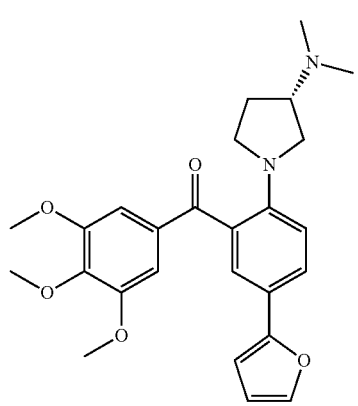
TABLE 5-continued
Compound Structure
Compound 386
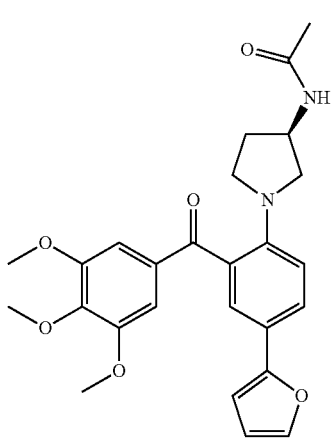
Compound 387
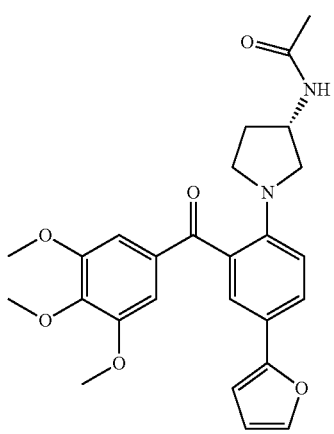
Compound 388
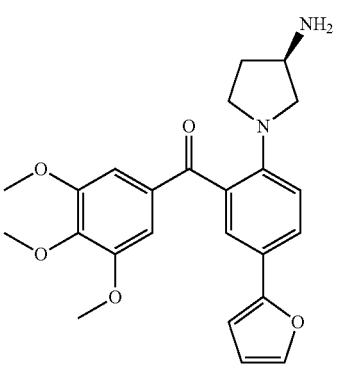

TABLE 5-continued
Compound Structure
Compound 389
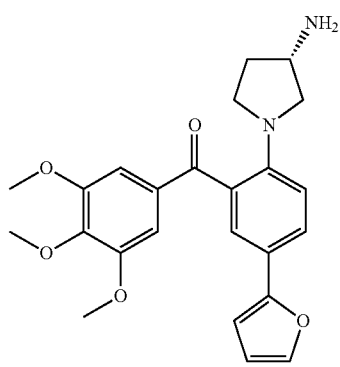
TABLE 6
Compound Structure
Compound 390
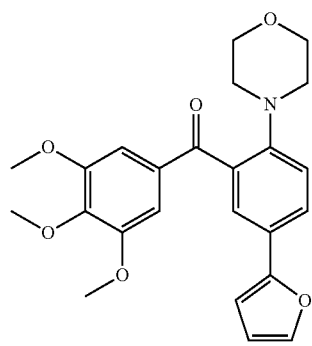
Compound 391
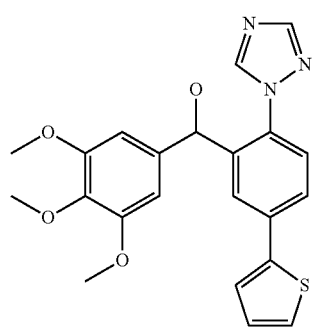
TABLE 6-continued
Compound Structure
Compound 392
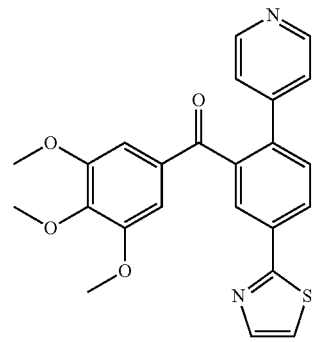
Compound 393
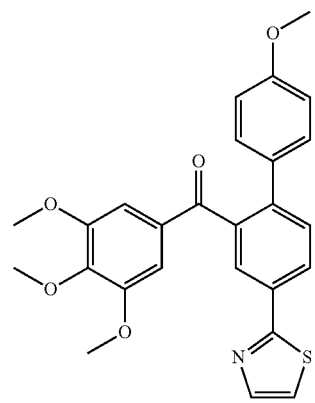
Compound 394
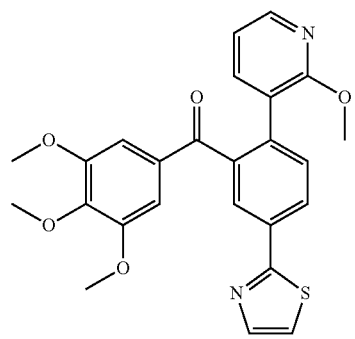
Compound 395
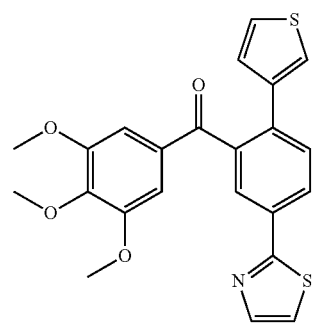

TABLE 6-continued
| Compound Structure |
|---|
| Compound 396 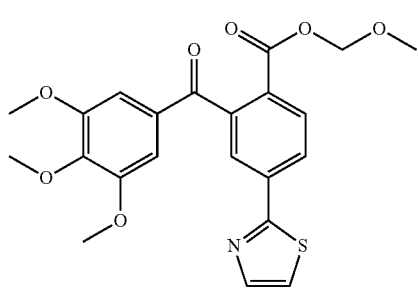 |
| Compound 397 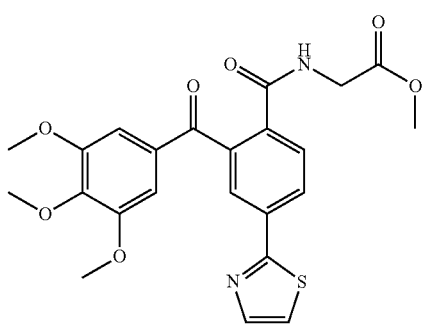 |
| Compound 399 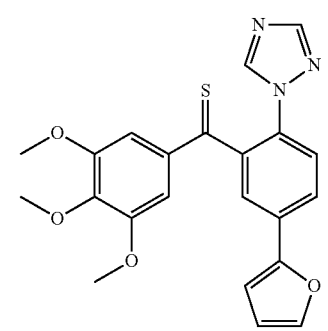 |
| Compound 400 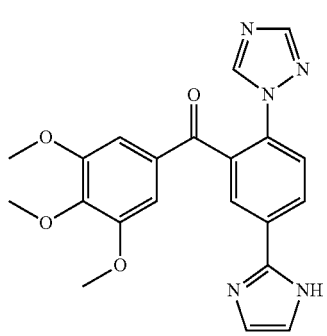 |
TABLE 6-continued
| Compound Structure |
|---|
| Compound 401 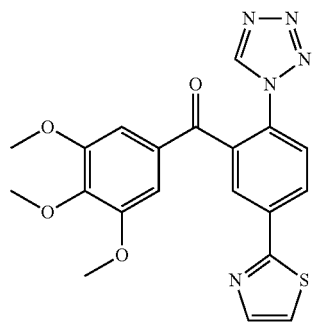 |
| Compound 402 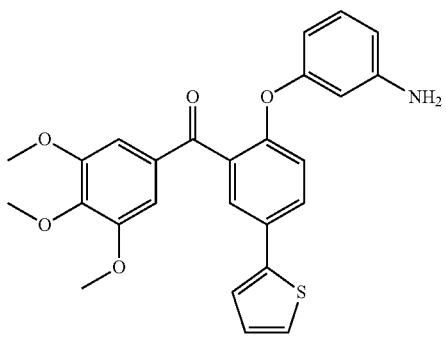 |
| Compound 403 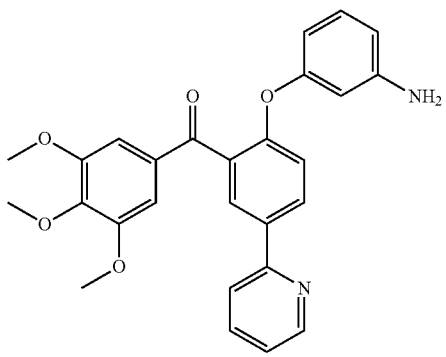 |
| Compound 406 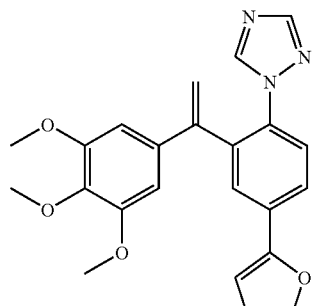 |

TABLE 6-continued
Compound Structure
Compound 408
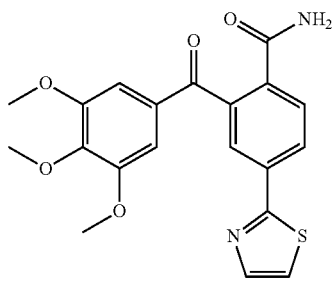
Compound 409
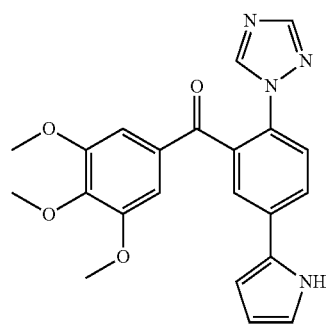
Compound 410
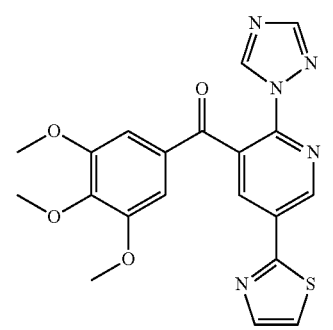
Compound 411
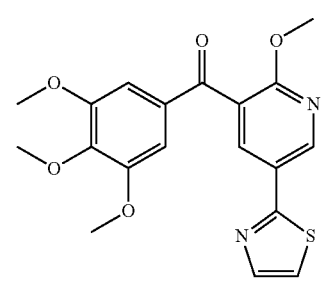
TABLE 6-continued
Compound Structure
Compound 420
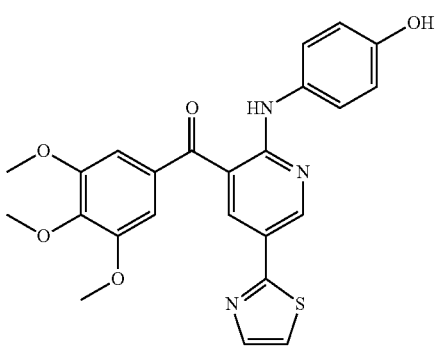
Compound 421
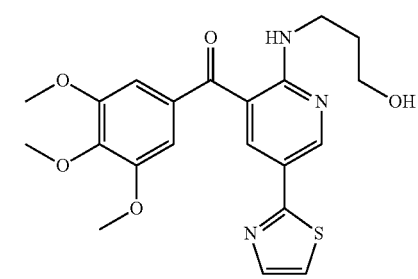
Compound 422
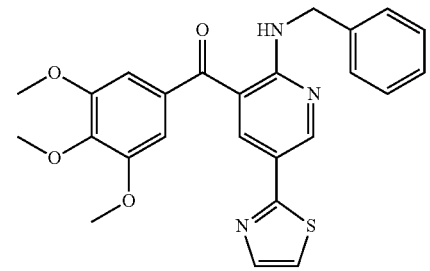
Compound 425
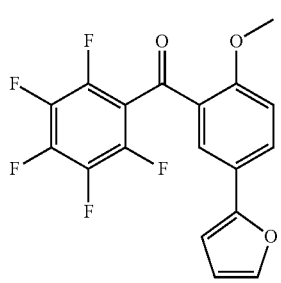

TABLE 6-continued
Compound Structure
Compound 426
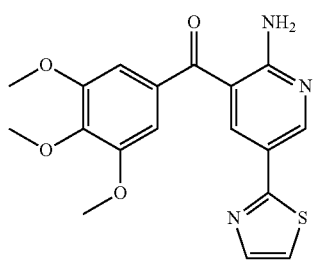
Compound 427
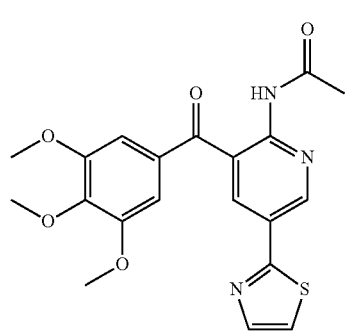
Compound 429
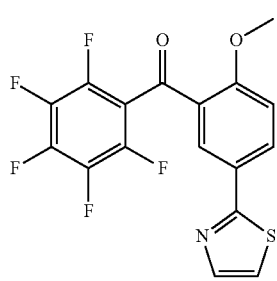
Compound 434
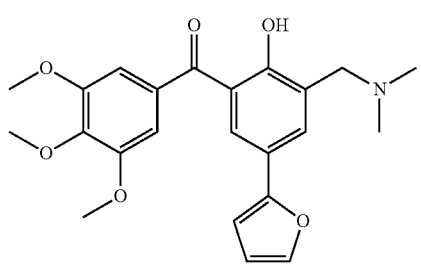
Compound 437
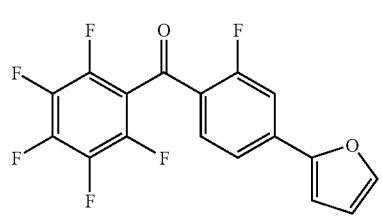
TABLE 6-continued
Compound Structure
Compound 443
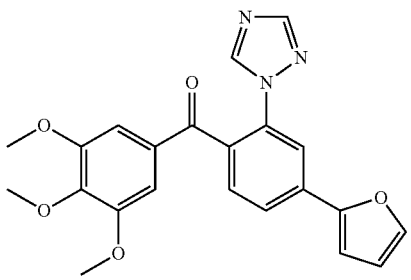
Compound 444
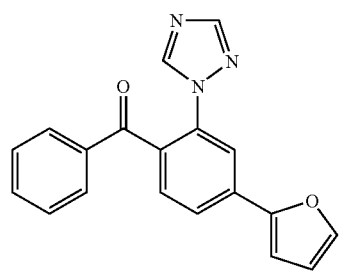
Compound 446
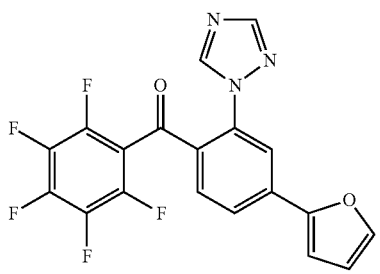
TABLE 7
Compound Structure
Compound 455
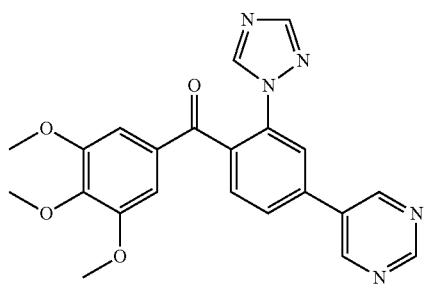

TABLE 7-continued

Compound Structure

Compound 456

Compound 457

Compound 458

Compound 462

Compound 463

Compound 464

Compound 469

Compound 474

Compound 475

TABLE 7-continued
| Compound Structure |
|---|
| Compound 476 |
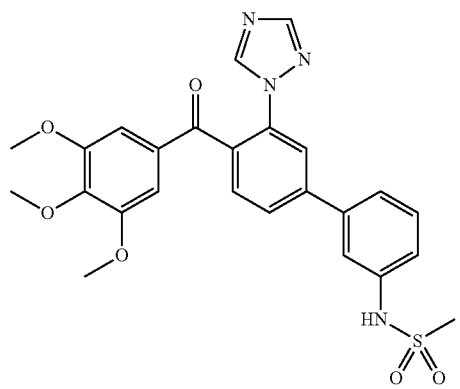
Compound 477
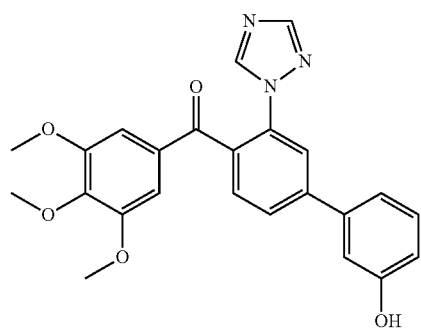
Compound 479
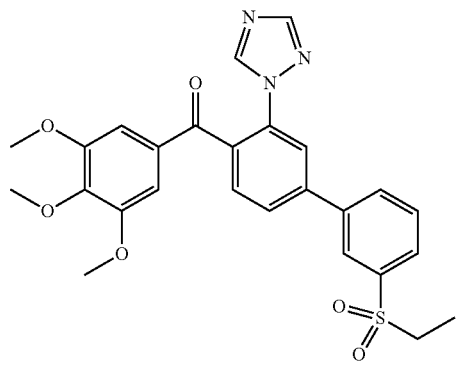
Compound 480
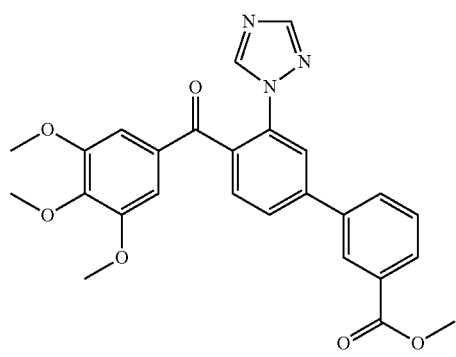
TABLE 7-continued
| Compound Structure |
|---|
| Compound 482 |
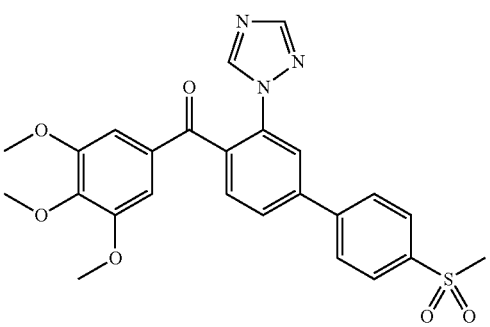
Compound 483
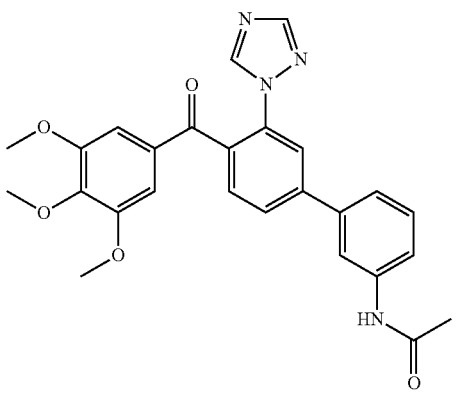
Compound 484
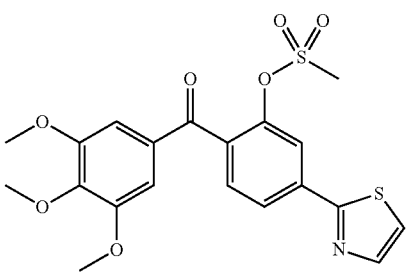
Compound 485
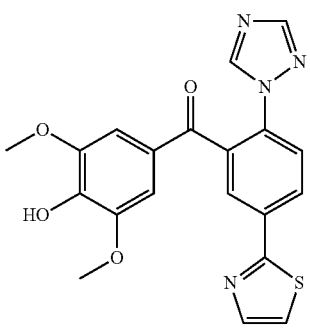

TABLE 7-continued
| Compound Structure |
|---|
| Compound 486 |
| 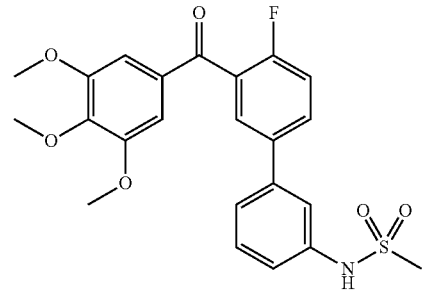 |
| Compound 492 |
| Compound 493 |
| Compound 494 |
| Compound 495 |
TABLE 7-continued
| Compound Structure |
|---|
| Compound 497 |
| 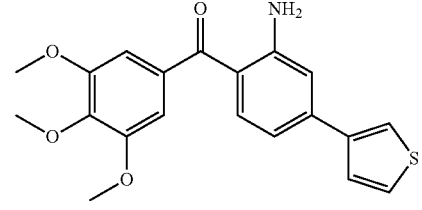 |
| Compound 499 |
| Compound 500 |
| Compound 501 |
| Compound 502 |

TABLE 7-continued
Compound Structure
Compound 503
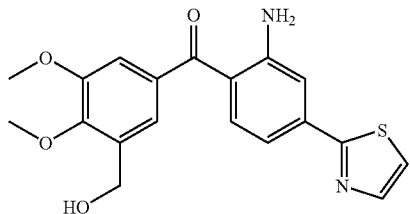
Compound 505
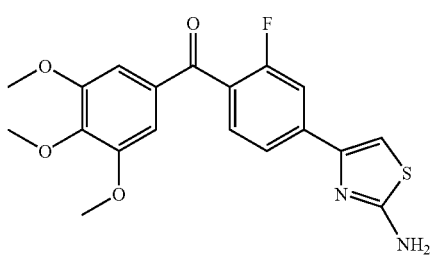
TABLE 8
Compound Structure
Compound 506
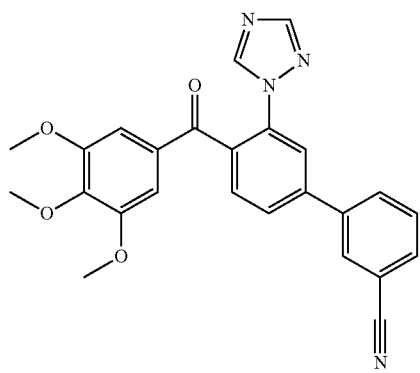
Compound 507
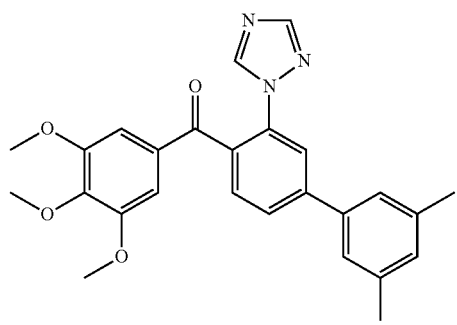
TABLE 8-continued
Compound Structure
Compound 508
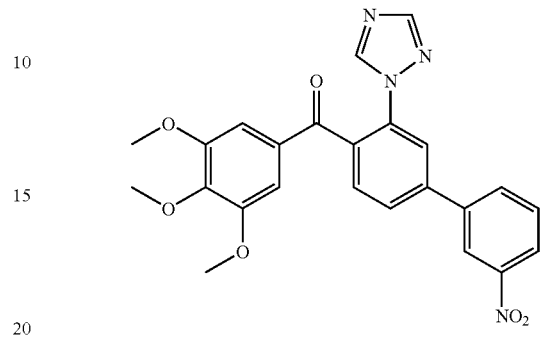
Compound 509
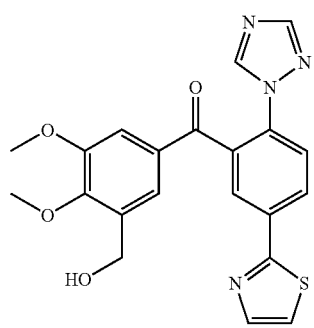
Compound 510
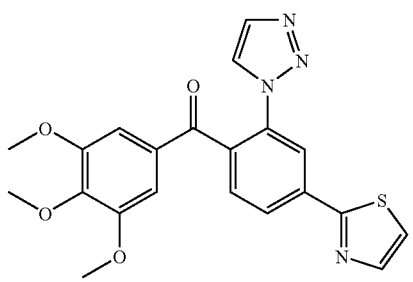
Compound 511
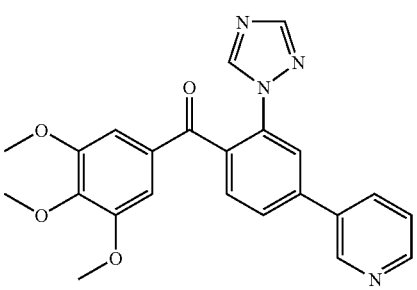

TABLE 8-continued
Compound Structure
Compound 512
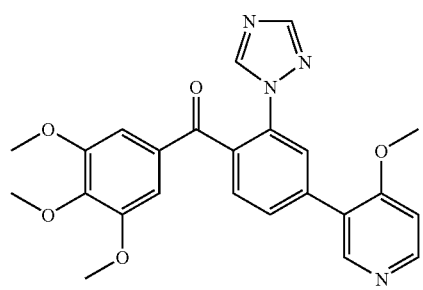
Compound 513
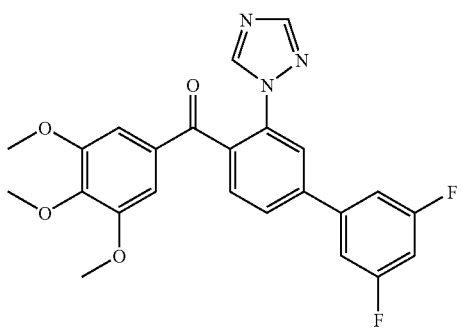
Compound 514
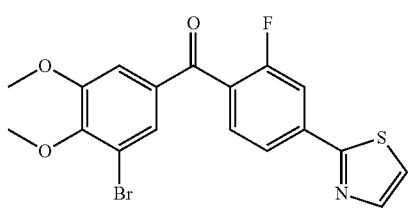
Compound 515
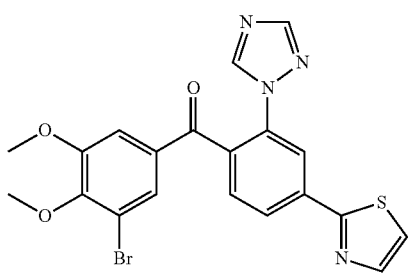
TABLE 8-continued
Compound Structure
Compound 516
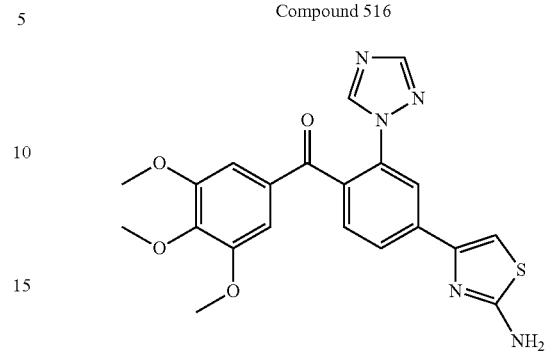
Compound 517
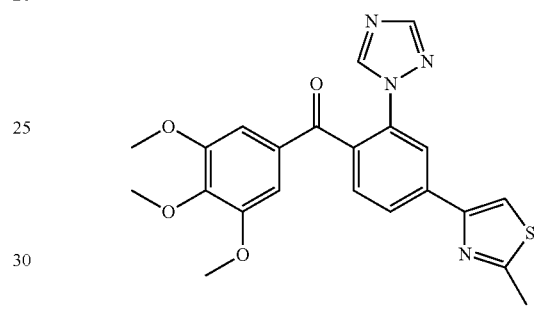
Compound 518
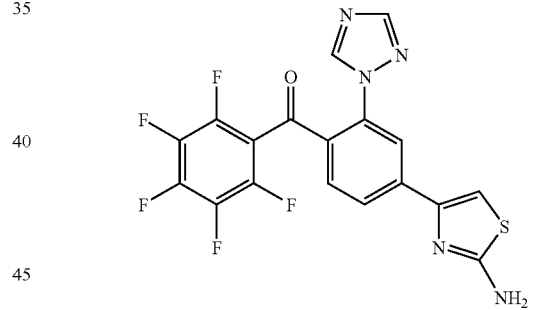
TABLE 9
Compound Structure
Compound 519
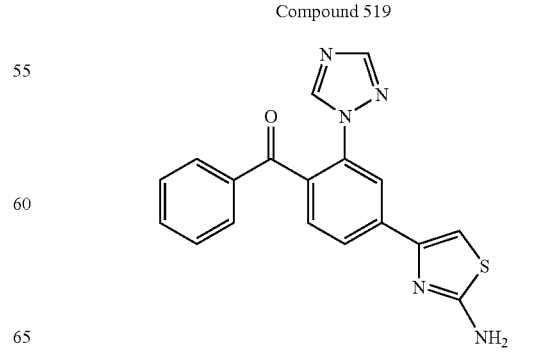

TABLE 9-continued
Compound Structure
Compound 525
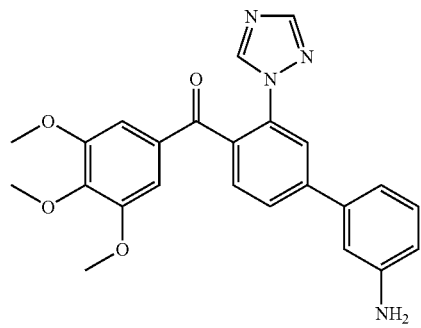
Compound 531
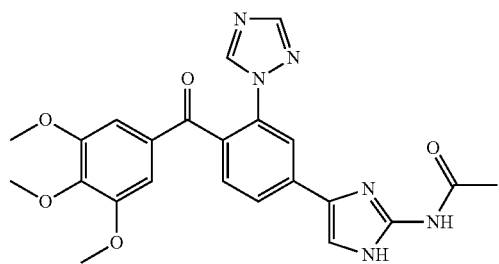
Compound 534
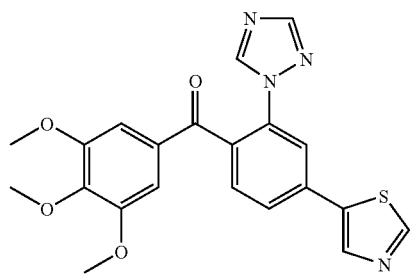
Compound 538
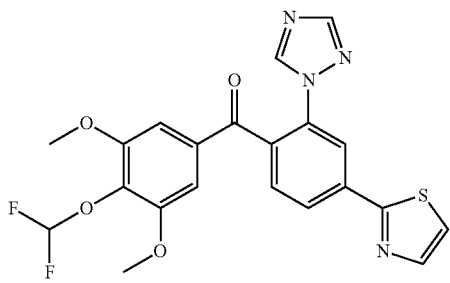
TABLE 9-continued
Compound Structure
Compound 547
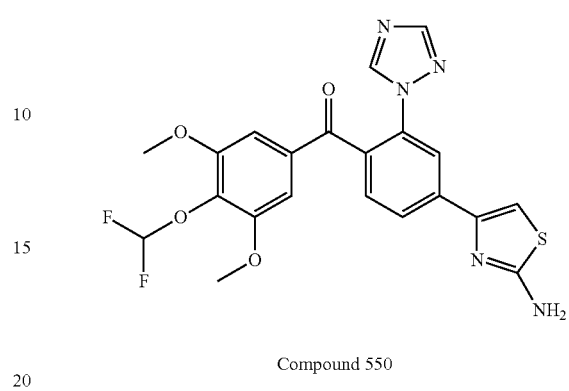
Compound 550
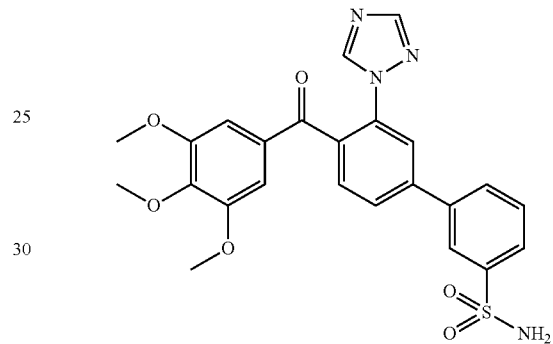
Compound 554
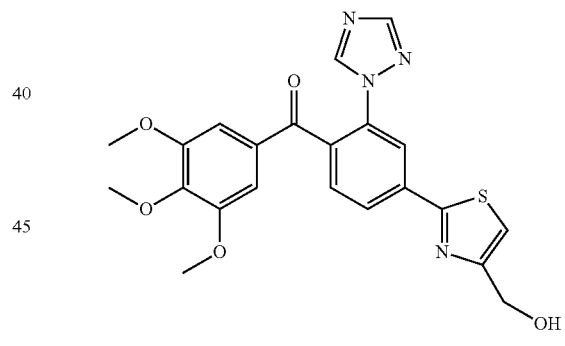
Compound 560
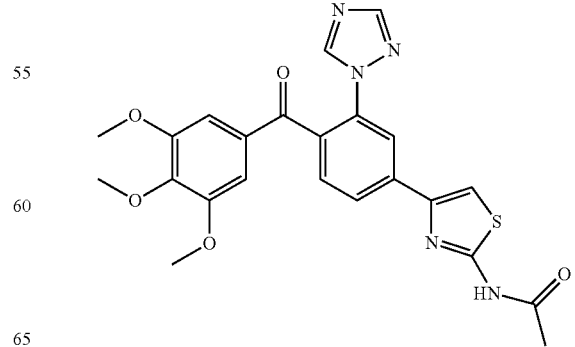

TABLE 9-continued
| Compound Structure |
|---|
| Compound 561 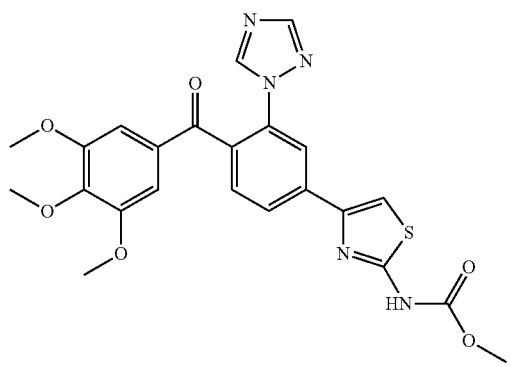 |
| Compound 562 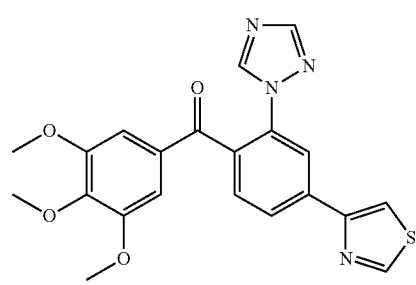 |
| Compound 563 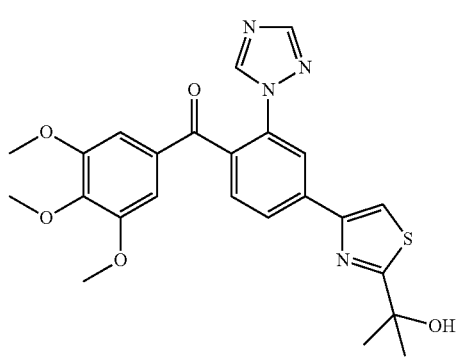 |
| Compound 564 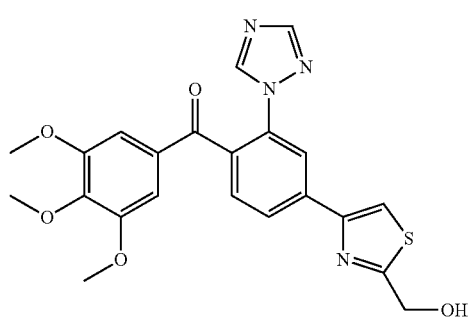 |
TABLE 9-continued
| Compound Structure |
|---|
| Compound 568 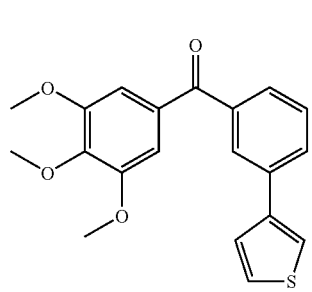 |
| Compound 570 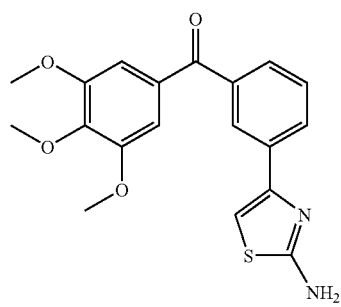 |
| Compound 571 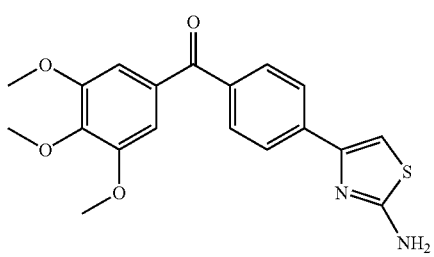 |
TABLE 10
| Compound Structure |
|---|
| Compound 581 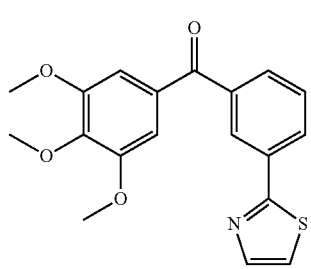 |

TABLE 10-continued
Compound Structure
Compound 583
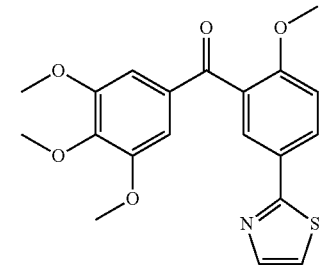
Compound 587
Compound 588
Compound 590
Compound 591
TABLE 10-continued
Compound Structure
Compound 594
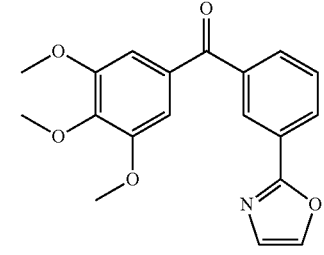
Compound 595
Compound 596
Compound 597

TABLE 10-continued

| Compound Structure |
|---|
| Compound 598 |
| Compound 599 |

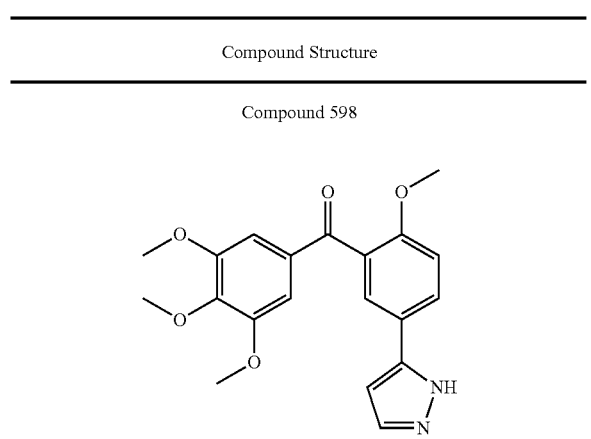
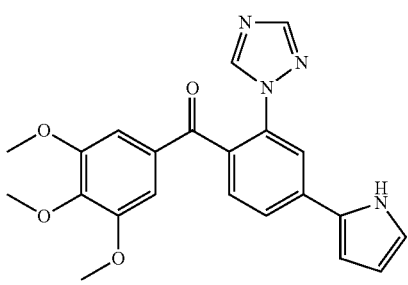

TABLE 10-continued

| Compound Structure |
|---|
| Compound 601 |
| Compound 602 |

Preparation Method of the Compound

The compounds of the present invention represented by the formula I can be prepared by a method widely known in a variety of literature (Jing-Ping Liou, et al., *Journal of Medicinal Chemistry*, 2002, 45, 2556-2562; Jing-Ping Liou, et al., *Journal of Medicinal Chemistry*, 2004, 47, 2897-2905; and Pettit, G. R., et al., *Journal of Medicinal Chemistry*, 2000, 43, 2731-2737). The method for preparing the compound represented by the formula I will be described in greater detail, together with reaction equations.

[Reaction 1]

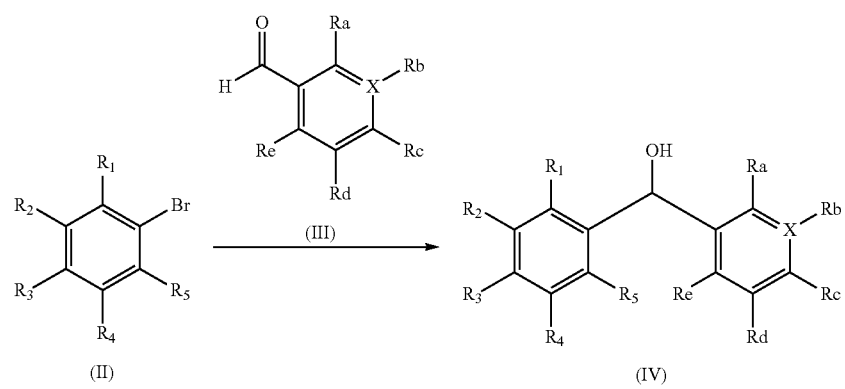

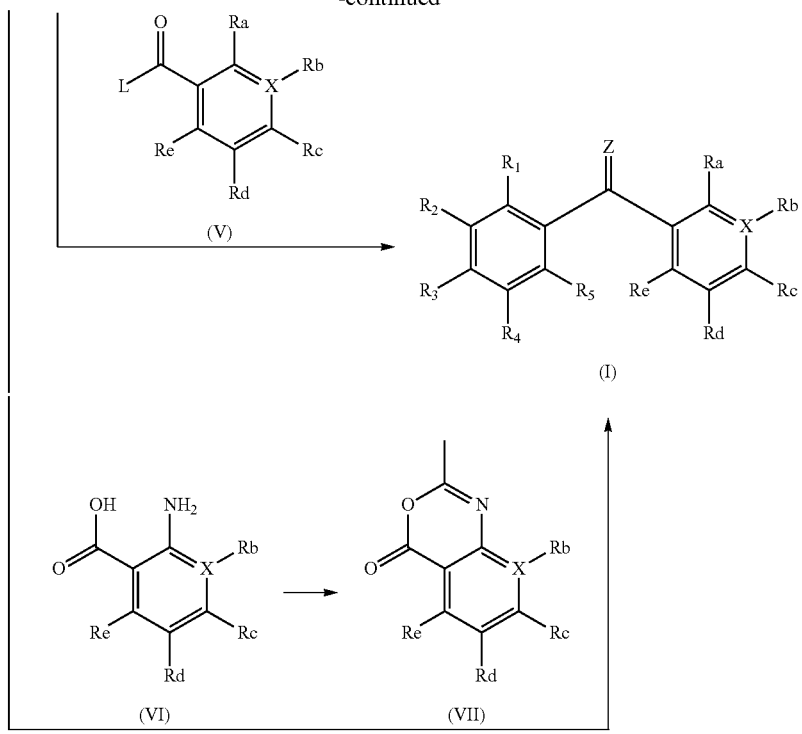

wherein, $R_1$, $R_2$, $R_3$, $R_4$, $R_5$, Ra, Rb, Rc, Rd, and Re are each independently the same as defined above. L is a leaving group, and preferably methoxymethylamine or halogen (e.g., chloro).

The reaction 1 is preferably carried out by, first, adding magnesium or n-butyllithium (n-BuLi) to Compound II as a starting material, and then, mixing Compound III, Compound V or Compound VII thereto.

Among the above reactions, the reaction using Compound III uses a solvent of tetrahydrofuran or ether, and has a reaction temperature of −100 to 70° C., preferably −78 to 20° C. The obtained compound represented by Compound IV is subjected to an oxidation reaction using various oxidants to obtain the desired Compound I (the compound represented by the formula I). As the oxidant, pyridinium dichromate (PDC), pyridinium chromate (PCC) or the like can be used. As the solvent, tetrahydrofuran, ether, methylenechloride or the like can be used, and preferably tetrahydrofuran or ether. Furthermore, a reaction temperature at this step is 0 to 70° C., and preferably 0 to 40° C.

The reaction using Compound V uses a solvent of tetrahydrofuran, dimethylformamide (DMF), acetonitrile ($CH_3CN$) or the like, and preferably tetrahydrofuran. Moreover, a reaction temperature at this reaction is −100 to 70° C., and preferably −78 to 20° C.

For the reaction using Compound VII, a method widely known for preparing Compound VII from Compound VI can be used (Welch, W. M., et al., *Bioorg. med. Chem. Lett.,* 2001, 11, 177-182).

The compound of the present invention represented by the formula I can also be prepared by a method known in a variety of literature, as shown in the following reaction 2 (Doo Ok Jang, et al., *J Tetrahedron Lett.,* 2006, 47, 6063-6066; and D. C. Waite, et al., *Organic Process research & Development,* 1998, 2, 116-120).

[Reaction 2]

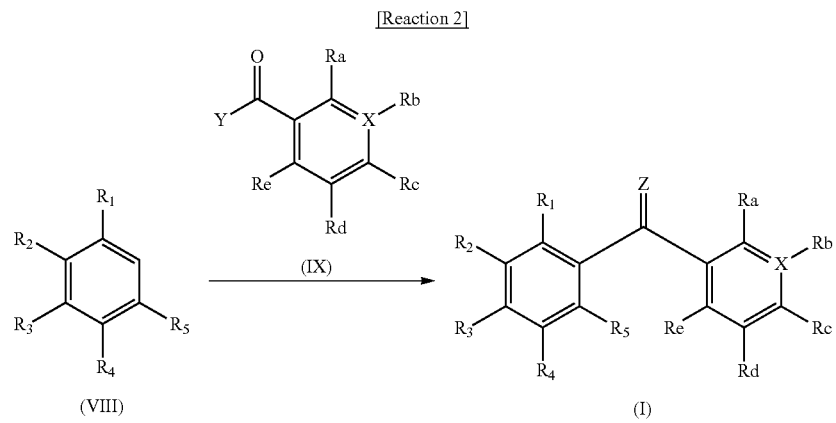

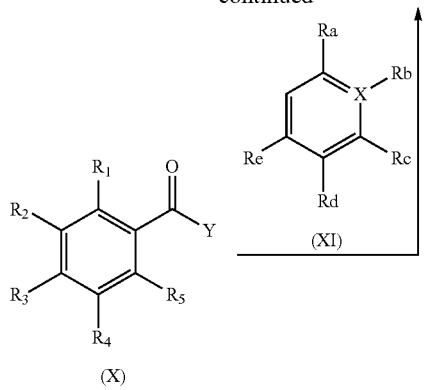

wherein, $R_1$, $R_2$, $R_3$, $R_4$, $R_5$, Ra, Rb, Rc, Rd, and Re are each independently the same as defined above. Y is a leaving group, and preferably hydroxyl or halogen (e.g., chloro).

The reaction 2 is preferably carried out by adding a Lewis acid or an organometal, and then mixing Compound IX or Compound X thereto. As the Lewis acid used herein, aluminum chloride ($AlCl_3$), zinc chloride ($ZnCl_2$), tin chloride ($SnCl_4$) or the like can be used. As the solvent, sulfuric acid, methylenechloride, dimethylacetamide, dimethylformamide (DMF), dimethylsulfoxide (DMSO) or the like can be used. Furthermore, a reaction temperature is −20 to 150° C., and preferably 0 to 80° C.

In general, Compound I of the present invention can be prepared by the above reaction 1 or 2. In the following reactions 3,4,5, and 6, more specific methods for preparing the compounds will be described.

[Reaction 3]

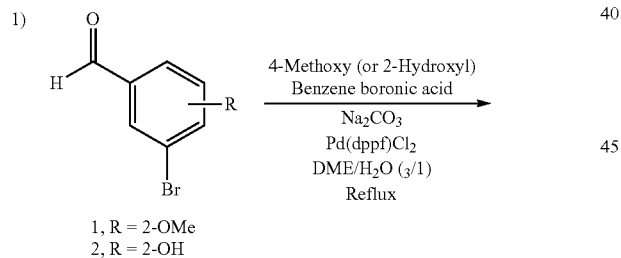

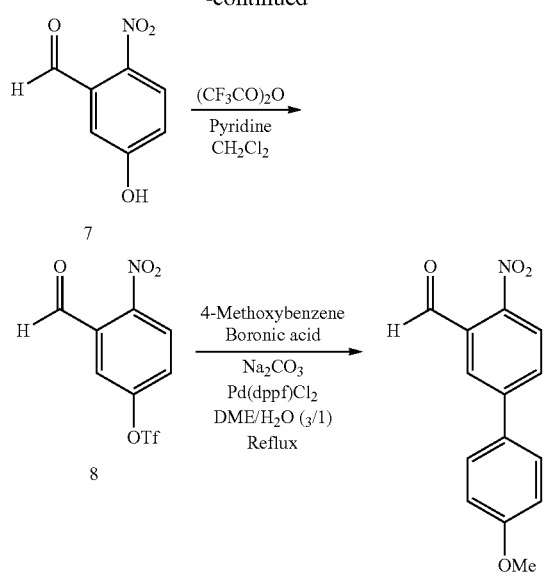

The reaction 3 is a typical process for preparing Compound III. Boronic acid is bonded to Compound I or Compound 2 by a Suzuki reaction (Morris, G. A., et al., *Tetrahedron Lett.*, 2001, 42, 2093) to prepare Compound 3 or Compound 4.

[Reaction 4]

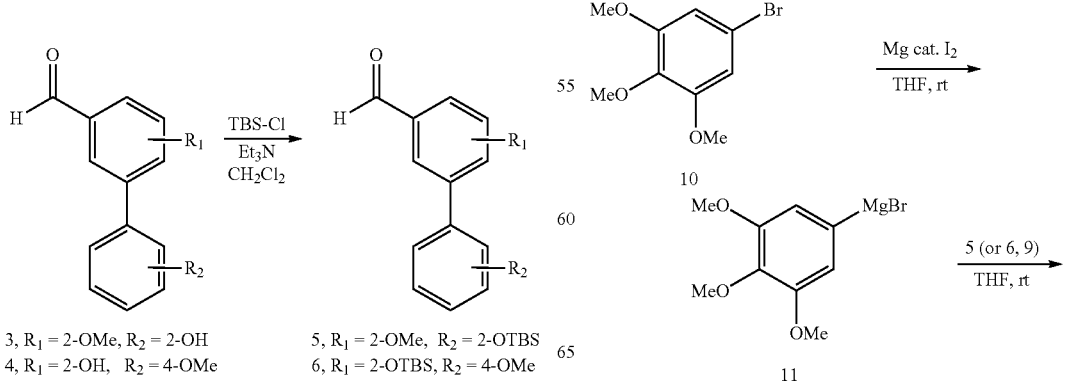

-continued

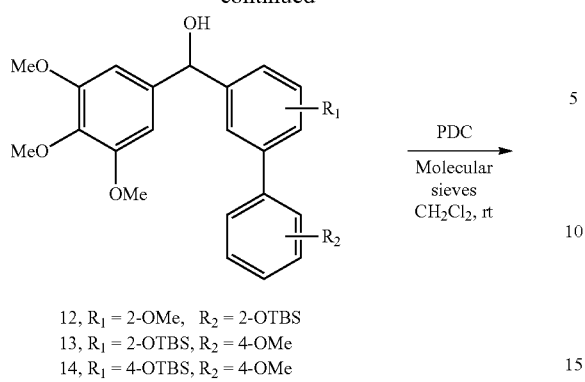

12, R₁ = 2-OMe, R₂ = 2-OTBS
13, R₁ = 2-OTBS, R₂ = 4-OMe
14, R₁ = 4-OTBS, R₂ = 4-OMe

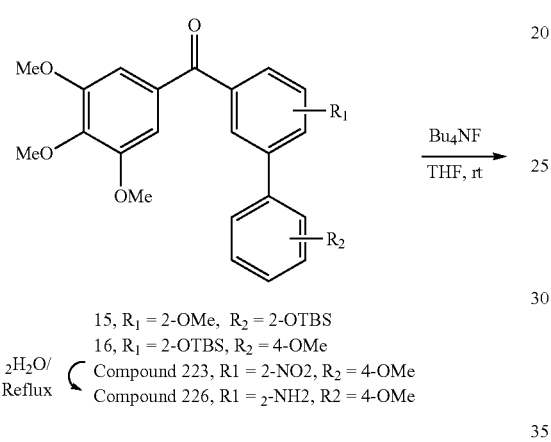

15, R₁ = 2-OMe, R₂ = 2-OTBS
16, R₁ = 2-OTBS, R₂ = 4-OMe

SnCl₂, 2H₂O/ EtOH, Reflux
Compound 223, R1 = 2-NO2, R2 = 4-OMe
Compound 226, R1 = 2-NH2, R2 = 4-OMe Compound 218, R₁ = 2-OMe, R₂ = 2-OH
Compound 220, R₁ = 2-OH, R₂ = 4-OMe The reaction 4 is a specific process for synthesizing Compounds 218, 220, 223, and 226 of the present invention. The other compounds of the present invention can also be prepared according to the above reaction. Metal magnesium is added to Compound 10, and iodide in a catalytic amount is added thereto to obtain Compound 11. Thus obtained Compound 11 is reacted with a variety of aldehydes obtained in the reaction 3 to obtain Compound 12, Compound 13, or Compound 14. Thus obtained benzhydrol derivatives are subjected to an oxidation reaction using various oxidants to prepare Compound 223 or Compound 226 of the present invention. In other cases, a typical deprotection reaction is carried out to prepare Compound 218 or Compound 220 of the present invention.

[Reaction 5]

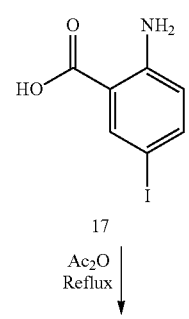

17

Ac₂O Reflux

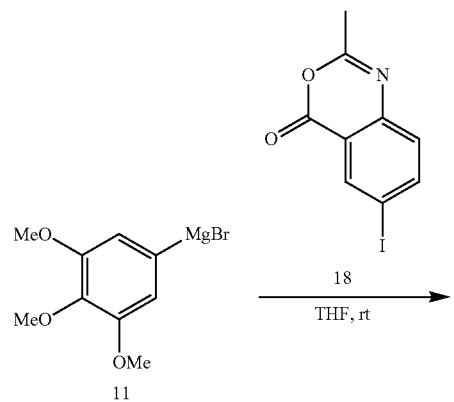

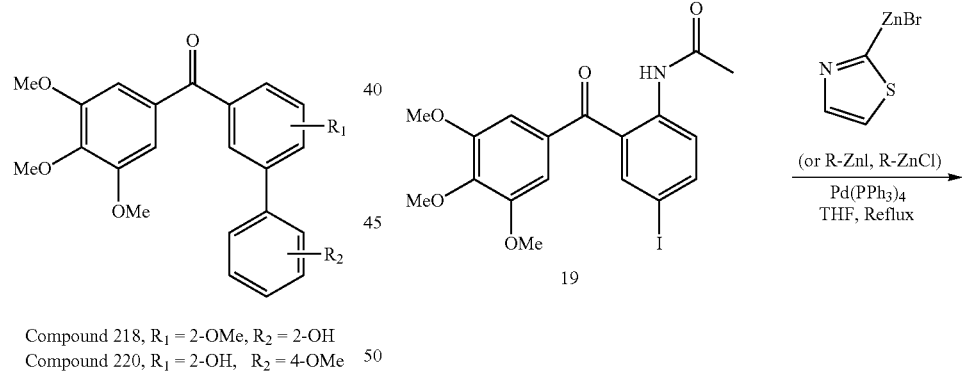

19

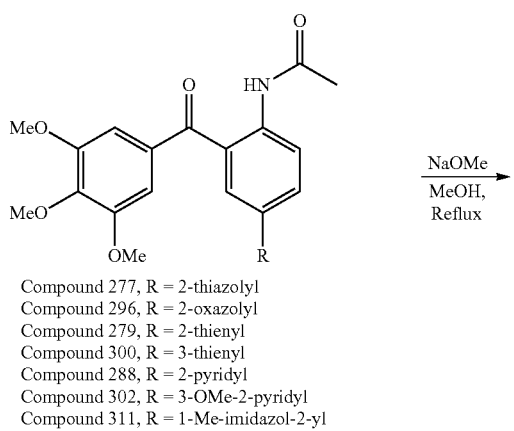

Compound 277, R = 2-thiazolyl
Compound 296, R = 2-oxazolyl
Compound 279, R = 2-thienyl
Compound 300, R = 3-thienyl
Compound 288, R = 2-pyridyl
Compound 302, R = 3-OMe-2-pyridyl
Compound 311, R = 1-Me-imidazol-2-yl

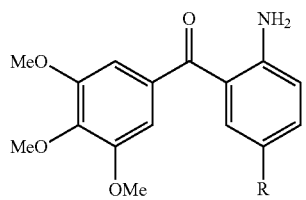

Compound 278, R = 2-thiazolyl
Compound 289, R = 2-oxazolyl
Compound 283, R = 2-thienyl
Compound 301, R = 3-thienyl
Compound 293, R = 2-pyridyl
Compound 303, R = 3-OMe-2-pyridyl
Compound 312, R = 1-Me-imidazol-2-yl The reaction 5 is a typical synthesis process of Compounds 227, 278, 296, 289, 279, 283, 300, 301, 288, 293, 302, 303, 311, and 312 of the present invention. The other compound of the present invention can also be prepared according to the above reaction. Compound 18 obtained from Compound 17 is reacted with Compound 11 of the reaction 4 to obtain Compound 19. From thus obtained Compound 19, the above compounds according to the present invention are prepared by a reaction described in a literature using a variety of commercially available ZnBr derivatives and a palladium catalyst (Michael R. Reeder, et al., *Organic Process research & Development*, 2003, 7, 696-699). When the ZnBr derivative and palladium catalyst are not commercially available, they can be synthesized in accordance with the literature. Thus obtained Compounds 277, 296, 279, 300, 288, 302, and 311 are deprotected in an acidic or alkaline condition to obtain Compounds 278, 289, 283, 301, 293, 303, and 312, respectively.

[Reaction 6]

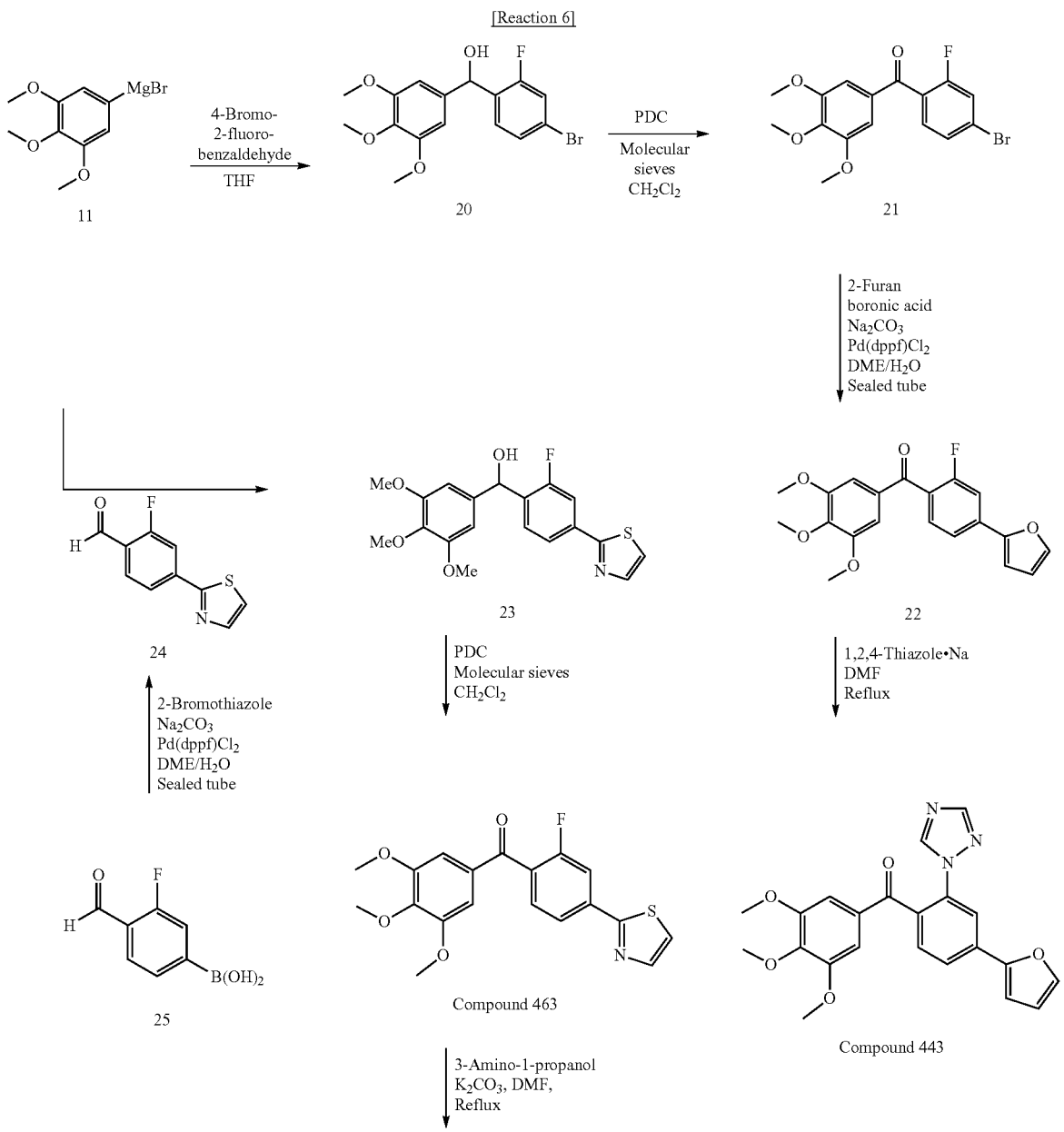

-continued

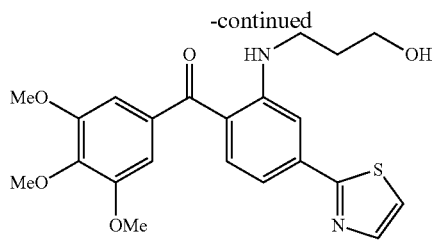

Compound 469

The reaction 6 is a typical synthesis process of Compounds 443 and 469. The other compounds of the present invention can also be prepared according to the above reaction. Compound 11 of the reaction 4 is reacted with a variety of aldehydes to prepare Compound 20 and Compound 23. Thus obtained benzhydrol derivatives are subjected to an oxidation reaction using various oxidants, as in the reaction 3, to obtain Compound 21. Boronic acid is bonded to Compound 21 by the Suzuki reaction (Morris, G. A., et al., *Tetrahedron Lett.*, 2001, 42, 2093) to prepare Compound 22. Compound 22 is reacted with various amines or heterocyclic rings to prepare Compound 443 of the present invention (Francois D. Bellamy, et al., *Journal of Medicinal Chemistry*, 1991, 34, 1545-1552).

Now, the present invention will be described in more detail with reference to the following Examples. These examples are provided only for illustrating the present invention and should not be construed as limiting the scope and spirit of the present invention.

EXAMPLES

Compound 200

Synthesis of (2-methoxy-5-(pyridin-3-yl)phenyl)(3,4,5-trimethoxyphenyl)methanone First, to 1-bromo-3,4,5-trimethoxy benzene as a starting material, magnesium was added, as shown in Reaction 1, and then a substituted aldehyde is added thereto through the Suzuki reaction, as shown in Reaction 3, to obtain (2-methoxy-5-(pyridin-3-yl)phenyl)(3,4,5-trim ethoxyphenyl) methanol. Thus obtained (2-Methoxy-5-(pyridin-3-yl)phenyl)(3,4,5-trimethoxyphenyl)methanol (28 mg, 0.07 mmol) was dissolved in dichloromethane (5 ml), whereto 4 Å molecular sieves (20 mg) and pyridinium chlorochromate (PCC) (24 mg, 0.11 mmol) were added at room temperature. The resulting mixture was stirred for 3 hours. After completion of the reaction, the precipitates were filtered out from the reaction mixture using Celite. The filtrate was vacuum evaporated to remove the solvent. Then, the resulting residue was purified by column chromatography (SiO$_2$, n-Hex/EA=2/1→1/1) to obtain Compound 200 (8 mg, 30%) in a form of white foam.

$^1$H NMR (CDCl$_3$+D$_2$O) δ 8.82 (s, 1H), 8.56 (d, 1H), 7.85 (d, 1H), 7.70 (d, 1H), 7.56 (s, 1H), 7.35 (dd, 1H), 7.13 (s, 2H), 7.12 (d, 1H), 3.93 (s, 3H), 3.84 (s, 6H), 3.82 (s, 3H).

Compound 203

Synthesis of (5-(furan-2-yl)-2-methoxyphenyl)(3,4,5-trimethoxyphenyl)methanone (5-Furan-2-yl)-2-methoxyphenyl)(3,4,5-trimethoxyphenyl)methanol (59 mg, 0.16 mmol) obtained in the same manner as in the synthesis of Compound 200 was acidified with PCC to obtain Compound 203 (15 mg, 25%) in a form of white foam.

$^1$H NMR (CDCl$_3$) δ 7.76 (d, 1H), 7.63 (s, 1H), 7.43 (s, 1H), 7.12 (s, 2H), 7.70 (d, 1H), 6.55 (s, 1H), 6.45 (s, 1H), 3.93 (s, 3H), 3.83 (s, 6H), 3.79 (s, 3H).

Compound 206

Synthesis of (5-(furan-2-yl)-2,3-dimethoxyphenyl)(3,4,5-trimethoxyphenyl)methanone In the same manner as in the synthesis of Compound 203, Compound 206 (50 mg, 38%) in a form of a white solid was obtained.

$^1$H NMR (CDCl$_3$) δ 7.44 (s, 1H), 7.35 (s, 1H), 7.18 (s, 1H), 7.12 (s, 2H), 6.59 (s, 1H), 6.46 (s, 1H), 3.97 (s, 3H), 3.92 (s, 3H), 3.83 (s, 6H), 3.78 (s, 3H).

Compound 207

Synthesis of (2,3-dimethoxy-5-(pyridin-3-yl)phenyl)(3,4,5-trimethoxyphenyl)methanone In the same manner as in the synthesis of Compound 203, Compound 207 (34 mg, 24%) in a form of a white solid was obtained.

$^1$H NMR (CDCl$_3$) δ 8.83 (b, 1H), 8.58 (b, 1H), 7.85 (d, 1H), 7.36 (b, 1H), 7.22 (s, 1H), 7.12 (s, 2H), 7.08 (s, 1H), 3.98 (s, 3H), 3.91 (s, 3H), 3.83 (s, 6H), 3.80 (s, 3H).

Compound 211

Synthesis of (4-methoxy-5'-nitrobiphenyl-3-yl)(3,4,5-trimethoxyphenyl)methanone

In the same manner as in the synthesis of Compound 203, Compound 211 (31 mg, 67%) in a form of a white solid was obtained.

$^1$H NMR (CDCl$_3$) δ 8.43 (s, 1H), 8.18 (d, 1H), 7.89 (d, 1H), 7.75 (d, 1H), 7.62~7.58 (m, 2H), 7.13 (m, 3H), 3.94 (s, 3H), 3.85 (s, 6H), 3.84 (s, 3H).

Compound 212

Synthesis of (5'-amino-4-methoxybiphenyl-3-yl)(3,4,5-trimethoxyphenyl)methanone

Compound 211 [(4-methoxy-5'-nitrobiphenyl-3-yl)(3,4,5-trimethoxyphenyl)methanone] (29 mg, 0.07 mmol), was dissolved in ethanol (4 ml), and SnCl$_2$.2H$_2$O (77 mg, 0.34 mmol) was added thereto. 3 Drops of concentrated hydrochloric acid was added to the reaction mixture, and then the resulting mixture was refluxed with stirring for 3 hours. After completion of the reaction, the resulting reaction mixture was vacuum concentrated. To this concentrated reaction mixture, water (10 ml) and a saturated aqueous sodium hydrogen carbonate solution were added, and the resulting solution was extracted with EtOAc (40 ml). The organic layer was washed with brine and dried over anhydrous $MgSO_4$. The solid substance was filtered off, and the filtrate was vacuum concentrated to obtain Compound 212 (26 mg, 94%) in a form of a white solid.

$^1$H NMR (CDCl$_3$) δ 7.66 (d, 1H), 7.54 (s, 1H), 7.21 (t, 1H), 7.13 (s, 2H), 7.04 (d, 1H), 6.98 (d, 1H), 6.92 (s, 1H), 6.69 (d, 1H).

Compound 213

Synthesis of (4,4'-dimethoxybiphenyl-3-yl)(3,4,5-trimethoxyphenyl)methanone

In the same manner as in the synthesis of Compound 203, Compound 213 (95 mg, 80%) in a form of a white solid was obtained.

$^1$H NMR (CDCl$_3$) δ 7.63 (d, 1H), 7.52 (s, 1H), 7.48 (d, 2H), 7.14 (s, 1H), 7.04 (d, 1H), 6.94 (d, 2H), 3.92 (s, 3H), 3.83 (s, 6H), 3.82 (s, 3H), 3.78 (s, 3H).

Compound 214

Synthesis of (4,6'-dimethoxybiphenyl-3-yl)(3,4,5-trimethoxyphenyl)methanone

In the same manner as in the synthesis of Compound 203, Compound 214 (82 mg, 74%) in a form of a white solid was obtained.

$^1$H NMR (CDCl$_3$) δ 7.65 (d, 1H), 7.55 (s, 1H), 7.31~7.27 (m, 2H), 7.17 (s, 2H), 7.05 (d, 1H), 7.00 (t, 1H), 6.96 (d, 1H), 3.92 (s, 3H), 3.85 (s, 6H), 3.81 (s, 3H), 3.79 (s, 3H).

Compound 216

Synthesis of (4-ethoxy-4'-methoxybiphenyl-3-yl)(3,4,5-trimethoxyphenyl)methanone In the same manner as in the synthesis of Compound 203, Compound 216 (44 mg, 40%) in a form of a white solid was obtained.

$^1$H NMR (CDCl$_3$) δ 7.62 (d, 1H), 7.55 (s, 1H), 7.49 (d, 2H), 7.12 (s, 2H), 7.02 (d, 1H), 6.95 (d, 2H), 4.03 (q, 2H), 3.92 (s, 3H), 3.84 (s, 6H), 3.82 (s, 3H), 1.18 (t, 3H).

Compound 218

Synthesis of (6'-hydroxy-4-methoxybiphenyl-3-yl)(3,4,5-trimethoxyphenyl)methanone As shown in Reaction 4, Compound 11 was added to a substituted benzaldehyde obtained through the Suzuki reaction of Reaction 3 to obtain Compound 12. Compound 15 [(6'-(tert-butyldimethylsilyloxy)-4-methoxybiphenyl-3-yl)(3,4,5-trimethoxyphenyl)methanone] (138 mg, 0.27 mmol) obtained by the oxidation of Compound 12 was dissolved in anhydrous tetrahydrofuran (5 ml). To this reaction solution, tetrabutylammonium fluoride (1 M, 0.8 ml, 5 mmol) dissolved in anhydrous tetrahydrofuran (5 ml) was added slowly. The reaction mixture was stirred for 2 hours at room temperature. After completion of the reaction, water (10 ml) was added to the reaction mixture, and the resulting solution was extracted with EtOAc (30 ml). The organic layer was washed with brine, and dried over anhydrous $MgSO_4$. The solid substance was filtered off, and the filtrate was vacuum concentrated. The resulting residue was purified by column chromatography (SiO$_2$, n-Hex/EA=5/1) to obtain Compound 218 (106 mg, 99%).

$^1$H NMR (CDC$_3$) δ 7.62 (dd, J=8.5, 2.1 Hz, 1H), 7.49 (d, J=2.1 Hz, 1H), 7.26~7.22 (m, 3H), 7.15 (s, 2H), 7.12 (d, J=8.5 Hz, 1H), 6.98 (m, 2H), 3.94 (s, 3H), 3.86 (s, 6H), 3.84 (s, 3H). MS (ESI) m/z 395 (M$^+$+H).

Compound 220

Synthesis of (4-hydroxy-4'-methoxybiphenyl-3-yl)(3,4,5-trimethoxyphenyl)methanone As shown in Reaction 4, in the same manner as in the synthesis of Compound 218, Compound 220 (120 mg, 99%) having the tert-butyldimethylsilyl group removed was obtained in a form of a white solid.

$^1$H NMR (CDCl$_3$) δ 11.77 (s, 1H), 7.82 (d, J=2.3 Hz, 1H), 7.71 (dd, J=8.6, 2.3 Hz, 1H), 7.38 (d, J=8.7 Hz, 2H), 7.13 (d, J=8.6 Hz, 1H), 6.99 (s, 2H), 6.93 (d, J=8.7 Hz, 2H), 3.95 (s, 3H), 3.89 (s, 6H), 3.82 (s, 3H). MS (ESI) m/z 393M$^+$−H).

Compound 223

Synthesis of (4'-methoxy-4-nitrobiphenyl-3-yl)(3,4,5-trimethoxyphenyl)methanone

The compound [(4'-methoxy-4-nitrobiphenyl-3-yl)(3,4,5-trimethoxyphenyl)methanol] (145 mg, 0.34 mmol) obtained in the same manner as in the synthesis of Compound 218 was dissolved in dichloromethane (8 ml), whereto 4 Å molecular sieves (300 mg) and pyridinium dichromate (PDC) (192 mg, 0.51 mmol) were added. The reaction mixture was stirred for 4 hours at room temperature. After completion of the reaction, the precipitates were filtered off using Celite. The filtrate was vacuum evaporated to remove the solvent. The resulting residue was purified by column chromatography (SiO$_2$, n-Hex/EA=9/1→2/1) to obtain Compound 223 (115 mg, 80%) in a form of a solid.

$^1$H NMR (CDCl$_3$) δ 8.28 (d, J=8.6 Hz, 1H), 7.82 (dd, J=8.6, 2.0 Hz, 1H), 7.63 (d, J=2.0 Hz, 1H), 7.60 (d, J=8.8 Hz, 2H), 7.04 (d, 2H), 7.01 (d, J=8.8 Hz, 2H), 3.93 (s, 3H), 3.87 (s, 3H), 3.83 (s, 6H). MS (ESI) m/z 424 (M$^+$+H).

Compound 224

Synthesis of (5-(furan-2-yl)-2-nitrophenyl)(3,4,5-trimethoxyphenyl) methanone

In the same manner as in the synthesis of Compound 223, Compound 224 (50 mg, 77%) in a form of a white solid was obtained.

$^1$H NMR (CDCl$_3$) δ 8.26 (d, J=8.7 Hz, 1H), 7.90 (dd, J=8.7, 1.9 Hz, 1H), 7.72 (d, J=1.9 Hz, 1H), 7.58 (d, J=1.5 Hz, 1H), 7.03 (s, 2H), 6.92 (d, J=3.5 Hz, 1H), 6.57 (dd, J=3.4, 1.7 Hz, 1H), 3.93 (s, 3H), 3.82 (s, 6H).

Compound 225

Synthesis of (2-amino-5-(furan-2-yl)phenyl)(3,4,5-trimethoxyphenyl)methanone

Compound 224 [(5-(furan-2-yl)-2-nitrophenyl)(3,4,5-trimethoxyphenyl)methanone](49 mg, 0.13 mmol) was dissolved in ethanol (6 ml), and SnCl$_2$.2H$_2$O (144 mg, 0.64 mmol) was added thereto. 2 to 3 Drops of concentrated hydrochloric acid was added to the reaction mixture, and then the reaction mixture was refluxed with stirring for 4 hours. After completion of the reaction, the resulting reaction mixture was vacuum concentrated. To this concentrated reaction mixture, water (10 ml) and a saturated aqueous sodium hydrogen carbonate solution were added, and the resulting solution was extracted with EtOAc (40 ml). The organic layer was washed with brine and dried over anhydrous MgSO$_4$. The solid substance was filtered off, and the filtrate was vacuum concentrated. The resulting residue was purified by column chromatography (SiO$_2$, n-Hex/EA=10/1→5/1) to obtain Compound 225 (26 mg, 94%) in a form of a yellow solid.

$^1$H NMR (DMSO-d6) δ 7.70 (d, J=2.1 Hz, 1H), 7.63 (dd, J=8.7, 2.1 Hz, 1H), 7.37 (d, J=1.6 Hz, 1H), 6.98 (s, NH2, 2H), 6.91 (d, J=8.7 Hz, 1H), 6.91 (s, 2H), 6.58 (d, J=3.3 Hz, 1H), 6.47 (dd, J=3.3, 1.8 Hz, 1H), 3.78 (s, 6H), 3.76 (s, 3H). MS (ESI) m/z 354 (M$^+$+H).

Compound 226

Synthesis of (4-amino-4'-methoxybiphenyl-3-yl)(3,4,5-trimethoxyphenyl)methanone

In the same manner as in the synthesis of Compound 225, Compound 223 [(4'-methoxy-4-nitrobiphenyl-3-yl)(3,4,5-trimethoxyphenyl)methanane] was subjected to the reduction reaction to obtain Compound 226 (52 mg, 53%) in a form of a yellow solid.

$^1$H NMR (CDCl$_3$) δ 7.70 (d, J=2.2 Hz, 1H), 7.56 (dd, J=8.5, 2.1 Hz, 1H), 7.36 (d, J=8.7 Hz, 2H), 6.93 (m, 3H), 3.93 (s, 3H), 3.87 (s, 6H), 3.82 (s, 3H). MS (ESI) m/z 394 (M$^+$+H).

Compound 227

Synthesis of (5-(furan-2-yl)-2-methoxyphenyl)(3,4,5-trimethoxyphenyl)methanone oxime Compound 203 [(5-(furan-2-yl)-2-methoxyphenyl)(3,4,5-trimethoxyphenyl)methanone] (20 mg, 0.05 mmol) was dissolved in ethanol (5 ml), hydroxylamine.HCl (6 mg, 0.08 mmol) was added thereto. A solution of sodium hydroxide (4 mg, 0.1 mmol) in water (3 ml) was added to the reaction mixture, and then the resulting solution was refluxed with stirring for 24 hours. After completion of the reaction, the reaction mixture was vacuum concentrated. Then, the concentrated reaction mixture was extracted with water (10 ml) and EtOAc (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=7/1) to obtain Compound 227 (10 mg, 52%).

$^1$H NMR (CDCl$_3$) δ 7.74 (d, 1H), 7.47 (s, 1H), 7.42 (s, 1H), 7.08 (d, 1H), 6.78 (s, 2H), 6.54 (s, 1H), 6.45 (s, 1H), 3.86 (s, 3H), 3.81 (s, 3H), 3.78 (s, 6H). MS (ESI) m/z 384 (M$^+$+H).

Compound 228

Synthesis of (4-methoxy-3-(3,4,5-trimethoxybenzoyl)phenyl)-1H-pyrrole-1-carboxylic acid tert-butyl ester In the same manner as in the synthesis of Compound 223, Compound 228 (890 mg, 72%) in a form of a white solid was obtained.

$^1$H NMR (CDCl$_3$) δ 7.46 (dd, J=8.5, 2.1 Hz, 1H), 7.31 (m, 2H), 7.14 (s, 2H), 6.99 (d, J=8.5 Hz, 1H), 6.20~6.16 (m, 2H), 3.92 (s, 3H), 3.85 (s, 6H), 3.80 (s, 3H), 1.42 (s, 9H). MS (ESI) m/z 468 (M$^+$+H).

Compound 229

Synthesis of (2-methoxy-5-(1H-pyrrol-2-yl)phenyl)(3,4,5-trimethoxyphenyl)methanone Compound 228 [(4-methoxy-3-(3,4,5-trimethoxybenzoyl)phenyl)-1H-pyrrole-1-carboxylic acid tert-butyl ester] (850 mg, 1.82 mmol) was dissolved in methanol (7 ml), and NaOMe (589 mg, 10.91 mmol) was added thereto. The mixture was stirred for 2 hours at room temperature. After completion of the reaction, the reaction mixture was extracted with water (10 ml) and EtOAc (30 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=3/1→1/1) to obtain Compound 229 (420 mg, 63%) in a form of a white foam.

$^1$H NMR (CDCl$_3$) δ 7.58 (dd, J=8.7, 2.4 Hz, 1H), 7.43 (d, J=2.3 Hz, 1H), 7.12~7.07 (m, 3H), 7.01 (d, J=8.6 Hz, 1H), 6.85 (m, 1H), 6.45 (m, 1H), 6.29 (m, 1H), 3.93 (s, 3H), 3.83 (s, 6H), 3.78 (s, 3H). MS (ESI) m/z 368 (M$^+$+H).

Compound 231

Synthesis of N-(4-(furan-2-yl)-2-(3,4,5-trimethoxybenzoyl)phenyl)acetamide

Compound 225 [(2-amino-5-(furan-2-yl)phenyl)(3,4,5-trimethoxyphenyl)methanone] (40 mg, 0.11 mmol) was dissolved in dichloromethane (5 ml), and an excessive amount of pyridine and acetylchloride (11 mg, 0.13 mmol) were sequentially added thereto. The reaction mixture was stirred for 3 days at room temperature, and vacuum concentrated. The resulting residue was purified by column chromatography (SiO$_2$, n-Hex/EA=3/1→1/1) to obtain Compound 231 (20 mg, 46%).

$^1$H NMR (CDCl$_3$) δ 10.45 (brs, NH, 1H), 8.59 (d, J=8.7 Hz, 1H), 7.90 (d, J=2.0 Hz, 1H), 7.83 (dd, J=8.7, 2.0 Hz, 1H), 7.42 (d, J=1.0 Hz, 1H), 7.03 (s, 2H), 6.57 (d, J=3.2 Hz, 1H), 6.45 (dd, J=3.2, 1.7 Hz, 1H), 3.97 (s, 3H), 3.87 (s, 6H), 2.22 (s, 3H).

Compound 232

Synthesis of (2-(benzylamino)-5-(furan-2-yl)phenyl)(3,4,5-trimethoxyphenyl)methanone Compound 225 [(2-amino-5-(furan-2-yl)phenyl)(3,4,5-trimethoxyphenyl)methanone] (46 mg, 0.13 mmol) was dissolved in N,N-dimethylformamide (DMF) (5 ml), potassium carbonate (54 mg, 0.39 mmol) and benzylbromide (27 mg, 0.16 mmol) were added thereto. The reaction mixture was stirred for 3 days at room temperature, and vacuum concentrated. The resulting reaction mixture was extracted with water (5 ml) and EtOAc (10 ml). The organic layer was dried over anhydrous MgSO$_4$. The solid substance was filtered off, and the filtrate was vacuum concentrated. The resulting residue was purified by column chromatography (SiO$_2$, n-Hex/EA=10/1) to obtain Compound 232 (15 mg, 26%).

$^1$H NMR (CDCl$_3$) δ 7.92 (d, J=2.1 Hz, 1H), 7.75 (dd, J=8.7, 2.1 Hz, 1H), 7.40~7.27 (m, 8H), 6.89 (s, 2H), 6.47 (d, J=3.4 Hz, 1H), 6.43 (m, 1H), 4.55 (s, 2H), 3.97 (s, 3H), 3.89 (s, 6H).

Compound 233

Synthesis of (3-(1,3-dioxan-2-yl)-4,5-dimethoxyphenyl)(5-(furan-2-yl)-2-methoxyphenyl)methanone As shown in Reaction 1, first, magnesium was added to 2-(5-bromo-2,3-dimethoxyphenyl)-1,3-dioxane as a starting material, which substituted an aldehyde group with an acetyl group. Then, Compound (III) derivative was substituted thereto to synthesize (3-(1,3-dioxan-2-yl)-4,5-dimethoxyphenyl)(5-(furan-2-yl)-2-methoxyphenyl)methanol. Thus obtained (3-(1,3-dioxan-2-yl)-4,5-dimethoxyphenyl)(5-(furan-2-yl)-2-methoxyphenyl)methanol (1.7 g, 4.0 mmol) was dissolved in 40 ml of anhydrous dichloromethane, whereto 4 Å molecular sieves (0.6 g) and pyridinium dichromate (PDC) (2.24 g, 6.0 mmol) were added sequentially at 0° C. The mixture was reacted at room temperature for 24 hours. After completion of the reaction, diethylether (150 ml) was added to the reaction mixture, and the precipitates were filtered off using Celite. An organic layer was extracted out from the filtrate using brine, and the organic layer was dried over $Na_2SO_3$. The solvent was removed, and the resulting residue was purified by column chromatography ($SiO_2$, n-Hex/EA=1/1) to synthesize Compound 233 (1.02 g, 60%).

$^1$H NMR ($CDCl_3$) δ 7.77 (dd, J=8.50, 2.29 Hz, 1H), 7.62 (m, 2H), 7.56 (d, J=2.02 Hz, 1H), 7.43 (d, J=1.53 Hz, 1H), 7.02 (d, J=8.70 Hz, 1H), 6.55 (d, J=3.17 Hz, 1H), 6.45 (dd, J=3.32, 1.76 Hz, 1H), 5.80 (s, 1H), 4.18 (m, 2H), 3.98 (m, 2H), 3.94 (s, 3H), 3.91 (s, 3H), 3.76 (s, 3H), 2.15 (m, 2H), 1.59 (bs, 1H).

Compound 234

Synthesis of 5-(5-(furan-2-yl)-2-methoxybenzoyl)-2,3-dimethoxybenzaldehyde

Compound 233 [(3-(1,3-dioxan-2-yl)-4,5-dimethoxyphenyl)(5-(furan-2-yl)-2-methoxyphenyl)methanone] (262 mg, 0.62 mmol) was dissolved in 6 ml of a mixed solution of tetrahydrofuran and methanol (5/1). 1 N hydrochloric acid (0.2 ml, 0.20 mmol) was added dropwise thereto. The mixture was reacted for 24 hours at room temperature, and an organic layer was extracted out using dichloromethane and brine, and the organic layer was dried over $Na_2SO_3$. The solvent was removed, and the resulting residue was purified by column chromatography ($SiO_2$, n-Hex/EA=2/1→1/1) to obtain Compound 234 (105 mg, 47%) in a form of a solid.

$^1$H NMR ($CDCl_3$) δ 10.39 (s, 1H), 7.86 (d, J=2.00 Hz, 1H), 7.78 (dd, J=8.68, 2.20 Hz, 1H), 7.68 (d, J=2.00 Hz, 1H), 7.62 (d, J=2.24 Hz, 1H), 7.43 (s, 1H), 7.03 (d, J=8.72 Hz, 1H), 6.55 (d, J=3.32 Hz, 1H), 6.45 (dd, J=3.32, 1.80 Hz, 1H), 4.10 (s, 3H), 4.00 (s, 3H), 3.76 (s, 3H).

Compound 235

Synthesis of N-(4-(furan-2-yl)-2-(3,4,5-trimethoxybenzoyl)phenyl)methanesulfonamide Compound 225 [(2-amino-5-(furan-2-yl)phenyl)(3,4,5-trimethoxyphenyl)methanone] (20.9 mg, 0.06 mmol) was dissolved in dichloromethane (3 ml), and pyridine (5.74 µl), methanesulfonyl chloride (5.94 µl) were added thereto at room temperature. The mixture was stirred at room temperature for 12 hours. Pyridine (5.74 µl) and methanesulfonyl chloride (20 µl) was further added to the reaction mixture, and the resulting mixture was stirred at room temperature for 3 days. After completion of the reaction, the solvent was removed by vacuum evaporation, and the resulting residue was purified by column chromatography ($SiO_2$, $CH_2Cl_2$/MeOH=5/1→3/1) to obtain Compound 235 (16.9 mg, 66.5%) in a form of a bright yellow solid.

$^1$H NMR ($CDCl_3$) δ 9.863 (S, 1H), 7.974 (dd, J=1.80 Hz, 1H), 7.867-7.807 (m, 2H), 7.448 (d, J=1.38 Hz, 1H), 7.026 (s, 2H), 6.601 (d, J=3.31 Hz, 1H), 6.471 (dd, J=3.34, 1.74 Hz, 1H), 3.979 (s, 3H), 3.879 (s, 6H), 3.099 (s, 3H).

Compound 236

Synthesis of 4-(4-(furan-2-yl)-2-(3,4,5-trimethoxybenzoyl)phenylamino)-4-oxobutanoic acid Compound 225 [(2-amino-5-(furan-2-yl)phenyl)(3,4,5-trimethoxyphenyl)methanone] (14.9 mg, 0.04 mmol) was dissolved in dichloromethane (3 ml), and pyridine (5.74 µl) and succinic anhydride (5.05 mg) were added thereto at room temperature. The mixture was stirred at room temperature for 3 days. After completion of the reaction, the solvent was removed by vacuum evaporation. The resulting residue was purified by column chromatography ($SiO_2$, $CH_2Cl_2$/MeOH=10/1) to obtain Compound 236 (~10 mg, 52.6%) in a form of a bright yellow solid.

$^1$H NMR ($CDC_3$) δ10.590 (s, 1H), 8.579 (d, J=8.76 Hz, 1H), 7.907 (d, J=2.08 Hz, 1H), 7.830 (dd, J=8.72, 2.08 Hz, 1H), 7.431 (d, J=1.60 Hz, 1H), 7.031 (s, 2H), 6.582 (d, J=3.24 Hz, 1H), 6.456 (dd, J=3.40, 1.88 Hz, 1H), 3.973 (s, 3H), 3.872 (s, 6H), 2.777 (m, 4H).

Compound 237

Synthesis of 2-amino-N-(4-(furan-2-yl)-2-(3,4,5-trimethoxybenzoyl)phenyl)acetamide Compound 225 [(2-amino-5-(furan-2-yl)phenyl)(3,4,5-trimethoxyphenyl)methanone] (30 mg, 0.08 mmol) was dissolved in dichloromethane (5 ml), and Fmoc-glycine (30 mg, 0.10 mmol), N-(3-dimethylaminopropyl)-N'-ethylcarboimide (EDC) (33 mg, 0.17 mmol) and N,N-dimethylaminopyridine (DMAP) (10 mg, 0.08 mmol) were added thereto. The mixture was stirred at room temperature for 3 days. The reaction mixture was vacuum concentrated, and the resulting residue was purified by column chromatography ($SiO_2$, n-Hex/EA=5/1→1/1) to obtain a compound. The compound thus obtained was dissolved in DMF (2 ml), and piperidine (1 ml) was added thereto. The mixture was stirred for 2 hours at room temperature. The reaction mixture was vacuum concentrated, and the resulting residue was purified by column chromatography ($SiO_2$, n-Hex/EA=2/1) to obtain Compound 237 (1.62 mg, 20%).

$^1$H NMR ($CDCl_3$) δ 8.17 (m, 1H), 7.83 (m, 1H), 7.74 (s, 1H), 7.45 (d, J=1.2 Hz, 1H), 7.19 (s, 2H), 7.15 (m, 1H), 6.85 (brs, NH2, 2H), 6.61 (d, J=3.1 Hz, 1H), 6.47 (dd, J=3.3, 1.7 Hz, 1H), 4.32 (m, 2H), 3.92~3.84 (m, 9H).

Compound 238

Synthesis of (2-(allylamino)-5-(furan-2-yl)phenyl)(3,4,5-trimethoxyphenyl)methanone Compound 225 [(2-amino-5-(furan-2-yl)phenyl)(3,4,5-trimethoxyphenyl)methanone] (27.6 mg, 0.08 mmol) and potassium carbonate (32.4 mg) were dissolved in DMF (3 ml), and allyl bromide (10 µl) was added thereto at room temperature. The mixture was stirred for 5 hours at 130° C. After completion of the reaction, the solvent was removed by vacuum evaporation. The resulting residue was purified by column chromatography (SiO$_2$, CH$_2$Cl$_2$/MeOH=10/1) to obtain Compound 238 (10.7 mg, 35%) in a form of yellow oil.

$^1$H NMR (CDCl$_3$) δ 7.946 (d, J=2.12 Hz, 1H), 7.740 (dd, J=8.73, 2.10 Hz, 1H), 7.389 (dd, J=1.56, 0.67 Hz, 1H), 7.082 (d, J=8.76 Hz, 1H), 6.964 (s, 2H), 6.450-6.402 (m, 2H), 6.019-5.977 (m, 1H), 5.389-5258 (m, 2H), 3.975 (m, 6H), 3.896 (s, 6H).

Compound 239

Synthesis of (R)-2-amino-N-(4-(furan-2-yl)-2-(3,4,5-trimethoxybenzoyl)phenyl)-3-methylbutanamide Compound 225 [(2-amino-5-(furan-2-yl)phenyl)(3,4,5-trimethoxyphenyl)methanone] (25 mg, 0.07 mmol), Fmoc-valine (28.5 mg), and N,N-dimethylaminopyridine (8.6 mg) were dissolved in dichloromethane (3 ml), and N-(3-dimethylaminopropyl)-N'-ethylcarboimide (EDC) (26.8 mg) was added thereto at room temperature. The mixture was stirred for 2 days at room temperature. After completion of the reaction, the solvent was removed by vacuum evaporation. The resulting residue was purified by column chromatography (SiO$_2$, CH$_2$Cl$_2$/MeOH=1/1) to obtain a bright yellow solid compound. The compound thus obtained was dissolved in DMF (3 ml), and piperidine (1 drop) was added thereto at room temperature. The mixture was stirred for 1 hour at room temperature. After completion of the reaction, the solvent was removed by vacuum evaporation. The resulting residue was purified by column chromatography (SiO$_2$, CH$_2$Cl$_2$/MeOH=1/1→1/2) to obtain Compound 239 (6.84 mg, 42%, 2 steps) in a form of yellow oil.

$^1$H NMR (CDCl$_3$) δ 11.401 (s, 1H), 8.649 (d, J=8.28 Hz, 1H), 7.889 (d, J=1.68 Hz, 1H), 7.832 (m, 2H), 7.427 (d, J=1.36 Hz, 1H), 7.113 (s, 2H), 6.579 (d, J=3.36 Hz, 1H), 6.454 (dd, J=3.24, 1.72 Hz, 1H), 3.963 (s, 3H), 3.828 (m, 7H), 2.437 (s, 1H), 1.083-0.961 (m, 6H).

Compound 240

Synthesis of (5-(furan-2-yl)-2-hydroxyphenyl)(3,4,5-trimethoxyphenyl)methanone

Compound 15 derivative [(2-(tert-butyldimethylsilyloxy)-5-(furan-2-yl)phenyl)(3,4,5-trimethoxyphenyl)methanone] (137 mg, 0.29 mmol) obtained according to Reaction 3 was dissolved in tetrahydrofuran (5 ml), and tetrabutylammonium fluoride (229 mg, 0.88 mmol) was added thereto. The mixture was stirred at room temperature. After completion of the reaction, water (10 ml) was added to the reaction mixture, and the resulting solution was extracted with EtOAc (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=10/1→3/1) to obtain Compound 240 (100 mg, 97%).

$^1$H NMR (CDCl$_3$) δ 11.89 (s, OH, 1H), 8.02 (d, J=2.2 Hz, 1H), 7.80 (dd, J=8.7, 2.2 Hz, 1H), 7.41 (s, 1H), 7.11 (d, J=8.7 Hz, 1H), 7.01 (s, 2H), 6.49 (d, J=3.2 Hz, 1H), 6.44 (dd, J=3.3, 1.7 Hz, 1H), 3.96 (s, 3H), 3.91 (s, 6H).

Compound 241

Synthesis of methanesulfonic acid 4-(furan-2-yl)-2-(3,4,5-trimethoxybenzoyl)phenyl Compound 240 [(5-(furan-2-yl)-2-hydroxyphenyl)(3,4,5-trimethoxyphenyl)methanone] (13 mg, 0.04 mmol) was dissolved in dichloromethane (4 ml), and an excessive amount of triethylamine and methanesulfonyl chloride (5 mg, 0.04 mmol) were sequentially added thereto.

After stirring the reaction mixture for 4 hours at room temperature, the resulting residue was purified by column chromatography (SiO$_2$, n-Hex/EA=3/1→1/1) to obtain Compound 241 (12 mg, 75%).

$^1$H NMR (CDCl$_3$) δ 7.83 (dd, J=8.6, 2.3 Hz, 1H), 7.74 (d, J=2.2 Hz, 1H), 7.55 (d, J=8.6 Hz, 1H), 7.48 (d, J=1.6 Hz, 1H), 7.09 (s, 2H), 6.70 (d, J=3.3 Hz, 1H), 6.49 (dd, J=3.3, 1.7 Hz, 1H), 3.95 (s, 3H), 3.85 (s, 6H), 3.04 (s, 3H).

Compound 242

Synthesis of (2-(2-(dimethylamino)ethoxy)-5-(furan-2-yl)phenyl (3,4,5-trimethoxyphenyl)methanone Compound 240 [(5-(furan-2-yl)-2-hydroxyphenyl)(3,4,5-trimethoxyphenyl)methanone] (23 mg, 0.07 mmol) and N,N-dimethylethyleneamine.HCl (11.2 mg) were dissolved in DMF (3 ml), and sodium hydride (6.5 mg) was added thereto at 0° C. The mixture was stirred for 2 hours at 130° C. After completion of the reaction, the reaction mixture was cooled to room temperature and diluted with an EtOAc solution. The organic layer was washed with a saturated ammonium chloride solution and brine. The extracted organic layer was dried over anhydrous MgSO$_4$, and the solid substance was filtered out. The filtrate was vacuum dried to obtain Compound 242 (12 mg, 43.5%) in a form of a yellow solid.

$^1$H NMR (CDCl$_3$) δ 7.757 (dd, J=8.65, 2.33 Hz, 1H), 7.661 (d, J=2.27 Hz, 1H), 7.431 (dd, J=2.03, 1.44 Hz, 1H), 7.066 (s, 2H), 7.015 (d, J=8.74 Hz, 1H), 6.562 (d, J=3.20 Hz, 1H), 6.453 (dd, J=3.32, 1.72 Hz, 1H), 4.116 (t, J=5.67 Hz, 2H), 3.923 (s, 3H), 3.831 (s, 6H), 2.571 (t, J=5.28 Hz, 2H), 2.213 (s, 6H).

Compound 243

Synthesis of 2-(4-furan-2-yl)-2-(3,4,5-trimethoxybenzoyl)phenoxy)acetic acid methyl ester Compound 240 [(5-(furan-2-yl)-2-hydroxyphenyl)(3,4,5-trimethoxyphenyl)methanone] (27 mg, 0.08 mmol) and potassium carbonate (52.5 mg) were dissolved in acetone (5 ml), and methyl 2-bromoacetate (21.7 μl) was added thereto at room temperature. The mixture was stirred for 10 hours at 130° C. After completion of the reaction, the reaction mixture was cooled to room temperature, and the precipitates were filtered off using Celite. Then, the remaining solvent was removed by vacuum evaporation. The resulting residue was purified by column chromatography (SiO$_2$, CH$_2$Cl$_2$/MeOH=2/1) to obtain Compound 243 (10 mg, 30.9%) in a form of yellow oil.

$^1$H NMR (CDCl$_3$) δ 7.729 (dd, J=8.66, 2.19 Hz, 1H), 7.664 (d, J=2.26 Hz, 1H), 7.436 (dd, J=2.21, 0.58 Hz, 1H), 7.184 (s, 2H), 6.858 (d, J=8.69 Hz, 1H), 6.572 (dd, J=3.33, 0.56 Hz, 1H), 6.454 (dd, J=3.35, 1.76 Hz, 1H), 4.626 (s, 2H), 3.391 (s, 3H), 3.864 (s, 6H), 3.737 (s, 3H).

Compound 244

Synthesis of 2-(4-(furan-2-yl)-2-(3,4,5-trimethoxybenzoyl)phenoxy)acetic acid

Compound 243 [2-(4-(furan-2-yl)-2-(3,4,5-trimethoxybenzoyl)phenoxy)acetic acid methyl ester] (8 mg, 0.02 mmol) was dissolved in methanol/water (2 ml, 4/1), and lithium hydroxide (2.25 mg) was added thereto at room temperature. The mixture was stirred for 12 hours. After completion of the reaction, the reaction mixture was diluted with dichloromethane, and the organic layer was discarded. The obtained aqueous layer was adjusted to about pH 2 with a 1 M hydrochloric acid solution, and the resulting solution was extracted with an EtOAc solution. The organic layer was washed with brine. The extracted EtOAc layer was dried over anhydrous $MgSO_4$, and the solid substance was filtered off. The filtrate was vacuum dried to obtain Compound 244 (5.4 mg, 69.2%) in a form of a yellow solid.

$^1$H NMR ($CDCl_3$) δ 7.833 (dd, J=8.65, 2.14 Hz, 1H), 7.747 (d, J=2.14 Hz, 1H), 7.449 (d, J=1.45 Hz, 1H), 7.168 (s, 2H), 7.122 (d, J=8.68 Hz, 1H), 6.593 (d, J=3.29 Hz, 1H), 6.469 (dd, J=3.34, 1.87 Hz, 1H), 4.823 (s, 2H), 4.976 (s, 3H), 3.869 (s, 6H).

Compound 245

Synthesis of (5-(furan-2-yl)-2-methoxyphenyl)(phenyl)methanone

As shown in Reaction 1, (5-(furan-2-yl)-2-methoxyphenyl)(phenyl)methanol (61 mg, 0.22 mmol) obtained by adding a substituted benzaldehyde to phenyl magnesium as a starting material was dissolved in dichloromethane (8 ml), and 4 Å molecular sieves (100 mg) and pyridinium dichromate (PDC) (123 mg, 0.33 mmol) were added thereto. The reaction mixture was stirred for 4 hours at room temperature. After completion of the reaction, the precipitates were filtered off using Celite. The remaining solvent was removed by vacuum evaporation. Then, the resulting residue was purified by column chromatography ($SiO_2$, n-Hex/EA=10/1→4/1) to obtain Compound 245 (15 mg, 25%).

$^1$H NMR ($CDCl_3$) δ 7.85~7.83 (m, 2H), 7.77 (dd, J=8.7, 2.2 Hz, 1H), 7.65 (d, J=2.2 Hz, 1H), 7.56 (m, 1H), 7.46~7.42 (m, 3H), 7.02 (d, J=8.7 Hz, 1H), 6.55 (d, J=3.3 Hz, 1H), 6.45 (dd, J=3.3, 1.7 Hz, 1H), 3.75 (s, 3H).

Compound 246

Synthesis of (5-(furan-2-yl)-2-methoxyphenyl)(4-methoxyphenyl)methanone

In the same manner as in the synthesis of Compound 245, Compound 246 (20 mg, 22%) was obtained.

$^1$H NMR ($CDCl_3$) δ 7.83 (d, J=8.8 Hz, 2H), 7.75 (dd, J=8.6, 2.2 Hz, 1H), 7.61 (d, J=2.2 Hz, 1H), 7.42 (d, J=1.5 Hz, 1H), 7.01 (d, J=8.7 Hz, 1H), 6.91 (d, J=8.8 Hz, 2H), 6.54 (d, J=3.3 Hz, 1H), 6.44 (dd, J=3.2, 1.8 Hz, 1H), 3.85 (s, 3H), 3.78 (s, 3H).

Compound 247

Synthesis of (3,4-dimethoxyphenyl)(5-(furan-2-yl)-2-methoxyphenyl)methanone

In the same manner as in the synthesis of Compound 245, Compound 247 (20 mg, 22%) was obtained.

$^1$H NMR ($CDCl_3$) δ 7.74 (dd, J=8.7, 2.1 Hz, 1H), 7.60~7.58 (m, 2H), 7.41 (s, 1H), 7.30 (d, J=8.4 Hz, 1H), 7.00 (d, J=8.7 Hz, 1H), 6.82 (d, J=8.4 Hz, 1H), 6.53 (d, J=3.3 Hz, 1H), 6.43 (m, 1H), 3.93 (s, 6H), 3.77 (s, 3H).

Compound 248

Synthesis of benzo[d][1,3]dioxol-5-yl(5-(furan-2-yl)-2-methoxyphenyl)methanone

In the same manner as in the synthesis of Compound 245, Compound 248 (35 mg, 36%) was obtained.

$^1$H NMR ($CDCl_3$) δ 7.74 (dd, J=8.7, 2.3 Hz, 1H), 7.59 (d, J=2.3 Hz, 1H), 7.42~7.40 (m, 2H), 7.36 (dd, J=8.2, 1.6 Hz, 1H), 7.00 (d, J=8.7 Hz, 1H), 6.81 (d, J=8.1 Hz, 1H), 6.53 (d, J=3.3 Hz, 1H), 6.44 (dd, J=3.3, 1.7 Hz, 1H), 6.04 (s, 2H), 3.77 (s, 3H).

Compound 249

Synthesis of (5-(furan-2-yl)-2-methoxyphenyl)(3-(hydroxymethyl)-4,5-dimethoxyphenyl)methanone Compound 234 [(5-5-(furan-2-yl)-2-methoxybenzoyl)-2,3-dimethoxybenzaldehyde] (16 mg, 0.44 mmol) was dissolved in 1% acetic acid/methanol (10 ml), and $NaBH_3$ CN (2.74 mg, 0.44 mmol) was added thereto at 0° C. The mixture was reacted for 24 hours at room temperature. Using EtOAc and water, an organic layer was extracted out. The organic layer was dried over $Na_2SO_3$, and the remaining solvent was removed. The resulting residue was purified by column chromatography ($SiO_2$, n-Hex/EA=2/1→1/1) to obtain Compound 249 (16 mg, 99%).

$^1$H NMR ($CDCl_3$) δ 7.76 (dd, J=8.69, 2.36 Hz, 1H), 7.60 (d, J=2.29 Hz, 1H), 7.57 (d, J=1.96 Hz, 1H), 7.43 (m, 1H), 7.30 (d, J=1.99 Hz, 1H), 7.02 (d, J=8.70 Hz, 1H), 6.55 (d, J=3.23 Hz, 1H), 6.45 (dd, J=3.37, 1.78 Hz, 1H), 4.65 (s, 2H), 3.98 (s, 3H), 3.92 (s, 3H), 3.78 (s, 3H).

Compound 253

Synthesis of (4,5-dimethoxy-3-((methylamino)methyl)phenyl)(5-furan-2-yl)-2-methoxyphenyl)methanone To 5-(5-(furan-2-yl)-2-methoxybenzoyl)-2,3-dimethoxybenzaldehyde (92 mg, 0.25 mmol) in anhydrous THF (3.0 mL) was added 2.0 M methylamine in methanol (0.20 mL, 0.40 mmol) at room temperature. After 2 hours, sodium cyanoborohydride (25 mg, 0.40 mmol) was added to the reaction mixture. The mixture was stirred for 6 hours at room temperature. After completion of the reaction, a saturated ammonium chloride solution was added, and diluted with EtOAc solution. The organic layer was washed with water and brine. The extracted organic layer was dried over anhydrous $MgSO_4$, and the solid substance was filtered off. Then, the filtrate was vacuum dried to remove the solvent. The resulting residue was purified by column chromatography ($SiO_2$, n-Hex/EA=1/1) to obtain Compound 253 (32 mg, 34%) in a form of oil.

$^1$H NMR ($CDCl_3$) δ 7.800 (dd, J=8.70, 2.34 Hz, 1H), 7.640 (m, 2H), 7.621 (dd, J=7.96, 2.22 Hz, 1H), 7.433 (q, J=1.68 Hz, 2H), 7.140 (d, J=1.92 Hz, 1H), 7.042 (d, J=8.70 Hz, 1H), 6.560 (m, 1H), 6.460 (dd, J=3.36, 1.73 Hz, 1H), 4.098 (s, 3H), 3.943 (s, 3H), 3.770 (s, 3H), 2.522 (brs, 1H), 2.424 (d, J=5.78 Hz, 3H). MS (ESI) m/z 382 ($M^+$+H).

Compound 255

Synthesis of (5-(furan-2-yl)-2-methoxyphenyl)(3-methoxy-4-(methoxymethoxy)phenyl)methanone In the same manner as in the synthesis of Compound 245, Compound 255 (76.2 mg, 51%) was obtained.

$^1$H NMR ($CDCl_3$) δ 7.739 (dd, 1H), 7.604 (dd, 1H), 7.412 (d, 1H), 7.263 (dd, 1H), 7.109 (d, 1H), 7.002 (d, 1H), 6.5269 (d, 1H), 6.432 (dd, 1H), 5.251 (s, 2H), 3.932 (s, 3H), 3.768 (s, 3H), 3.501 (s, 3H).

Compound 256

Synthesis of (5-(furan-2-yl)-2-methoxyphenyl)(4-hydroxy-3-methoxyphenyl)methanone Compound 255 [(5-(furan-2-yl)-2-methoxyphenyl)(3-methoxy-4-(methoxymethoxy)phenyl)methanone] (53 mg, 0.144 mmol) was dissolved in methanol (3 ml), and 6 M hydrochloride (500 μl) was added thereto at room temperature. The mixture was stirred for 2 days at room temperature. After completion of the reaction, the reaction mixture was diluted with dichloromethane. The organic layer was washed with water and brine. The extracted organic layer was dried over anhydrous $MgSO_4$, and the solid substance was filtered off. The filtrate was vacuum dried to obtain Compound 256 (38 mg, 81.4%) in a form of a white solid.

$^1$H NMR ($CDCl_3$) δ 7.741 (dd, 1H), 7.602 (m, 2H), 7.421 (m, 1H), 7.006 (d, 1H), 6.884 (d, 1H), 6.536 (dd, 1H), 6.440 (dd, 1H), 6.240 (brs, 1H), 3.945 (s, 3H), 3.771 (s, 3H).

Compound 257

Synthesis of (3-((dimethylamino)methyl)-4-hydroxy-5-methoxyphenyl)(5-(furan-2-yl)-2-methoxyphenyl)methanone Compound 256 [(5-(furan-2-yl)-2-methoxyphenyl)(4-hydroxy-3-methoxyphenyl)methanone] (32 mg, 0.01 mmol) and p-formamide (9.05 mg) were dissolved in tetrahydrofuran (5 ml), and dimethylamine (0.1 ml) was added thereto at room temperature. The mixture was stirred for 30 hours at 70° C. After completion of the reaction, the reaction mixture was cooled to room temperature, and the solvent was removed by vacuum evaporation. The resulting residue was purified by column chromatography ($SiO_2$, n-Hex/EA=1/2) to obtain Compound 257 (12.6 mg, 37.8%) in a form of a white solid.

$^1$H NMR ($CDCl_3$) δ 7.423 (dd, 1H), 7.589 (d, 1H), 7.463 (d, 1H), 7.422 (d, 1H), 7.081 (dd, 1H), 7.010 (d, 1H), 6.537 (d, 1H), 6.444 (dd, 1N), 3.895 (s, 3H), 3.777 (s, 3H), 3.699 (s, 2H), 2.368 (s, 6H).

Compound 260

Synthesis of (5-(furan-2-yl)-2-nitrophenyl)(3-methoxy-4-(methoxymethoxyphenyl)methanone In the same manner as in the synthesis of Compound 245, Compound 260 (142 mg, 62%) was obtained.

$^1$H NMR ($CDCl_3$) δ 8.23 (d, J=8.7 Hz, 1H), 7.86 (dd, J=8.7, 1.8 Hz, 1H), 7.68 (d, J=1.7 Hz, 1H), 7.64 (d, J=1.6 Hz, 1H), 7.55 (s, 1H), 7.09~7.01 (m, 2H), 6.88 (d, J=3.4 Hz, 1H), 6.53 (dd, J=3.4, 1.7 Hz, 1H), 5.25 (s, 2H), 3.95 (s, 3H), 3.47 (s, 3H).

Compound 261

Synthesis of (5-(furan-2-yl)-2-nitrophenyl)(4-hydroxy-3-methoxyphenyl)methanone

In the same manner as in the synthesis of Compound 256), Compound 261 (102.4 mg, 81.6%) in a form of a yellow oil was obtained, except that Compound 260 [(5-(furan-2-yl)-2-nitrophenyl)(3-methoxy-4-(methoxymethoxyphenyl)methanone) (142 mg, 0.37 mmol) was used.

$^1$H NMR ($CDCl_3$) δ 8.235 (d, 1H), 7.861 (dd, 1H), 7.681 (d, 1H), 7.638 (d, 1H), 7.554 (d, 1H), 7.023 (dd, 1H), 6.890 (d, 1H), 6.840 (d, 1H), 6.538 (dd, 1H).

Compound 262

Synthesis of (5-(furan-2-yl)-2,4-dimethoxyphenyl)(3,4,5-trimethoxyphenyl)methanone (5-Bromo-2,4-dimethoxyphenyl)(3,4,5-trimethoxyphenyl)methanone (61 mg, 0.15 mmol) obtained in the same manner as in the synthesis of Compound 203 was dissolved in 1,2-dimethoxyethane (DME) (12 ml), and furan-2-boronic acid (22 mg, 0.19 mmol) and Pd(dppf)$Cl_2$ (6 mg, 0.007 mmol) were added thereto. The mixture was stirred. To this reaction mixture, sodium carbonate (47 mg, 0.44 mmol) dissolved in water (4 ml) was added, and the resulting mixture was refluxed with stirring for 24 hours. After completion of the reaction, water (20 ml) was added to the reaction mixture, and the resulting solution was extracted with EtOAc (40 ml). The organic layer was washed with brine, and dried over anhydrous $MgSO_4$. The solid substance was filtered off, and the filtrate was vacuum concentrated. The resulting residue was purified by column chromatography ($SiO_2$, n-Hex/EA=5/1→3/1) to obtain Compound 262 (6 mg, 10%).

MS (ESI) m/z 399 ($M^+$+H).

Compound 263

Synthesis of (3-((dimethylamino)methyl)-4,5-dimethoxyphenyl)(5-(furan-2-yl)-2-methoxyphenyl)methanone Compound 257 [(3-((dimethylamino)methyl)-4-hydroxy-5-methoxyphenyl) (5-(furan-2-yl)-2-methoxyphenyl)methanone] (34.1 mg, 0.09 mmol), triphenylphosphine (12 mg) and methanol (10 drops) were dissolved in tetrahydrofuran (5 ml), diisopropyl azodiimide diisopropyl azodicarboxylate (44.3 μl) was added thereto at room temperature. The mixture was stirred for 12 hours at room temperature. After completion of the reaction, the solvent was removed by vacuum evaporation. The resulting residue was purified by column chromatography ($SiO_2$, $CH_2Cl_2$/MeOH=10/1) to obtain Compound 263 (12.5 mg, 35.1%) in a form of a white solid.

$^1$H NMR ($CDCl_3$) δ 7.769 (dd, 1N), 7.633 (d, 1H), 7.594 (d, 1H), 7.458 (d, 1H), 7.424 (d, 1H), 7.018 (dd, 1H), 6.544 (d, 1H), 6.448 (dd, 1H), 3.937 (s, 3H), 3.916 (s, 3H), 3.733 (s, 2H), 2.242 (s, 6H). MS (ESI) m/z 396 ($M^+$+H).

Compound 264

Synthesis of (5-(furan-2-yl)-2-methoxyphenyl)(4-methoxy-3,5-dimethylphenyl)methanone In the same manner as in the synthesis of Compound 245, Compound 264 (18 mg, 11%) was obtained.

$^1$H NMR ($CDC_3$) δ 7.76 (dd, J=8.6, 1.3 Hz, 1H), 7.60 (s, 1H), 7.53 (s, 2H), 7.43 (s, 1H), 7.01 (m, 1H), 6.54 (m, 1H), 6.45 (m, 1H), 3.77 (s, 6H), 2.29 (s, 6H). MS (ESI) m/z 337 ($M^+$+H).

Compound 265

Synthesis of (5-(furan-2-yl)-2-methoxyphenyl)(4-(methoxymethoxy)-3,5-dimethylphenyl)methanone In the same manner as in the synthesis of Compound 245, Compound 265 (133 mg, 49%) was obtained.

$^1$H NMR ($CDCl_3$) δ 7.75 (m, 1H), 7.60 (s, 1H), 7.53 (s, 2H), 7.42 (s, 1H), 7.01 (m, 1H), 6.54 (m, 1H), 6.44 (m, 1H), 5.01 (s, 2H), 3.76 (s, 3H), 3.60 (s, 3H), 2.30 (s, 6H). MS (ESI) m/z 367 ($M^+$+H).

Compound 266

Synthesis of (5-(furan-2-yl)-2-methoxyphenyl)(4-hydroxy-3,5-dimethylphenyl)methanone Compound 265 [(5-(furan-2-yl)-2-methoxyphenyl)(4-(methoxymethoxy)-3,5-dimethylphenyl)methanone] (110 mg, 0.30 mmol) was dissolved in methanol (5 ml), and concentrated hydrochloric acid (1 ml) was added thereto. The reaction mixture was stirred for 4 hours at room temperature. After completion of the reaction, the reaction mixture was vacuum concentrated. The resulting residue was extracted with water (10 ml) and EtOAc (20 ml). The organic layer was washed with brine, and dried over anhydrous $MgSO_4$. The solid substance was filtered off, and the filtrate was vacuum concentrated to obtain Compound 266 (110 mg, 99%).

$^1$H NMR (CDCl$_3$) δ 7.94 (m, 1H), 7.68 (s, 1H), 7.58 (s, 2H), 7.43 (s, 1H), 7.02 (d, J=8.7 Hz, 1H), 6.54 (m, 1H), 6.45 (m, 1H), 5.08 (b, OH, 1H), 3.80 (s, 3H), 2.26 (s, 6H).

Compound 267

Synthesis of (4-(2-(dimethylamino)ethoxy)-3,5-dimethylphenyl)(5-(furan-2-yl)-2-methoxyphenyl)methanone Compound 266 [(5-(furan-2-yl)-2-methoxyphenyl)(4-hydroxy-3,5-dimethylphenyl)methanone] (33.1 mg, 0.09 mmol) and N,N-dimethylethyleneamine.HCl (15.6 mg) were dissolved in DMF (2 ml), and sodium hydride (9 mg) was added thereto. The mixture was stirred for 1 hour at 130° C. After completion of the reaction, the reaction mixture was cooled to room temperature, and diluted with an EtOAc solution. The organic layer was washed with a saturated ammonium chloride solution, water, and brine. The extracted EtOAc layer was dried over anhydrous $MgSO_4$, and the solid substance was filtered off. The filtrate was vacuum dried to remove the solvent. The resulting residue was purified by column chromatography (SiO$_2$, CH$_2$Cl$_2$/MeOH=10/1) to obtain Compound 267 (25.5 mg, 72%) in a form of a yellow solid.

$^1$H NMR (CDCl$_3$) δ 7.750 (dd, J=8.67, 2.30 Hz, 1H), 7.581 (d, J=2.27 Hz, 1H), 7.514 (s, 2H), 7.419 (d, J=1.39 Hz, 1H), 7.009 (d, J=8.70 Hz, 1H), 6.536 (d, J=3.29 Hz, 1H), 6.440 (dd, J=3.32, 1.87 Hz, 1H), 3.986 (t, J=5.76 Hz, 2H), 3.762 (s, 3H), 2.862 (t, J=5.66 Hz, 2H), 2.459 (s, 6H), 2.298 (s, 6H). MS (ESI) m/z 394 (M$^+$+H).

Compound 268

Synthesis of (4-(allyloxy)-3-methoxyphenyl)(5-(furan-2-yl)-2-methoxyphenyl)methanone Compound 256 [(5-(furan-2-yl)-2-methoxyphenyl)(4-hydroxy-3-methoxyphenyl)methanone] (140 mg, 0.38 mmol) and potassium carbonate (157.6 mg) were dissolved in acetone (10 ml), and allyl bromide (160 µl) was added thereto at room temperature. The mixture was stirred for 12 hours at 80° C. After completion of the reaction, the reaction mixture was cooled to room temperature. The precipitates were filtered off by vacuum filtration, and the solvent was removed. The resulting residue was purified by column chromatography (SiO$_2$, n-Hex/EA=1/2) to obtain Compound 268 (108.4 mg, 78.3%) in a form of colorless oil.

$^1$H NMR (CDCl$_3$) δ 7.788 (dd, J=8.66, 2.26 Hz, 1H), 7.651 (m, 2H), 7.465 (d, J=1.32 Hz, 1H), 7.324 (dd, J=8.41, 1.91 Hz, 1H), 7.052 (d, J=8.69 Hz, 1H), 6.873 (d, J=8.42 Hz, 1H), 6.584 (d, J=3.26 Hz, 1H), 6.486 (dd, J=3.29, 1.84 Hz, 1H), 6.140-6.084 (m, 1H), 5.464 (dd, J=17.3, 1.37 Hz, 1H), 5.360 (dd, J=10.4, 1.13 Hz, 1H), 4.716 (d, J=5.38 Hz, 2H), 3.976 (s, 3H), 3.817 (s, 3H). MS (ESI) m/z 365 (M$^+$+H).

Compound 269

Synthesis of (3-allyl-4-hydroxy-5-methoxyphenyl)(5-(furan-2-yl)-2-methoxyphenyl)methanone Compound 268 [(4-(allyloxy)-3-methoxyphenyl)(5-(furan-2-yl)-2-methoxyphenyl)methanone] (108 mg, 0.3 mmol) was dissolved in p-xylene (5 ml), and the solution was stirred in a pressurized high-temperature reactor at 140° C. for 12 hours. After completion of the reaction the reaction mixture was cooled to room temperature, and the solvent was removed by vacuum evaporation. The resulting residue was purified by column chromatography (SiO$_2$, n-Hex/EA=3/1→2/1) to obtain Compound 269 (61.4 mg, 56.9%) in a form of a yellow oil.

$^1$H NMR (CDCl$_3$) δ 7.753 (dd, J=8.64, 1.87 Hz, 1H), 7.614 (d, J=1.80 Hz, 1H), 7.425 (m, 2H), 7.194 (m, 1H), 7.009 (d, J=8.66 Hz, 1H), 6.540 (d, J=3.20 Hz, 1H), 6.449 (d, J=1.56 Hz, 1H), 6.222 (s, 1H), 5.971-5.904 (m, 1H), 5.033-4.994 (m, 2H), 3.928 (s, 3H), 3.766 (s, 3H), 3.372 (d, J=6.29 Hz, 2H). MS (ESI) m/z 365 (M$^+$+H).

Compound 271

Synthesis of N-(5-(1H-1,2,4-triazol-1-yl)-2-(3,4,5-trimethoxybenzoyl)phenyl)acetamide As shown in Reaction 1, first, magnesium was added to 1-bromo-3,4,5-trimethoxybenzene as a starting material. Then, Compound (VII) derivative was added thereto to obtain a compound [N-(5-fluoro-2-(3,4,5-trimethoxybenzoyl)phenyl)acetamide. Thus obtained compound [N-(5-fluoro-2-(3,4,5-trimethoxybenzoyl)phenyl)acetamide] (36.2 mg, 0.1 mmol) was dissolved in DMF (2 ml), and 1,2,4-triazole.Na (28.5 mg) was added thereto at room temperature. The mixture was heated with stirring for 2 hours. After completion of the reaction, the reaction mixture was cooled to room temperature and diluted with an EtOAc solution. The organic layer was washed with water, and brine. The extracted organic layer was dried over anhydrous $MgSO_4$, and the solid substance was filtered off. The remaining solvent was removed by vacuum evaporation. The resulting residue was purified by column chromatography (SiO$_2$, n-Hex/EA=2/1→1/1) to obtain Compound 271 (25.6 mg, 65%).

$^1$H NMR (CDCl$_3$) δ 10.812 (s, 1H), 9.077 (s, 1H), 8.788 (s, 1H), 8.144 (s, 1H), 7.767 (d, J=8.36 Hz, 1H), 7.564 (d, J=8.52 Hz, 1H), 6.956 (s, 2H), 3.954 (s, 3H), 3.879 (s, 6H), 2.264 (s, 3H). MS (ESI) m/z 397 (M$^+$+H).

Compound 272

Synthesis of (2-amino-4-(1H-1,2,4-triazol-1-yl)phenyl)(3,4,5-trimethoxyphenyl)methanone In the same manner as in the synthesis of Compound 278, Compound 272 was synthesized.

$^1$H NMR (CDCl$_3$) δ 8.786 (s, 1H), 8.145 (s, 1H), 7.648 (d, J=8.62 Hz, 1H), 7.187 (d, J=2.02 Hz, 1H), 6.949-6.901 (m, 3H), 3.928 (s, 3H), 3.879 (s, 6H). MS (ESI) m/z 355 (M$^+$+H).

Compound 273

Synthesis of 2-(4-acetamido-3-(3,4,5-trimethoxybenzoyl)phenyl)-1H-pyrrole-1-carboxylic acid tert-butyl ester As shown in Reaction 5, Compound 18 obtained from 2-amino-5-iodobenzoic acid (Compound 17) as a starting material was reacted with Compound 11 to obtain N-(4-iodo-2-(3,4,5-trimethoxybenzoyl)phenyl)acetamide (Compound 19). Thus obtained N-(4-iodo-2-(3,4,5-trimethoxybenzoyl)phenyl)acetamide (Compound 19, 100 mg, 0.22 mmol) was dissolved in 1,2-dimethoxyethane (12 ml), and 1-(tert-butoxycarbonyl)-1H-pyrrole-2-yl boronic acid (51 mg, 0.24 mmol) and Pd(dppf)Cl$_2$ (9 mg, 0.01 mmol) were added thereto. The mixture was stirred. To this reaction mixture, sodium carbonate (46 mg, 0.44 mmol) dissolved in water (4 ml) was added, and the resulting mixture was refluxed with stirring for 24 hours. After completion of the reaction, water (20 ml) was added to the reaction mixture, and the resulting solution was extracted with dichloromethane (30 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=5/1→3/1) to obtain Compound 273 (68 mg, 63%).

$^1$H NMR (CDCl$_3$) δ 10.42 (s, NH, 1H), 8.56 (d, J=8.3 Hz, 1H), 7.58 (m, 2H), 7.29 (m, 1H), 7.00 (s, 2H), 6.19 (m, 1H), 6.13 (m, 1H), 3.93 (s, 3H), 3.88 (s, 6H), 2.22 (s, 3H), 1.41 (s, 9H).

Compound 274

Synthesis of N-(4-(1H-pyrrole-2-yl)-2-(3,4,5-trimethoxybenzoyl)phenyl)acetamide

Compound 273 [(2-(4-acetamido-3-(3,4,5-trimethoxybenzoyl)phenyl)-1H-pyrrole-1-carboxylic acid tert-butyl ester](68 mg, 0.14 mmol) was dissolved in tetrahydrofuran (10 ml), and a solution of NaOMe (45 mg, 0.83 mmol) dissolved in methanol (2 ml) was added thereto. The reaction mixture was stirred for 12 hours at room temperature. After completion of the reaction, water (20 ml) was added to the reaction mixture, and the resulting solution was extracted with EtOAc (30 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=3/1→1/1) to obtain Compound 274 (16 mg, 30%).

$^1$H NMR (CDCl$_3$) δ 10.33 (s, NH, 1H), 8.70 (brs, NH, 1H), 8.56 (d, J=8.3 Hz, 1H), 7.70 (m, 2H), 7.02 (s, 2H), 6.85 (s, 1H), 6.43 (s, 1H), 6.27 (s, 1H), 3.96 (s, 3H), 3.86 (s, 6H), 2.22 (s, 3H). MS (ESI) m/z 395 (M$^+$+H).

Compound 275

Synthesis of (3-allyl-4,5-dimethoxyphenyl)((5-furan-2-yl)-2-methoxyphenyl)methanone Compound 269 [(3-allyl-4-hydroxy-5-methoxyphenyl)(5-(furan-2-yl)-2-methoxyphenyl)methanone] (24.5 mg, 0.07 mmol) and potassium carbonate (27.9 mg) were dissolved in acetone (5 ml), and iodomethane (228.5 mg) was added thereto at room temperature. The mixture was stirred for 4 hours at 80° C. After completion of the reaction, the reaction mixture was cooled to room temperature, and the precipitates were filtered off by vacuum filtration. The remaining solvent was removed, and the resulting residue was purified by column chromatography (SiO$_2$, n-Hex/EA=2/1→1/1) to obtain Compound 275 (26.3 mg, 99%) in a form of colorless oil.

$^1$H NMR (CDCl$_3$) δ 7.763 (dd, J=8.68, 2.24 Hz, 1H), 7.624 (d, J=2.22 Hz, 1H), 7.450-7.429 (m, 2H), 7.179 (d, J=1.98 Hz, 1H), 7.013 (d, J=8.70 Hz, 1H), 6.544 (d, J=3.20 Hz, 1H), 6.449 (dd, J=3.34, 1.92 Hz, 1H), 5.946-5.878 (m, 1H), 5.019-4.959 (m, 2H), 3.893 (s, 3H), 3.889 (s, 3H), 3.765 (s, 3H), 3.369 (d, J=6.39 Hz, 2H). MS (ESI) m/z 379 (M$^+$+H).

Compound 276

Synthesis of (3-(2,3-dihydroxypropyl)-4,5-dimethoxyphenyl)(5-(furan-2-yl)-2-methoxyphenyl)methanone Compound 275 [(3-allyl-4,5-dimethoxyphenyl)((5-(furan-2-yl)-2-methoxyphenyl)methanone) (23.9 mg, 0.06 mmol) and N-methylmorpholine-N-oxide (14.8 mg) were dissolved in acetone/water (5 ml, v/v 4:1), and OsO$_4$ (100 μl) was added thereto at room temperature. The mixture was stirred for 12 hours at room temperature. After completion of the reaction, sodium sulfite was added to the reaction mixture, and the resulting mixture was stirred for 1 hour at room temperature. The mixture was diluted with an EtOAc solution, and the organic layer was washed with water, and brine. The extracted organic layer was dried over anhydrous MgSO$_4$, and the solid substance was filtered off. The filtrate was vacuum dried to remove the solvent, and the resulting residue was purified by column chromatography (SiO$_2$, n-Hex/EA=1/2) to obtain Compound 276 (31.9 mg, 99%) in a form of a yellow solid.

$^1$H NMR (CDCl$_3$) δ 7.773 (dd, J=8.64, 2.20 Hz, 1H), 7.622 (d, J=2.16 Hz, 1H), 7.498 (d, J=1.72 Hz, 1H), 7.434 (m, 1H), 7.182 (d, J=1.80 Hz, 1H), 7.025 (d, J=8.72 Hz, 1H), 6.553 (d, J=3.32 Hz, 1H), 6.453 (dd, J=3.28, 1.80 Hz, 1H), 3.939 (s, 3H), 3.915 (s, 3H), 3.861-3.847 (m, 1H), 3.779 (s, 3H), 3.747 (m, 2H), 3.616-3.579 (m, 1H), 3.491-3.396 (m, 1H). MS (ESI) m/z 413 (M$^+$+H).

Compound 277

Synthesis of N-(4-(thiazol-2-yl)-2-(3,4,5-trimethoxybenzoyl)phenyl)acetamide

As shown in Reaction 5, Compound 19 [(N-(4-iodo-2-(3,4,5-trimethoxybenzoyl)phenyl)acetamide) (96.7 mg, 0.21 mol) was dissolved in tetrahydrofuran (10 ml), and tetrakis triphenylphosphine palladium (Pd(PPh$_3$)$_4$) (24.3 mg, 10 mole %) and 2-thiazol-ZnBr (552.3 μl) were added thereto at room temperature. The mixture was stirred for 12 hours at 70° C. After completion of the reaction, the reaction mixture was cooled to room temperature, and the solvent was removed by vacuum evaporation. Then, the resulting residue was purified by column chromatography (SiO$_2$, n-Hex/EA-2/1→1/2) to obtain Compound 277 (40 mg, 46.2%) in a form of a gray solid.

MS (ESI) m/z 413 (M$^+$+H).

Compound 278

Synthesis of (2-amino-5-(thiazol-2-yl)phenyl)(3,4,5-trimethoxyphenyl)methanone

Compound 277 [N-(4-(thiazol-2-yl)-2-(3,4,5-trimethoxybenzoyl)phenyl)acetamide](15.6 mg, 0.04 mmol) was dissolved in methanol (3 ml), and NaOMe (10.2 mg) was added thereto at room temperature. The mixture was stirred for 2 hours at 100° C. After completion of the reaction, the reaction mixture was cooled to room temperature, and the solvent was removed by vacuum evaporation. The resulting residue was purified by column chromatography (SiO$_2$, n-Hex/EA=1/1) to obtain Compound 278 (10 mg, 95%) in a form of a yellow solid.

$^1$H NMR (acetone-d6) δ 8.224 (d, J=8.22 Hz, 1H), 7.919 (dd, J=8.70, 2.16 Hz, 1H), 7.721 (d, J=3.24 Hz, 1H), 7.422 (d, J=3.29 Hz, 1H), 7.137 (brs, 2H), 7.035 (s, 2H), 7.016 (d, J=8.72 Hz, 1H). MS (ESI) m/z 371 (M$^+$+H).

Compound 279

Synthesis of N-(4-(thiophen-2-yl)-2-(3,4,5-trimethoxybenzoyl)phenyl)acetamide

In the same manner as in the synthesis of Compound 277, Compound 279 (63.4 mg, 67%) was obtained.

$^1$H NMR (CDCl$_3$) δ 10.444 (s, 1H), 8.591 (d, J=8.48 Hz, 1H), 7.823-7.789 (m, 2H), 7.256 (dd, J=4.88, 0.76 Hz, 1H), 7.221 (dd, J=3.52, 0.92 Hz, 1H), 7.066-7.039 (m, 3H), 3.970 (s, 3H), 3.879 (s, 6H), 2.225 (s, 3H). MS (ESI) m/z 412 (M$^+$+H).

Compound 281

Synthesis of N-(4-(furan-2-yl)-2-(3,4,5-trimethoxybenzoyl)phenyl)-N-methylacetamide Compound 231 [N-(4-furan-2-yl)-2-(3,4,5-trimethoxybenzoyl)phenyl]acetamide] (100 mg, 0.25 mmol) was dissolved in tetrahydrofuran (10 ml), and the solution was cooled to 0° C. Then, sodium hydride (60%, 30 mg, 0.76 mmol) and iodomethane (90 mg, 0.63 mmol) were added to the solution. The reaction mixture was stirred at 0° C. for 2 hours, and ice water (5 ml) was slowly added dropwise thereto to terminate the reaction. The reaction mixture was extracted with water (10 ml), and EtOAc (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=3/1→1/2) to obtain Compound 281 (75 mg, 73%).

$^1$H NMR (CDCl$_3$) δ 7.82 (dd, J=8.25, 2.0 Hz, 1H), 7.72 (d, J=2.0 Hz, 1H), 7.47 (d, J=1.6 Hz, 1H), 7.29 (d, J=8.25 Hz, 1H), 7.05 (s, 2H), 6.71 (d, J=3.4 Hz, 1H), 6.48 (dd, J=3.4, 1.7 Hz, 1H), 3.92 (s, 3H), 3.80 (s, 6H), 3.06 (s, 3H), 1.86 (s, 3H). MS (ESI) m/z 410 (M$^+$+H).

Compound 282

Synthesis of (5-(furan-2-yl)-2-(methylamino)phenyl)(3,4,5-trimethoxyphenyl)methanone In the same manner as in the synthesis of Compound 278, Compound 282 was obtained.

$^1$H NMR (acetone-d6) δ 8.38 (b, 1H), 7.92 (b, 1H), 7.80 (m, 1H), 7.49 (b, 1H), 6.97~6.92 (m, 3H), 6.54 (m, 1H), 6.45 (m, 1H), 3.86~3.84 (m, 9H), 3.02 (s, 3H). MS (ESI) m/z 368 (M$^+$+H).

Compound 283

Synthesis of (2-amino-5-(thiophen-2-yl)phenyl)(3,4,5-trimethoxyphenyl)methanone

In the same manner as in the synthesis of Compound 278, Compound 283 (22 mg, 40.6%) was obtained.

$^1$H NMR (CDCl$_3$) δ 7.798 (d, J=2.17 Hz, 1H), 7.579 (dd, J=8.47, 2.14 Hz, 1H), 7.158 (dd, J=3.61, 1.11 Hz, 1H), 7.086 (dd, J=3.61, 1.11 Hz, 1H), 7.021-6.987 (m, 3H), 6.833 (d, J=7.18 Hz, 1H), 3.950 (s, 3H), 3.887 (s, 6H). MS (ESI) m/z 370 (M$^+$+H).

Compound 284

Synthesis of (2-amino-5-(oxazol-5-yl)phenyl)(3,4,5-trimethoxyphenyl)methanone

N-(4-formyl-2-(3,4,5-trimethoxybenzoyl)phenyl)acetamide (55.6 mg, 0.16 mmol) as a starting material and sodium carbonate (66.3 mg) were dissolved in methanol (5 ml), and tosylmethyl isocyanide (93.7 mg) was added thereto at room temperature. The mixture was stirred for 7 hours at 80° C. After completion of the reaction, the reaction mixture was cooled to room temperature, and the solvent was removed by vacuum evaporation. The resulting residue was purified by column chromatography (SiO$_2$, n-Hex/EA=1/1→1/2) to obtain Compound 284 (15.3 mg, 26.9%) in a form of a yellow solid.

$^1$H NMR (CDCl$_3$) δ7.894 (s, 1H), 7.852 (d, J=2.03 Hz, 1H), 7.592 (dd, J=8.64, 2.06 Hz, 1H), 7.163 (s, 1H), 6.959 (s, 2H), 6.887 (d, J=8.57 Hz, 1H), 3.974 (s, 3H), 3.877 (s, 6H). MS (ESI) m/z 355 (M$^+$+H).

Compound 285

Synthesis of N-(2-(3-(hydroxymethyl)-4,5-dimethoxybenzoyl)-4-(thiazol-2-yl)phenyl)acetamide In the same manner as in the synthesis of Compound 277, a compound was obtained from Compound 19 derivative of Reaction 5 by introducing 2-thiazole. And, in the same manner as in the synthesis of Compound 249, aldehyde group of thus obtained compound was subjected to the reduction reaction to synthesize Compound 285.

MS (ESI) m/z 413 (M$^+$+H).

Compound 286

Synthesis of (2-amino-5-(thiazol-2-yl)phenyl)(3-(hydroxymethyl)-4,5-dimethoxyphenyl)methanone In the same manner as in the synthesis of Compound 278, Compound 286 was obtained.

$^1$H NMR (CDC$_3$) δ 8.52 (s, 1H), 7.95 (m, 2H), 7.50 (s, 1H), 7.38 (d, J=3.98 Hz, 1H), 7.34 (d, J=2.02 Hz, 1H), 6.88 (d, J=8.85 Hz, 1H), 4.78 (s, 2H), 3.98 (s, 3H), 3.92 (m, 5H), 1.26 (bs, 3H).

Compound 288

Synthesis of N-(4-(pyridin-2-yl)-2-(3,4,5-trimethoxybenzoyl)phenyl)acetamide

In the same manner as in the synthesis of Compound 277, Compound 288 (500 mg, 93%) was obtained.

$^1$H NMR (CDCl$_3$) δ 10.59 (s, NH, 1H), 8.67 (d, J=8.7 Hz, 1H), 8.60 (d, J=4.5 Hz, 1H), 8.35 (d, J=2.0 Hz, 1H), 8.16 (dd, J=8.7, 1.8 Hz, 1H), 7.72 (m, 1H), 7.64 (d, J=−8.1 Hz, 1H), 7.21~7.18 (m, 1H), 7.04 (s, 2H), 3.94 (s, 3H), 3.85 (s, 6H), 2.22 (s, 3H).

Compound 289

Synthesis of (2-amino-5-(oxazol-2-yl)phenyl)(3,4,5-trimethoxyphenyl)methanone

Compound 296 [N-(4-(oxazol-2-yl)-2-(3,4,5-trimethoxybenzoyl)phenyl)acetamide](594 mg, 1.50 mmol) was dissolved in methanol (30 ml), and NaOMe (810 mg) was added thereto at room temperature. The mixture was stirred for 3 hours at 80°. After completion of the reaction, the solvent was removed by vacuum evaporation. The resulting residue was purified by column chromatography (SiO$_2$, n-Hex/EA=3/1→1/5) to obtain Compound 289 (450 mg, 84.7%) in a form of a yellow solid.

$^1$H NMR (acetone-d6) δ 8.233 (d, J=2.04 Hz, 1H), 7.932 (dd, J=8.73, 2.05 Hz, 1H), 7.859 (d, J=0.67 Hz, 1H), 7.169 (brs, 2H), 7.153 (s, 1H), 7.031 (d, J=8.77 Hz, 1H), 7.014 (s, 2H), 3.874 (s, 3H), 3.848 (s, 6H). MS (ESI) m/z 355 (M$^+$+H).

Compound 290

Synthesis of (5-(1H-imidazol-1-yl)-2-nitrophenyl)(3,4,5-trimethoxyphenyl)methanone To 1-bromo-3,4,5-trimethoxybenzene as a starting material, magnesium was added, as shown in Reaction 1, and a substituted benzaldehyde was added thereto to obtain a Formula IV derivative. Thus obtained Formula IV derivative was oxidized to obtain (5-chloro-2-nitrophenyl)(3,4,5-trimethoxyphenyl)methanone. Thus obtained (5-chloro-2-nitrophenyl)(3,4,5-trimethoxyphenyl)methanone (59.2 mg, 0.17 mmol) was dissolved in DMF (3 ml), and imidazole.Na (22.7 mg) was added thereto at room temperature. The mixture was stirred for 6 hours at 130° C. After completion of the reaction, the reaction mixture was cooled to room temperature, and diluted with an EtOAc solution. The organic layer was washed with a saturated ammonium chloride solution, water, and brine. The extracted organic layer was dried over anhydrous MgSO$_4$, and the solid substance was filtered off. Then, the filtrate was vacuum dried to remove the solvent. The resulting residue was purified by column chromatography (SiO$_2$, n-Hex/EA=1/2) to obtain Compound 290 (17 mg, 26.4%) in a form of a yellow solid.

$^1$H NMR (CDCl$_3$) δ 8.407 (d, J=8.86 Hz, 1H), 8.357 (brs, 1H), 7.883 (dd, J=8.85, 2.46 Hz, 1H), 7.636 (d, J=2.45 Hz, 1H), 7.606 (brs, 1H), 7.274 (brs, 1H), 6.994 (s, 2H), 3.879 (s, 3H), 3.804 (s, 6H).

Compound 291

Synthesis of (2-nitro-5-(1H-1,2,4-triazol-1-yl)phenyl)(3,4,5-trimethoxyphenyl)methanone In the same manner as in the synthesis of Compound 290, Compound 291 (85 mg, 51%) was obtained.

$^1$H NMR (CD$_3$OD+CDCl$_3$) δ 9.28 (s, 1H), 8.44 (d, J=9.0 Hz, 1H), 8.25 (dd, J=9.0, 2.4 Hz, 1H), 8.20 (s, 1H), 8.08 (d, J=2.4 Hz, 1H), 7.05 (s, 2H), 3.89 (s, 3H), 3.81 (s, 6H). MS (ESI) m/z 385 (M$^+$+H).

Compound 293

Synthesis of (2-amino-5-(pyridin-2-yl)phenyl)(3,4,5-trimethoxyphenyl)methanone

In the same manner as in the synthesis of Compound 289, Compound 293 (260 mg, 58%) was obtained.

$^1$H NMR (acetone-d6) δ 8.53 (m, 1H), 8.44 (d, J=2.2 Hz, 1H), 8.08 (dd, J=8.7, 2.1 Hz, 1H), 7.74~7.71 (m, 2H), 7.16 (m, 1H), 7.04 (s, 2H), 7.01 (d, J=8.7 Hz, 1H), 6.92 (b, NH2, 2H), 3.88 (s, 6H), 3.84 (s, 3H). MS (ESI) m/z 365 (M$^+$+H).

Compound 294

Synthesis of N-(4-(2-aminothiazol-5-yl)-2-(3,4,5-trimethoxybenzoyl)phenyl)acetamide N-(4-(2-bromoacetyl)-2-(3,4,5-trimethoxybenzoyl)phenyl)acetamide (10 mg, 22 mmol) obtained from Compound 19 of Reaction 5 was dissolved in 3 ml of 95% ethanol, and thiourea (7.6 mg, 100 mmol) was added thereto. The mixture was reacted for 2 hours at room temperature, and then for 24 hours with heating. The solvent was removed by vacuum evaporation, the resulting residue was purified by column chromatography (SiO$_2$, n-Hex/EA=1/1→1/2) to obtain Compound 294 (9.7 mg, 100%).

$^1$H NMR (CDCl$_3$) δ 10.46 (s, 1H), 8.59 (d, J=8.76 Hz, 1H), 8.01 (d, J=2.04 Hz, 1H), 7.94 (dd, J=8.76, 2.04 Hz, 1H), 7.02 (s, 2H), 6.62 (s, 1H), 5.74 (bs, 2H), 3.96 (s, 3H), 3.87 (s, 6H), 2.22 (s, 3H).

Compound 295

Synthesis of N-(4-(2-methylthiazol-5-yl)-2-(3,4,5-trimethoxybenzoyl) phenyl)acetamide In the same manner as in the synthesis of Compound 294, Compound 295 was obtained.

$^1$H NMR (CDCl$_3$) δ 10.45 (s, 1H), 8.69 (d, J=8.64 Hz, 1H), 8.19 (d, J=8.64 Hz, 1H), 8.12 (s, 1H), 7.30 (s, 1H), 7.02 (s, 2H), 3.96 (s, 3H), 3.87 (s, 6H), 2.98 (s, 3H), 3.96 (s, 3H), 2.23 (s, 3H).

Compound 296

Synthesis of N-(4-(oxazol-2-yl)-2-(3,4,5-trimethoxybenzoyl)phenyl)acetamide

Oxazole (1.07 g, 15.5 mmol) as a starting material was dissolved in tetrahydrofuran (20 ml), and the solution was cooled to −78° C. Then, n-butyllithium (5 ml) was slowly added to the solution. The mixture was stirred at −78° C. for 20, and zinc chloride (15.5 ml) was added thereto. Then, the temperature of the resulting mixture was elevated to room temperature. Pd(PPh$_3$)$_4$ (330.5 mg) and Compound 19 [(N-(4-iodo-2-(3,4,5-trimethoxybenzoyl)phenyl)acetamide) (1.3 g, 2.86 mmol) of Reaction 5 were added to the reaction mixture, and the resulting mixture was stirred for 12 hours at 70° C. After completion of the reaction, the reaction mixture was cooled to room temperature, and diluted with an EtOAc solution. The organic layer was washed with a saturated ammonium chloride solution, water, and brine. The extracted organic layer was dried over anhydrous MgSO$_4$, and the solid substance was filtered off. The filtrate was vacuum dried to remove the solvent, and the resulting residue was purified by column chromatography (SiO$_2$, n-Hex/EA=1/1→1/5) to obtain Compound 296 (650 mg, 57.7%) in a form of a yellow solid.

$^1$H NMR (CDC$_3$) δ 10.61 (s, 1H), 8.738 (d, J=8.40 Hz, 1H), 8.322 (d, J=2.04 Hz, 1H), 8.235 (dd, J=8.76, 2.00 Hz, 1H), 7.694 (s, 1H), 7.216 (s, 1H), 7.015 (s, 2H), 3.984 (s, 3H), 3.871 (s, 6H), 2.252 (s, 3H). MS (ESI) m/z 397 (M$^+$+H).

Compound 297

Synthesis of (2-amino-5-(2-aminothiazol-4-yl)phenyl)(3,4,5-trimethoxyphenyl)methanone Compound 294 [N-(4-(2-aminothiazol-5-yl)-2-(3,4,5-trimethoxybenzoyl)phenyl)acetamide] (8 mg, 19 mmol) was dissolved in 3 ml of 35% hydrochloric acid, and the solution was heated with stirring for 3 hours. After cooling, the reaction solution was poured into ice water. The resulting solution was neutralized with 6 N sodium hydroxide, and extracted with dichloromethane. The organic layer was dried over $Na_2SO_3$, and the solid substance was filtered off. The filtrate was vacuum evaporated to remove the solvent, and the resulting residue was purified by column chromatography ($SiO_2$, n-Hex/EA=1/1→1/2) to obtain Compound 297 (5 mg, 65%).

$^1$H NMR (acetone-d6) δ 8.13 (d, J=2.07 Hz, 1H), 7.77 (dd, J=8.67, 2.07 Hz, 1H), 7.01 (s, 2H), 6.90 (d, J=8.67 Hz, 1H), 6.79 (bs, 2H), 6.62 (s, 1H), 6.30 (bs, 2H), 3.88 (s, 6H), 3.84 (s, 3H).

Compound 298

Synthesis of (2-amino-5-(2-methylthiazol-4-yl)phenyl)(3,4,5-trimethoxyphenyl)methanone In the same manner as in the synthesis of Compound 297, Compound 298 was obtained.

$^1$H NMR (acetone-d6) δ 8.27 (d, J=2.09 Hz, 1H), 7.88 (dd, J=8.62, 2.09 Hz, 1H), 7.40 (s, 1H), 7.04 (s, 2H), 6.96 (d, J=8.62 Hz, 1H), 6.86 (bs, 2H), 3.88 (s, 6H), 3.84 (s, 3H), 2.65 (s, 3H).

Compound 300

Synthesis of N-(4-(thiophen-3-yl)-2-(3,4,5-trimethoxybenzoyl)phenyl)acetamide

In the same manner as in the synthesis of Compound 277, Compound 300 (70 mg, 77%) was obtained.

$^1$H NMR (acetone-d6) δ 10.03 (b, NH, 1H), 8.37 (d, J=8.6 Hz, 1H), 7.93 (dd, J=8.6, 2.1 Hz, 1H), 7.90 (d, J=2.0 Hz, 1H), 7.74 (m, 1H), 7.55 (m, 1H), 7.49 (m, 1H), 7.12 (s, 2H), 3.85 (s, 9H), 2.08 (s, 3H).

Compound 301

Synthesis of (2-amino-5-(thiophen-3-yl)phenyl)(3,4,5-trimethoxyphenyl)methanone

In the same manner as in the synthesis of Compound 289, Compound 301 was obtained.

$^1$H NMR (acetone-d6) δ 7.81 (d, J=2.0 Hz, 1H), 7.67 (dd, J=8.5, 2.0 Hz, 1H), 7.45 (m, 2H), 7.31 (m, 1H), 7.00 (s, 2H), 6.97 (d, J=8.6 Hz, 1H), 6.76 (b, NH2, 2H), 3.86 (s, 6H), 3.81 (s, 3H). MS (ESI) m/z 370 (M$^+$+H).

Compound 302

Synthesis of N-(4-(6-methoxypyridin-2-yl)-2-(3,4,5-trimethoxybenzoyl)phenyl)acetamide In the same manner as in the synthesis of Compound 277, Compound 302 was obtained.

$^1$H NMR (CDCl$_3$) δ 10.641 (s, 1H), 8.664 (d, J=8.76 Hz, 1H), 8.368 (d, J=2.12 Hz, 1H), 8.211 (dd, J=8.76, 2.16 Hz, 1H), 7.581 (m, 1H), 7.228 (d, J=7.40 Hz, 1H), 7.040 (s, 2H), 6.646 (d, J=8.20 Hz, 1H), 3.936 (s, 3H), 3.881 (s, 3H), 3.851 (s, 6H), 2.233 (s, 3H). MS (ESI) m/z 437 (M$^+$+H).

Compound 303

Synthesis of (2-amino-5-(6-methoxypyridin-2-yl)phenyl)(3,4,5-trimethoxyphenyl)methanone In the same manner as in the synthesis of Compound 289, Compound 303 was obtained.

$^1$H NMR (CDCl$_3$) δ 8.434 (d, J=2.16 Hz, 1H), 8.072 (dd, J=8.72, 2.20 Hz, 1H), 7.629 (m, 1H), 7.283 (m, 1H), 7.019-6.985 (m, 4H), 6.559 (m, 1H), 3.858 (s, 6H), 3.830 (s, 3H), 3.825 (s, 3H). MS (ESI) m/z 395 (M$^+$+H).

Compound 306

Synthesis of (5-(furan-2-yl)-2-phenoxyphenyl)(3,4,5-trimethoxyphenyl)methanone

Compound 240 [(5-(furan-2-yl)-2-hydroxyphenyl)(3,4,5-trimethoxyphenyl)methanone] (31 mg, 0.08 mmol), benzeneboronic acid (21 mg, 0.17 mmol), Cu(OAc)$_2$ (16 mg, 0.08 mmol), triethylamine (44 mg, 0.44 mmol), and 4 Å molecular sieves (50 mg) were dissolved in dichloromethane (8 ml), and the mixture was stirred at room temperature. After terminating the reaction by adding an aqueous sodium hydroxide solution, water (10 ml) was added to the reaction mixture, and the resulting solution was extracted with dichloromethane (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=6/1) to obtain Compound 306 (6 mg, 17%).

$^1$H NMR (acetone-d6) δ 7.87 (dd, J=8.6, 2.2 Hz, 1H), 7.82 (d, J=2.2 Hz, 1H), 7.65 (d, J=1.4 Hz, 1H), 7.35~7.31 (m, 2H), 7.14 (s, 2H), 7.10~7.07 (m, 2H), 6.96 (d, J=8.7 Hz, 2H), 6.91 (d, J=3.3 Hz, 1H), 6.57 (dd, J=3.3, 1.7 Hz, 1H), 3.81 (s, 6H), 3.79 (s, 3H). MS (ESI) m/z 431 (M$^+$+H).

Compound 307

Synthesis of N-(4-(thiazol-2-yl)-2-(3,4,5-trimethoxybenzoyl)phenyl)propionamide

Compound 278 [(2-amino-5-(thiazol-2-yl)phenyl)(3,4,5-trimethoxyphenyl)methanone] (34.7 mg, 0.09 mmol) was dissolved in dichloromethane (3 ml), and pyridine (9.1 μl) and propionyl chloride (12.3 μl) were added thereto at room temperature. The mixture was stirred for 12 hours at room temperature. After completion of the reaction, the solvent was removed by vacuum evaporation. The resulting residue was purified by column chromatography (SiO$_2$, n-Hex/EA=1/1→1/2) to obtain Compound 307 (28 mg, 70%) in a form of a gray solid.

$^1$H NMR (acetone-d6) δ 10.357 (s, 1H), 8.551 (d, J=8.72 Hz, 1H), 8.285 (d, J=2.20 Hz, 1H), 8.182 (dd, J=8.72, 2.12 Hz, 1H), 7.852 (d, J=3.24 Hz, 1H), 7.618 (d, J=3.28 Hz, 1H), 7.141 (s, 2H), 3.864 (s, 9H), 2.422 (q, J=7.48 Hz, 2H), 1.147 (t, J=7.52 Hz, 3H). MS (ESI) m/z 427 (M$^+$+H).

Compound 308

Synthesis of N-(4-(thiazol-2-yl)-2-(3,4,5-trimethoxybenzoyl)phenyl)methanesulfonamide In the same manner as in the synthesis of Compound 307, Compound 308 (6 mg, 18.3%) was obtained.

$^1$H NMR (CDCl$_3$) 10.106 (s, 1H), 8.350 (d, J=2.16 Hz, 1H), 8.149 (dd, J=8.68, 2.12 Hz, 1H), 7.888 (d, J=8.72 Hz, 1H), 7.836 (d, J=3.20 Hz, 1H), 7.339 (d, J=3.28 Hz, 1H), 7.039 (s, 2H), 3.980 (s, 3H), 3.884 (s, 6H), 3.148 (s, 3H). MS (ESI) m/z 449 (M$^+$+H).

Compound 309

Synthesis of 4-(thiazol-2-yl)-2-(3,4,5-trimethoxybenzoyl)phenylcarboxylic acid methyl ester In the same manner as in the synthesis of Compound 307, Compound 309 (18 mg, 70%) was obtained.

$^1$H NMR (CDCl$_3$) δ 10.063 (s, 1H), 8.509 (d, J=8.80 Hz, 1H), 8.258 (d, J=1.08 Hz, 1H), 8.137 (dd, 1H), 7.814 (d, 1H), 7.305 (d, 1H), 7.038 (s, 2H), 3.969 (s, 3H), 3.869 (s, 6H), 3.808 (s, 3H). MS (ESI) m/z 429 (M$^+$+H).

Compound 311

Synthesis of N-(4-(1-methyl-1H-imidazol-2-yl)-2-(3,4,5-trimethoxybenzoyl)phenylacetamide In the same manner as in the synthesis of Compound 296, Compound 311 (12 mg, 18.7%) in a form of a gray solid was obtained.

$^1$H NMR (CDCl$_3$) δ 10.508 (s, 1H), 8.687 (d, J=8.68 Hz, 1H), 7.938 (d, J=2.12 Hz, 1H), 7.804 (dd, J=8.68, 2.12 Hz, 1H), 7.094 (s, 1H), 6.992 (s, 2H), 6.959 (s, 1H), 3.971 (s, 3H), 3.869 (s, 6H), 3.733 (s, 3H). MS (ESI) m/z 368 (M$^+$+H).

Compound 312

Synthesis of (2-amino-5-(1-methyl-1H-imidazol-2-yl)phenyl)(3,4,5-trimethoxyphenyl)methanone In the same manner as in the synthesis of Compound 289, Compound 312 (6.2 mg, 56.4%) in a form of yellow oil was obtained.

$^1$H NMR (CDCl$_3$) δ 7.713 (d, J=2.07 Hz, 1H), 7.616 (dd, J=8.48, 2.09 Hz, 1H), 7.047 (d, J=1.14 Hz, 1H), 6.911 (s, 2H), 6.888 (d, J=1.09 Hz, 1H), 6.833 (d, J=8.57 Hz, 1H), 6.147 (brs, 2H), 3.942 (s, 3H), 3.862 (s, 6H), 3.625 (s, 3H). MS (ESI) m/z 410 (M$^+$+H).

Compound 313

Synthesis of N-(4-(1H-pyrazol-5-yl)-2-(3,4,5-trimethoxybenzoyl)phenyl)acetamide (Z)-N-(4-(1-hydroxy-3-oxoprop-1-enyl)-2-(3,4,5-trimethoxybenzoyl)phenyl)acetamide (13 mg, 0.03 mmol) obtained from Compound 19 of Reaction 5 through a two step reaction was dissolved in 3 ml of ethanol, and hydrazine.H$_2$O (excessive amount) was added thereto. The reaction mixture was heated for 3 hours, and then vacuum concentrated. The resulting residue was extracted with a saturated aqueous sodium bicarbonate solution (2 ml) and EtOAc (10 ml). The organic layer was washed with brine, and dried over anhydrous MgSO$_4$. The solid substance was filtered off, and the filtrate was vacuum dried to remove the solvent. The resulting residue was purified by column chromatography (SiO$_2$, n-Hex/EA=3/1→1/10) to obtain Compound 313 (5 mg, 42%) in a form of a solid.

$^1$H NMR (acetone-d6) δ 10.17 (s, NH, 1H), 8.42 (dd, J=8.6, 3.6 Hz, 1H), 8.14 (d, J=1.7 Hz, 1H), 8.05 (dd, J=8.6, 2.0 Hz, 1H), 7.73 (s, 1H), 7.12 (s, 2H), 6.69 (s, 1H), 3.85 (s, 9H), 2.10 (s, 3H).

Compound 314

Synthesis of 3-chloro-N-(4-(thiazol-2-yl)-2-(3,4,5-trimethoxybenzoyl)phenyl)propanamide Compound 278 [(2-amino-5-(thiazol-2-yl)phenyl)(3,4,5-trimethoxyphenyl)methanone] (5.2 mg, 13.5 mmol) was dissolved in 2 ml of dichloromethane, and 3-chloro-propionyl chloride (5 ml, 51 mmol) and pyridine (5 ml, 62 mmol) were added thereto. The mixture was reacted for 3 hours at room temperature. An organic layer was extracted using EtOAc and water, and the organic layer was dried over Na$_2$SO$_3$. The solid substance was filtered off, and the filtrate was vacuum dried to remove the solvent. The resulting residue was purified by column chromatography (SiO$_2$, n-Hex/EA=2/1→1/1) to obtain Compound 314 (6.2 mg, 99%) in a form of a solid.

$^1$H NMR (CDCl$_3$) δ 10.77 (s, 1H), 8.74 (d, 1H), 8.31 (d, 1H), 8.14 (dd, 1H), 7.83 (d, 1H), 7.33 (d, 1H), 7.05 (s, 2H), 3.98 (s, 3H), 3.90 (t, 2H), 3.88 (s, 6H), 2.92 (t, 2H).

Compound 315

Synthesis of 4-(thiazol-2-yl)-2-(3,4,5-trimethoxybenzoyl)phenylcarboxylic acid isobutyl ester In the same manner as in the synthesis of Compound 314, Compound 315 was obtained.

$^1$H NMR (CDCl$_3$) δ 8.55 (d, 1H, J=8.8 Hz), 8.27 (d, 1H, J=2.1 Hz), 8.19 (dd, 1H, J=2.1 Hz, 8.8 Hz), 7.84 (d, 1H, J=3.3 Hz), 7.33 (d, 1H, J=3.3 Hz), 7.04 (s, 2H), 4.02-3.99 (m, 2H), 3.97 (s, 3H), 3.87 (s, 6H), 2.04-1.96 (m, 1H), 1.00 (s, 3H), 0.99 (s, 3H). MS (ESI) m/z 471 (M$^+$+H).

Compound 316

Synthesis of N-(4-(thiazol-2-yl)-2-(3,4,5-trimethoxybenzoyl)phenyl)formamide

Compound 278 [(2-amino-5-(thiazol-2-yl)phenyl)(3,4,5-trimethoxyphenyl)methanone] (20 mg, 0.054 mmol) was dissolved in formic acid (2 ml), and the solution was refluxed with stirring for 20 hours. After completion of the reaction, the reaction solution was cooled to room temperature, and cold water was poured thereto. An organic layer was extracted out using EtOAc and water, and the organic layer was dried over anhydrous MgSO$_4$. The solid substance was filtered out, and the filtrate was vacuum dried to remove the solvent. The resulting residue was purified by column chromatography (SiO$_2$, n-Hex/EA=2/1→1/1) to obtain Compound 316 (12.87 mg, 60%) in a form of a yellow solid.

$^1$H NMR (acetone-d6) δ 8.62 (d, 1H, J=8.6 Hz), 8.52 (s, 1H), 8.25 (s, 1H), 8.19 (dd, 1H, J=2.1 Hz, 8.6 Hz), 7.85 (d, 1H, J=3.2 Hz), 7.62 (d, 2H, J=3.2 Hz), 7.16 (s, 2H), 3.86 (s, 9H). MS (ESI) m/z 399 (M$^+$+H).

Compound 317

Synthesis of (5-(furan-2-yl)-2-(4-methylpiperazin-1-yl)phenyl)(3,4,5-trimethoxyphenyl)methanone First, magnesium was added to 1-bromo-3,4,5-trimethoxybenzene as a starting material, as shown in Reaction 1, and a substituted benzaldehyde was added thereto to obtain formula IV derivative. Thus obtained formula IV derivative was oxidized, and methylpiperazine was added thereto to obtain (5-bromo-2-(4-methylpiperazin-1-yl)phenyl)(3,4,5-trimethoxyphenyl)methanone. Thus obtained (5-bromo-2-(4-methylpiperazin-1-yl)phenyl)(3,4,5-trimethoxyphenyl)methanone (65 mg, 0.14 mmol), furan-2-boronic acid (24 mg, 0.22 mmol), and Pd(dppf)Cl$_2$ (6 mg, 0.007 mmol) were dissolved in 1,2-dimethoxyethane (6 ml), and sodium carbonate (31 mg, 0.29 mmol) dissolved in water (2 ml) was added dropwise. The mixture was refluxed with stirring for 12 hours. After completion of the reaction, the reaction mixture was cooled to room temperature, and diluted with an EtOAc solution. The organic layer was washed with a saturated aqueous ammonium chloride solution, water, and brine. The extracted organic layer was dried over anhydrous MgSO$_4$, and the solid substance was filtered out. The filtrate was vacuum evaporated to remove the solvent. The resulting residue was purified by column chromatography (SiO$_2$, CH$_2$Cl$_2$/MeOH=30/1) to obtain Compound 317 (14 mg, 23%) in a form of oil.

$^1$H NMR (CDCl$_3$) δ 7.74 (dd, J=8.5, 2.2 Hz, 1H), 7.67 (d, J=2.1 Hz, 1H), 7.43 (d, J=1.4 Hz, 1H), 7.08 (m, 3H), 6.58 (d, J=3.3 Hz, 1H), 6.45 (dd, J=3.3, 1.7 Hz, 1H), 3.93 (s, 3H), 3.82 (s, 6H), 3.00 (m, 4H), 2.18 (m, 7H). MS (ESI) m/z 437 (M$^+$+H).

Compound 318

Synthesis of (2-amino-5-(thiazol-2-yl)phenyl)(3,4,5-trimethoxyphenyl)methanone oxime Compound 278 [(2-amino-5-(thiazol-2-yl)phenyl)(3,4,5-trimethoxyphenyl)methanone] (25 mg, 0.07 mmol) was dissolved in 2 ml of pyridine, and hydroxylamine.HCl (9 mg, 0.13 mmol) was added thereto. The reaction mixture was refluxed for 24 hours. After completion of the reaction, the reaction mixture was cooled to room temperature, and vacuum concentrated. The resulting residue was purified by column chromatography (SiO$_2$, n-Hex/EA=3/1→1/1) to obtain Compound 318 (12 mg, 44%).

$^1$H NMR (acetone-d6) δ 10.20 (s, OH, 1H), 7.62 (dd, J=8.5, 2.1 Hz, 1H), 7.57 (d, J=3.2 Hz, 1H), 7.45 (d, J=2.1 Hz, 1H), 7.26 (d, J=3.2 Hz, 1H), 6.82 (d, J=8.5 Hz, 1H), 6.69 (b, NH2, 2H), 6.58 (s, 2H), 3.77 (s, 6H), 3.76 (s, 3H). MS (ESI) m/z 386 (M$^+$+H).

Compound 320

Synthesis of 4-(thiazol-2-yl)-2-(3,4,5-trimethoxybenzoyl)phenylcarboxylic acid hexyl ester In the same manner as in the synthesis of Compound 314, Compound 320 was obtained.

$^1$H NMR (acetone-d6) δ 10.0 (bs, 1H), 8.40 (d, 1H, J=8.8 Hz), 8.27 (d, 1H, J=2.1 Hz), 8.15 (dd, 1H J=2.1 Hz, 8.8 Hz), 7.79 (d, 1H, J=3.3 Hz), 7.56 (d, 2H, J=3.3 Hz), 7.10 (s, 2H), 4.14-4.10 (m, 2H), 3.82 (s, 9H), 1.65-1.61 (m, 2H), 1.37-1.26 (m, 6H), 0.86-0.82 (m, 3H). MS (ESI) m/z 499 (M$^+$+H).

Compound 321

Synthesis of 4-methoxy-N-(4-(thiazol-2-yl)-2-(3,4,5-trimethoxybenzoyl)phenyl)benzenesulfonamide Compound 278 [(2-amino-5-(thiazol-2-yl)phenyl)(3,4,5-trimethoxyphenyl)methanone] (10 mg, 0.027 mmol) and 4-methoxybenzenesulfonyl chloride (8.34 mg, 0.040 mmol) were dissolved in dichloromethane, and pyridine (4.35 μl, 0.054 mmol) was added thereto. The mixture was refluxed with stirring for 3 days. After completion of the reaction, the reaction mixture was diluted with dichloromethane, and washed with a saturated sodium bicarbonate solution. The organic layer was dried over anhydrous MgSO$_4$, and the solid substance was filtered off. The filtrate was vacuum concentrated, and the resulting residue was purified by column chromatography (SiO$_2$, n-Hex/EA=1/2) to obtain Compound 321 (8.61 mg, 52.9%) in a form of a yellow oil.

$^1$H NMR (CDCl$_3$) δ 9.84 (s, 1H), 8.16 (bs, 2H), 7.88 (d, 2H, J=7.0 Hz), 7.66 (d, 2H, J=8.9 Hz), 7.26 (bs, 1H), 6.76 (s, 2H), 6.72 (d, 2H, J=8.9 Hz), 3.96 (s, 3H), 3.82 (s, 6H), 3.70 (s, 3H). MS (ESI) m/z 541 (M$^+$+H).

Compound 322

Synthesis of (5-(furan-2-yl)-2-(1H-1,2,4-triazol-1-yl)phenyl)(3,4,5-trimethoxyphenyl)methanone In the same manner as in the synthesis of Compound 347, triazole was added to Compound 327, which is a derivative of Compound 21, as shown in Reaction 6, to obtain Compound 322 (6.2 mg, 56.4%).

$^1$H NMR (acetone-d6) δ 8.71 (s, 1H), 8.08 (dd; J=8.5, 2.0 Hz, 1H), 7.94 (d, J=2.0 Hz, 1H), 7.84 (m, 2H), 7.73 (d, J=1.2 Hz, 1H), 7.12 (d, J=3.3 Hz, 1H), 7.00 (s, 2H), 6.63 (dd, J=3.3, 1.7 Hz, 1H), 3.78 (s, 9H). MS (ESI) m/z 406 (M$^+$+H).

Compound 323

Synthesis of (5-(furan-2-yl)-2-(2-hydroxyethylamino)phenyl)(3,4,5-trimethoxyphenyl)methanone Compound 327 [(2-fluoro-5-(furan-2-yl)phenyl)(3,4,5-trimethoxyphenyl)methanone] (43 mg, 0.12 mmol) was dissolved in N,N-dimethylformamide (DMF) (2 ml), and potassium carbonate (83 mg, 0.60 mmol) and ethanolamine (22 mg, 0.36 mmol) were added thereto. The mixture was refluxed with stirring for 3 hours. After completion of the reaction, the reaction mixture was vacuum concentrated. Water (5 ml) was added to the concentrated reaction mixture, and the resulting solution was extracted with EtOAc (10 ml). The organic layer was washed with a 1 N aqueous hydrochloric acid solution, and brine, and dried over anhydrous MgSO$_4$. The solid substance was filtered off, and the filtrate was vacuum concentrated. The resulting residue was purified by column chromatography (SiO$_2$, n-Hex/EA=3/1→1/1) to obtain Compound 323 (7 mg, 15%).

$^1$H NMR (acetone-d6) δ 8.67 (b, NH, 1H), 7.93 (d, J=2.1 Hz, 1H), 7.76 (dd, J=8.8, 2.1 Hz, 1H), 7.48 (d, J=1.4 Hz, 1H), 6.98 (m, 3H), 6.54 (d, J=3.2 Hz, 1H), 6.45 (dd, J=3.3, 1.7 Hz, 1H), 3.86~3.83 (m, 11H), 3.45 (m, 2H). MS (ESI) m/z 398 (M$^+$+H).

Compound 324

Synthesis of N-(4-(2-formamidethiazol-4-yl)-2-(3,4,5-trimethoxybenzoyl)phenyl)acetamide Compound 294 [N-(4-(2-aminothiazol-5-yl)-2-(3,4,5-trimethoxybenzoyl)phenyl)acetamide] (14.8 mg, 34.6 mmol) was dissolved in 7 ml of toluene, and formic acid (3 ml, 78 mmol) was added thereto. The mixture was heated with stirring for 24 hours. Water (5 ml) was added to the reaction mixture, and the resulting solution was extracted with EtOAc (10 ml). The organic layer was dried over Na$_2$SO$_3$, and the solid substance was filtered out. The filtrate was vacuum evaporated to remove the solvent. The resulting residue was purified by column chromatography (SiO$_2$, n-Hex/EA=2/1→1/1) to obtain Compound 324 (11.6 mg, 74%).

$^1$H NMR (CDC$_3$) δ 10.54 (s, 1H), 9.52 (bs, 1H), 8.64 (d, 1H), 8.50 (s, 1H), 8.10 (d, 1H), 8.00 (dd, 1H), 7.11 (s, 1H), 7.04 (s, 2H), 3.96 (s, 3H), 3.87 (s, 6H), 2.24 (s, 3H).

Compound 326

Synthesis of (2-amino-5-(thiazol-2-yl)phenyl)(4-hydroxy-3,5-diethoxyphenyl)methanone 1 N hydrochloric acid was added to Compound 278 (2-amino-5-(thiazol-2-yl)phenyl)(3,4,5-trimethoxyphenyl)methanone to obtain Compound 326.

MS (ESI) m/z 357 ($M^++H$).

Compound 327

Synthesis of (2-fluoro-5-(furan-2-yl)phenyl)(3,4,5-trimethoxyphenyl)methanone First, magnesium was added to 1-bromo-3,4,5-trimethoxybenzene as a starting material, as shown in Reaction 5, and benzaldehyde having a 2-fluoro substituent group was added thereto to obtain Compound 20 derivative. Thus obtained Compound 20 derivative was oxidized to obtain (5-bromo-2-fluorophenyl)(3,4,5-trimethoxyphenyl)methanone. Thus obtained (5-bromo-2-fluorophenyl)(3,4,5-trimethoxyphenyl)methanone (250 mg, 0.68 mmol), furan-2-boronic acid (114 mg, 1.02 mmol), and Pd(dppf)Cl$_2$ (28 mg, 0.03 mmol) were dissolved in 1,2-dimethoxyethane (3 ml), and sodium carbonate (143 mg, 1.35 mmol) dissolved in water (1 ml) was added thereto. The reaction mixture was reacted using a microwave (200° C., 500 s). After completion of the reaction, water (10 ml) was added to the reaction mixture, and the resulting solution was extracted with EtOAc (20 ml). The organic layer was washed with brine, and dried over anhydrous MgSO$_4$. The solid substance was filtered off, and the filtrate was vacuum concentrated. The resulting residue was purified with a column chromatography (SiO$_2$, n-Hex/EA=5/1→3/1) to obtain Compound 327 (180 mg, 74%).

$^1$H NMR (CDCl$_3$) δ 7.82 (m, 2H), 7.47 (d, J=1.6 Hz, 1H), 7.20 (dd, J=9.3 Hz, 1H), 7.13 (s, 2H), 6.65 (d, J=3.3 Hz, 1H), 6.57 (dd, J=3.3, 1.7 Hz, 1H), 3.95 (s, 3H), 3.86 (s, 6H). MS (ESI) m/z 357 ($M^++H$).

Compound 328

Synthesis of (2-(methoxyamino)-5-(thiazol-2-yl)phenyl)(3,4,5-trimethoxyphenyl)methanone O-methyl oxime Compound 327 [(2-fluoro-5-(furan-2-yl)phenyl)(3,4,5-trimethoxyphenyl)methanone] (24 mg, 0.07 mmol) was dissolved in N,N-dimethylformamide (2 ml), and potassium carbonate (46 mg, 0.34 mmol) and methoxylamine.HCl (17 mg, 0.20 mmol) were added thereto. The mixture was refluxed for 24 hours. After completion of the reaction, the reaction mixture was vacuum concentrated, and water (5 ml) was added thereto. The resulting solution was extracted with EtOAc (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=7/1→3/1) to obtain Compound 328 (3 mg, 11%).

$^1$H NMR (acetone-d6) δ 7.40 (dd, J=8.7, 2.2 Hz, 1H), 7.58 (d, J=2.2 Hz, 1H), 7.54 (d, J=1.5 Hz, 1H), 7.16 (s, 2H), 7.12 (b, NH, 1H), 7.11 (d, J=8.7 Hz, 1H), 6.70 (d, J=3.3 Hz, 1H), 6.50 (dd, J=3.3, 1.7 Hz, 1H), 3.82 (s, 9H), 2.75 (s, 6H).

Compound 329

Synthesis of (5-(furan-2-yl)-2-(1H-1,2,4-triazol-1-yl)phenyl)(4-hydroxy-3,5-dimethoxyphenyl)methanone In the same manner as in the synthesis of Compound 322, Compound 329 was obtained.

$^1$H NMR (acetone-d6) δ 8.65 (s, 1H), 8.06 (dd, J=8.4, 2.0 Hz, 1H), 7.92 (d, J=2.0 Hz, 1H), 7.84 (s, 1H), 7.81 (d, J=8.4 Hz, 1H), 7.73 (d, J=1.6 Hz, 1H), 7.12 (d, J=3.3 Hz, 1H), 7.01 (s, 2H), 6.63 (dd, J=3.3, 1.7 Hz, 1H), 3.78 (s, 6H). MS (ESI) m/z 392 ($M^++H$).

Compound 330

Synthesis of (2-(dimethoxyamino)-5-(furan-2-yl)phenyl)(3,4,5-trimethoxyphenyl)methanone Compound 327 [(2-fluoro-5-(furan-2-yl)phenyl)(3,4,5-trimethoxyphenyl)methanone] (40 mg, 0.11 mmol) was dissolved in DMF (4 ml), and potassium carbonate (77 mg, 0.56 mmol) and dimethylamine (2.0 M, 170 μl, 0.34 mmol) were added thereto. The mixture was refluxed for 24 hours. After completion of the reaction, the reaction mixture was vacuum concentrated, and water (5 ml) was added thereto. The resulting solution was extracted with EtOAc (10 ml). The organic layer was washed with brine, and dried over anhydrous MgSO$_4$. The solid substance was vacuum concentrated. The resulting residue was purified by column chromatography (SiO$_2$, n-Hex/EA=3/1) to obtain Compound 330 (10 mg, 24%).

$^1$H NMR (CDCl$_3$) δ 7.68 (dd, J=8.40, 2.14 Hz, 1H), 7.59 (d, J=2.14 Hz 1H), 7.40 (d, 1H), 7.16 (s, 2H), 7.11 (d, J=9.36 Hz, 1H), 6.49 (d, J=3.2 Hz, 1H), 6.42 (dd, J=3.2, 1.6 Hz, 1H), 3.94 (s, 3H), 3.84 (s, 6H), 2.79 (s, 6H). MS (ESI) m/z 382 ($M^++H$).

Compound 331

Synthesis of (2-(difluoromethoxy)-5-(furan-2-yl)phenyl(3,4,5-trimethoxyphenyl)methanone (5-(furan-2-yl)-2-hydroxyphenyl)(3,4,5-trimethoxyphenyl)methanone (52.3 mg, 0.15 mmol), which substituted a 2-fluoro group of Compound 327 with a hydroxyl group, and cesium carbonate (7.2 mg) were dissolved in DMF (3 ml), and methyl-2-chloro-2,2-difluoroacetate (24 μl) was added thereto at room temperature. The mixture was stirred for 3 hours at 130° C. After completion of the reaction, the reaction mixture was cooled to room temperature, and diluted with an EtOAc solution. The organic layer was washed with a saturated aqueous ammonium chloride solution, water, and brine. The extracted organic layer was dried over anhydrous MgSO$_4$, and the solid substance was filtered out. The filtrate was vacuum evaporated to remove the solvent. The resulting residue was purified by column chromatography (SiO$_2$, n-Hex/EA=3/1→1/1) to obtain Compound 331 (174.1 mg, 42%) in a form of a yellow solid.

$^1$H NMR (CDCl$_3$) δ 7.739 (dd, J=8.56, 1.94 Hz, 1H), 7.585 (d, J=1.80 Hz, 1H), 7.432 (d, J=1.40 Hz, 1H), 7.099 (d, J=8.58 Hz, 1H), 6.625 (s, 2H), 6.573 (dd, J=3.33, 0.49 Hz, 1H), 6.456 (dd, J=3.35, 1.75 Hz, 1H), 3.932 (s, 3H), 3.796 (s, 6H), 2.943 (d, J=2.71 Hz, 1H). MS (ESI) m/z 405 ($M^++H$).

Compound 332

Synthesis of (3-allyl-5-(furan-2-yl)-2-hydroxyphenyl)(3,4,5-trimethoxyphenyl)methanone (5-(furan-2-yl)-2-hydroxyphenyl)(3,4,5-trimethoxyphenyl)methanone (190.7 mg, 0.55 mmol), which substituted a 2-fluoro group of Compound 327 with a hydroxyl group, and potassium carbonate (228.9 mg) were dissolved in DMF (3 ml), and allyl bromide (232.6 µl) was added thereto at room temperature. The mixture was stirred for 1 hour at 130° C. After completion of the reaction, the reaction mixture was cooled to room temperature, and diluted with an EtOAc solution. The organic layer was washed with a saturated aqueous ammonium chloride solution, water, and brine. The extracted organic layer was dried over anhydrous $MgSO_4$, and the solid substance was filtered off. The filtrate was vacuum evaporated to remove the solvent. The crude product was dissolved in p-xylene (5 ml), and the reaction solution was stirred for 5 hours with a high-temperature, high-pressure reaction at 140° C. After completion of the reaction, the reaction solution was cooled to room temperature, and the solvent was removed by vacuum evaporation. The resulting residue was purified by column chromatography ($SiO_2$, n-Hex/EA=3/1→1/1) to obtain Compound 332 (93.5 mg, 43.2%) in a form of a yellow solid.

$^1$H NMR ($CDCl_3$) δ 12.242 (s, 1H), 7.899 (d, J=2.20 Hz, 1H), 7.688 (d, J=1.92 Hz, 1H), 7.400 (d, J=1.36 Hz, 1H), 7.007 (s, 2H), 6.482 (dd, J=3.28, 0.6 Hz, 1H), 6.433 (dd, J=3.36, 1.76 Hz, 1H), 6.109-6.024 (m, 1H), 5.027-5.131 (m, 2H), 3.972 (s, 3H), 3.899 (s, 6H), 3.525 (d, J=6.60 Hz, 1H). MS (ESI) m/z 395 ($M^+$+H).

Compound 333

Synthesis of (3-allyl-2-(difluoromethoxy)-5-(furan-2-yl)phenyl)(3,4,5-trimethoxyphenyl)methanone Compound 332 [(3-allyl-5-(furan-2-yl)-2-hydroxyphenyl)(3,4,5-trimethoxyphenyl)methanone] (93 mg, 0.24 mmol) and cesium carbonate (156.4 mg) were dissolved in DMF (3 ml), and methyl-2-chloro-2,2-difluoroacetate (38.4 µl) was added thereto at room temperature. The mixture was stirred for 3 hours at 130° C. After completion of the reaction, the reaction mixture was cooled to room temperature, and diluted with an EtOAc solution. The organic layer was washed with a saturated aqueous ammonium chloride solution, water, and brine. The extracted organic layer was dried over anhydrous $MgSO_4$, and the solid substance was filtered off. The filtrate was vacuum evaporated to remove the solvent. The resulting residue was purified by column chromatography ($SiO_2$, n-Hex/EA=1/1→1/3) to obtain Compound 333 (92.6 mg, 86.8%) in a form of a yellow solid.

$^1$H NMR ($CDCl_3$) δ 7.563 (d, J=1.81 Hz, 1H), 7.453 (d, J=1.87 Hz, H), 7.421 (d, J=2.12 Hz, 1H), 6.622 (s, 2H), 6.554 (d, J=3.32 Hz, 1H), 6.443 (dd, J=3.39, 1.81 Hz, 1H), 6.059-5.992 (m, 1H), 5.197-5.146 (m, 2H), 3.875 (s, 3H), 3.781 (s, 6H), 3.479 (dd, J=6.26, 0.66 Hz, 2H), 3.125 (d, J=2.30 Hz, 1H). MS (ESI) m/z 445 ($M^+$+H).

Compound 334

Synthesis of 4-(thiazol-2-yl)-2-(3,4,5-trimethoxybenzoyl)phenylcarboxylic acid 2-methoxymethyl ester In the same manner as in the synthesis of Compound 314, Compound 334 was obtained.

$^1$H NMR ($CDCl_3$) 10.03 (s, 1H), 8.50 (d, 1H), 8.25 (d, 1H), 8.12 (d, 1H), 7.81 (d, 1H), 7.30 (d, 1H), 7.04 (s, 2H), 3.35 (m, 2H), 3.97 (s, 3H), 3.87 (s, 6H), 3.65 (m, 2H), 3.41 (s, 3H).

Compound 335

Synthesis of N-(4-(pyridin-2-yl)-2-(3,4,5-trimethoxybenzoyl)phenyl)methanesulfonamide In the same manner as in the synthesis of Compound 307, Compound 335 was obtained.

$^1$H NMR ($CDCl_3$) δ 10.09 (s, NH), 8.63 (d, J=4.08 Hz, 1H), 8.43 (s, 1H), 8.20 (d, J=8.8 Hz, 1H), 7.90 (d, J=8.8 Hz, 1H), 7.75 (t, 1H), 7.65 (d, J=7.88 Hz, 1H), 7.25 (m, 1H), 7.05 (s, 2H), 3.96 (s, 3H), 3.87 (s, 6H), 3.13 (s, 3H). MS (ESI) m/z 443 ($M^+$+H).

Compound 336

Synthesis of (5-(furan-2-yl)-2-(1H-pyrazol-1-yl)phenyl)(3,4,5-trimethoxyphenyl)methanone In the same manner as in the synthesis of Compound 323, Compound 336 was obtained.

$^1$H NMR (acetone-d6) δ 8.04~8.00 (m, 2H), 7.86 (d, J=2.0 Hz, 1H), 7.77 (d, J=8.8 Hz, 1H), 7.70 (s, 1H), 7.37 (d, J=1.6 Hz, 1H), 7.06 (d, J=3.28 Hz, 1H), 6.94 (s, 2H), 6.61 (d, J=3.6 Hz, 1H), 6.30 (dd, J=2.4, 1.76 Hz, 1H), 3.75 (s, 3H), 3.74 (s, 6H). MS (ESI) m/z 405 ($M^+$+H).

Compound 337

Synthesis of (4,5'-diaminophenyl-3-yl)(3,4,5-trimethoxyphenyl)methanone

In the same manner as in the synthesis of Compound 289, Compound 337 was obtained from Compound 338 by deprotection, as shown in Reaction 5.

$^1$H NMR ($CDCl_3$) δ 7.71 (d, J=2.1 Hz, 1H), 7.55 (dd, J=8.5, 2.1 Hz, 1H), 7.17 (t, J=7.8 Hz, 1H), 6.96 (s, 2H), 6.89 (d, J=7.6 Hz, 1H), 6.81 (m, 2H), 6.67 (dd, J=7.8, 1.4 Hz, 1H), 3.93 (s, 3H), 3.87 (s, 6H). MS (ESI) m/z 379 ($M^+$+H).

Compound 338

Synthesis of N-(5'-amino-3-(3,4,5-trimethoxybenzoyl)biphenyl-4-yl)acetamide

Compound 19 [N-(4-iodo-2-(3,4,5-trimethoxybenzoyl)phenyl)acetamide] (100 mg, 0.22 mmol) of Reaction 5, 3-aminophenyl boronic acid (45 mg, 0.33 mmol), and Pd(dppf)$Cl_2$ (9 mg, 0.01 mmol) were dissolved in 1,2-dimethoxyethane (3 ml), and sodium carbonate (46 mg, 0.44 mmol) dissolved in water (1 ml) was added thereto. The reaction mixture was reacted using a microwave (200° C., 500 s). After completion of the reaction, water (10 ml) was added to the reaction mixture, and the resulting solution was extracted with EtOAc (20 ml). The organic layer was washed with brine, and dried over anhydrous $MgSO_4$. The solid substance was filtered off, and the filtrate was vacuum concentrated. The resulting residue was purified by column chromatography ($SiO_2$, n-Hex/EA=3/1→1/1) to obtain Compound 338 (34 mg, 37%).

$^1$H NMR (acetone-d6) δ 10.10 (b, NH), 8.39 (d, J=8.5 Hz, 1H), 7.82~7.77 (m, 2H), 7.11 (m, 3H), 6.92 (m, 1H), 6.83 (d, 1H), 6.63 (dd, 1H), 4.75 (b, NH2), 3.84 (s, 9H), 2.09 (s, 3H).

Compound 339

Synthesis of N-(4-(pyrimidin-5-yl)-2-(3,4,5-tri-methoxybenzoyl)phenyl)acetamide

In the same manner as in the synthesis of Compound 338, Compound 339 was obtained.
$^1$H NMR (CDC$_3$) δ 10.46 (s, NH), 9.20 (s, 1H), 8.89 (b, 2H), 8.76 (d, J=8.5 Hz, 1H), 7.79 (m, 2H), 6.99 (s, 2H), 3.96 (s, 3H), 3.86 (s, 6H), 2.25 (s, 3H). MS (ESI) m/z 408 (M$^+$+H).

Compound 340

Synthesis of (2-amino-5-(pyrimidin-5-yl)phenyl)(3,4,5-trimethoxyphenyl)methanone In the same manner as in the synthesis of Compound 289, Compound 340 was obtained from Compound 339 by the deprotection, as shown in Reaction 5.
$^1$H NMR (CDCl$_3$) δ 9.14 (s, 1H), 8.86 (b, 2H), 7.76 (d, J=2.0 Hz, 1H), 7.56 (dd, J=8.5, 2.0 Hz, 1H), 6.93 (s, 2H), 6.91 (d, J=8.7 Hz, 1H), 3.95 (s, 3H), 3.87 (s, 6H). MS (ESI) m/z 366 (M$^+$+H).

Compound 341

Synthesis of (5-(furan-2-yl)-2-(3-hydroxypropy-lamino)phenyl)(3,4,5-trimethoxyphenyl)methanone In the same manner as in the synthesis of Compound 323, Compound 341 was obtained.
$^1$H NMR (CDCl$_3$) δ 7.91 (d, J=1.8 Hz, 1H), 7.68 (dd, J=8.8, 1.9 Hz, 1H), 7.35 (s, 1H), 6.93 (s, 2H), 6.86 (d, J=8.8 Hz, 1H), 6.39 (m, 1H), 6.35 (m, 1H), 3.94 (s, 3H), 3.86 (m, 8H), 3.43 (m, 2H), 1.98 (m, 2H). MS (ESI) m/z 412 (M$^+$+H).

Compound 342

Synthesis of N-(4-(oxazol-2-yl)-2-(3,4,5-trimethoxy-benzoyl)phenyl)methanesulfonamide Compound 289 [(2-amino-5-(oxazol-2-yl)phenyl)(3,4,5-trimethoxyphenyl)methanone](~5 mg, 0.014 mmol) was dissolved in dichloromethane (1 ml), and pyridine (excessive amount) and methanesulfonyl chloride (excessive amount) were added thereto at room temperature. The mixture was stirred for 2 days at room temperature. After completion of the reaction, the reaction mixture was diluted with an EtOAc solution. The organic layer was washed with 1 M hydrochloride, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=2/1→1/2) to obtain Compound 342 (2.91 mg, 48.1%) in a form of a white solid.
$^1$H NMR (CDCl$_3$) δ 10.175 (s, 1H), 8.393 (d, J=2.04 Hz, 1H), 8.240 (dd, J=8.72, 2.08 Hz, 1H), 7.9001 (d, J=8.76 Hz, 1H), 7.704 (d, J=0.76 Hz, 1H), 7.216 (d, J=0.76 Hz, H), 7.012 (s, 2H), 3.978 (s, 3H), 3.877 (s, 6H), 3.164 (s, 3H). MS (ESI) m/z 433 (M$^+$+H).

Compound 346

Synthesis of (5-(pyridin-2-yl)-2-(1H-1,2,4-triazol-1-yl)phenyl)(3,4,5-trimethoxyphenyl)methanone In the same manner as in the synthesis of Compound 347, Compound 346 was obtained.
$^1$H NMR (CDCl$_3$) δ 8.73 (m, 1H), 8.70 (dd, J=8.4, 1.9 Hz, 1H), 8.31 (s, 1H), 8.22 (d, J=2.0 Hz, 1H), 7.93 (s, 1H), 7.83 (m, 2H), 7.76 (d, J=8.4 Hz, 1H), 7.35 (m, 1H), 6.98 (s, 2H), 3.89 (s, 3H), 3.80 (s, 6H). MS (ESI) m/z 417 (M$^+$+H).

Compound 347

Synthesis of (5-(thiazol-2-yl)-2-(1H-1,2,4-thiazol-1-yl)phenyl)(3,4,5-trimethoxyphenyl)methanone First, magnesium was added to 1-bromo-3,4,5-trimethoxybenzene as a starting material, as shown in Reaction 1, and a Compound V derivative (2-fluoro-5-iodobenzoyl chloride) was added thereto to obtain Compound I derivative. Thus obtained Compound I derivative was substituted with thiazol-2-ZnBr to obtain (2-fluoro-5-(thiazol-2-yl)phenyl)(3,4,5-trimethoxyphenyl)methanone. Thus obtained (2-fluoro-5-(thiazol-2-yl)phenyl)(3,4,5-trimethoxyphenyl)methanone (30 mg, 0.08 mmol) was dissolved in N,N-dimethylformamide (3 ml), and 1,2,4-triazole-Na (22 mg, 0.24 mmol) was added thereto. The mixture was heated for 3 hours. After completion of the reaction, the reaction mixture was vacuum concentrated. The resulting residue was purified by column chromatography (SiO2, n-Hex/EA=1/1→1/2) to obtain Compound 347 (16 mg, 47%) in a form of a white solid.
$^1$H NMR (CDCl$_3$) δ 8.32 (s, 1H), 8.29 (dd, J=8.3, 2.0 Hz, 1H), 8.16 (d, J=2.0 Hz, 1H), 7.93 (m, 2H), 7.74 (d, J=8.4 Hz, 1H), 7.44 (d, J=3.27 Hz, 1H), 6.98 (s, 2H), 3.89 (s, 3H), 3.80 (s, 6H). MS (ESI) m/z 423 (M$^+$+H).

Compound 348

Synthesis of (2-(3-hydroxypropylamino)-5-(thiazol-2-yl)phenyl)(3,4,5-trimethoxyphenyl)methanone (2-Fluoro-5-(thiazol-2-yl)phenyl)(3,4,5-trimethoxyphenyl)methanone (37 mg, 0.10 mmol), which is a starting material of Compound 347, was dissolved in DMF (3 ml), and potassium carbonate (68 mg, 0.50 mmol) and 3-amino-1-propanol (22 mg, 0.30 mmol) were added thereto. The mixture was heated for 3 hours. After completion of the reaction, the reaction mixture was vacuum concentrated. A saturated aqueous ammonium chloride solution (10 ml) was added to the concentrated reaction mixture, and the resulting solution was extracted with EtOAc (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA-2/1→1/2) to obtain Compound 348 (20 mg, 47%) in a form of a yellow solid.
$^1$H NMR (CDCl$_3$) δ 8.75 (brs, NH), 8.21 (d, J=2.17 Hz, 1H), 8.08 (m, 1H), 7.73 (d, J=3.3 Hz, 1H), 7.17 (d, J=3.3 Hz, 1H), 6.95 (s, 2H), 6.90 (d, J=8.9 Hz, 1H), 3.95 (s, 3H), 3.86 (m, 8H), 3.47 (t, J=6.6 Hz, 2H), 2.00 (m, 2H). MS (ESI) m/z 429 (M$^+$+H).

Compound 350

Synthesis of N-(4-(pyridin-4-yl)-2-(3,4,5-tri-methoxybenzoyl)phenyl)acetamide

In the same manner as in the synthesis of Compound 338, Compound 350 was obtained through the Suzuki reaction.
$^1$H NMR (acetone-d6) δ 10.17 (b, NH), 8.65 (b, 2H), 8.50 (dd, J=8.6, 3.7 Hz, 1H), 8.04 (dd, J=8.6, 2.2 Hz, 1H), 8.00 (d, J=2.1 Hz, 1H), 7.69 (b, 2H), 7.13 (s, 2H), 3.85 (s, 9H), 2.12 (s, 3H). MS (ESI) m/z 407 (M⁺+H).

Compound 352

Synthesis of (2-amino-5-(pyridin-4-yl)phenyl)(3,4,5-trimethoxyphenyl)methanone

In the same manner as in the synthesis of Compound 289, Compound 352 was obtained from Compound 351 by the deprotection, as shown in Reaction 5.

¹H NMR (acetone-d6) δ 8.51 (dd, J=4.6, 1.6 Hz, 2H), 7.95 (d, J=2.2 Hz, 1H), 7.78 (dd, J=8.7, 2.3 Hz, 1H), 7.48 (dd, J=4.6, 1.6 Hz, 2H), 7.06 (d, J=8.7 Hz, 1H), 7.01 (s, 2H), 6.97 (b, NH2), 3.87 (s, 6H), 3.83 (s, 3H). MS (ESI) m/z 365 (M⁺+H).

Compound 354

Synthesis of (5-(furan-2-yl)-2-(1H-imidazol-1-yl)phenyl)(3,4,5-trimethoxyphenyl)methanone In the same manner as in the synthesis of Compound 330, Compound 354 was obtained.

¹H NMR (acetone-d6) δ 8.04 (dd, J=8.3, 2.08 Hz, 1H), 7.90 (d, J=2.0 Hz, 1H), 7.71 (s, 1H), 7.63 (, J=8.3 Hz, 1H), 7.61 (s, 1H), 7.20 (s, 1H), 7.09 (d, J=3.36 Hz, 1H), 7.02 (s, 2H), 6.87 (d, 1H), 6.62 (dd, J=3.36, 1.7 Hz, 1H), 3.78 (s, 9H). MS (ESI) m/z 405 (M⁺+H).

Compound 357

Synthesis of (2-fluoro-5-(isoxazol-5-yl)phenyl)(3,4,5-trimethoxyphenyl)methanone Compound 357 was synthesized from Compound 21 derivative [(2-fluoro-5-iodophenyl)(3,4,5-trimethoxyphenyl)methanone] of Reaction 6 by the two step reaction.

MS (ESI) m/z 358 (M⁺+H).

Compound 359

Synthesis of (5-(oxazol-2-yl)-2-(H-1,2,4-triazol-1-yl)phenyl)(3,4,5-trimethoxyphenyl)methanone In the same manner as in the synthesis of Compound 347, Compound 359 was obtained.

¹H NMR (CDCl₃) δ 8.376-8.350 (m, 2H), 8.262 (d, J=1.88 Hz, 1H), 7.965 (s, 1H), 7.788-7.759 (m, 2H), 7.310 (s, 1H), 6.982 (s, 2H), 3.908 (s, 3H), 3.808 (s, 6H). MS (ESI) m/z 407 (M⁺+H).

Compound 360

Synthesis of (2-(3-hydroxypropylamino)-5-(oxazol-2-yl)phenyl)(3,4,5-trimethoxyphenyl)methanone In the same manner as in the synthesis of Compound 348, Compound 360 was obtained.

¹H NMR (CDCl₃) δ 8.292 (m, 1H), 8.134 (m, 1H), 7.641 (d, J=1.45 Hz, 1H), 7.161 (s, 1H), 6.922-6.903 (m, 3H), 3.949 (s, 3H), 3.847-3.808 (m, 8H), 3.480 (t, J=3.31 Hz, 2H), 2.002 (m, 2H). MS (ESI) m/z 413 (M⁺+H).

Compound 363

Synthesis of (2-(3-hydroxypropylamino)-5-(1H-pyrrole-2-yl)phenyl)(3,4,5-trimethoxyphenyl)methanone In the same manner as in the synthesis of Compound 348, Compound 363 was obtained.

¹H NMR (acetone-d6) δ 7.81 (d, 1H, J=2.2 Hz), 7.73 (dd, 1H, J=2.2 Hz, 8.8 Hz), 6.95 (s, 2H), 6.94 (d, 1H, J=7.2 Hz), 6.70 (d, 1H, J=2.6 Hz), 6.25 (d, 1H, J=5.7 Hz), 6.07 (dd, 1H, J=2.6 Hz, 5.7 Hz), 3.85 (s, 3H), 3.82 (s, 6H), 3.76-3.71 (m, 2H), 3.46-3.41 (m, 2H), 1.96-1.88 (m, 2H). MS (ESI) m/z 411 (M⁺+H).

Compound 364

Synthesis of (3-(2,3-dihydroxypropyl)-5-(furan-2-yl)-2-methoxyphenyl)(3,4,5-trimethoxyphenyl)methanone (3-allyl-5-(furan-2-yl)-2-methoxyphenyl)(3,4,5-trimethoxyphenyl)methanone, which substituted a hydroxyl group of Compound 332 with a methyl group, was treated in the same manner as in the synthesis of Compound 276 to obtain Compound 364.

MS (ESI) m/z 443 (M⁺+H).

Compound 365

Synthesis of (2-(pyrimidin-5-yl)-5-(thiazol-2-yl)phenyl)(3,4,5-trimethoxyphenyl)methanone In the same manner as in the synthesis of Compound 383, Compound 365 was synthesized through the Suzuki reaction.

¹H NMR (CDCl₃) δ 9.141 (brs, 1H), 8.742 (brs, 2H), 8.269 (dd, J=8.05, 1.78 Hz, 1H), 8.192 (d, J=1.79 Hz, 1H), 7.936 (d, J=3.26 Hz, 1H), 7.584 (d, J=8.04 Hz, 1H), 7.440 (d, J=3.26 Hz, 1H), 7.010 (s, 2H), 3.909 (s, 3H), 3.802 (s, 6H). MS (ESI) m/z 434 (M⁺+H).

Compound 366

Synthesis of (5-(furan-2-yl)-2-(pyrazin-2-ylamino)phenyl)(3,4,5-trimethoxyphenyl)methanone Compound 327 [(2-fluoro-5-(furan-2-yl)phenyl)(3,4,5-trimethoxyphenyl)methanone] (40 mg, 0.11 mmol) was dissolved in N,N-dimethylformamide (3 ml), and sodium hydride (60%, 14 mg, 0.34 mmol) and 2-aminopyrazine (32 mg, 0.34 mmol) was added thereto. The mixture was refluxed for 4 hours. After completion of the reaction, the reaction mixture was vacuum concentrated, and water (5 ml) was added thereto. The resulting solution was extracted with EtOAc (10 ml). The organic layer was washed with brine, and dried over anhydrous MgSO₄. The solid substance was filtered off, and the filtrate was vacuum concentrated. The resulting residue was purified by column chromatography (SiO₂, n-Hex/EA=5/1→3/1) to obtain Compound 366 (5 mg, 11%) in a form of a solid.

¹H NMR (acetone-d6) δ 10.23 (b, NH), 8.63 (dd, J=8.8, 3.7 Hz, 1H), 8.35 (s, 1H), 8.16 (s, 1H), 8.04 (d, J=1.0 Hz, 1H), 7.99 (d, J=2.1 Hz, 1H), 7.93 (dd, J=8.8, 2.1 Hz, 1H), 7.59 (d, J=1.0 Hz, 1H), 7.12 (s, 2H), 6.80 (d, J=3.7 Hz, 1H), 6.53 (dd, J=3.3, 1.7 Hz, 1H), 3.85 (s, 9H). MS (ESI) m/z 432 (M⁺+H).

Compound 367

Synthesis of (5-(furan-2-yl)-2-(pyridin-2-ylamino)phenyl)(3,4,5-trimethoxyphenyl)methanone In the same manner as in the synthesis of Compound 366, Compound 367 was obtained.
$^1$H NMR (acetone-d6) δ 8.72 (d, 1H, J=8.8 Hz), 8.24 (d, 1H, J=1.3 Hz), 8.00 (d, 1H, J=2.2 Hz), 7.90 (dd, 1H, J=2.2 Hz, 8.8 Hz), 7.67-7.65 (m, 1H), 7.57 (s, 1H), 7.11 (s, 2H), 6.99 (d, 1H, J=8.3 Hz), 6.91-6.88 (m, 1H), 6.75 (d, 1H, J=3.3 Hz), 6.52 (dd, 1H, J=2.0 Hz, 3.3 Hz), 3.86 (s, 9H). MS (ESI) m/z 431 (M$^+$+H).

Compound 368

Synthesis of (2-(2-(1H-imidazol-4-yl)ethylamino)-5-(furan-2-yl)phenyl)(3,4,5-trimethoxyphenyl)methanone In the same manner as in the synthesis of Compound 323, Compound 368 was obtained.
$^1$H NMR (CDCl$_3$) δ 8.38 (bs, 1H), 7.89 (d, J=4.40 Hz, 1H), 7.74 (s, 1H), 7.67 (dd, J=8.86, 4.40 Hz, 1H), 7.34 (d, J=1.38 Hz, 1H), 7.00 (s, 1H), 6.91 (s, 2H), 6.85 (d, J=8.86 Hz, 1H), 6.40 (dd, J=3.22, 1.38 Hz, 1H), 6.35 (d, J=3.22 Hz, 1H), 3.94 (s, 3H), 3.86 (s, 6H), 3.62 (t, J=6.72 Hz, 2H), 3.05 (t, J=6.72 Hz, 2H).

Compound 369

Synthesis of (5-(furan-2-yl)-2-(3-hydroxypyrrolidin-1-yl)phenyl)(3,4,5-trimethoxyphenyl)methanone In the same manner as in the synthesis of Compound 330, Compound 369 was obtained.
$^1$H NMR (CDCl$_3$) δ 7.67 (dd, J=8.80, 2.14 Hz, 1H), 7.59 (d, J=2.14 Hz, 1H), 7.37 (s, 1H), 7.24 (s, 2H), 6.91 (d, J=8.80 Hz, 1H), 6.42 (m, 2H), 4.50 (m, 1H), 3.96 (s, 3H), 3.87 (s, 6H), 3.52 (m, 2H), 3.31 (m, 1H), 2.95 (d, J=11.12 Hz, 1H), 2.09 (m, 1H), 2.01 (m, 2H).

Compound 370

Synthesis of (S)-(5-(furan-2-yl)-2-(2-(hydroxymethyl)pyrrolidin-1-yl) phenyl)(3,4,5-trimethoxyphenyl)methanone In the same manner as in the synthesis of Compound 330, Compound 370 was obtained.
$^1$H NMR (CDCl$_3$) δ 7.66 (dd, J=8.7, 1.9 Hz, 1H), 7.61 (d, J=2.1 Hz, 1H), 7.39 (s, 1H), 7.19 (s, 2H), 7.08 (m, 1H), 6.46 (d, J=2.8 Hz, 1H), 6.42 (dd, J=3.2, 1.7 Hz, 1H), 3.95 (s, 3H), 3.86 (m, 8H), 3.50 (m, 1H), 3.29 (m, 1H), 2.84 (m, 1H), 2.06 (m, 2H), 1.86 (m, 1H), 1.73 (m, 1H). MS (ESI) m/z 438 (M$^+$+H).

Compound 371

Synthesis of (5-(furan-2-yl)-2-(4-(2-hydroxyethyl)piperazin-1-yl)phenyl)(3,4,5-trimethoxyphenyl)methanone In the same manner as in the synthesis of Compound 330, Compound 371 was obtained.
$^1$H NMR (CDCl$_3$) δ 7.75 (dd, J=8.4, 2.1 Hz, 1H), 7.67 (d, J=2.1 Hz, 1H), 7.44 (m, 1H), 7.07 (m, 3H), 6.58 (d, J=3.2 Hz, 1H), 6.45 (dd, J=3.3, 1.7 Hz, 1H), 3.93 (s, 3H), 3.82 (s, 6H), 3.64 (m, 3H), 3.03 (m, 4H), 249~2.36 (m, 6H). MS (ESI) m/z 467 (M$^+$+H).

Compound 372

Synthesis of (2-(1,2-dihydroxyethyl)-5-(thiazol-2-yl)phenyl)(3,4,5-trimethoxyphenyl)methanone (5-(thiazol-2-yl)-2-vinylphenyl)(3,4,5-trimethoxyphenyl)methanone (85 mg, 0.223 mmol) as a starting material was dissolved in acetone/water (10 ml), and NMMO (1.5 ml) and OsO$_4$ (1 ml) were added thereto at room temperature. The mixture was stirred for 24 hours at room temperature. After completion of the reaction, sodium sulfite was added to the reaction mixture. The resulting mixture was stirred for 1 hour, and extracted with EtOAc (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=5/1→3/1) to obtain Compound 372 (67.7 mg, 73%) in a form of a white solid.
$^1$H NMR (CD$_3$OD) δ 7.759 (d, J=2.24 Hz, 1H), 7.486-7.470 (m, 2H), 7.118 (s, 2H), 6.692 (t, J=3.26 Hz, 1H), 6.445 (dd, J=3.32, 1.73 Hz, 1H), 3.889 (m, 1H), 3.808 (s, 3H), 3.761 (s, 6H), 3.577 (s, 3H), 3.498 (m, 2H), 2.938 (dd, J=13.7, 5.0 Hz, 1H), 2.729 (dd, J=13.7, 8.14 Hz, 1H).

Compound 373

Synthesis of 4-(thiazol-2-yl)-2-(3,4,5-trimethoxybenzoyl)benzoic acid

Compound 372 [(2-(1,2-dihydroxyethyl)-5-(thiazol-2-yl)phenyl)(3,4,5-trimethoxyphenyl)methanone] (44 mg, 0.1 mmol) was dissolved in acetone/water (3 ml, 2/1), and NaIO$_4$ (45.3 mg), potassium permanganate (1.6 mg), and sodium bicarbonate (0.42 mg) were added thereto at room temperature. The mixture was stirred for 7 hours at room temperature. After completion of the reaction, the reaction mixture was extracted with EtOAc (10 ml). The organic layer was washed with brine, and dried over anhydrous MgSO$_4$. The solid substance was filtered off, and the filtrate was vacuum concentrated to obtain Compound 373 (21 mg, 52.6%) in a form of oil.
$^1$H NMR (CD$_3$OD) δ 8.149 (dd, J=8.25, 1.71 Hz, 1H), 8.107 (d, J=8.18 Hz, 1H), 7.953 (d, J=1.59 Hz, 1H), 7.891 (d, J=3.13 Hz, 1H), 7.668 (d, J=3.29 Hz, 1H), 3.780 (s, 3H), 3.733 (s, 6H). MS (ESI) m/z 400 (M$^+$+H).

Compound 374

Synthesis of 4-(thiazol-2-yl)-2-(3,4,5-trimethoxybenzoyl)benzoic acid methyl ester Compound 373 [4-(thiazol-2-yl)-2-(3,4,5-trimethoxybenzoyl)benzoic acid] (18 mg, 0.045 mmol) and potassium carbonate (18.8 mg) were dissolved in DMF (3 ml), and iodomethane (14 µl) was added thereto at room temperature. The mixture was heated for 2 hours. After completion of the reaction, the reaction mixture was cooled to room temperature, and diluted with an EtOAc solution. The organic layer was washed with a saturated aqueous ammonium chloride solution, water, and brine. The extracted organic layer dried over anhydrous MgSO$_4$, and the solid substance was filtered off. The filtrate was vacuum concentrated. The resulting residue was purified by column chromatography (SiO$_2$, n-Hex/EA=2/1→1/2) to obtain Compound 374 (15.3 mg, 82%) in a form of a white solid.
$^1$H NMR (CDCl$_3$) δ 8.179 (dd, J=8.14, 1.69 Hz, 1H), 8.123 (d, J=8.16 Hz, 1H), 7.991 (d, J=1.55 Hz, 1H), 7.931 (d, J=3.15 Hz, 1H), 7.446 (d, J=3.19 Hz, 1H), 7.046 (s, 2H), 3.917 (s, 3H), 3.816 (s, 6H), 3.707 (s, 3H). MS (ESI) m/z 414 (M$^+$+H).

Compound 375

Synthesis of (2-(oxazol-5-yl)-5-(thiazol-2-yl)phenyl)(3,4,5-trimethoxyphenyl)methanone A compound [4-(thiazol-2-yl)-2-(3,4,5-trimethoxybenzoyl)benzaldehyde] (21.7 mg, 0.06 mmol) obtained by oxidizing Compound 372 and potassium carbonate (23.2 mg) were dissolved in methanol (5 ml), and TosMIC (33.1 mg) was added thereto at room temperature. The mixture was refluxed for 4 hours. After completion of the reaction, the reaction mixture was cooled to room temperature, and vacuum concentrated. The resulting residue was purified by column chromatography (SiO$_2$, n-Hex/EA=2/1→1/1) to obtain Compound 375 (11.3 mg, 47.9%) in a form of a white solid.
$^1$H NMR (CDCl$_3$) δ 8.213 (dd, J=8.26, 1.65 Hz, 1H), 7.998 (d, J=1.56 Hz, 1H), 7.919 (d, J=3.13 Hz, 1H), 7.870 (d, J=8.26 Hz, 1H), 8.267 (s, 1H), 7.422 (d, J=3.12 Hz, 1H), 7.211 (s, 1H), 7.073 (s, 2H), 3.916 (s, 3H), 3.801 (s, 6H). MS (ESI) m/z 423 (M$^+$+H).

Compound 376

Synthesis of (2-(3-amino-1H-1,2,4-triazol-1-yl)-5-(thiazol-2-yl)phenyl)(3,4,5-trimethoxyphenyl)methanone In the same manner as in the synthesis of Compound 366, Compound 376 (9 mg, 15.4%) was obtained.
$^1$H NMR (CDCl$_3$) δ 8.243 (dd, J=8.40, 2.04 Hz, 1H), 8.117 (d, J=2.01 Hz, 1H), 8.026 (s, 1H), 7.914 (d, J=3.27 Hz, 1H), 7.720 (t, J=8.91 Hz, 1H), 7.129 (s, 2H), 3.955 (s, 3H), 3.864 (s, 6H). MS (ESI) m/z 438 (M$^+$+H).

Compound 377

Synthesis of (3-(1,3-dioxan-2-yl)-4,5-dimethoxyphenyl)(5-(furan-2-yl)-2-(1H-1,2,4-triazol-1-yl)phenyl)methanone In the same manner as in the synthesis of Compound 347, triazole was added to (3-(1,3-Dioxan-2-yl)-4,5-dimethoxyphenyl)(2-fluoro-5-(furan-2-yl)phenyl)methanone prepared according to Reaction 6 using Compound 233 as a starting material to obtain Compound 377.
MS (ESI) m/z 462 (M$^+$+H).

Compound 378

Synthesis of (5-(furan-2-yl)-2-(1H-1,2,4,-triazol-1-yl)phenyl)(3-(hydroxymethyl)-4,5-dimethoxyphenyl)methanone Deprotected aldehyde derivative was obtained from Compound 377. Then, in the same manner as in the synthesis of Compound 249, Compound 378 was obtained by the reduction reaction.

$^1$H NMR (CDCl$_3$) δ 8.36 (s, 1H), 7.94 (dd, 1H, J=2.0, 8.4 Hz), 7.88 (s, 1H), 7.85 (d, 1H, J=2.0 Hz), 7.62 (d, 1H, J=8.4 Hz), 7.53 (d, 1H, J=1.6 Hz), 7.441 (d, 1H, J=2.0 Hz), 7.17 (d, 2H, J=2.0 Hz), 6.80 (d, 1H, J=3.3 Hz), 6.53 (dd, 1H, J=1.7, 3.3, Hz), 4.60 (s, 2H), 3.94 (s, 3H), 3.89 (s, 3H). MS (ESI) m/z 406 (M$^+$+H).

Compound 379

Synthesis of (5-(furan-2-yl)-2-(1H-1,2,3,-triazol-1-yl)phenyl)(3,4,5-trimethoxyphenyl)methanone Compound 327 [(2-fluoro-5-(furan-2-yl)phenyl)(3,4,5-trimethoxyphenyl)methanone] (70 mg, 0.20 mmol) and 1,2,3-triazole (34.2 µl, 0.59 mmol) were dissolved in N,N-dimethylformamide (3 ml), and potassium carbonate (81.4 mg, 0.59 mmol) was added thereto. The mixture was stirred for 24 hours at about 120° C. After completion of the reaction, the reaction mixture was diluted with EtOAc, and washed with a saturated aqueous ammonium chloride solution. The organic layer was dried over anhydrous MgSO$_4$, and the solid substance was filtered off. The filtrate was vacuum concentrated, and the resulting residue was purified by column chromatography (SiO$_2$, n-Hex/EA=7/3) to obtain Compound 379 (12.1 mg, 15.2%) in a form of a yellow solid.
$^1$H NMR (CDCl$_3$) δ 7.97 (dd, 1H, J=2.0, 8.3 Hz), 7.87 (d, 1H, J=2.0 Hz), 7.78 (s, 1H), 7.69 (d, 1H, J=8.3 Hz), 7.64 (s, 1H), 7.54 (d, 1H, J=1.5 Hz), 6.97 (s, 1H), 6.81 (d, 1H, J=3.3 Hz), 6.54 (dd, 1H, J=1.7, 3.3 Hz), 3.89 (s, 3H), 3.80 (s, 3H). MS (ESI) m/z 406 (M$^+$+H).

Compound 380

Synthesis of (2-(3-hydroxypropylamino)-5-(pyridin-2-yl)phenyl)(3,4,5-trimethoxyphenyl)methanone In the same manner as in the synthesis of Compound 348, Compound 380 was obtained.
$^1$H NMR (acetone-d6) δ 8.53-8.50 (m, 2H), 8.20 (dd, 1H, J=2.2 Hz, 8.9 Hz), 7.74-7.72 (m, 2H), 7.17-7.14 (m, 1H), 7.02-7.01 (m, 3H), 3.87 (s, 6H), 3.84 (s, 3H), 3.78-3.74 (m, 2H), 3.51-3.47 (m, 2H), 2.02-1.90 (m, 2H). MS (ESI) m/z 423 (M$^+$+H).

Compound 381

Synthesis of (5-(pyridin-2-yl)-2-(1H-1,2,3,-triazol-1-yl)phenyl)(3,4,5-trimethoxyphenyl)methanone In the same manner as in the synthesis of Compound 379, Compound 381 was obtained.
$^1$H NMR (acetone-d6) δ 8.69-8.68 (m, 1H), 8.50 (dd, 1H, J=2.1, 8.4 Hz), 8.40 (d, 1H, J=2.1 Hz), 8.31 (s, 1H), 8.10 (d, 1H, J=7.3 Hz), 7.90-7.80 (m, 2H), 7.65 (s, 1H), 7.40-7.39 (m, 1H), 6.98 (s, 2H), 3.74 (s, 9H). MS (ESI) m/z 417 (M$^+$+H).

Compound 382

Synthesis of (5-(furan-2-yl)-2-(4-hydroxybutylamino)phenyl(3,4,5-trimethoxyphenyl)methanone In the same manner as in the synthesis of Compound 323, Compound 382 was obtained.
$^1$H NMR (CDCl$_3$) δ 7.91 (d, J=2.0 Hz, 1H), 7.69 (dd, J=8.8, 2.0 Hz, 1H), 7.35 (d, 1H), 6.94 (s, 2H), 6.84 (d, J=8.8 Hz, 1H), 6.40 (m, 1H), 6.36 (m, 1H), 3.94 (s, 3H), 3.87 (s, 6H), 3.73 (m, 1H), 334 (m, 1H), 1.87~1.73 (m, 4H). MS (ESI) m/z 426 (M$^+$+H).

Compound 383

Synthesis of (5-(furan-2-yl)-2-(pyridin-3-yl)phenyl)(3,4,5-trimethoxyphenyl)methanone 4-(Furan-2-yl)-2-(3,4,5-trimethoxybenzoyl)phenyl trifluoromethanesulfonic acid was obtained from Compound 327 by substituting with a hydroxyl group, and then substituting with a trifluoromethanesulfonic acid group. Thus obtained 4-(furan-2-yl)-2-(3,4,5-trimethoxybenzoyl)phenyl trifluoromethanesulfonic acid (100 mg, 0.20 mmol), 3-pyridine boronic acid (38 mg, 0.31 mmol) and Pd(dppf)Cl$_2$ (8 mg, 0.01 mmol) were dissolved in 1,2-dimethoxyethane (3 ml), and sodium carbonate (44 mg, 0.41 mmol) dissolved in water (1 ml) was added thereto. The mixture was reacted using a sealed tube (150° C., 1 hour). After completion of the reaction, water (10 ml) was added to the reaction mixture, and the resulting solution was extracted with EtOAc (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=3/1→1/2) to obtain Compound 383 (19 mg, 23%).

$^1$H NMR (CDCl$_3$) δ 8.57 (m, 1H), 8.45 (m, 1H), 7.89 (dd, J=8.0, 1.8 Hz, 1H), 7.83 (d, J=1.8 Hz, 1H), 7.62 (m, 1H), 7.50 (m, 2H), 7.19 (m, 1H), 6.97 (s, 2H), 6.76 (d, J=3.3 Hz, 1H), 6.51 (dd, J=3.3, 1.8 Hz, 1H), 3.86 (s, 3H), 3.77 (s, 6H). MS (ESI) m/z 416 (M$^+$+H).

Compound 384

Synthesis of (S)-(2-(3-(dimethylamino)pyrrolidin-1-yl)-5-(furan-2-yl)phenyl)(3,4,5-trimethoxyphenyl)methanone In the same manner as in the synthesis of Compound 330, Compound 384 was obtained.

$^1$H NMR (CDCl$_3$) δ 7.63 (dd, J=8.8, 2.2 Hz, 1H), 7.56 (d, J=2.2 Hz, 1H), 7.35 (t, J=1.1 Hz, 1H), 7.21 (s, 2H), 6.82 (d, J=8.8 Hz, 1H), 6.40 (m, 2H), 3.94 (s, 3H), 3.85 (s, 6H), 3.33 (m, 2H), 3.18 (t, J=8.7 Hz, 1H), 3.11 (td, J=8.7, 1.8 Hz, 1H), 2.80 (m, 1H), 2.25 (s, 6H), 2.07 (m, 1H), 1.82 (m, 1H). MS (ESI) m/z 451 (M$^+$+H).

Compound 385

Synthesis of (R)-(2-(3-(dimethylamino)pyrrolidin-1-yl)-5-(furan-2-yl)phenyl)(3,4,5-trimethoxyphenyl)methanone In the same manner as in the synthesis of Compound 330, Compound 385 was obtained.

$^1$H NMR (CDCl$_3$) δ 7.65 (dd, J=8.8, 2.2 Hz, 1H), 7.57 (d, J=2.2 Hz, 1H), 7.31 (t, J=1.1. Hz, 1H), 7.21 (s, 2H), 6.84 (d, J=8.8 Hz, 1H), 6.41 (m, 2H), 3.96 (s, 3H), 3.87 (s, 6H), 3.34 (m, 4H), 3.13 (td, J=10.2, 1.9 Hz, 1H), 2.34 (s, 6H), 2.13 (m, 1H), 1.91 (m, 1H). MS (ESI) m/z 451 (M$^+$+H).

Compound 386

Synthesis of (S)—N-(1-(4-(furan-2-yl)-2-(3,4,5,-trimethoxybenzoyl)phenyl)pyrrolidin-3-yl)acetamide In the same manner as in the synthesis of Compound 330, Compound 386 was obtained.

$^1$H NMR (CDCl$_3$) δ 7.71 (dd, J=8.7, 2.1 Hz, 1H), 7.63 (d, J=2.1 Hz, 1H), 7.40 (d, J=1.4 Hz, 1H), 7.20 (s, 2H), 7.12 (m, 1H), 6.49 (d, J=3.3 Hz, 1H), 6.44 (dd, J=3.3, 1.7 Hz, 1H), 4.63 (s, 1H), 3.97 (s, 3H), 3.87 (s, 6H), 3.52 (m, 2H), 3.21 (m, 2H), 2.26 (m, 1H), 1.96 (s, 3H), 1.94 (m, 1H). MS (ESI) m/z 465 (M$^+$+H).

Compound 387

Synthesis of (R)—N-(1-(4-(furan-2-yl)-2-(3,4,5,-trimethoxybenzoyl)phenyl)pyrrolidin-3-yl)acetamide In the same manner as in the synthesis of Compound 330, Compound 387 was obtained.

$^1$H NMR (CDCl$_3$) δ 7.69 (d, J=8.6 Hz, 1H), 7.62 (d, J=1.7 Hz, 1H), 7.39 (d, 1H), 7.20 (s, 2H), 7.00 (m, 1H), 6.47 (s, 1H), 6.43 (t, J=1.5 Hz, 1H), 4.60 (s, 1H), 3.97 (s, 3H), 3.87 (s, 6H), 3.47 (m, 2H), 3.19 (m, 2H), 2.23 (m, 1H), 1.95 (s, 3H), 1.92 (m, 1H). MS (ESI) m/z 465 (M$^+$+H).

Compound 388

Synthesis of (S)-(2-(3-aminopyrrolidin-1-yl)-5-(furan-2-yl)phenyl)(3,4,5-trimethoxyphenyl)methanone Compound 386 [(S)—N-(1-(4-(furan-2-yl)-2-(3,4,5-trimethoxybenzoyl)phenyl)pyrrolidin-3-yl)acetamide] (10 mg, 21 mmol) was dissolved in methanol (3 ml), and 1 N potassium hydroxide (1 ml) was added thereto. The mixture was heated with stirring for 24 hours, and the solvent water removed in vacuo. The resulting residue was purified by column chromatography (SiO$_2$, CH2Cl2/MeOH=8/1) to obtain Compound 388 (5.3 mg, 60%).

$^1$H NMR (CDCl$_3$) δ 7.64 (dd, J=8.8, 2.1 Hz, 1H), 7.58 (d, J=2.1 Hz, 1H), 7.37 (t, J=2.4 Hz, 1H), 7.23 (s, 2H), 6.82 (d, J=8.8 Hz, 2H), 6.42 (m, 2H), 3.96 (s, 3H), 3.87 (s, 6H), 3.70 (m, 1H), 3.37 (m, 2H), 3.17 (m, 1H), 3.05 (m, 1H), 2.14 (m, 1H), 1.90 (m, 1H). MS (ESI) m/z 423 (M$^+$+H).

Compound 389

Synthesis of (R)-(2-(3-aminopyrrolidin-1-yl)-5-(furan-2-yl)phenyl)(3,4,5-trimethoxyphenyl)methanone In the same manner as in the synthesis of Compound 388, Compound 389 was obtained.

$^1$H NMR (CDCl$_3$) δ 7.63 (dd, J=8.8, 2.1 Hz, 1H), 7.58 (d, J=2.1 Hz, 1H), 7.37 (t, J=2.1 Hz, 1H), 7.22 (s, 2H), 6.81 (d, J=8.8 Hz, 2H), 6.42 (m, 2H), 3.95 (s, 3H), 3.86 (s, 6H), 3.73 (m, 1H), 3.38 (m, 2H), 3.14 (m, 2H), 2.16 (m, 1H), 1.95 (m, 1H). MS (ESI) m/z 423 (M$^+$+H).

Compound 390

Synthesis of (5-(furan-2-yl)-2-morpholinophenyl)(3,4,5-trimethoxyphenyl)methanone In the same manner as in the synthesis of Compound 330, Compound 390 was obtained.

$^1$H NMR (CDCl$_3$) δ 7.77 (dd, J=8.50, 2.21 Hz, 1H), 7.68 (d, J=2.21 Hz, 1H), 7.45 (d, J=1.50 Hz, 1H), 7.21 (d, J=8.50 Hz, 1H), 7.08 (s, 2H), 6.61 (d, J=3.41 Hz, 2H), 6.47 (dd, J=3.41, 1.50 Hz, 1H), 3.94 (s, 3H), 3.82 (s, 6H), 3.49 (m, 4H), 3.01 (m, 4H).

Compound 391

Synthesis of (5-(thiophen-2-yl)-2-(1H-1,2,4,-triazol-1-yl)phenyl)(3,4,5-trimethoxyphenyl)methanone In the same manner as in the synthesis of Compound 347, Compound 391 was obtained.

$^1$H NMR (acetone-d6) δ 8.70 (s, 1H), 8.04 (dd, J=8.4, 2.2 Hz, 1H), 7.90 (d, J=2.1 Hz, 1H), 7.84 (s, 1H), 7.82 (d, J=8.4 Hz, 1H), 7.67 (m, 1H), 7.58 (m, 1H), 7.19 (m, 1H), 7.01 (s, 2H), 3.78 (s, 9H). MS (ESI) m/z 422 (M$^+$+H).

Compound 392

Synthesis of (2-pyridin-4-yl)-5-(thiazol-2-yl)phenyl)(3,4,5-trimethoxyphenyl)methanone In the same manner as in the synthesis of Compound 383, Compound 392 was synthesized through the Suzuki reaction.
$^1$H NMR (CDCl$_3$) δ 8.56 (m, 2H), 8.21 (m, 1H), 8.11 (s, 1H), 7.90 (d, J=3.1 Hz, 1H), 7.58 (m, 1H), 7.41 (d, J=3.1 Hz, 1H), 726 (m, 2H), 6.97 (s, 2H), 3.88 (s, 6H), 3.77 (s, 3H). MS (ESI) m/z 433 (M$^+$+H).

Compound 393

Synthesis of (4'-methoxy-4-(thiazol-2-yl)biphenyl-2-yl)(3,4,5-trimethoxyphenyl)methanone In the same manner as in the synthesis of Compound 383, Compound 393 was synthesized through the Suzuki reaction.
$^1$H NMR (CDCl$_3$) δ 8.16 (dd, J=8.0, 1.8 Hz, 1H), 8.04 (d, J=1.8 Hz, 1H), 7.88 (d, J=3.2 Hz, 1H), 7.56 (d, J=8.0 Hz, 1H), 7.37 (d, J=3.2 Hz, 1H), 7.23 (m, 2H), 6.96 (s, 2H), 6.78 (m, 2H), 3.86 (s, 3H), 3.76 (s, 9H), 3.75 (s, 3H). MS (ESI) m/z 462 (M$^+$+H).

Compound 394

Synthesis of (2-(2-methoxypyridin-3-yl)-5-(thiazol-2-yl)phenyl)(3,4,5-trimethoxyphenyl)methanone In the same manner as in the synthesis of Compound 383, Compound 394 was synthesized through the Suzuki reaction.
$^1$H NMR (CDCl$_3$) δ 8.15 (dd, J=8.0, 1.8 Hz, 1H), 8.11 (d, J=1.6 Hz, 1H), 8.05 (m, 1H), 7.87 (d, J=3.2 Hz, 1H), 7.57 (dd, J=7.2, 1.8 Hz, 1H), 7.52 (d, J=8.0 Hz, 1H), 7.36 (d, J=3.1 Hz, 1H), 7.04 (s, 2H), 6.90 (m, 1H), 3.89 (s, 3H), 3.80 (s, 9H), 3.57 (s, 3H). MS (ESI) m/z 463 (M$^+$+H).

Compound 395

Synthesis of (5-(thiazol-2-yl)-2-(thiophen-3-yl)phenyl)(3,4,5-trimethoxyphenyl)methanone In the same manner as in the synthesis of Compound 383, Compound 395 was synthesized through the Suzuki reaction.
$^1$H NMR (CDCl$_3$) δ 8.14 (dd, J=8.1, 1.8 Hz, 1H), 8.02 (d, J=1.8 Hz, 1H), 7.88 (d, J=3.2 Hz, 1H), 7.62 (d, J=8.1 Hz, 1H), 7.36 (d, J=3.2 Hz, 1H), 7.20 (m, 2H), 7.06 (m, 1H), 6.98 (s, 2H), 3.86 (s, 3H), 3.76 (s, 6H). MS (ESI) m/z 438 (M$^+$+H).

Compound 396

Synthesis of 4-(thiazol-2-yl)-2-(3,4,5-trimethoxybenzoyl)benzoic acid methoxymethyl ester Compound 373 [4-(thiazol-2-yl)-2-(3,4,5-trimethoxybenzoyl)benzoic acid] (16 mg, 0.04 mmol) and potassium carbonate (27.6 mg) were dissolved in N,N-dimethylformamide (3 ml), and methoxymethyl chloride (15.2 µl) was added thereto at room temperature. The mixture was heated with stirring for 30 minutes. After completion of the reaction, the reaction mixture was cooled to room temperature, and diluted with an EtOAc solution. The organic layer was washed with a saturated aqueous ammonium chloride solution, water, and brine. The extracted organic layer was dried over anhydrous MgSO$_4$, and the solid substance was filtered off. The filtrate was vacuum concentrated. The resulting residue was purified by column chromatography (SiO$_2$, n-Hex/EA=3/1→1/1) to obtain Compound 396 (5.94 mg, 33.6%) in a form of oil.
$^1$H NMR (CDCl$_3$) δ 8.204 (d, J=0.86 Hz, 2H), 7.989 (t, J=1.10 Hz, 1H), 7.948 (d, J=3.27 Hz, 1H), 7.469 (d, J=3.21 Hz, 1H), 5.290 (s, 2H), 3.915 (s, 3H), 3.817 (s, 6H), 3.623 (s, 3H). MS (ESI) m/z 444 (M$^+$+H).

Compound 397

Synthesis of 2-(4-(thiazol-2-yl)-2-(3,4,5-trimethoxybenzoyl)benzamido) acetic acid methyl ester Compound 373 [4-(thiazol-2-yl)-2-(3,4,5-trimethoxybenzoyl)benzoic acid] (13 mg, 0.03 mmol), glycine methyl ester (6.27 mg), and N,N-dimethylaminopyridine (4.4 mg) were dissolved in dichloromethane (3 ml), and EDC (17.3 mg) was added thereto at room temperature. The mixture was stirred for 24 hours at room temperature. After completion of the reaction, the reaction mixture was vacuum concentrated. The resulting residue was purified by column chromatography (SiO$_2$, n-Hex/EA=1/3→1/5) to obtain Compound 397 (2.33 mg, 16.5%) in a form of oil.
$^1$H NMR (CDC$_3$) δ 8.047 (dd, J=7.89, 1.36 Hz, 1H), 7.967 (t, J=0.66 Hz, 1H), 7.913-7.882 (m, 2H), 7.684 (d, J=3.16 Hz, 1H), 6.672 (s, 2H), 4.556 (d, J=17.7 Hz, 1H), 3.836 (s, 3H), 3.810 (s, 6H), 3.772 (s, 3H), 3.703 (d, J=17.7 Hz, 1H). MS (ESI) m/z 471 (M$^+$+H).

Compound 399

Synthesis of (5-(furan-2-yl)-2-(1H-1,2,4-triazol-1-yl)phenyl)(3,4,5-trimethoxyphenyl)methanethione Compound 322 [(5-(furan-2-yl)-2-(1H-1,2,4-triazol-1-yl)phenyl)(3,4,5-trimethoxyphenyl)methanone] (50 mg, 0.12 mmol) was dissolved in toluene (3 ml), and a Lawesson reagent (100 mg, 0.25 mmol) was added thereto. The mixture was refluxed for 2 hours. After completion of the reaction, the reaction mixture was vacuum concentrated, and extracted with EtOAc (20 ml) and water (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=2/1→1/1) to obtain Compound 399 (15 mg, 30%).
$^1$H NMR (CDCl$_3$) δ 8.14 (s, 1H), 7.88 (dd, J=8.3, 2.0 Hz, 1H), 7.85 (s, 1H), 7.83 (d, J=2.0 Hz, 1H), 7.58 (d, J=8.3 Hz, 1H), 7.52 (d, J=1.5 Hz, 1H), 7.04 (s, 2H), 6.79 (d, J=3.3 Hz, 1H), 6.52 (dd, J=3.3, 1.7 Hz, 1H), 3.90 (s, 3H), 3.80 (s, 6H). MS (ESI) m/z 422 (M$^+$+H).

Compound 400

Synthesis of (5-(1H-imidazol-2-yl)-2-(H-1,2,4-triazol-1-yl)phenyl)(3,4,5-trimethoxyphenyl)methanone In the same manner as in the synthesis of Compound 347, Compound 400 was synthesized.
MS (ESI) m/z 406 (M$^+$+H).

Compound 401

Synthesis of (2-(1H-tetrazol-1-yl)-5-(thiazol-2-yl)phenyl)(3,4,5-trimethoxyphenyl)methanone (2-Fluoro-5-(thiazol-2-yl)phenyl)(3,4,5-trimethoxyphenyl)methanone (100 mg, 0.27 mmol) as a starting material of Compound 347 and triethyl orthoformate (134.2 μl, 0.81 mmol) were dissolved in acetic acid (5 ml), and NaN$_3$ (52.5 mg, 0.81 mmol) was added thereto. The mixture was stirred at room temperature for 3 hours. After completion of the reaction, the reaction mixture was diluted with EtOAc, and the resulting solution was washed with water, and brine. The organic layer was dried over anhydrous MgSO$_4$, and the solid substance was filtered off. The filtrate was vacuum concentrated. The resulting residue was purified by column chromatography (SiO$_2$, n-Hex/EA=6/4→4/6) to obtain Compound 401 (8.2 mg, 7.8%) in a form of a yellow solid.

$^1$H NMR (CDCl$_3$) δ 8.88 (s, 1H), 8.33 (dd, J=2.0 Hz, 8.3 Hz, 1H), 8.23 (d, J=2.0 Hz, 1H), 7.96 (d, J=3.2 Hz, 1H), 7.76 (d, J=8.3 Hz, 1H), 7.49 (d, J=3.2 Hz, 1H), 6.99 (s, 2H), 3.92 (s, 3H), 3.81 (s, 6H). MS (ESI) m/z 424 (M$^+$+H).

Compound 402

Synthesis of (2-(3-aminophenoxy)-5-(thiophen-2-yl) phenyl)(3,4,5-trimethoxyphenyl)methanone (2-Fluoro-5-(thiophen-2-yl)phenyl)(3,4,5-trimethoxyphenyl)methanone (75 mg, 0.20 mmol) as a starting material of Compound 391 and 3-aminophenol (135 mg, 0.60 mmol) was dissolved in DMF (2 ml), and sodium hydride (26.4 mg, 0.60 mmol; 55% in paraffin liquid) was added thereto. The mixture was stirred at about 60° C. for 3 hours. After completion of the reaction, the reaction mixture was diluted with EtOAc, and the resulting solution was washed with a saturated aqueous sodium bicarbonate solution. The organic layer was dried over anhydrous MgSO$_4$, and the solid substance was filtered off. The filtrate was vacuum concentrated. The resulting residue was purified by column chromatography (SiO$_2$, n-Hex/EA=7/3) to obtain Compound 402 (57.2 mg, 61.6%) in a form of an oil.

MS (ESI) m/z 462 (M$^+$+H).

Compound 403

Synthesis of (2-(3-aminophenoxy)-5-(pyridin-2-yl) phenyl)(3,4,5-trimethoxyphenyl)methanone In the same manner as in the synthesis of Compound 402, Compound 403 (67.1 mg, 40%) in a form of clear oil was obtained.

$^1$H NMR (acetone-d6) δ 8.66-8.65 (m, 1H), 8.28-8.28 (m, 2H), 7.97 (d, J=7.1 Hz, 1H), 7.88-7.86 (m, 1H), 7.33-7.31 (m, 1H), 7.18 (s, 2H), 7.12 (d, J=8.5 Hz, 1H), 7.00 (t, J=8.0 Hz, 1H), 6.44-6.41 (m, 1H), 6.32-6.31 (m, 1H), 6.23-6.20 (m, 1H), 4.79 (bs, NH2), 3.83 (s, 6H), 3.81 (s, 3H). MS (ESI) m/z 457 (M$^+$+H).

Compound 406

Synthesis of 1-(4-(furan-2-yl)-2-(1-(3,4,5-trimethoxyphenyl)vinyl)phenyl)-1-1H-1,2,4-triazole Methyl magnesiumbromide was added to Compound 322 to obtain 1-(5-(furan-2-yl)-2-(1H-1,2,4-triazol-1-yl)phenyl)-1-(3,4,5-trimethoxyphenyl)ethanol. Thus obtained 1-(5-(furan-2-yl)-2-(1H-1,2,4-triazol-1-yl)phenyl)-1-(3,4,5-trimethoxyphenyl)ethanol (25 mg, 0.06 mmol) was dissolved in acetic acid (3 ml). The solution was refluxed for 5 hours. The reaction solution was vacuum concentrated. The concentrated reaction solution was extracted with a saturated aqueous ammonium chloride solution (5 ml) and EtOAc (20 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=1/1→1/2) to obtain Compound 406 (8 mg, 33%) in a form of oil.

$^1$H NMR (acetone-d6) δ 8.34 (s, 1H), 7.92 (dd, J=8.3, 2.0 Hz, 1H), 7.84 (d, J=2.0 Hz, 1H), 7.82 (s, 1H), 7.72 (d, J=1.6 Hz, 1H), 7.62 (d, J=8.3 Hz, 1H), 7.07 (d, J=3.4 Hz, 1H), 6.62 (dd, J=3.4, 1.7 Hz, 1H), 6.47 (s, 2H), 5.80 (s, 1H), 5.42 (s, 1H), 3.70 (s, 6H), 3.68 (s, 3H). MS (ESI) m/z 404 (M$^+$+H).

Compound 408

Synthesis of 4-(thiazol-2-yl)-2-(3,4,5-trimethoxybenzoyl)benzamide

Compound 373 [4-(thiazol-2-yl)-2-(3,4,5-trimethoxybenzoyl)benzoic acid] (9.5 mg, 0.02 mmol) was dissolved in toluene (1 ml), and thionyl chloride (5 drops) was added thereto at room temperature. The mixture was stirred for 2 hours at 100° C. After completion of the reaction, the reaction mixture was cooled to room temperature, and the solvent was removed by vacuum evaporation. The resulting residue was dissolved in tetrahydrofuran (2 ml), and ammonia water (1 ml) was added thereto at room temperature. The mixture was stirred for 30 minutes. After completion of the reaction, the reaction mixture was cooled to room temperature, and the solvent was removed by vacuum evaporation. The resulting residue was purified by column chromatography (SiO$_2$, n-Hex/EA=1/5→1/10) to obtain Compound 408 (2.1 mg, 22.9%) in a form of a white solid.

$^1$H NMR (CDCl$_3$) δ 8.099 (dd, J=7.90, 1.49 Hz, 1H), 7.989 (d, J=1.44 Hz, 1H), 7.902 (d, J=3.27 Hz, 1H), 7.847 (d, J=7.88 Hz, 1H), 7.672 (d, J=3.28 Hz, 1H). MS (ESI) m/z 399 (M$^+$+H).

Compound 409

Synthesis of (5-(1H-pyrrole-2-yl)-2-(1H-1,2,4-triazol-1-yl)phenyl)(3,4,5-trimethoxyphenyl)methanone In the same manner as in the synthesis of Compound 457, Compound 409 (27.1 mg, 32%) in a form of a white solid was obtained through the Suzuki reaction.

$^1$H NMR (CDCl$_3$) δ 8.744 (brs, 1H), 8.283 (s, 1H), 7.916 (s, 1H), 7.758 (s, 1H), 7.758 (dd, J=8.34, 1.99 Hz, 1H), 7.639-7.595 (m, 2H), 6.958-6.942 (m, 3H), 6.662 (m, 1H), 6.346 (m, 1H), 3.888 (s, 3H), 3.795 (s, 6H). MS (ESI) m/z 405 (M$^+$+H).

Compound 410

Synthesis of (5-(thiazol-2-yl)-2-(1H-1,2,4-triazol-1-yl)pyridin-3-yl)(3,4,5-trimethoxyphenyl)methanone In the same manner as in the synthesis of Compound 347, a chloride group of (2-chloro-5-(thiazol-2-yl)pyridin-3-yl)(3,4,5-trimethoxyphenyl)methanone as a starting material was substituted with a triazole group to obtain Compound 410.

MS (ESI) m/z 424 (M$^+$+H).

Compound 411

Synthesis of (2-methoxy-5-(thiazol-2-yl)pyridin-3-yl)(3,4,5-trimethoxyphenyl)methanone (2-Chloro-5-(thiazol-2-yl)pyridin-3-yl)(3,4,5-trimethoxyphenyl)methanone (39 mg, 0.1 mmol) as a starting material was dissolved in methanol (3 ml), and NaOMe (16.2 mg) was added thereto at room temperature. The mixture was stirred for 3 hours at 80° C. After completion of the reaction, the reaction mixture was cooled to room temperature, and the solvent was removed by vacuum evaporation. The resulting residue was purified by column chromatography (SiO$_2$, n-Hex/EA=2/1→1/2) to obtain Compound 411 (10 mg, 25.9%) in a form of a solid.

$^1$H NMR (CDCl$_3$) δ 8.908 (d, J=2.42 Hz, 1H), 8.254 (d, J=2.44 Hz, 1H), 7.878 (d, J=3.28 Hz, 1H), 7.366 (d, J=3.28 Hz, 1H), 7.094 (s, 2H), 3.993 (s, 3H), 3.949 (s, 3H), 3.853 (s, 6H). MS (ESI) m/z 387 (M$^+$+H).

Compound 420

Synthesis of (2-(4-hydroxyphenylamino)-5-(thiazol-2-yl)pyridin-3-yl)(3,4,5-trimethoxyphenyl)methanone (2-chloro-5-(thiazol-2-yl)pyridin-3-yl-3,4,5-trimethoxyphenyl)methanone (33.3 mg, 0.09 mmol) as a starting material was dissolved in 2-propanol (5 ml), and 4-aminophenol (12.1 mg) was added thereto at room temperature. The mixture was stirred for 3 hours using a high-temperature, high-pressure reactor at 140° C. After completion of the reaction, the reaction mixture was cooled to room temperature, and the solvent was removed by vacuum evaporation. The resulting residue was purified by column chromatography (SiO$_2$, n-Hex/EA=1/1→1/5) to obtain Compound 420 (25.9 mg, 62%) in a form of a red solid.

$^1$H NMR (CDCl$_3$) δ 10.684 (s, 1H), 8.924 (d, J=2.24 Hz, 1H), 8.604 (d, J=2.28 Hz, 1H), 7.802 (d, J=3.28 Hz, 1H), 7.489 (d, J=8.68 Hz, 1H), 7.287 (d, J=3.28 Hz, 1H), 6.978 (s, 2H), 6.862 (d, J=8.72 Hz, 1H), 3.975 (s, 3H), 3.907 (s, 6H). MS (ESI) m/z 464 (M$^+$+H).

Compound 421

Synthesis of (2-(3-hydroxypropylamino)-5-(thiazol-2-yl)pyridin-3-yl) (3,4,5-trimethoxyphenyl)methanone In the same manner as in the synthesis of Compound 348, Compound 421 (19.4 mg, 88.4%) in a form of a yellow solid was obtained $^1$H NMR (CDCl$_3$) δ 8.84 (d, J=2.4 Hz, 1H), 8.62 (s, 1H), 7.78 (d, J=3.2 Hz, 1H), 7.73 (d, J=3.2 Hz, 1H), 6.92 (s, 2H), 3.96 (s, 3H), 3.89 (s, 6H), 3.89 (m, 2H), 3.73 (t, J=5.4 Hz, 2H), 1.93 (m, 2H). MS (ESI) m/z 430 (M$^+$+H).

Compound 422

Synthesis of (2-(benzylamino)-5-(thiazol-2-yl)pyridin-3-yl)(3,4,5-trimethoxyphenyl)methanone In the same manner as in the synthesis of Compound 348, Compound 422 (106.6 mg, 81.3%) in a form of a yellow solid was obtained.

$^1$H NMR (CDCl$_3$) δ 9.16 (s, 1H), 8.92 (d, J=2.2 Hz, 1H), 8.50 (d, J=2.2 Hz, 1H), 7.77 (d, J=3.2 Hz, 1H), 7.33 (m, 5H), 7.23 (d, J=3.2 Hz, 1H), 6.93 (s, 2H), 4.89 (d, J=5.5 Hz, 2H), 3.96 (s, 3H), 3.88 (s, 6H). MS (ESI) m/z 462 (M$^+$+H).

Compound 425

Synthesis of (5-(furan-2-yl)-2-methoxyphenyl)(pentafluorophenyl)methanone

First, magnesium was added to 1-bromo-pentafluorobenzene as a starting material, as shown in Reaction 1, and a substituted benzaldehyde was added thereto to obtain (5-(furan-2-yl)-2-methoxyphenyl)(pentafluorophenyl)methanol. Thus obtained (5-(furan-2-yl)-2-methoxyphenyl)(pentafluorophenyl)methanol (117 mg, 0.32 mmol) was dissolved in dichloromethane (10 ml), and 4 Å molecular sieves (150 mg) and pyridinium dichromate (PDC) (179 mg, 0.47 mmol) were added sequentially at 0° C. The mixture reacted at room temperature for 24 hours. After completion of the reaction, the precipitates were filtered off using Celite. The resulting residue was purified by column chromatography (SiO$_2$, n-Hex/EA=9/1) to obtain Compound 425 (30 mg, 25%).

$^1$H NMR (acetone-d6) δ 8.11 (d, J=2.3 Hz, 1H), 8.02 (dd, J=8.7, 2.3 Hz, 1H), 7.64 (d, J=1.4 Hz, 1H), 7.28 (d, J=8.7 Hz, 1H), 6.87 (d, J=3.3 Hz, 1H), 6.56 (dd, J=3.3, 1.9 Hz, 1H), 3.80 (s, 3H). MS (ESI) m/z 369 (M$^+$+H).

Compound 426

Synthesis of (2-amino-5-(thiazol-2-yl)pyridin-3-yl)(3,4,5-trimethoxyphenyl)methanone (2-Chloro-5-(thiazol-2-yl)pyridin-3-yl)(3,4,5-trimethoxyphenyl)methanone (65 mg, 0.16 mmol) as a starting material was dissolved in isopropyl alcohol (3 ml), and ammonia water (10 ml) was added thereto. The mixture was heated for 3 hours in a Steel Bomb. After completion of the reaction, the reaction mixture was vacuum concentrated, and extracted with dichloromethane (30 ml) and water (10 ml). The organic layer was washed with brine, and dried over anhydrous MgSO$_4$. The solid substance filtered off, and the filtrate was vacuum concentrated. The resulting residue was purified by column chromatography (SiO$_2$, n-Hex/EA=1/1) to obtain a desired yellow solid compound (24.0 mg, 38.84%).

$^1$H NMR (CDCl$_3$) δ 8.85 (s, 1H), 8.48 (d, J=2.0 Hz, 1H), 7.79 (d, J=3.3 Hz, 1H), 7.27 (d, J=3.3 Hz, 1H), 6.94 (s, 2H), 3.96 (s, 3H), 3.89 (s, 6H). MS (ESI) m/z 372 (M$^+$+H).

Compound 427

Synthesis of N-(5-(thiazol-2-yl)-3-(3,4,5-trimethoxybenzoyl)pyridin-2-yl)acetamide Compound 426 [(2-amino-5-(thiazol-2-yl)pyridin-3-yl)(3,4,5-trimethoxyphenyl)methanone] (14.3 mg, 0.038 mmol) was dissolved in dichloromethane (3 ml), and pyridine (3.1 µl, 0.038 mmol) was added thereto. Acetylchloride (2.7 µl, 0.038 mmol) was added to the mixture, and the resulting mixture was stirred for 5 minutes. After completion of the reaction, the reaction mixture was vacuum concentrated, and extracted with dichloromethane (20 ml) and water (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=2/1) to obtain a desired yellow solid compound (24.0 mg, 38.84%).

$^1$H NMR (CDCl$_3$) δ 9.62 (s, 1H), 9.09 (s, 1H), 8.45 (s, 1H), 7.88 (d, J=3.2 Hz, 1H), 7.40 (s, J=3.2 Hz, 1H), 7.09 (s, 2H), 3.97 (s, 3H), 3.88 (s, 6H), 2.31 (s, 3H). MS (ESI) m/z 414 (M$^+$+H).

Compound 429

Synthesis of (2-methoxy-5-(thiazol-2-yl)phenyl)(pentafluorophenyl)methanone

In the same manner as in the synthesis of Compound 425, Compound 429 was obtained.

$^1$H NMR (acetone-d6) δ 8.35 (d, J=2.4 Hz, 1H), 8.24 (dd, J=8.7, 2.4 Hz, 1H), 7.83 (d, J=3.2 Hz, 1H), 7.59 (d, J=3.2 Hz, 1H), 7.30 (d, J=8.7 Hz, 1H), 3.79 (s, 3H). MS (ESI) m/z 386 (M$^+$+H).

Compound 434

Synthesis of (3-((dimethylamino)methyl)-5-(furan-2-yl)-2-hydroxyphenyl) (3,4,5-trimethoxyphenyl) methanone In the same manner as in the synthesis of Compound 457, Compound 434 was synthesized by subjecting (3-((dimethylamino)methyl-2-hydroxy-5-iodophenyl)(3,4,5-trimethoxyphenyl)methanone as a starting material and furan-2-boronic acid to the Suzuki reaction.

$^1$H NMR (CDCl$_3$) δ 7.761 (brs, 1H), 7.410 (s, 1H), 7.087 (s, 2H), 6.605 (s, 1H), 6.447 (m, 1H), 3.954 (s, 3H), 3.877 (s, 6H), 3.837 (s, 2H), 2.502 (s, 6H). MS (ESI) m/z 412 (M$^+$+H).

Compound 437

Synthesis of (2-fluoro-4-(furan-2-yl)phenyl)(pentafluorophenyl)methanone

In the same manner as in the synthesis of Compound 425, Compound 437 was obtained.

$^1$H NMR (acetone-d6) δ 7.97 (t, J=8.1 Hz, 1H), 7.81 (m, 1H), 7.75 (dd, J=8.3, 1.5 Hz, 1H), 7.63 (dd, J=12.6, 1.5 Hz, 1H), 7.26 (d, J=3.1 Hz, 1H), 6.67 (m, 1H). MS (ESI) m/z 357 (M$^+$+H).

Compound 443

Synthesis of (4-(furan-2-yl)-2-(1H-1,2,4-triazol-1-yl)phenyl)(3,4,5-trimethoxyphenyl)methanone First, magnesium was added to 1-bromo-3,4,5-trimethoxybenzene as a starting material, as shown in Reaction 6, and 4-bromo-2-fluorobenzaldehyde was added thereto to obtain Compound 20. Thus obtained Compound 20 was oxidized to obtain Compound 21. In the same manner as in the synthesis of Compound 457, thus obtained Compound 21 and furan-2-boronic acid were subjected to the Suzuki reaction to obtain Compound 22. In the same manner as in the synthesis of Compound 455, triazole was added to Compound 22 to obtain Compound 443.

$^1$H NMR (acetone-d6) δ 8.78 (s, 1H), 8.07 (d, J=1.6 Hz, 1H), 7.98 (dd, J=8.1, 1.6 Hz, 1H), 7.85 (s, 1H), 7.79 (d, J=1.6 Hz, 1H), 7.70 (d, J=8.1 Hz, 1H), 7.20 (d, J=3.2 Hz, 1H), 6.98 (s, 2H), 6.67 (dd, J=3.4, 1.8 Hz, 1H), 3.78 (s, 6H), 3.77 (s, 3H). MS (ESI) m/z 406 (M$^+$+H).

Compound 444

Synthesis of (4-(furan-2-yl)-2-(1H-1,2,4-triazol-1-yl)phenyl)(phenyl)methanone

Phenyl magnesium bromide as a starting material was added to a benzaldehyde substituted with furan and triazole to obtain a Formula IV derivative. In the same manner as in the synthesis of Compound 425, Compound 444 was obtained by subjecting the Formula IV derivative to the oxidation reaction.

$^1$H NMR (acetone-d6) 8.80 (s, 1H), 8.09 (d, J=1.6 Hz, 1H), 7.99 (dd, J=8.2 Hz, 1H), 7.78 (d, J=1.4 Hz, 1H), 7.76 (s, 1H), 7.71~7.66 (m, 3H), 7.54 (t, 1H), 7.42~7.38 (m, 2H), 7.21 (d, J=3.3 Hz, 1H), 6.67 (dd, J=3.5, 1.8 Hz, 1H). MS (ESI) m/z 316 (M$^+$+H).

Compound 446

Synthesis of (4-(furan-2-yl)-2-(1H-1,2,4,-triazol-1-yl)phenyl)(pentafluorophenyl)methanone In the same manner as in the synthesis of Compound 425, Compound 446 was synthesized.

$^1$H NMR (acetone-d6) δ 8.90 (s, 1H), 8.07~8.04 (m, 2H), 7.96 (m, 2H), 7.82 (d, J=1.6 Hz, 1H), 7.28 (d, J=3.3 Hz, 1H), 6.69 (dd, J=3.4, 1.8 Hz, 1H). MS (ESI) m/z 406 (M$^+$+H).

Compound 455

Synthesis of (4-(pyrimidin-5-yl)-2-(1H-1,2,4,-triazol-1-yl)phenyl)(3,4,5-trimethoxyphenyl)methanone In the same manner as in the synthesis of Compound 457, Compound 21 of Reaction 6 and pyrimidine were subjected to the Suzuki reaction to obtain a Compound 22 derivative [(2-fluoro-4-(pyrimidin-5-yl)phenyl)(3,4,5-trimethoxyphenyl)methanone]. Thus obtained Compound 22 derivative [(2-fluoro-4-(pyrimidin-5-yl)phenyl)(3,4,5-trimethoxyphenyl)methanone] (50 mg, 0.13 mmol) was dissolved in N,N-dimethylformamide (5 ml), and 1,2,4-triazole-Na (37 mg, 0.41 mmol) was added thereto. The mixture was heated for 1 hour. After completion of the reaction, the reaction mixture was vacuum concentrated, and extracted with water (5 ml) and EtOAc (10 ml). The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=1/2→1/9) to obtain Compound 455 (20 mg, 37%).

$^1$H NMR (CDCl$_3$) δ 9.30 (s, 1H), 9.07 (s, 2H), 8.34 (s, 1H), 7.96 (s, 1H), 7.89 (d, J=0.9 Hz, 1H), 7.80 (dd, J=7.9, 1.2 Hz, 1H), 7.75 (d, J=7.9 Hz, 1H), 6.96 (s, 2H), 3.89 (s, 3H), 3.81 (s, 6H).

Compound 456

Synthesis of (2'-hydroxy-3-(1H-1,2,4-triazol-1-yl)biphenyl-4-yl)(3,4,5-trimethoxyphenyl)methanone In the same manner as in the synthesis of Compound 455, Compound 456 was synthesized.

$^1$H NMR (acetone-d6) δ 8.92 (s, 1H), 8.78 (s, 1H), 8.01 (d, J=1.6 Hz, 1H), 7.93 (dd, J=8.0, 1.6 Hz, 1H), 7.85 (s, 1H), 7.69 (d, J=8.0 Hz, 1H), 7.52 (dd, J=7.7, 1.6 Hz, 1H), 7.28 (t, J=7.5 Hz, 1H), 7.07 (dd, J=8.2, 0.9 Hz, 1H), 7.03 (m, 3H), 3.79 (s, 6H), 3.78 (s, 3H).

Compound 457

Synthesis of (2'-hydroxy-3-(fluoro)biphenyl-4-yl)(3,4,5-trimethoxyphenyl)methanone Sodium carbonate (40 mg, 0.38 mmol) was dissolved in water (1 ml), and then a solution of Compound 21 [(4-bromo-2-fluorophenyl)(3,4,5-trimethoxyphenyl)methanone] (70 mg, 0.19 mmol) of Reaction 6, 2-hydroxybenzeneboronic acid (39 mg, 0.28 mmol), and Pd(dppf)Cl$_2$ (8 mg, 0.01 mmol) dissolved in 1,2-dimethoxyethane (3 ml) was added thereto. The mixture was heated (150° C.) for 2 hours using a sealed tube. After completion of the reaction, water (10 ml) was added to the reaction mixture, and the resulting solution was extracted with EtOAc (20 ml). The organic layer was washed with brine, and dried over anhydrous $MgSO_4$. The solid substance was filtered off, and the filtrate was vacuum concentrated. The resulting residue was purified by column chromatography ($SiO_2$, n-Hex/EA=7/1→4/1) to obtain Compound 457 (70 mg, 96%) in a form of a solid $^1$H NMR ($CDCl_3$) δ 7.62 (dd, J=7.6 Hz, 1H), 7.46 (dd, J=7.9, 1.2 Hz, 1H), 7.41 (dd, J=11.0, 1.0 Hz, 1H), 7.33 (dd, J=7.6, 1.3 Hz, 1H), 7.28 (t, 1H), 7.15 (s, 2H), 7.03 (t, J=7.5 Hz, 1H), 7.98 (dd, J=8.0 Hz, 1H), 5.29 (b, OH), 3.95 (s, 3H), 3.87 (s, 6H).

Compound 458

Synthesis of (2-fluoro-4-(thiophen-3-yl)phenyl)(3,4,5-trimethoxyphenyl)methanone In the same manner as in the synthesis of Compound 457, Compound 458 was synthesized.

$^1$H NMR ($CDCl_3$) δ 7.97 (dd, J=2.8, 1.6 Hz, 1H), 7.67 (dd, J=8.0, 1.6 Hz, 1H), 7.62~7.54 (m, 4H), 7.10 (s, 2H), 3.79 (s, 3H), 3.78 (s, 6H).

Compound 462

Synthesis of (4-(thiophen-3-yl)-2-(1H-1,2,4,-triazol-1-yl)phenyl)(3,4,5-trimethoxyphenyl)methanone In the same manner as in the synthesis of Compound 455, Compound 462 was synthesized from Compound 458 by adding triazole.

$^1$H NMR (acetone-d6) δ 8.81 (s, 1H), 8.13 (d, J=1.6 Hz, 1H), 8.09 (dd, J=2.9, 1.3 Hz, 1H), 8.01 (dd, J=8.1, 1.7 Hz, 1H), 7.84 (s, 1H), 7.75 (dd, J=5.0, 1.3 Hz, 1H), 7.70~7.67 (m, 2H), 6.98 (s, 2H), 3.78 (s, 3H), 3.77 (s, 6H).

Compound 463

Synthesis of (2-fluoro-4-(thiazol-2-yl)phenyl)(3,4,5-trimethoxyphenyl)methanone

First, Compound 25 and 2-bromothiazole were subjected to the Suzuki reaction, as shown in Reaction 6, to obtain 4-thiazol-2-fluorobenzaldehyde. 3,4,5-Trimethoxybenzene magnesiumbromide was added to 4-thiazol-2-fluorobenzaldehyde to obtain Compound 23. In the same manner as in the synthesis of Compound 425, thus obtained Compound 23 was subjected to the oxidation reaction to obtain Compound 463.

$^1$H NMR ($CDCl_3$) δ 7.95 (d, J=3.2 Hz, 1H), 7.87~7.82 (m, 2H), 7.62 (dd, J=7.7 Hz, 1H), 7.46 (d, J=3.2 Hz, 1H), 7.12 (s, 2H), 3.95 (s, 3H), 3.87 (s, 6H). MS (ESI) m/z 374 (M$^+$H).

Compound 464

Synthesis of (4-(thiazol-2-yl)-2-(1H-1,2,4-triazol-1-yl)phenyl)(3,4,5-trimethoxyphenyl)methanone In the same manner as in the synthesis of Compound 455, Compound 464 was synthesized from Compound 463 by adding triazole.

$^1$H NMR ($CDCl_3$) δ 8.38 (s, 1H), 8.26 (d, J=1.2 Hz, 1H), 8.13 (dd, J=8.0, 1.4 Hz, 1H), 7.96 (d, J=3.2 Hz, 1H), 7.93 (s, 1H), 7.67 (d, J=8.0 Hz, 1H), 7.49 (d, J=3.2 Hz, 1H), 6.97 (s, 2H), 3.89 (s, 3H), 3.80 (s, 6H).

Compound 469

Synthesis of (2-(3-hydroxypropylamino)-4-(thiazol-2-yl)phenyl)(3,4,5-trimethoxyphenyl)methanone In the same manner as in the synthesis of Compound 425, Compound 23 was subjected to an oxidation reaction to obtain Compound 463, as shown in Reaction 6. Then, in the same manner as in the synthesis of Compound 348, 3-amino-1-propanol was added to Compound 463 to synthesize Compound 469.

MS (ESI) m/z 430 (M$^+$+H).

Compound 474

Synthesis of (4'-methoxy-4-[1,2,4]triazol-1-yl-biphenyl-3-yl)(3,4,5-trimethoxyphenyl)methanone In the same manner as in the synthesis of Compound 455, triazole was added to (4-fluoro-4'-methoxybiphenyl-3-yl)(3,4,5-trimethoxyphenyl)methanone (84 mg, 0.21 mmol) to obtain Compound 474 (31.8 mg, 34%) in a form of a white solid.

$^1$H NMR ($CDC_3$) δ 8.304 (s, 1H), 7.928 (s, 1H), 7.849 (dd, J=8.33, 2.12 Hz, 1H), 7.746 (d, J=2.06 Hz, 1H), 7.671 (d, J=8.32 Hz, 1H), 7.588 (d, J=2.02 Hz, 1H), 7.568 (m, 2H), 7.023-6.992 (m, 4H), 3.893 (s, 3H), 3.866 (s, 3H), 3.810 (s, 6H). MS (ESI) m/z 446 (M$^+$+H).

Compound 475

Synthesis of (4-(3,5-dimethyl-isoxazol-4-yl)-2-[1,2,4]triazol-1-yl-phenyl)(3,4,5-trimethoxyphenyl)methanone In the same manner as in the synthesis of Compound 443, 475 was synthesized, as shown in Reaction 6.

$^1$H NMR ($CDCl_3$) δ 8.01 (d, J=2.2 Hz, 1H), 7.65 (dd, J=8.7, 2.2 Hz, 1H), 7.08 (d, J=8.7 Hz, 1H), 6.99 (d, J=16.2 Hz, 1H), 6.90 (d, J=16.2 Hz, 1H), 6.73 (s, 2H), 3.99 (s, 3H), 3.92 (s, 6H), 3.88 (s, 3H). MS (ESI) m/z 435 (M$^+$+H).

Compound 476

Synthesis of N-(3'-[1,2,4]triazol-1-yl-4'-(3,4,5-trimethoxybenzoyl)biphenyl-3-yl)methanesulfonamide Compound 21 was synthesized, and then triazole was added thereto, as shown in Reaction 6. Then, in the same manner as in the synthesis of Compound 457, Compound 476 was synthesized through the Suzuki reaction.

$^1$H NMR (acetone-d6) δ 8.83 (s, 1H), 8.77 (s, NH), 8.06 (d, J=1.5 Hz, 1H), 7.95 (dd, J=8.0, 1.5 Hz, 1H), 7.87 (s, 1H), 7.80 (s, 1H), 7.77 (d, J=8.0 Hz, 1H), 7.66 (d, J=7.7 Hz, 1H), 7.54 (t, J=7.9 Hz, 1H), 7.45 (d, J=7.9 Hz, 1H), 7.00 (s, 2H), 3.78 (s, 9H), 3.07 (s, 3H). MS (ESI) m/z 509 (M$^+$+H).

Compound 477

Synthesis of (3'-hydroxy-3-[1,2,4]triazol-1-yl-biphenyl-4-yl)(3,4,5-trimethoxyphenyl)methanone In the same manner as in the synthesis of Compound 443, Compound 477 was synthesized, as shown in Reaction 6.

$^1$H NMR (acetone-d6) δ 8.84 (s, 1H), 8.61 (s, OH), 8.02 (d, J=1.7 Hz, 1H), 7.92 (dd, J=8.0, 1.7 Hz, 1H), 7.84 (s, 1H), 7.72

(d, J=8.0 Hz, 1H), 7.37~7.29 (m, 3H), 7.00~6.94 (m, 3H), 3.79 (s, 9H). MS (ESI) m/z 432 (M$^+$+H).

Compound 479

Synthesis of (3'-ethanesulfonyl-3-[1,2,4]triazol-1-yl-biphenyl-4-yl)(3,4,5-trimethoxyphenyl)methanone In the same manner as in the synthesis of Compound 443, Compound 479 was synthesized, as shown in Reaction 6.
$^1$H NMR (CDCl$_3$) δ 8.37 (s, 1H), 8.21 (d, J=1.2 Hz, 1H), 7.98~7.94 (m, 3H), 7.89 (s, 1H), 7.82 (d, J=8.0 Hz, 1H), 7.74~7.69 (m, 2H), 6.96 (s, 2H), 3.88 (s, 3H), 3.80 (s, 6H), 3.18 (q, J=7.4 Hz, 2H), 1.31 (t, J=7.4 Hz, 3H). MS (ESI) m/z 508 (M$^+$+H).

Compound 480

Synthesis of 3'-[1,2,4]triazol-1-yl-4'-(3,4,5-trimethoxybenzoyl)-biphenyl-3-carboxylic acid methyl ester In the same manner as in the synthesis of Compound 476, Compound 480 was synthesized.
$^1$H NMR (CDCl$_3$) δ 8.37 (s, 2H), 8.12 (d, J=7.6 Hz, 1H), 7.96 (s, 1H), 7.88 (m, 2H), 7.84 (d, J=8.0 Hz, 1H), 7.70 (d, J=7.9 Hz, 1H), 7.60 (t, J=7.6 Hz, 1H), 6.99 (s, 2H), 3.97 (s, 3H), 3.90 (s, 3H), 3.82 (s, 6H). MS (ESI) m/z 474 (M$^+$+1).

Compound 482

Synthesis of (4'-methanesulfonyl-3-[1,2,4]triazol-1-yl-biphenyl-4-yl)(3,4,5-trimethoxyphenyl)methanone In the same manner as in the synthesis of Compound 443, Compound 482 was synthesized, as shown in Reaction 6.
$^1$H NMR (CDCl$_3$) δ 8.36 (brs, 1H), 8.10 (d, J=8.4 Hz, 2H), 7.97 (brs, 1H), 7.89 (m, 3H), 7.83 (dd, J=8.0, 1.4 Hz, 1H), 7.73 (d, J=8.0 Hz, 1H), 6.98 (s, 2H), 3.91 (s, 3H), 3.82 (s, 6H), 3.12 (s, 3H). MS (ESI) m/z 494 (M$^+$+H).

Compound 483

Synthesis of N-(3'-[1,2,4]triazol-1-yl-4'-(3,4,5-trimethoxybenzoyl)-biphenyl-3-yl)acetamide In the same manner as in the synthesis of Compound 443, Compound 483 was synthesized, as shown in Reaction 6.
$^1$H NMR (CDCl$_3$) δ 8.44 (brs, 1H), 8.01 (s, 1H), 7.96 (s, 1H), 7.83 (s, 1H), 7.79 (d, J=8.0 Hz, 1H), 7.65 (d, J=7.9 Hz, 1H), 7.53~7.40 (m, 4H), 6.99 (s, 2H), 3.90 (s, 3H), 3.82 (s, 6H), 2.21 (s, 3H). MS (ESI) m/z 473 (M$^+$+H).

Compound 484

Synthesis of methanesulfonic acid 5-(thiazol-2-yl)-2-(3,4,5-trimethoxybenzoyl)phenyl ester The fluoro group of Compound 463 was substituted with a hydroxyl group to obtain (2-hydroxy-4-(thiazol-2-yl)phenyl)(3,4,5-trimethoxyphenyl)methanone. Thus obtained (2-hydroxy-4-(thiazol-2-yl)phenyl)(3,4,5-trimethoxyphenyl)methanone (70 mg, 0.19 mmol) was dissolved in dichloromethane (3 ml), and methanesulfonyl chloride (32 mg, 0.28 mmol) and triethylamine (38 mg, 0.38 mmol) were added thereto. The mixture was heated for 24 hours. After completion of the reaction, the reaction mixture was cooled, and vacuum concentrated. Then, the resulting residue was purified by column chromatography (SiO$_2$, n-Hex/EA=3/1→1/1) to obtain Compound 484 (20 mg, 23%) in a form of a solid.
$^1$H NMR (CDCl$_3$) δ 8.12 (s, 1H), 8.02~7.95 (m, 2H), 7.57 (d, J=7.9 Hz, 1H), 7.46 (m, 1H), 7.07 (s, 2H), 3.94 (s, 3H), 3.85 (s, 6H), 3.11 (s, 3H). MS (ESI) m/z 450 (M$^+$+H).

Compound 485

Synthesis of (4-hydroxy-3,5-dimethoxyphenyl)(5-thiazol-2-yl-2-[1,2,4]thiazol-1-yl-phenyl)methanone Compound 347 [(5-(thiazol-2-yl)-2-(1H-1,2,4-triazol-1-yl)phenyl)(3,4,5-trimethoxyphenyl)methanone] (41.7 mg, 0.1 mmol) was dissolved in DMF (3 ml), and 1,2,4-triazole.Na (27 mg) was added thereto at room temperature. The mixture was reacted at 130° C. for 12 hours. After completion of the reaction, the reaction mixture was cooled to room temperature, and diluted with an EtOAc solution. The organic layer was washed with a saturated ammonium chloride solution, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, CH$_2$Cl$_2$/MeOH=40/1→10/1) to obtain Compound 485 (78.7 mg, 73%) in a form of a white solid.
$^1$H NMR (CDCl$_3$) δ 8.375 (brs, 1H), 8.345 (dd, J=10.5, 8.40, 1H), 8.173 (d, J=2.10 Hz, 1H), 7.965 (m, 2H), 7.773 (d, J=8.40 Hz, 1H), 7.476 (d, J=3.0 Hz, 1H), 3.857 (s, 6H). MS (ESI) m/z 409 (M$^+$+H).

Compound 486

Synthesis of N-[4'-fluoro-3'-(3,4,5-trimethoxybenzoyl)-biphenyl-3-yl]-methanesulfonamide In the same manner as in the synthesis of Compound 457, Compound 21 derivative of Reaction 6 was subjected to the Suzuki reaction to synthesize Compound 486.
$^1$H NMR (CDCl$_3$) δ 7.71~7.68 (m, 2H), 7.44~7.38 (m, 3H), 7.26~7.23 (m, 2H), 7.13 (s, 2H), 7.03 (s, NH), 3.94 (s, 3H), 3.86 (s, 6H), 3.04 (s, 3H).

Compound 492

Synthesis of (2-amino-4-thiophen-3-yl-phenyl)(3,4,5-trimethoxyphenyl)methanone (2-Amino-4-bromophenyl)(3,4,5-trimethoxyphenyl)methanone (85 mg, 0.23 mmol) obtained by adding amine to Compound 21 of Reaction 6, 3-thiophene boronic acid (44.5 mg), Pd(dppf)$_2$Cl$_2$ (9.4 mg), and sodium carbonate (48.7 mg) were dissolved in water (3 ml), and after 10 minutes DME (9 ml) was added thereto. The mixture was stirred for 1 hour with a high-temperature, high-pressure reactor at 140° C. After completion of the reaction, the reaction mixture was cooled to room temperature, and diluted with an EtOAc solution. The organic layer was washed, with a saturated ammonium chloride, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=2/1→1/2) to obtain Compound 492 (27.2 mg, 32%) in a form of a white solid.

$^1$H NMR (acetone-d6) δ 7.810 (dd, J=2.91, 4.29 Hz, 1H), 7.579 (dd, J=5.07, 8.01 Hz, 1H), 7.537 (s, 1H), 7.508 (dd, J=5.07, 6.45 Hz, 1H), 7.239 (d, J=1.77 Hz, 1H), 6.959-6.925 (m, 3H), 3.866 (s, 6H), 3.809 (s, 3H). MS (ESI) m/z 370 (M$^+$+H).

Compound 493

Synthesis of (2-amino-4-furan-2-yl-phenyl)(3,4,5-trimethoxyphenyl)methanone

In the same manner as in the synthesis of Compound 492, Compound 493 was synthesized through the Suzuki reaction.

$^1$H NMR (acetone-d6) δ 7.678 (dd, J=1.80, 0.72 Hz, 1H), 7.514 (d, J=8.43 Hz, 1H), 7.242 (d, J=1.65 Hz, 1H), 6.947-6.888 (m, 6H), 6.574 (dd, J=3.45, 1.83 Hz, 1H). 3.856 (s, 6H), 3.801 (s, 3H). MS (ESI) m/z 354 (M$^+$+H).

Compound 494

Synthesis of N-(3'-amino-4'-(3,4,5-trimethoxybenzoyl)-biphenyl-3-yl)methanesulfonamide In the same manner as in the synthesis of Compound 492, Compound 494 was synthesized through the Suzuki reaction.

$^1$H NMR (acetone-d6) δ 7.671-7.656 (m, 1H), 7.591 (d, J=8.34 Hz, 1H), 7.489-7.456 (m, 2H), 7.394-7.356 (m, 1H), 7.179 (d, J=1.80 Hz, 1H), 6.953 (s, 2H), 6.897-6.850 (m, 3H), 3.878 (s, 6H), 3.821 (s, 3H), 3.042 (s, 3H). MS (ESI) m/z 457 (M$^+$+H).

Compound 495

Synthesis of pentafluorophenyl-(4-thiazol-2-yl-2-[1,2,4]thiazol-1-yl-phenyl)methanone In the same manner as in the synthesis of Compound 425, Compound 495 was synthesized.

$^1$H NMR (acetone-d6) δ 8.98 (s, 1H), 8.34~8.29 (m, 2H), 8.02~7.97 (m, 3H), 7.84 (d, J=3.2 Hz, 1H). MS (ESI) m/z 423 (M$^+$+H).

Compound 497

Synthesis of (2-amino-4-thiazol-2-yl-phenyl)(3,4,5-trimethoxyphenyl)methanone

Compound 499 [(2-(4-methoxybenzylamino)-4-(thiazol-2-yl)phenyl)(3,4,5-trimethoxyphenyl)methanone] (401.5 mg, 0.82 mmol) was added to trifluoroacetic acid (3 ml), and the mixture was stirred for 6 hours at room temperature. After completion of the reaction, the reaction mixture was diluted with an EtOAc solution. The organic layer was washed with saturated sodium bicarbonate, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=2/1→1/2) to obtain Compound 497 (187 mg, 61.5%) in a form of a yellow solid.

$^1$H NMR (acetone-d6) δ 7.945 (d, J=3.21 Hz, 1H), 7.718 (d, J=3.21 Hz, 1H), 7.626-7.584 (m, 2H), 7.222 (dd, J=1.77, 8.34 Hz, 1H), 6.970 (s, 2H), 3.885 (s, 6H), 3.832 (s, 3H). MS (ESI) m/z 371 (M$^+$+H).

Compound 499

Synthesis of (2-(4-methoxy-benzylamino)-4-(thiazol-2-yl)-phenyl)(3,4,5-trimethoxyphenyl)methanone Compound 463 [(2-fluoro-4-(thiazol-2-yl)phenyl)(3,4,5-trimethoxyphenyl)methanone] (408 mg, 1.09 mmol) and potassium carbonate (453.05 mg) were dissolved in DMF (5 ml), and 4-methoxybenzylamine (213.6 μl) was added thereto at room temperature. The mixture was stirred for 5 hours at 130° C. After completion of the reaction, the reaction mixture was diluted with an EtOAc solution. The organic layer was washed with a saturated aqueous ammonium chloride solution, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=2/1→1/2) to obtain Compound 499 (401.5 mg, 75%) in a form of a yellow solid.

MS (ESI) m/z 491 (M$^+$+H).

Compound 500

Synthesis of (3,4-dimethoxy-5-((methoxymethoxy)methyl)phenyl)(4-(thiazol-2-yl)-2-(1H-1,2,4-triazol-1-yl)phenyl)methanone In the same manner as in the synthesis of Compound 425, Compound 500 was synthesized.

$^1$H NMR (CDCl$_3$) δ 8.48 (s, 1H), 8.27 (d, J=1.3 Hz, 1H), 8.11 (dd, J=8.0, 1.4 Hz, 1H), 7.97 (d, J=3.2 Hz, 1H), 7.90 (s, 1H), 7.65 (d, J=8.0 Hz, 1H), 7.49 (d, J=3.2 Hz, 1H), 7.40 (d, J=2.0 Hz, 1H), 7.22 (d, J=2.0 Hz, 1H), 4.62 (s, 2H), 4.52 (s, 2H), 3.89 (s, 3H), 3.86 (s, 3H), 3.33 (s, 3H). MS (ESI) m/z 467 (M$^+$+H).

Compound 501

Synthesis of (3-hydroxymethyl-4,5-dimethoxyphenyl)(4-thiazol-2-yl-2-[1,2,4]triazol-1-yl-phenyl)methanone Compound 500 [(3,4-dimethoxy-5-((methoxymethoxy)methyl)phenyl)(4-(thiazol-2-yl)-2-(1H-1,2,4-triazol-1-yl)phenyl)methanone] (20 mg, 0.04 mmol) was dissolved in anhydrous tetrahydrofuran (1 ml), and the solution was cooled to 0° C. 6 N hydrochloric acid (1 ml) was added dropwise to the reaction solution, and then the mixture was stirred for 5 hours at room temperature. After completion of the reaction, water (3 ml) was added to the reaction mixture, and the resulting solution was extracted with EtOAc (6 ml). The organic layer was washed with brine, and dried over anhydrous MgSO$_4$. The solid substance was filtered off, and the filtrate was vacuum concentrated to obtain Compound 501 (10 mg, 59%).

$^1$H NMR (CDCl$_3$) δ 8.56 (s, 1H), 8.27 (d, J=1.4 Hz, 1H), 8.13 (dd, J=8.0, 1.6 Hz, 1H), 7.97 (d, J=3.3 Hz, 1H), 7.91 (s, 1H), 7.67 (d, J=8.0 Hz, 1H), 7.50 (d, J=3.3 Hz, 1H), 7.42 (d, J=2.0 Hz, 1H), 7.16 (d, J=2.0 Hz, 1H), 4.59 (s, 2H), 3.92 (s, 6H), 3.87 (s, 3H). MS (ESI) m/z 423 (M$^+$+H).

Compound 502

Synthesis of (2-(2-hydroxyethylamino)-4-(thiazol-2-yl)phenyl)(3-hydroxymethyl-4,5-dimethoxyphenyl)methanone In the same manner as in the synthesis of Compound 501, Compound 502 was synthesized.

$^1$H NMR (acetone-d6) δ 7.933 (d, J=3.24 Hz, 1H), 7.709 (d, J=3.24 Hz, 1H), 7.549 (m, 1H), 7.499 (d, J=1.56 Hz, 1H), 7.361 (d, J=2.04 Hz, 1H), 7.232 (d, J=2.01 Hz, 1H), 7.56 (dd, J=1.68, 8.28 Hz, 1H), 4.702 (s, 2H), 3.902-3.844 (m, 8H), 3.516-3.462 (m, 2H). MS (ESI) m/z 414 (M$^+$+H).

Compound 503

Synthesis of (2-amino-4-thiazol-2-yl-phenyl)(3-hydroxymethyl-4,5-dimethoxyphenyl)methanone Trifluoroacetic acid (3 ml) was added to (3,4-dimethoxy-5-((methoxymethoxy)methyl)phenyl)(2-(4-methoxybenzylamine)-4-(thiazol-2-yl)phenyl)methanone (127 mg, 0.23 mmol) as a starting material at room temperature. The mixture was stirred for 6 hours at room temperature. After completion of the reaction, the reaction mixture was diluted with an EtOAc solution. The organic layer was washed with saturated sodium carbonate, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=2/1→1/2) to obtain Compound 503 (10 mg, 11.7%) in a form of a yellow solid.

$^1$H NMR (acetone-d6) δ 7.924 (d, J=3.21 Hz, 1H), 7.696 (d, J=3.24 Hz, 1H), 7.586-7.557 (m, 2H), 7.397 (d, J=2.04 Hz, 1H), 7.257 (d, J=2.04 Hz, 1H), 7.189 (dd, J=1.74, 8.37), 4.718 (s, 2H), 3.907 (s, 3H), 3.883 (s, 3H). MS (ESI) m/z 371 (M$^+$+H).

Compound 505

Synthesis of (4-(2-amino-thiazol-4-yl)-2-fluoro-phenyl)(3,4,5-trimethoxyphenyl)methanone 2-Bromo-1-(3-fluoro-4-(3,4,5-trimethoxybenzoyl)phenyl)ethanone (360 mg, 0.88 mmol) obtained from Compound 21 of Reaction 6 was dissolved in 95% ethanol (15 ml), and urea chloride thiourea (336.2 mg) was added thereto at room temperature. The mixture was stirred for 2 hours at 80° C. After completion of the reaction, the reaction mixture was diluted with an EtOAc solution. The organic layer was washed with water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, CH$_2$Cl$_2$/MeOH=30/1→20/1) to obtain Compound 505 (218.7 mg, 64%) in a form of a white solid.

$^1$H NMR (DMSO-d6) δ 7.792-7308 (m, 2H), 7.569 (t, J=7.62 Hz, 1H), 7.353 (s, 1H), 7.196 (s, 2H), 7.051 (s, 2H), 3.782 (s, 6H), 3.766 (s, 3H). MS (ESI) m/z 389 (M$^+$+H).

Compound 506

Synthesis of 3'-[1,2,4]triazol-1-yl-4'-(3,4,5-trimethoxybenzoyl)-biphenyl-3-carbonitrile In the same manner as in the synthesis of Compound 443, Compound 506 was synthesized, as shown in Reaction 6.

$^1$H NMR (acetone-d6) δ 8.88 (s, 1H), 8.30 (d, J=0.5 Hz, 1H), 8.21 (m, 2H), 8.05 (dd, J=8.0, 1.8 Hz, 1H), 7.85~7.75 (m, 4H), 6.98 (s, 2H), 3.76 (s, 9H). MS (ESI) m/z 441 (M$^+$+H).

Compound 507

Synthesis of (3',5'-dimethyl-3-[1,2,4]thiazol-1-yl-biphenyl-4-yl)(3,4,5-trimethoxyphenyl)methanone In the same manner as in the synthesis of Compound 443, Compound 507 was synthesized, as shown in Reaction 6.

$^1$H NMR (CDCl$_3$) δ 8.50 (s, 1H), 8.00 (brs, 1H), 7.81~7.78 (m, 2H), 7.65 (d, J=8.0 Hz, 1H), 7.29 (s, 2H), 7.08 (s, 1H), 6.98 (s, 2H), 3.89 (s, 3H), 3.81 (s, 6H), 2.40 (s, 6H). MS (ESI) m/z 444 (M$^+$+H).

Compound 508

Synthesis of (3'-nitro-3-[1,2,4]thiazol-1-yl-biphenyl-4-yl)(3,4,5-trimethoxyphenyl)methanone In the same manner as in the synthesis of Compound 443; Compound 508 was synthesized, as shown in Reaction 6.

$^1$H NMR (acetone-d6) δ 8.91 (s, 1H), 8.70 (d, J=0.4 Hz, 1H), 8.36 (m, 2H), 8.28 (dd, J=1.8, 0.4 Hz, 1H), 8.11 (dd, J=8.0, 1.8 Hz, 1H), 7.88~7.81 (m, 4H), 7.02 (s, 2H), 3.79 (s, 9H). MS (ESI) m/z 461 (M$^+$+H).

Compound 509

Synthesis of (3-hydroxymethyl-4,5-dimethoxy-phenyl)(5-thiazol-2-yl-2-[1,2,4]thiazol-1-yl-phenyl)methanone In the same manner as in the synthesis of Compound 501, Compound 509 (74.5 mg, 82.14%) was obtained in a form of a white solid.

$^1$H NMR (CDCl$_3$) δ 8.41 (s, 1H), 8.27 (dd, J=8.4, 2.1, 1H), 8.16 (d, J=1.8, 1H), 7.93 (d, J=3.0, 1H), 7.90 (s, 1H), 7.72 (d, J=8.4, 1H), 7.46 (d, J=2.1, 1H), 7.46 (d, J=3.3, 1H), 7.20 (d, J=2.1, 1H), 4.60 (s, 1H), 3.93 (s, 3H), 3.89 (s, 6H). MS (ESI) m/z 423 (M$^+$+H).

Compound 510

Synthesis of (4-thiazol-2-yl-2-[1,2,3]thiazol-1-yl-phenyl)(3,4,5-trimethoxyphenyl)methanone Compound 463 [(2-fluoro-4-(thiazol-2-yl)phenyl)(3,4,5-trimethoxyphenyl)methanone] (55 mg, 0.15 mmol) and potassium carbonate (60.9 mg) were dissolved in DMF (3 ml), and 1,2,3-triazole (12.4 μl) was added thereto at room temperature. The mixture was stirred for 12 hours at 130° C. After completion of the reaction, the reaction mixture was diluted with an EtOAc solution. The organic layer was washed with a saturated aqueous ammonium chloride solution, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=1/1→1/5) to obtain Compound 510 (14.3 mg, 23%) in a form of a white solid.

$^1$H NMR (CDCl$_3$) δ 8.303 (d, J=1.62 Hz, 1H), 8.195 (dd, J=8.04, 1.68 Hz, 1H), 7.978 (d, J=3.24 Hz, 1H), 7.872 (d, J=0.08 Hz, 1H), 7.721-7.676 (m, 2H), 7.501 (d, J=3.24 Hz, 1H), 6.968 (s, 2H), 3.893 (s, 3H), 3.814 (s, 6H). MS (ESI) m/z 423 (M$^+$+H).

Compound 511

Synthesis of (4-pyridin-3-yl-2-[1,2,4]thiazol-1-yl-phenyl)(3,4,5-trimethoxyphenyl)methanone In the same manner as in the synthesis of Compound 443, Compound 511 was synthesized, as shown in Reaction 6.

$^1$H NMR (CDCl$_3$) δ 9.07 (s, 1H), 8.77 (s, 1H), 8.36 (s, 1H), 8.25 (d, J=7.8, 1H), 7.96 (s, 1H), 7.93 (s, 1H), 7.83 (dd, J=8.0, 1.2, 1H), 7.76 (d, J=7.8, 1H), 7.69 (s, 1H), 6.89 (s, 2H), 3.91 (s, 3H), 3.83 (s, 6H). MS (ESI) m/z 417 (M$^+$+H).

Compound 512

Synthesis of (4-(4-methoxypyridin-3-yl)-2-(1H-1,2,4-triazol-1-yl)phenyl)(3,4,5-trimethoxyphenyl)methanone In the same manner as in the synthesis of Compound 443, Compound 512 was synthesized, as shown in Reaction 6.

$^1$H NMR (CDCl$_3$) δ 8.51 (s, 1H), 8.32 (s, 1H), 7.94 (s, 1H), 7.90 (s, 1H), 7.73 (m, 3H), 6.90 (s, 2H), 6.89 (d, J=6.3, 1H), 4.02 (s, 3H), 3.89 (s, 3H), 3.82 (s, 6H). MS (ESI) m/z 447 (M$^+$+H).

Compound 513

Synthesis of (3',5'-difluoro-3-[1,2,4]triazol-1-yl-biphenyl-4-yl)(3,4,5-trimethoxyphenyl)methanone As shown in Reaction 6, Compound 21 was synthesized, and then triazole was added thereto. Then, in the same manner as in the synthesis of Compound 457, Compound 513 was synthesized through the Suzuki reaction.

$^1$H NMR (acetone-d6) δ 8.90 (s, 1H), 8.19 (dd, J=1.8, 0.4 Hz, 1H), 8.04 (dd, J=8.0, 1.8 Hz, 1H), 7.84 (s, 1H), 7.76 (dd, J=8.0, 0.4 Hz, 1H), 7.61~7.58 (m, 2H), 7.15 (m, 1H), 6.99 (s, 2H), 3.77 (s, 9H). MS (ESI) m/z 452 (M$^+$+H).

Compound 514

Synthesis of (3-bromo-4,5-dimethoxyphenyl)(2-fluoro-4-(thiazol-2-yl)phenyl)methanone As shown in Reaction 6, 1-bromo-3,4-dimethoxybenzene as a starting material was added to Compound 24 to obtain a Compound 23 derivative. Thus obtained Compound 23 derivative was oxidized using PDC to obtain (3,4-dimethoxyphenyl)(2-fluoro-4-(thiazol-2-yl)phenyl)methanone. Thus obtained (3,4-dimethoxyphenyl)(2-fluoro-4-(thiazol-2-yl)phenyl)methanone (70 mg, 0.20 mmol) was dissolved in a mixed solution of tetrahydrofuran and water (2 ml/2 ml), and N-bromosuccinimide (NBS) (36.3 mg, 0.20 mmol) was added thereto. The mixture was stirred for 30 minutes at room temperature. After completion of the reaction, the reaction mixture was extracted with dichloromethane, and the filtrate was vacuum evaporated. The resulting residue was purified by column chromatography (SiO$_2$, n-Hex/EA=1/3→1/2) to obtain Compound 514 (72.0 mg, 83.6%) in a form of a yellow solid.

$^1$H NMR (CDCl$_3$) δ 7.94 (d, J=3.3 Hz, 1H), 7.90 (s, 1H), 7.80 (dd, J=8.1, 1.8 Hz, 1H), 7.75~7.68 (m, 2H); 7.45 (d, J=3.3 Hz, 1H), 6.45 (s, 1H), 3.98 (s, 3H), 3.69 (s, 3H). MS (ESI) m/z 421 (M$^+$−H), 423 (M$^+$+H).

Compound 515

Synthesis of (3-bromo-4,5-dimethoxyphenyl)(4-(thiazol-2-yl)-2-(1,2,4-triazol-1-yl)phenyl)methanone Compound 514 [(3-bromo-4,5-dimethoxyphenyl)(2-fluoro-4-(thiazol-2-yl)phenyl)methanone] (31 mg, 0.07 mmol) was dissolved in DMF (3 ml), and 1,2,4-triazole (10.0 mg, 0.15 mmol) and potassium carbonate (20 mg, 0.15 mmol) were added thereto. The mixture was heat refluxed with stirring for 8 hours. After completion of the reaction, the reaction mixture was vacuum evaporated. The resulting residue was purified by column chromatography (SiO$_2$, n-Hex/EA=1/3→1/2) to obtain Compound 515 (15.4 mg, 44.5%) in a white solid.

MS (ESI) m/z 470 (M$^+$−H), 472 (M$^+$+H).

Compound 516

Synthesis of (4-(2-aminothiazol-4-yl)-2-(1H-1,2,4-triazol-1-yl)phenyl)(3,4,5-trimethoxyphenyl)methanone In the same manner as in the synthesis of Compound 515, 1,2,4-triazole was added to Compound 21 of Reaction 6. Then, tributyl(1-ethoxyvinyl)tin was added to the mixture, and the resulting mixture was reacted to obtain (4-(1-ethoxyvinyl)-2-(1H-1,2,4-triazol-1-yl)phenyl)(3,4,5-trimethoxyphenyl)methanone. Thus obtained (4-(1-ethoxyvinyl)-2-(1H-1,2,4-triazol-1-yl)phenyl)(3,4,5-trimethoxyphenyl)methanone was dissolved in a mixed solution of tetrahydrofuran and water (1/1), and N-bromosuccinimide (NBS) was added thereto. The mixture was stirred for 3 hours at room temperature. After completion of the reaction, the reaction mixture was extracted with EtOAc. The organic layer was washed with a saturated aqueous Na$_2$SO$_3$ solution, water, and brine. The extracted organic layer was dried over anhydrous MgSO$_4$, and the solid substance was filtered off. The filtrate was vacuum evaporated to remove the solvent. The resulting residue was purified by column chromatography (SiO$_2$, n-Hex/EA=3/1→1/2) to obtain 1-(3-(1H-1,2,4-triazol-1-yl)-4-(3,4,5-trimethoxybenzoyl)phenyl)-2-bromoethanone. Thus obtained 1-(3-(1H-1,2,4-triazol-1-yl)-4-(3,4,5-trimethoxybenzoyl)phenyl)-2-bromoethanone (65 mg, 0.14 mmol) was dissolved in 3 ml of 95% ethanol, and thiourea (16 mg) was added thereto. The mixture was refluxed for 2 hours. After completion of the reaction, the reaction mixture was cooled to room temperature, and vacuum evaporated to remove the solvent. The resulting residue was purified by column chromatography (SiO$_2$, CH$_2$Cl$_2$/MeOH=30/1→10/1) to obtain Compound 516 (29.3 mg, 48%).

$^1$H NMR (DMSO-d6) δ 9.03 (s, 1H), 8.15 (d, J=1.5 Hz, 1H), 8.05 (dd, J=8.0, 1.5 Hz, 1H), 7.96 (s, 1H), 7.65 (d, J=8.0 Hz, 1H), 7.42 (s, 1H), 6.85 (s, 2H), 3.72 (s, 6H), 3.70 (s, 3H). MS (ESI) m/z 438 (M$^+$+H).

Compound 517

Synthesis of (4-(2-methylthiazol-4-yl)-2-(1H-1,2,4-triazol-1-yl)phenyl)(3,4,5-trimethoxyphenyl)methanone In the same manner as in the synthesis of Compound 516, Compound 517 was synthesized.

$^1$H NMR (CDCl$_3$) δ 8.78 (s, 1H), 8.29 (d, J=1.5 Hz, 1H), 8.12 (dd, J=8.0, 1.5 Hz, 1H), 7.98 (s, 1H), 7.66 (m, 2H), 6.97 (s, 2H), 3.90 (s, 6H), 3.81 (s, 3H), 2.93 (s, 3H). MS (ESI) m/z 437 (M$^+$+H).

Compound 518

Synthesis of (4-(2-aminothiazol-4-yl)-2-(1H-1,2,4-triazol-1-yl)phenyl)(pentafluorophenyl)methanone In the same manner as in the synthesis of Compounds 495 and 516, Compound 518 was synthesized.
MS (ESI) m/z 438 (M$^+$+1).

Compound 519

Synthesis of (4-(2-aminothiazol-4-yl)-2-(1H-1,24-triazol-1-yl)phenyl)(phenyl)methanone In the same manner as in the synthesis of Compound 516 using bromobenzene as a starting material, Compound 519 was synthesized.
$^1$H NMR (DMSO-d6) δ 9.003 (s, 1H), 8.155 (d, J=1.53 Hz, 1H), 8.055 (dd, J=7.98, 1.50 Hz, 1H), 7.882 (s, 1H), 7.645-7.533 (m, 4H), 7.467-7.375 (m, 3H), 7.217 (s, 2H). MS (ESI) m/z 348 (M$^+$+H).

Compound 525

Synthesis of (3'-amino-3-(1H-1,2,4-triazol-1-yl)biphenyl-4-yl)(3,4,5-trimethoxyphenyl)methanone As shown in Reaction 6, Compound 21 was synthesized, and triazole was added thereto to obtain (4-bromo-2-(1H-1,2,4-triazol-1-yl)phenyl)(3,4,5-trimethoxyphenyl)methanone. Then, thus obtained (4-bromo-2-(1H-1,2,4-triazol-1-yl)phenyl)(3,4,5-trimethoxyphenyl)methanone and 3-aminobenzeneboronic acid were subjected to the Suzuki reaction to obtain Compound 525.
$^1$H NMR (DMSO-d6) δ 9.12 (s, 1H), 7.97 (m, 2H), 7.84 (dd, J=8.1, 1.8 Hz, 1H), 7.69 (d, J=8.1 Hz, 1H), 7.18 (t, J=7.8 Hz, 1H), 7.04~7.00 (m, 2H), 6.89 (s, 2H), 6.69~6.65 (m, 1H), 5.26 (brs, NH2), 3.74 (s, 6H), 3.72 (s, 3H). MS (ESI) m/z 431 (M$^+$+H).

Compound 531

Synthesis of N-(4-(3-(1H-1,2,4-triazol-1-yl)-4-(3,4,5-trimethoxybenzoyl)phenyl)-1H-imidazol-2-yl)acetamide 1-(3-(1H-1,2,4-triazol-1-yl)-4-(3,4,5-trimethoxybenzoyl)phenyl)-2-bromoethanone (80.2 mg, 0.2 mmol) obtained as a synthetic intermediate of Compound 516 was dissolved in acetonitrile (5 ml), and 1-acetylguanidine (25.6 mg) was added thereto at room temperature. Then, the mixture was stirred for 3 hours at 90° C. After completion of the reaction, the reaction mixture was cooled to room temperature, and vacuum dried to remove the solvent. The resulting residue was purified by column chromatography (SiO$_2$, CH$_2$Cl$_2$/MeOH=20/1→10/1) to obtain Compound 531 (29.3 mg, 48%) in a yellow solid.
$^1$H NMR (300 MHz, Acetone-d6) 8.694 (s, 1H), 8.079 (m, 1H), 8.077 (m, 1H), 7.831 (s, 1H), 7.621-7.599 (m, 2H), 6.977 (s, 2H), 3.788 (s, 6H), 3.772 (s, 3H). MS (ESI) m/z 463 (M$^+$+H).

Compound 534

Synthesis of (4-(thiazol-5-yl)-2-(1H-1,2,4-triazol-1-yl)phenyl)(3,4,5-trimethoxyphenyl)methanone To (2-fluoro-4-(thiazol-5-yl)phenyl)(3,4,5-trimethoxyphenyl)methanone obtained in the same manner as in the synthesis of Compound 463 of Reaction 6 using 5-bromothiazole as a starting material, 1,2,4-triazole was added in the same manner as in the synthesis of Compound 455 to synthesize Compound 534.
$^1$H NMR (Acetone-d6) δ 9.12 (s, 1H), 8.84 (s, 1H), 8.52 (s, 1H), 8.16 (d, J=1.8 Hz, 1H), 7.97 (dd, J=8.0, 1.8 Hz, 1H), 7.86 (s, 1H), 7.74 (d, J=8.0 Hz, 1H), 7.00 (s, 2H), 3.79 (s, 6H), 3.78 (s, 3H). MS (ESI) m/z 423 (M$^+$+H).

Compound 538

Synthesis of (4-(difluoromethoxy)-3,5-dimethoxyphenyl)(4-(thiazol-2-yl)-2-(1H-1,2,4-triazol-1-yl)phenyl)methanone In the same manner as in the synthesis of Compound 455, triazole was added to Compound 463 to obtain (4-Hydroxy-3,5-dimethoxyphenyl)(4-(thiazol-2-yl)-2-(1H-1,2,4-triazol-1-yl)phenyl)methanone. Thus obtained (4-hydroxy-3,5-dimethoxyphenyl)(4-(thiazol-2-yl)-2-(1H-1,2,4-triazol-1-yl)phenyl)methanone (33.6 mg, 0.08 mmol) and Cs$_2$CO$_3$ (52.1 mg) were dissolved in N,N-dimethylformamide (3 ml), and methyl 2-chloro-2,2-difluoroacetate (11.4 μl) was added thereto at room temperature. The mixture was stirred for 1 hour at 130° C. The reaction mixture was diluted with an EtOAC solution. The organic layer was washed with water, and brine, and dried over anhydrous MgSO$_4$. The solid substance was filtered off, and the filtrate was vacuum dried to remove the solvent. The resulting residue was purified by column chromatography (SiO$_2$, Hex/EtOAc=1/1→1/5) to obtain Compound 538 (19.9 mg, 54%) in a white solid.
$^1$H NMR (Acetone-d6) δ 8.913 (s, 1H), 8.385~8.378 (m, 1H), 8.270 (dd, J=8.04, 1.68 Hz, 1H), 8.036 (d, J=3.21 Hz, 1H), 7.868~7.800 (m, 3H), 7.081 (s, 2H), 3.845 (s, 6H), 3.819 (d, J=11.4 Hz, 1H). MS (ESI) m/z 459 (M$^+$+H).

Compound 547

Synthesis of (4-(2-aminothiazol-4-yl)-2-(1H-1,2,4-triazol-1-yl)phenyl)(4-(difluoromethoxy)-3,5-dimethoxyphenyl)methanone In the same manner as in the synthesis of Compound 538, Compound 547 was synthesized.
$^1$H NMR (Acetone-d6) δ 8.770 (s, 1H), 8.199 (dd, J=1.59, 0.33 Hz, 1H), 8.130 (dd, J=807, 1.62 Hz, 1H), 7.843 (s, 1H), 7.671 (dd, J=8.07, 0.39 Hz, 1H), 7.336 (d, J=0.72 Hz, 1H), 7.029 (s, 2H), 6.605 (brs, 2H), 3.843 (s, 7H). MS (ESI) m/z 474 (M$^+$+H).

Compound 550

Synthesis of (5'-(1H-1,2,4-triazol-1-yl)-4'-(3,4,5-trimethoxybenzoyl)biphenyl-3-sulfonamide As shown in Reaction 6, triazole was added to 5'-fluoro-4'-(3,4,5-trimethoxybenzoyl)biphenyl-3-sulfonamide obtained in the same manner as in the synthesis of Compound 463 to synthesize Compound 550.
$^1$H NMR (CDCl$_3$) δ 8.90 (s, 1H), 8.33 (t, J=1.8 Hz, 1H); 8.08 (d, J=1.8 Hz, 1H), 8.05 (dd, J=1.8, 1.2 Hz, 1H), 8.02 (dd, J=8.1, 1.8 Hz, 1H), 7.98 (dd, J=1.8, 1.2 Hz, 1H), 7.95 (s, 1H), 7.80 (d, J=8.1 Hz, 1H), 7.72 (t, J=7.8 Hz, 1H), 6.99 (s, 2H), 3.81 (s, 3H), 3.80 (s, 6H). MS (ESI) m/z 495 (M$^+$+H).

Compound 554

Synthesis of ((4-(4-hydroxymethyl)thiazol-2-yl)-2-(1H-1,2,4-triazol-1-yl)phenyl)(3,4,5-trimethoxyphenyl)methanone (4-(4-((methoxymethoxy)methyl)thiazol-2-yl)-2-(1H-1,2,4-triazol-1-yl)phenyl)(3,4,5-trimethoxyphenyl)methanone (30 mg, 0.06 mmol) obtained in the same manner as in the synthesis of Compound 464 was dissolved in anhydrous tetrahydrofuran (2 ml), and 6 N hydrochloric acid (1 ml) was added thereto. Then, the mixture was stirred for 24 hours at room temperature. After completion of the reaction, the reaction mixture was extracted with water (2 ml) and EtOAc (6 ml). The organic layer was washed with brine, and dried over anhydrous $MgSO_4$. The solid substance was filtered off, and the filtrate was vacuum concentrated. The resulting residue was purified by column chromatography ($SiO_2$, n-Hex/EA=1/1→1/99) to obtain Compound 554 (106 mg, 99%).

$^1$H NMR ($CDCl_3$+MeOH-d4) δ 8.84 (1H), 8.33 (d, J=1.56 Hz, 1H), 8.20 (dd, J=8.0, 1.68 Hz, 1H), 7.94 (s, 1H), 7.74 (d, J=8.0 Hz, 1H), 7.53 (s, 1H), 6.97 (s, 2H), 4.79 (s, 2H), 3.82 (s, 3H), 3.79 (s, 6H). MS (ESI) m/z 453 (M$^+$+H).

Compound 560

Synthesis of N-(4-(3-(1H-1,2,4-triazol-1-yl)-4-(3,4,5-trimethoxybenzoyl) phenyl)thiazol-2-yl)acetamide Compound 516 (36.9 mg, 0.08 mmol) was dissolved in dichloromethane (3 ml), and pyridine (8.2 µl) and acetylbromide (9.4 µl) were added thereto. The mixture was stirred for 24 hours at room temperature. After completion of the reaction; the reaction mixture was vacuum dried. The resulting residue was purified by column chromatography ($SiO_2$, $CH_2Cl_2$/MeOH-20/1→10/1) to obtain Compound 560 (13.1 mg, 32.4%) in a white solid.

$^1$H NMR ($CDCl_3$) δ 8.726 (d, J=4.80 Hz, 1H), 8.346 (s, 1N), 8.082 (d, J=1.60 Hz, 1H), 7.970~7.943 (m, 2H), 7.625 (m, 1H), 7.343 (s, 1H), 6.973 (s, 2H). MS (ESI) m/z 480 (M$^+$+H).

Compound 561

Synthesis of methyl 4-(3-(1H-1,2,4-triazol-1-yl)-4-(3,4,5-trimethoxybenzoyl)phenyl)thiazol-2-yl carbamate In the same manner as in the synthesis of Compound 560, Compound 561 was synthesized.

$^1$H NMR (DMSO-d6) δ 12.029 (s, 1H), 9.029 (s, 1H), 8.236 (d, J=1.60 Hz, 1H), 8.118 (dd, J=8.00, 1.60 Hz, 1H), 7.966 (s, 1H), 7.960 (s, 1H), 7.686 (d, J=8.00 Hz, 1H), 6.845 (s, 2H), 3.852 (s, 3H), 3.750 (s, 6H), 3.705 (s, 3H). MS (ESI) m/z 496 (M$_+$+H).

Compound 562

Synthesis of (4-(thiazol-4-yl)-2-(1H-1,2,4-triazol-1-yl)phenyl)(3,4,5-trimethoxyphenyl)methanone In the same manner as in the synthesis of Compound 464, Compound 562 was synthesized.

$^1$H NMR ($CDCl_3$) δ 8.94 (d, J=2.0 Hz, 1H), 8.51 (s, 1H), 8.26 (d, J=1.6 Hz, 1H), 8.13 (dd, J=8.0, 1.6 Hz, 1H), 7.95 (s, 1H), 7.80 (d, J=2.0 Hz, 1H), 7.66 (d, J=8.4 Hz, 1H), 6.97 (s, 2H), 3.88 (s, 3H), 3.80 (s, 6H). MS (ESI) m/z 423 (M$^+$+H).

Compound 563

Synthesis of (4-(2-(2-hydroxypropan-2-yl)thiazol-4-yl)-2-(1H-1,2,4-triazol-1-yl)phenyl)(3,4,5-trimethoxyphenyl)methanone In the same manner as in the synthesis of Compound 464, Compound 563 was synthesized.

$^1$H NMR ($CDCl_3$) δ 8.56 (s, 1H), 8.24 (d, J=1.5 Hz, 1H), 8.09 (dd, J=8.0, 1.5 Hz, 1H), 7.97 (s, 1H), 7.67 (s, 1H), 7.64 (d, J=8.0 Hz, 1H), 6.97 (s, 2H), 3.89 (s, 3H), 3.83 (s, 6H), 1.75 (s, 6H). MS (ESI) m/z 481 (M$^+$+H).

Compound 564

Synthesis of (4-(2-(hydroxymethyl)thiazol-4-yl)-2-(1H-1,2,4-triazol-1-yl)phenyl)(3,4,5-trimethoxyphenyl)methanone In the same manner as in the synthesis of Compound 554, Compound 564 was synthesized.

$^1$H NMR (MeOH-d4+$CDCl_3$) δ 8.53 (s, 1H), 8.20 (d, J=1.6 Hz, 1H), 8.08 (dd, J=8.0, 1.6 Hz, 1H), 7.93 (s, 1H), 7.78 (s, 1H), 7.65 (d, J=8.0 Hz, 1H), 6.99 (s, 2H), 4.96 (s, 2H), 3.89 (s, 3H), 3.81 (s, 6H). MS (ESI) m/z 453 (M$^+$+H).

Compound 568

Synthesis of (3-(thiophen-3-yl)phenyl)(3,4,5-trimethoxyphenyl)methanone

First, magnesium was added to 1-bromo-3,4,5-trimethoxybenzene as a starting material, as shown in Reaction 6, and then 3-bromobenzaldehyde was added thereto to obtain a compound. Thus obtained compound was oxidized using PDC to obtain a Compound 21 derivative [(3-bromophenyl)(3,4,5-trimethoxyphenyl)methanone]. Thus obtained compound and thiophen-3-boronic acid were subjected to the Suzuki reaction, in the same manner as in the synthesis of Compound 457, to obtain Compound 568.

MS (ESI) m/z 355 (M$^+$+H).

Compound 570

Synthesis of (3-(2-aminothiazol-4-yl)phenyl)(3,4,5-trimethoxyphenyl)methanone

Using (3-bromophenyl)(3,4,5-trimethoxyphenyl)methanone, which is a synthetic intermediate of Compound 568, as a starting material, aminothiazole was introduced in the same manner as in the synthesis of Compound 516 to obtain Compound 570.

MS (ESI) m/z 371 (M$^+$+H).

Compound 571

Synthesis of (4-(2-aminothiazol-4-yl)phenyl)(3,4,5-trimethoxyphenyl)methanone

First, magnesium was added to 1-bromo-3,4,5-trimethoxybenzene as a starting material, as shown in Reaction 6, and then 4-bromobenzaldehyde was added thereto to obtain a compound. Thus obtained compound was oxidized using PDC to obtain a Compound 21 derivative [(4-bromophenyl)

(3,4,5-trimethoxyphenyl)methanone]. Using thus obtained compound as a starting material aminothiazole was introduced in the same manner as in the synthesis of Compound 516 to obtain Compound 571 in a form of a white solid.

$^1$H NMR (Acetone-d6) δ 8.12 (d, J=8.3 Hz, 2H), 7.92 (d, J=8.6 Hz, 2H), 7.46 (s, 1H), 7.12 (s, 2H), 3.87 (s, 6H), 3.84 (s, 3H).

Compound 581

Synthesis of (3-(thiazol-2-yl)phenyl(3,4,5-trimethoxyphenyl)methanone

First, magnesium was added to 1-bromo-3,4,5-trimethoxybenzene as a starting material, as shown in Reaction 6, and then 3-iodobenzoyl chloride was added thereto to obtain a Compound 21 derivative [(3-iodophenyl)(3,4,5-trimethoxyphenyl)methanone]. Thus obtained compound (88 mg, 0.250 mmol) was dissolved in tetrahydrofuran (2.5 ml), and 2-(tributylstannyl)thiazole (135 μl, 0.425 mmol) and Pd(PPh$_3$)$_2$Cl$_2$ (8.79 mg, 0.012 mmol) were slowly added thereto at room temperature. The mixture was refluxed for 2 hours. After completion of the reaction, the reaction mixture was diluted with EtOAc, and an aqueous sodium bicarbonate solution was added thereto. An organic layer was extracted out from the resulting solution. The organic layer was washed with water, and brine, and dried over anhydrous MgSO$_4$. The solid substance was filtered off, and the filtrate was vacuum concentrated. The resulting residue was purified by column chromatography (SiO$_2$, n-Hex/EA=2/1→1/1) to obtain Compound 581 (20 mg, 22%) in a form of a yellow solid.

$^1$H NMR (CDCl$_3$) δ 8.36 (dd, J=0.28 Hz, 1H), 8.21 (dt, J=4.76 Hz, 1H), 7.89 (d, J=3.36 Hz, 1H), 7.89~7.82 (m, 1H), 7.06~7.56 (m, 1H), 7.381 (d, J=3.28 Hz, 1H), 7.09 (s, 2H), 3.94 (s, 3H), 3.86 (s, 6H). MS (ESI) m/z 336 (M+1).

Compound 583

Synthesis of (2-methoxy-5-(thiazol-2-yl)phenyl)(3,4,5-trimethoxyphenyl)methanone First, magnesium was added to 1-bromo-3,4,5-trimethoxybenzene as a starting material, as shown in Reaction 6, and then 2-fluoro-5-iodobenzoyl chloride was added thereto to obtain a Compound 21 derivative [(2-fluoro-5-iodophenyl) (3,4,5-trimethoxyphenyl)methanone]. Using NaOMe, the fluoro group of thus obtained compound was substituted with a methoxy group to obtain (2-methoxy-5-iodophenyl)(3,4,5-trimethoxyphenyl)methanone. Thus obtained (2-methoxy-5-iodophenyl)(3,4,5-trimethoxyphenyl)methanone (320 mg, 0.75 mmol) was dissolved in tetrahydrofuran (50 ml), and 2-(tributylstannyl)thiazole (475 mg, 1.27 mmol) and Pd(PPh$_3$)$_2$Cl$_2$ (26 mg, 0.04 mmol) were slowly added thereto at room temperature. The mixture was heat refluxed for 8 hours. After completion of the reaction, the reaction mixture was extracted with water and EtOAc. The organic layer was washed with brine, and dried over anhydrous MgSO$_4$. The solid substance was filtered off, and the filtrate was vacuum concentrated. The resulting residue was purified by column chromatography (SiO$_2$, n-Hex/EA=1/2) to obtain Compound 583 (140 mg, 49%).

$^1$H NMR (CDCl$_3$) δ 8.11 (dd, J=2.32, 8.68 Hz, 1H), 7.93 (d, J=2.24 Hz, 1H), 7.83 (d, J=3.68 Hz, 1H), 7.30 (d, J=3.28 Hz, 1H), 7.13 (s, 21-H), 7.09 (d, J=8.68 Hz, 1H), 3.94 (s, 3H), 3.84 (s, 9H). MS (ESI) m/z 358 (M$^+$+H).

Compound 587

Synthesis of (3-(oxazol-2-yl)phenyl)(3,4,5-trimethoxyphenyl)methanone

In the same manner as in the synthesis of Compound 581, Compound 587 was obtained in a form of a white solid.

$^1$H NMR (CDCl$_3$) δ 8.45 (s, 1H), 8.29 (d, J=8 Hz, 1H), 7.89~7.87 (m, 1H), 7.82 (s, 1H), 7.77~7.75 (m, 1H), 7.35 (s, 1H), 7.08 (s, 2H), 3.9 (s, 3H), 3.87 (s, 6H). MS (ESI) m/z 340 (M+1).

Compound 588

Synthesis of (2-methoxy-5-(thiophen-3-yl)phenyl)(3,4,5-trimethoxyphenyl)methanone (2-Methoxy-5-iodophenyl)(3,4,5-trimethoxyphenyl) methanone, which is a synthetic intermediate of Compound 583, and thiophen-3-boronic acid were subjected to the Suzuki reaction, in the same manner as in the synthesis of Compound 457, to obtain Compound 588.

MS (ESI) m/z 385 (M$^+$+H).

Compound 590

Synthesis of (2-methoxy-5-(oxazol-2-yl)phenyl)(3,4,5-trimethoxyphenyl)methanone

In the same manner as in the synthesis of Compound 583, Compound 590 was obtained.

$^1$H NMR (CDCl$_3$) δ 8.17 (dd, J=2.20, 8.72 Hz, 1H), 8.02 (d, J=2.16 Hz, 1H), 7.69 (s, 1H), 7.11 (s, 2H), 3.94 (s, 3H), 3.85 (s, 3H), 3.84 (s, 6H). MS (ESI) m/z 370 (M$^+$+H).

Compound 591

Synthesis of (3-(1H-pyrrol-2-yl)phenyl)(3,4,5-trimethoxyphenyl)methanone (3-Iodophenyl)(3,4,5-trimethoxyphenyl)methanone, which is which is a synthetic intermediate of Compound 581, and (1-(tert-butoxycarbonyl)-1H-pyrrole-2-yl)boronic acid were subjected to the Suzuki reaction in the same manner as in the synthesis of Compound 457 to obtain Compound 591.

MS (ESI) m/z 338 (M$^+$+H).

Compound 594

Synthesis of (2-methoxy-5-(thiophen-2-yl)phenyl)(3,4,5-trimethoxyphenyl)methanone In the same manner as in the synthesis of Compound 583, Compound 594 was obtained.

$^1$H NMR (CDCl$_3$) δ 7.71 (dd, J=2.36, 8.62 Hz, 1H), 7.59 (d, J=2.36 Hz, 1H), 7.25 (m, 2H), 7.14 (s, 2H), 7.06 (m, 2H), 3.95 (s, 3H), 3.85 (s, 6H), 3.81 (s, 3H). MS (ESI) m/z 385 (M$^+$+H).

Compound 595

Synthesis of (2-methoxy-5-(methylthiazol-4-yl)phenyl)(3,4,5-trimethoxyphenyl)methanone (2-Fluoro-5-(2-methylthiazol-4-yl)phenyl)(3,4,5-trimethoxyphenyl)methanone (50 mg, 0.13 mmol) as a synthetic intermediate of Compound 596 was dissolved in NaOMe (2 ml) and methanol (5 ml). The solution was heat refluxed for 3 hours. After completion of the reaction, the reaction solution was extracted with water and dichloromethane, and the organic layer was vacuum concentrated.

The resulting residue was purified by column chromatography (SiO$_2$, n-Hex/EA=1/1) to obtain Compound 595 (41 mg, 80%).

MS (ESI) m/z 400 (M$^+$+H).

Compound 596

Synthesis of (5-(2-methylthiazol-4-yl)-2-(1H-1,2,4-triazol-1-yl)phenyl)(3,4,5-trimethoxyphenyl)methanone 1,2,4-Triazole was added to (2-fluoro-5-(2-methylthiazol-4-yl)phenyl) (3,4,5-trimethoxyphenyl)methanone obtained in the same manner as in the synthesis of Compound 463 to synthesize Compound 596.

$^1$H NMR (Acetone-d6) δ 8.71 (s, 1H), 8.35 (dd, J=8.4, 2.0 Hz, 1H), 8.23 (d, J=2.0 Hz, 1H), 8.02 (s, 1H), 7.84 (d, J=8.4 Hz, 1H), 7.84 (s, 1H), 7.01 (s, 2H), 3.78 (s, 9H), 2.75 (s, 3H). MS (ESI) m/z 437 (M$^+$+H).

Compound 597

Synthesis of (2-amino-5-(1H-pyrrol-2-yl)phenyl)(3,4,5-trimethoxyphenyl)methanone In the same manner as in the synthesis of Compound 457, Compound 19 shown in Reaction 5 and (1-(tert-butoxycarbonyl)-1H-pyrrole-2-yl)boronic acid were subjected to the Suzuki reaction to obtain N-(4-(1H-pyrrole-2-yl)-2-(3,4,5-trimethoxybenzoyl)phenyl)acetamide. Thus obtained N-(4-(1H-pyrrole-2-yl)-2-(3,4,5-trimethoxybenzoyl)phenyl)acetamide (20 mg, 0.05 mmol) was dissolved in methanol (3 ml), and NaOMe (30 µl, 0.5 mmol, 1.0 M/tetrahydrofuran) was added thereto at room temperature. The mixture was refluxed with stirring for 3 hours at 80° C. After completion of the reaction, the reaction mixture was cooled to room temperature, and diluted with an EtOAc solution. The organic layer was washed with water, and brine. The extracted organic layer was dried over anhydrous MgSO$_4$, and the solid substance was filtered off. The filtrate was vacuum concentrated. The resulting residue was purified by column chromatography (SiO$_2$, n-Hex/EA=2/1→1/2) to obtain Compound 597 (8 mg, 45%) in a form of a yellow solid.

$^1$H NMR (CDCl$_3$) δ 7.74 (s, 1H), 7.62-7.60 (m, 1H), 6.97 (s, 1H), 6.92 (d, J=8.64 Hz, 1H), 6.69~6.68 (m, 1H), 6.61 (s, 1H), 6.26~6.25 (m, 1H), 6.07~6.05 (m, 1H), 3.86~3.82 (m, 9H). MS (ESI) m/z 353 (M+1).

Compound 598

Synthesis of (2-methoxy-5-(1H-pyrazol-5-yl)phenyl)(3,4,5-trimethoxyphenyl)methanone In the same manner as in the synthesis of Compound 457, (2-methoxy-5-iodophenyl)(3,4,5-trimethoxyphenyl)methanone as a synthetic intermediate Compound 583 and pyrazoleboronic acid pinacole ester were subjected to the Suzuki reaction to obtain Compound 598.

MS (ESI) m/z 369 (M$^+$+H).

Compound 599

Synthesis of (4-(1H-pyrrol-2-yl)-2-(1H-1,2,4-triazol-1-yl)phenyl)(3,4,5-trimethoxyphenyl)methanone In the same manner as in the synthesis of Compound 443 shown in Reaction 6, Compound 599 was obtained.

MS (ESI) m/z 405 (M$^+$+H).

Compound 601

Synthesis of (2-hydroxy-5-(thiazol-2-yl)phenyl)(3,4,5-trimethoxyphenyl)methanone In the same manner as in the synthesis of Compound 240, Compound 601 was obtained.

MS (ESI) m/z 372 (M$^+$+H).

Compound 602

Synthesis of (4-(oxazol-2-yl)-2-(1H-1,2,4-triazol-1-yl)phenyl)(3,4,5-trimethoxyphenyl)methanone In the same manner as in, the synthesis of Compound 443 shown in Reaction 6, Compound 602 was obtained.

$^1$H NMR (CDCl$_3$) δ 8.53 (s, 1H), 8.36 (s, 1H), 8.27 (dd, J=1.16, 8.04 Hz, 1H), 8.01 (s, 1H), 7.84 (s, 1H), 7.72 (d, J=8.00 Hz, 1H), 7.37 (s, 1H), 6.99 (s, 2H), 3.93 (s, 3H), 3.86 (s, 6H). MS (ESI) m/z 407 (M$^+$+H).

Active Measurement-Experiment Protocol for Compounds of the Present Invention

1. Inhibition Effect of HL60 Cell Line Growth

A 10% FBS-contained RPMI1640 badge was used for culturing HL60 cells. The test substance was prepared by dissolving in DMSO to a concentration of 10 mg/ml, and continuously diluting with PBS to a final concentration of 100 µg/ml to 0.03 µg/ml. In a 96-well microplate, 180 µl of the badge containing 6.0×10$^4$ cells/ml of cells and 20 µl of continuously diluted test substance were added. The mixture was cultured at 37° C. with 5% CO$_2$ atmosphere for 3 days. After completion of the cultivation, 50 µl of a solution of 1.25 mg/ml MTT (3-(4,5-dimethylthiazol-2-yl)-2,5-diphenyltetrazolium bromide) dissolved in PBS was added to all wells, and the resulting mixture was reacted at 37° C. for 3 hours. Thus formed formazan crystals were dissolved in 150 µl of DMSO, and an absorbance was measured at 570 nm.

2. Inhibition Effect of Tubulin Polymerization

In order to measure the inhibition effect of a tubulin polymer formation, HTS-Tubulin Polymerization Assay Kit (Cytoskeleton, CDS01) was used, and a turbidity was measured using Molecular Device SPECTRA MAX Plus model. The test substance was dissolved in DMSO, and then diluted. All reagents were added to a microplate, which has been cooled to 0° C. An absorbance measured at 340 nm was standardized. The polymerization was carried out at 37° C.

(See *J. Med. Chem.*, 42, 3789-3799, 1999; *Cancer Res.*, 64, 4621-4628, 2004; *Mol. Pharmacol.*, 65, 77-84, 2004)

The following Tables 11 to 13 are lists of anticancer activity and inhibition effect of a microtubule formation of each compound.

TABLE 11

| Compound | HL60 Growth Inhibition (μM) | Tubulin Polymerization Inhibition (μM) |
|---|---|---|
| 200 | 0.13 | |
| 203 | 0.035 | 3.2 |
| 206 | 0.145 | |
| 209 | 0.54 | |
| 213 | 0.137 | 5.9 |
| 224 | 0.11 | 2.5 |
| 225 | 0.058 | 8.07 |
| 226 | 0.37 | 1.07 |
| 231 | 0.12 | 3.03 |
| 235 | 0.28 | 4.47 |
| 237 | 0.27 | 6.03 |
| 238 | 0.34 | 6.74 |
| 241 | 0.09 | 4.48 |
| 249 | 0.12 | 6.68 |
| 264 | 0.48 | 8.23 |
| 265 | 0.39 | 7.43 |
| 269 | 1.69 | 7.92 |
| 272 | 1.34 | >10 |
| 277 | 0.11 | |
| 278 | 0.03 | 3.91 |
| 279 | 0.13 | |
| 282 | 0.15 | |
| 283 | 0.048 | |
| 286 | 0.07 | 1.34 |
| 289 | 0.007 | 2.31 |
| 293 | 0.017 | |
| 296 | 1.23 | 1.33 |
| 294 | 0.10 | |
| 297 | 0.035 | 3.61 |
| 298 | 0.16 | 2.60 |
| 300 | 0.17 | |
| 301 | 0.08 | |
| 308 | 0.19 | 2.51 |
| 316 | 0.14 | 1.39 |
| 322 | 0.17 | 2.37 |
| 323 | 0.17 | 2.01 |
| 327 | 0.09 | |
| 335 | 0.22 | 5.57 |
| 337 | 0.19 | |
| 341 | 0.11 | 4.33 |
| 346 | 0.10 | 3.37 |
| 347 | 0.03 | 3.22 |
| 348 | 0.10 | 3.95 |
| 354 | 0.11 | |
| 359 | 0.10 | 7.71 |
| 363 | 0.11 | 2.47 |

TABLE 12

| Compound | HL60 Growth Inhibition (μM) | Tubulin Polymerization Inhibition (μM) |
|---|---|---|
| 365 | 0.07 | 1.84 |
| 372 | 0.11 | 8.57 |
| 374 | 0.1 | 2.15 |
| 375 | 0.04 | 1.70 |
| 379 | 0.11 | 5.41 |
| 380 | 0.11 | 3.11 |
| 391 | 0.12 | 3.45 |
| 399 | 0.11 | |
| 401 | 0.03 | 2.66 |
| 409 | 0.03 | 3.31 |
| 410 | 0.10 | |
| 442 | 0.033 | 4.51 |
| 443 | 0.08 | |
| 446 | 0.17 | 5.53 |
| 455 | 3.10 | |
| 457 | 11.58 | |
| 458 | 3.18 | |
| 462 | 0.033 | 4.64 |
| 464 | 0.09 | 8.70 |
| 476 | 0.025 | |
| 479 | 0.025 | |
| 484 | 4.24 | |
| 486 | 0.16 | |
| 494 | 0.12 | |
| 506 | 0.16 | |
| 511 | 0.10 | |

TABLE 13

| Compound | HL60 Growth Inhibition (μM) |
|---|---|
| 519 | 25 |
| 525 | 0.09 |
| 531 | 0.33 |
| 534 | 0.06 |
| 538 | 0.28 |
| 547 | 0.03 |
| 550 | 0.02 |
| 554 | 0.09 |
| 560 | 0.09 |
| 561 | 0.32 |
| 562 | 0.08 |
| 563 | 0.25 |
| 564 | 0.09 |
| 568 | 0.36 |
| 570 | 0.12 |
| 571 | 0.11 |
| 581 | 0.04 |
| 583 | 0.01 |
| 587 | 0.04 |
| 588 | 0.12 |
| 590 | 0.01 |
| 591 | 0.20 |
| 594 | 0.12 |
| 595 | 0.12 |
| 596 | 0.23 |
| 597 | 0.22 |
| 598 | 0.39 |
| 599 | 0.14 |
| 601 | 0.09 |
| 602 | 0.17 |

INDUSTRIAL APPLICABILITY

As seen from the above, the benzophenone derivative according to the present invention has an inhibition activity of microtubule formation, and can be used as a therapeutic agent for malignant tumors by killing the actively proliferating cells, viral or bacterial infections, vascular restenosis, inflammatory diseases, autoimmune diseases, and psoriasis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A compound represented by the following formula 1, a pharmaceutically acceptable salt thereof:

[Formula 1]

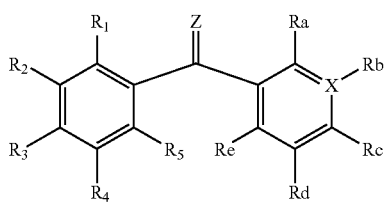

wherein,
$R_1$, $R_2$, $R_3$, $R_4$, and $R_5$ may be identical to or different from each other, may form a dioxane or dioxolane ring by connecting with adjacent carbons; wherein,
$R_1$, $R_3$ and $R_5$ are each independently hydrogen, hydroxyl, hydroxyalkyl, fluoro, bromo, chloro, substituted or unsubstituted $C_{1-6}$ alkyl, $C_{1-3}$ alkoxy, formyl, [1,3]dioxane, or a functional group represented by the following structural formula 1,

[Structural Formula 1]

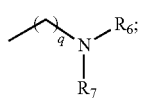

$R_2$ and $R_4$ are each independently hydroxyl, hydroxyalkyl, fluoro, bromo, chloro, substituted or unsubstituted $C_{1-6}$ alkyl, $C_{1-3}$ alkoxy, formyl, [1,3]dioxane, or a functional group represented by the structural formula 1;
wherein, q is 1 or 2, and $R_6$ and $R_7$ are each independently hydrogen or $C_{1-3}$ alkyl;
Z is O;
X is C or N, provided that when X is C, Rb is hydrogen, $C_{1-3}$ alkoxy, substituted or unsubstituted $C_{1-6}$ alkyl, or a functional group represented by the structural formula 1, and when X is N, Rb does not exist;
Ra is fluoro, —$CONH_2$, —COOH, nitro, —O—$R_9$ (wherein, $R_9$ is hydrogen, substituted or unsubstituted $C_{1-6}$ alkyl, phenyl, —$SO_2$—$R_{10}$, or —$CO_2R_{10}$, wherein $R_{10}$ is substituted or unsubstituted $C_{1-6}$ alkyl, or substituted or unsubstituted phenyl), —CO—$R_{10}$ or —COO—$R_{10}$ (wherein, $R_{10}$ is the same as defined above), or a functional group represented by the following structural formula 3,

[Structural formula 3]

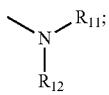

wherein, $R_{11}$ and $R_{12}$ are each independently hydrogen, formyl, $C_{1-3}$ alkoxy, pyridine, pyrimidine, substituted or unsubstituted $C_{1-6}$ alkyl, hydroxyalkyl, —CO—$R_{10}$, —COO—$R_{10}$, or —$SO_2$—$R_{10}$, wherein $R_{10}$ is the same as defined above,
or a $C_5$ or $C_6$ heterocyclic ring containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, thiol, amino, nitro, thiomethyl, carboxylic acid, methylcarboxylate, —$CF_3$, or —$NR_{13}R_{14}$, wherein $R_{13}$ and $R_{14}$ are each independently hydrogen, substituted or unsubstituted $C_{1-6}$ alkyl, hydroxyalkyl, CO—$R_{10}$, —COO—$R_{10}$, or —$SO_2$—$R_{10}$, wherein $R_{10}$ is the same as defined above);
Rc and Rd are each independently hydrogen, a $C_5$ or $C_6$ heterocyclic ring containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, or —$NR_{13}R_{14}$, wherein $R_{13}$ and $R_{14}$ are the same as defined above, and the ring may not have two oxygen), or a $R_{15}$-substituted phenyl (wherein, $R_{15}$ is hydroxyl, nitro, substituted or unsubstituted $C_{1-6}$ alkyl, $C_{1-3}$ alkoxy, fluoro, nitrile, —$NR_{11}R_{12}$, —COO—$R_{10}$, or —$SO_2$—$R_{10}$, wherein $R_{10}$, $R_{11}$, and $R_{12}$ are the same as defined above), provided that Rc and Rd may not be hydrogen simultaneously; and
Re is hydrogen or halogen.

2. The compound according to claim 1, which is a compound represented by the following formula 1, a pharmaceutically acceptable salt thereof:

[Formula I]

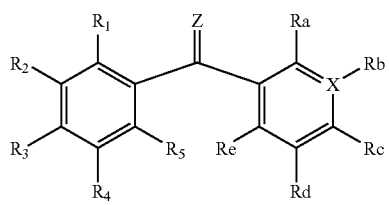

wherein, $R_1$, $R_2$, $R_3$, $R_4$, and $R_5$ may be identical to or different from each other;
$R_1$, $R_2$, $R_4$, and $R_5$ are each independently hydroxyl, hydroxyalkyl, fluoro, bromo, substituted or unsubstituted $C_{1-6}$ alkyl, $C_{1-3}$ alkoxy, formyl, or a functional group represented by the following structural formula 1,

[Structural Formula 1]

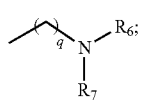

$R_3$ is selected from the group consisting of hydroxyl, hydroxyalkyl, fluoro, bromo, substituted $C_{1-6}$ alkyl, $C_{1-3}$ alkoxy, formyl, or a functional group represented by the structural formula 1.
wherein, q is 1 or 2, and $R_6$ and $R_7$ are each independently hydrogen or $C_{1-3}$ alkyl;
Z is O;
X is C or N, provided that when X is C, Rb is hydrogen, $C_{1-3}$ alkoxy, substituted or unsubstituted $C_{1-6}$ alkyl, or a functional group represented by the structural formula 1, and when X is N, Rb does not exist;
Ra is fluoro, —$CONH_2$, —COOH, nitro, —O—$R_9$ (wherein, $R_9$ is hydrogen, substituted or unsubstituted $C_{1-6}$ alkyl, —$SO_2$—$R_{10}$, or —$CO_2R_{10}$, wherein $R_{10}$ is substituted or unsubstituted $C_{1-6}$ alkyl, or substituted or unsubstituted phenyl), or a functional group represented by the following structural formula 3,

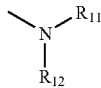

[Structural formula 3]

wherein, $R_{11}$ and $R_{12}$ are each independently hydrogen, formyl, $C_{1-3}$ alkoxy, pyridine, pyrimidine, substituted or unsubstituted $C_{1-6}$ alkyl, hydroxyalkyl, —CO—$R_{10}$, —COO—$R_{10}$, or —$SO_2$—$R_{10}$, wherein $R_{10}$ is the same as defined above, or a $C_5$ or $C_6$ heterocyclic ring containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, amino, nitro, thiomethyl, carboxylic acid, methylcarboxylate, —$CF_3$, or —$NR_{13}R_{14}$, wherein $R_{13}$ and $R_{14}$ are each independently hydrogen, substituted or unsubstituted $C_{1-6}$ alkyl);

Rc and Rd are each independently hydrogen, a $C_5$ or $C_6$ heterocyclic ring containing at least one hetero atom selected from the group consisting of O, S, and N (the ring may not have a substituent, or may be arbitrarily substituted with at least one of substituted or unsubstituted $C_{1-6}$ alkyl, $C_{1-3}$ alkoxy, or —$NR_{13}R_{14}$, wherein $R_{13}$ and $R_{14}$ are the same as defined above, and the ring may not have two oxygen), or a $R_{15}$—substituted phenyl (wherein, $R_{15}$ is hydroxyl, nitro, substituted or unsubstituted $C_{1-6}$ alkyl, $C_{1-3}$ alkoxy, fluoro, nitrile, —$NR_{11}R_{12}$, —COO—$R_{10}$, or —$SO_2$—$R_{10}$, wherein $R_{10}$, $R_{11}$, and $R_{12}$ are the same as defined above), provided that Rc and Rd may not be hydrogen simultaneously; and Re is hydrogen.

3. The compound according to claim 1, a pharmaceutically acceptable salt thereof, wherein Rc or Rd is a functional group selected from the group consisting of the following structural formulas,

[Structural Formula 4]

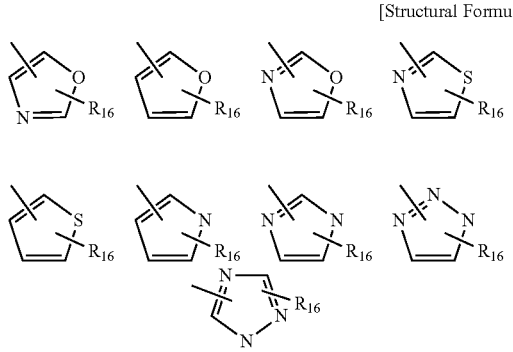

wherein, $R_{16}$ is hydrogen, amino, or $C_{1-3}$ alkyl.

4. The compound according to claim 1, a pharmaceutically acceptable salt thereof, wherein Rc or Rd is a functional group selected from the group consisting of the following structural formula,

[Structural Formula 5]

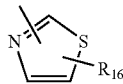

wherein, $R_{16}$ is the same as defined above.

5. The compound according to claim 1, a pharmaceutically acceptable salt thereof, wherein Rc or Rd is a functional group selected from the group consisting of the following structural formulas,

[Structural Formula 6]

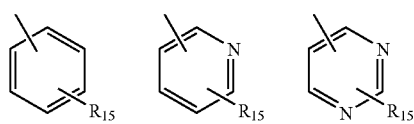

wherein, $R_{15}$ is the same as defined above.

6. The compound according to claim 1, a pharmaceutically acceptable salt thereof, wherein Ra is a functional group selected from the group consisting of the following structural formulas,

[Structural Formula 7]

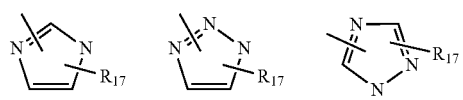

wherein, $R_{17}$ is hydrogen, substituted or unsubstituted $C_{1-6}$ alkyl, $C_{1-3}$ alkoxy, thiol, amino, nitro, thiomethyl, carboxylic acid, methylcarboxylate, or $CF_3$.

7. The compound according to claim 1, a pharmaceutically acceptable salt thereof, wherein Ra is a functional group selected from the group consisting of the following structural formulas,

[Structural Formula 7]

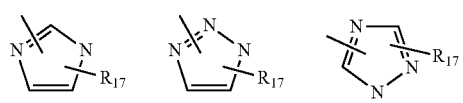

wherein, $R_{17}$ is hydrogen, methyl, amino, nitro, thiomethyl, carboxylic acid, methylcarboxylate, or $CF_3$, wherein Rc or Rd is a functional group selected from the group consisting of the following structural formulas,

[Structural Formula 8]

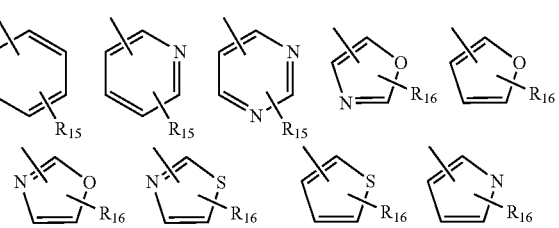

-continued

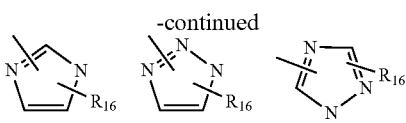

wherein, $R_{15}$ is hydrogen, hydroxyl, nitro, substituted or unsubstituted $C_{1-6}$ alkyl, $C_{1-3}$ alkoxy, fluoro, nitrile, —$NR_{11}R_{12}$, —COO—$R_{10}$, or —$SO_2$—$R_{10}$, wherein $R_{11}$, and $R_{12}$ are each independently the same as defined above; and $R_{16}$ is hydrogen or $C_{1-3}$ alkyl.

8. The compound according to claim 1, a pharmaceutically acceptable salt thereof, wherein Ra is a functional group selected from the group consisting of the following structural formula,

[Structural formula 3]

wherein, $R_{11}$ and $R_{12}$ are each independently the same as defined above, wherein Rc or Rd is a functional group selected from the group consisting of the following structural formulas,

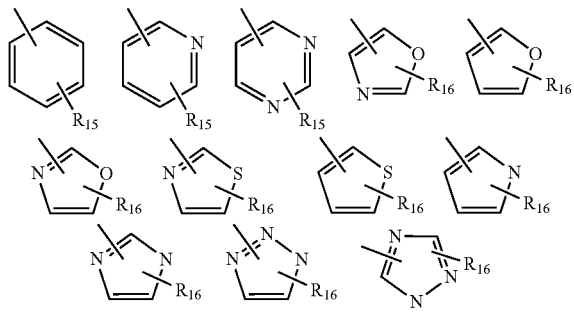
[Structural Formula 8]

wherein, $R_{15}$ and $R_{16}$ are each independently the same as defined above.

9. The compound according to claim 1, a pharmaceutically acceptable salt thereof, wherein Ra is a functional group selected from the group consisting of the following structural formula

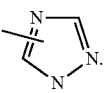
[Structural Formula 9]

10. The compound according to claim 1, a pharmaceutically acceptable salt thereof, wherein Ra is $NH_2$.

11. The compound according to claim 1, a pharmaceutically acceptable salt thereof, wherein Ra is $C_{1-3}$ alkoxy.

12. The compound according to claim 1, a pharmaceutically acceptable salt thereof, wherein $R_1$, $R_2$, $R_3$, $R_4$ and $R_5$ are each independently fluorine.

13. The compound according to claim 1, a pharmaceutically acceptable salt thereof, wherein $R_2$, $R_3$ and $R_4$ are each independently methoxy.

14. The compound according to claim 1, wherein the compound is selected from the following compounds, a pharmaceutically acceptable salt thereof:

Compound 200
(2-methoxy-5-(pyridin-3-yl)phenyl)(3,4,5-trimethoxyphenyl)methanone;

Compound 203
(5-(furan-2-yl)-2-methoxyphenyl)(3,4,5-trimethoxyphenyl)methanone;

Compound 206
(5-(furan-2-yl)-2,3-dimethoxyphenyl)(3,4,5-trimethoxyphenyl)methanone;

Compound 207
(2,3-dimethoxy-5-(pyridin-3-yl)phenyl)(3,4,5-trimethoxyphenyl)methanone;

Compound 211
(4-methoxy-5'-nitrobiphenyl-3-yl)(3,4,5-trimethoxyphenyl)methanone;

Compound 212
(5'-amino-4-methoxybiphenyl-3-yl)(3,4,5-trimethoxyphenyl)methanone;

Compound 213
(4,4'-dimethoxybiphenyl-3-yl)(3,4,5-trimethoxyphenyl)methanone;

Compound 214
(4,6'-dimethoxybiphenyl-3-yl)(3,4,5-trimethoxyphenyl)methanone;

Compound 216
(4-ethoxy-4'-methoxybiphenyl-3-yl)(3,4,5-trimethoxyphenyl)methanone;

Compound 218
(6'-hydroxy-4-methoxybiphenyl-3-yl)(3,4,5-trimethoxyphenyl)methanone;

Compound 220
(4-hydroxy-4'-methoxybiphenyl-3-yl)(3,4,5-trimethoxyphenyl)methanone;

Compound 223
(4'-methoxy-4-nitrobiphenyl-3-yl)(3,4,5-trimethoxyphenyl)methanone;

Compound 224
(5-(furan 2-yl)-2-nitrophenyl)(3,4,5-trimethoxyphenyl)methanone;

Compound 225
(2-amino-5-(furan-2-yl)phenyl)(3,4,5-trimethoxyphenyl)methanone;

Compound 226
(4-amino-4'-methoxybiphenyl-3-yl)(3,4,5-trimethoxyphenyl)methanone;

Compound 228
(4-methoxy-3-(3,4,5-trimethoxybenzoyl)phenyl)-1H-pyrrol-1-carboxylic acid tert-butyl ester, Compound 229
(2-methoxy-5-(1H pyrrol-2-yl)phenyl)(3,4,5-trimethoxyphenyl)methanone;

Compound 231
N-(4-(furan-2-yl)-2-(3,4,5-trimethoxybenzoyl)phenyl)acetamide;

Compound 232
(2-(benzylamino)-5-(furan-2-yl)phenyl)(3,4,5-trimethoxyphenyl)methanone;

Compound 233
(3-(1,3-dioxan-2-yl)-4,5-dimethoxyphenyl)(5-(furan-2-yl)-2-methoxyphenyl)methanone;

Compound 234
5-(5-(furan-2-yl)-2-methoxybenzoyl)-2,3-dimethoxybenzaldehyde;

Compound 235
N-(4-(furan-2-yl)-2-(3,4,5-trimethoxybenzoyl)phenyl)methanesulfonamide;
Compound 236
4-(4-(furan-2-yl)-2-(3,4,5-trimethoxybenzoyl)phenylamino)-4-oxobutanoic acid;
Compound 237
2-amino-N-(4-(furan-2-yl)-2-(3,4,5-trimethoxybenzoyl)phenyl)acetamide;
Compound 238
(2-(allylamino)-5-(furan-2-yl)phenyl)(3,4,5-trimethoxyphenyl)methanone;
Compound 239
(R)-2-amino-N-(4-(furan-2-yl)-2-(3,4,5-trimethoxybenzoyl)phenyl)-3-methylbutanamide;
Compound 240
(5-(furan-2-yl)-2-hydroxyphenyl)(3,4,5-trimethoxyphenyl)methanone;
Compound 241
methanesulfonic acid 4-(furan-2-yl)-2-(3,4,5-trimethoxybenzoyl)phenyl;
Compound 242
(2-(2-(dimethylamino)ethoxy)-5-(furan-2-yl)phenyl)(3,4,5-trimethoxyphenyl)methanone;
Compound 243
2-(4-furan-2-yl)-2-(3,4,5-trimethoxybenzoyl)phenoxy)acetic acid methyl ester;
Compound 244
2-(4-(furan-2-yl)-2-(3,4,5-trimethoxybenzoyl)phenoxy)acetic acid;
Compound 247
(3,4-dimethoxyphenyl)(5-(furan-2-yl)-2-methoxyphenyl)methanone;
Compound 249
(5-(furan-2-yl)-2-methoxyphenyl)(3-(hydroxymethyl)-4,5-dimethoxyphenyl)methanone;
Compound 253
(4,5-dimethoxy-3-((methylamino)methyl)phenyl)(5-furan-2-yl)-2-methoxyphenyl)methanone;
Compound 257
(3-((dimethylamino)methyl)-4-hydroxy-5-methoxyphenyl)(5-(furan-2-yl)-2-methoxyphenyl)methanone;
Compound 262
(5-(furan-2-yl)-2,4-dimethoxyphenyl)(3,4,5-trimethoxyphenyl)methanone;
Compound 263
(3-((dimethylamino)methyl)-4,5-dimethoxyphenyl)(5-(furan-2-yl)-2-methoxyphenyl)methanone;
Compound 264
(5-(furan-2-yl)-2-methoxyphenyl)(4-methoxy-3,5-dimethylphenyl)methanone;
Compound 265
(5-(furan-2-yl)-2-methoxyphenyl)(4-(methoxymethoxy)-3,5-dimethylphenyl)methanone;
Compound 266
(5-(furan-2-yl)-2-methoxyphenyl)(4-hydroxy-3,5-dimethylphenyl)methanone;
Compound 267
(4-(2-(dimethylamino)ethoxy)-3,5-dimethylphenyl)(5-(furan-2-yl)-2-methoxyphenyl)methanone;
Compound 268
(4-(allyloxy)-3-methoxyphenyl)(5-(furan-2-yl)-2-methoxyphenyl)methanone;
Compound 269
(3-allyl-4-hydroxy-5-methoxyphenyl)(5-(furan-2-yl)-2-methoxyphenyl)methanone;
Compound 271
N-(5-(1H-1,2,4-triazol-1-yl)-2-(3,4,5-trimethoxybenzoyl)phenyl)acetamide;
Compound 272
(2-amino-4-(1H-1,2,4-triazol-1-yl)phenyl)(3,4,5-trimethoxyphenyl)methanone;
Compound 273
2-(4-acetamido-3-(3,4,5-trimethoxybenzoyl)phenyl)-1H-pyrrol-1-carboxylic acid tert-butyl ester;
Compound 274
N-(4-(1H-pyrrol-2-yl)-2-(3,4,5-trimethoxybenzoyl)phenyl)acetamide;
Compound 275
(3-allyl-4,5-dimethoxyphenyl)((5-furan-2-yl)-2-methoxyphenyl)methanone;
Compound 276
(3-(2,3-dihydroxypropyl)-4,5-dimethoxyphenyl)(5-(furan-2-yl)-2-methoxyphenyl)methanone;
Compound 277
N-(4-(thiazol-2-yl)-2-(3,4,5-trimethoxybenzoyl)phenyl)acetamide;
Compound 278
(2-amino-5-(thiazol-2-yl)phenyl)(3,4,5-trimethoxyphenyl)methanone;
Compound 279
N-(4-(thiophen-2-yl)-2-(3,4,5-trimethoxybenzoyl)phenyl)acetamide;
Compound 281
N-(4-(furan-2-yl)-2-(3,4,5-trimethoxybenzoyl)phenyl)-N-methylacetamide;
Compound 282
(5-(furan-2-yl)-2-(methylamino)phenyl)(3,4,5-trimethoxyphenyl)methanone;
Compound 283
(2-amino-5-(thiophen-2-yl)phenyl)(3,4,5-trimethoxyphenyl)methanone;
Compound 284
(2-amino-5-(oxazol-5-yl)phenyl)(3,4,5-trimethoxyphenyl)methanone;
Compound 285
N-(2-(3-(hydroxymethyl)-4,5-dimethoxybenzoyl)-4-(thiazol-2-yl)phenyl)acetamide;
Compound 286
(2-amino-5-(thiazol-2-yl)phenyl)(3-(hydroxymethyl)-4,5-dimethoxyphenyl)methanone;
Compound 289
(2-amino-5-(oxazol-2-yl)phenyl)(3,4,5-trimethoxyphenyl)methanone;
Compound 290
(5-(1H-imidazol-1-yl)-2-nitrophenyl)(3,4,5-trimethoxyphenyl)methanone;
Compound 291
(2-nitro-5-(1H-1,2,4-triazol-1-yl)phenyl)(3,4,5-trimethoxyphenyl)methanone;
Compound 293
(2-amino-5-(pyridin-2-yl)phenyl)(3,4,5-trimethoxyphenyl)methanone;
Compound 294
N-(4-(2-aminothiazol-5-yl)-2-(3,4,5-trimethoxybenzoyl)phenyl)acetamide;
Compound 295
N-(4-(2-methylthiazol-5-yl)-2-(3,4,5-trimethoxybenzoyl)phenyl)acetamide;
Compound 296
N-(4-(oxazol-2-yl)-2-(3,4,5-trimethoxybenzoyl)phenyl)acetamide;

Compound 297
2-amino-5-(2-aminothiazol-4-yl)phenyl)(3,4,5-tri-methoxyphenyl)methanone;
Compound 298
(2-amino-5-(2-methylthiazol-4-yl)phenyl)(3,4,5-tri-methoxyphenyl)methanone;
Compound 300
N-(4-(thiophen 3-yl)-2-(3,4,5-trimethoxybenzoyl)phenyl)acetamide;
Compound 301
(2-amino-5-(thiophen-3-yl)phenyl)(3,4,5-trimethoxyphenyl)methanone;
Compound 302
N-(4-(6-methoxypyridin-2-yl)-2-(3,4,5-trimethoxybenzoyl)phenyl)acetamide;
Compound 303
(2-amino-5-(6-methoxypyridin-2-yl)phenyl)(3,4,5-tri-methoxyphenyl)methanone;
Compound 306
(5-(furan-2-yl)-2-phenoxyphenyl)(3,4,5-trimethoxyphenyl)methanone;
Compound 307
N-(4-(thiazol-2-yl)-2-(3,4,5-trimethoxybenzoyl)phenyl)propionamide;
Compound 308
N-(4-(thiazol-2-yl)-2-(3,4,5-trimethoxybenzoyl)phenyl)methanesulfonamide;
Compound 309
4-(thiazol-2-yl)-2-(3,4,5-trimethoxybenzoyl)phenylcarboxylic acid methyl ester;
Compound 311
N-(4-(1-methyl-1H-imidazol-2-yl)-2-(3,4,5-trimethoxybenzoyl)phenyl)acetamide;
Compound 312
(2-amino-5-(1-methyl-1H-imidazol-2-yl)phenyl)(3,4,5-trimethoxyphenyl)methanone;
Compound 313
N-(4-(1H-pyrazol-5-yl)-2-(3,4,5-trimethoxybenzoyl)phenyl)acetamide;
Compound 314
3-chloro-N-(4-(thiazol-2-yl)-2-(3,4,5-trimethoxybenzoyl)phenyl)propanamide;
Compound 315
4-(thiazol-2-yl)-2-(3,4,5-trimethoxybenzoyl)phenylcarboxylic acid isobutyl ester;
Compound 316
N-(4-(thiazol-2-yl)-2-(3,4,5-trimethoxybenzoyl)phenyl)formamide;
Compound 317
(5-(furan-2-yl)-2-(4-methylpiperazin-1-yl)phenyl)(3,4,5-trimethoxyphenyl)methanone;
Compound 320
4-(thiazol-2-yl)-2-(3,4,5-trimethoxybenzoyl)phenylcarboxylic acid hexyl ester;
Compound 321
4-methoxy-N-(4-(thiazol-2-yl)-2-(3,4,5-trimethoxybenzoyl)phenyl)benzenesulfonamide;
Compound 322
(5-(furan 2-yl)-2-(1H-1,2,4-triazol-1-yl)phenyl)(3,4,5-tri-methoxyphenyl)methanone;
Compound 323
(5-(furan-2-yl)-2-(2 hydroxyethylamino)phenyl)(3,4,5-trimethoxyphenyl)methanone;
Compound 324
N-(4-(2-formamidethiazol-4-yl)-2-(3,4,5-trimethoxybenzoyl)phenyl)acetamide;
Compound 326
(2-amino-5-(thiazol-2-yl)phenyl)(4-hydroxy-3,5-diethoxyphenyl)methanone;
Compound 327
(2-fluoro-5-(furan-2-yl)phenyl)(3,4,5-trimethoxyphenyl)methanone;
Compound 329
(5-(furan-2-yl)-2-(1H-1,2,4-triazol-1-yl)phenyl)(4-hydroxy-3,5-dimethoxyphenyl)methanone;
Compound 330
(2-(dimethoxyamino)-5-(furan-2-yl)phenyl)(3,4,5-tri-methoxyphenyl)methanone;
Compound 331
(2-(difluoromethoxy)-5-(furan-2-yl)phenyl)(3,4,5-tri-methoxyphenyl)methanone;
Compound 332
(3-allyl-5-(furan-2-yl)-2-hydroxyphenyl)(3,4,5-tri-methoxyphenyl)methanone;
Compound 333
(3-allyl-2-(difluoromethoxy)-5-(furan-2-yl)phenyl)(3,4,5-trimethoxyphenyl)methanone;
Compound 334
4-(thiazol-2-yl)-2-(3,4,5-trimethoxybenzoyl)phenylcarboxylic acid 2-methoxymethyl ester;
Compound 335
N-(4-(pyridin-2-yl)-2-(3,4,5-trimethoxybenzoyl)phenyl)methanesulfonamide;
Compound 336
(5-(furan-2-yl)-2-(1H pyrazol-1-yl)phenyl)(3,4,5-tri-methoxyphenyl)methanone;
Compound 337
(4,5'-diaminophenyl-3-yl)(3,4,5-trimethoxyphenyl)methanone;
Compound 338
N-(5'-amino-3-(3,4,5-trimethoxybenzoyl)biphenyl-4-yl)acetamide;
Compound 339
N-(4-(pyrimidin-5-yl)-2-(3,4,5-trimethoxybenzoyl)phenyl)acetamide;
Compound 340
(2-amino-5-(pyrimidin-5-yl)phenyl)(3,4,5-trimethoxyphenyl)methanone;
Compound 341
(5-(furan-2-yl)-2-(3-hydroxypropylamino)phenyl)(3,4,5-trimethoxyphenyl)methanone;
Compound 342
N-(4-(oxazol-2-yl)-2-(3,4,5-trimethoxybenzoyl)phenyl)methanesulfonamide;
Compound 346
(5-(pyridin-2-yl)-2-(1H-1,2,4-triazol-1-yl)phenyl)(3,4,5-trimethoxyphenyl)methanone;
Compound 347
(5-(thiazol-2-yl)-2-(1H-1,2,4-thiazol-1-yl)phenyl)(3,4,5-trimethoxyphenyl)methanone;
Compound 348
(2-(3-hydroxypropylamino)-5-(thiazol-2-yl)phenyl)(3,4,5-trimethoxyphenyl)methanone;
Compound 350
N-(4-(pyridin-4-yl)-2-(3,4,5-trimethoxybenzoyl)phenyl)acetamide;
Compound 352
(2-amino-5-(pyridin-4-yl)phenyl)(3,4,5-trimethoxyphenyl)methanone;
Compound 354
(5-(furan-2-yl)-2-(1H-imidazol-1-yl)phenyl)(3,4,5-tri-methoxyphenyl)methanone;

Compound 357
(2-fluoro-5-(isoxazol-5-yl)phenyl)(3,4,5-trimethoxyphenyl)methanone;
Compound 359
(5-(oxazol-2-yl)-2-(1H-1,2,4-triazol-1-yl)phenyl)(3,4,5-trimethoxyphenyl)methanone;
Compound 360
(2-(3 hydroxypropylamino)-5-(oxazol-2-yl)phenyl(3,4,5-trimethoxyphenyl)methanone;
Compound 363
(2-(3-hydroxypropylamino)-5-(1H-pyrrol-2-yl)phenyl)(3,4,5-trimethoxyphenyl)methanone;
Compound 364
(3-(2,3-dihydroxypropyl)-5-(furan-2-yl)-2-methoxyphenyl)(3,4,5-trimethoxyphenyl)methanone;
Compound 365
(2-(pyrimidin-5-yl)-5-(thiazol-2-yl)phenyl)(3,4,5-trimethoxyphenyl)methanone;
Compound 366
(5-(furan-2-yl)-2-(pyrazin-2-ylamino)phenyl)(3,4,5-trimethoxyphenyl)methanone;
Compound 367
(5-(furan-2-yl)-2-(pyridin-2-ylamino)phenyl)(3,4,5-trimethoxyphenyl)methanone;
Compound 368
(2-(2-(1H-imidazol-4-yl)ethylamino)-5-(furan-2-yl)phenyl)(3,4,5-trimethoxyphenyl)methanone;
Compound 369
(5-(furan-2-yl)-2-(3-hydroxypyrrolidin-1-yl)phenyl)(3,4,5-trimethoxyphenyl)methanone;
Compound 370
(S)-(5-(furan-2-yl)-2-(2-(hydroxymethyl)pyrrolidin-1-yl)phenyl)(3,4,5-trimethoxyphenyl)methanone;
Compound 371
(5-(furan-2-yl)-2-(4-(2-hydroxyethyl)piperazin-1-yl)phenyl)(3,4,5-trimethoxyphenyl)methanone;
Compound 372
(2-(1,2-dihydroxyethyl)-5-(thiazol-2-yl)phenyl)(3,4,5-trimethoxyphenyl)methanone;
Compound 373
4-(thiazol-2-yl)-2-(3,4,5-trimethoxybenzoyl)benzoic acid;
Compound 374
4-(thiazol-2-yl)-2-(3,4,5-trimethoxybenzoyl)benzoic acid methyl ester;
Compound 375
(2-(oxazol-5-yl)-5-(thiazol-2-yl)phenyl)(3,4,5-trimethoxyphenyl)methanone;
Compound 376
(2-(3-amino-1H-1,2,4-triazol-1-yl)-5-(thiazol-2-yl)phenyl)(3,4,5-trimethoxyphenyl)methanone;
Compound 377
(3-(1,3-dioxan-2-yl)-4,5-dimethoxyphenyl)(5-(furan-2-yl)-2-(1H-1,2,4-triazol-1-yl)phenyl)methanone;
Compound 378
(5-(furan-2-yl)-2-(1H-1,2,4-triazol-1-yl)phenyl)(3-(hydroxymethyl)-4,5-dimethoxyphenyl)methanone;
Compound 379
(5-(furan-2-yl)-2-(1H-1,2,3,-triazol-1-yl)phenyl)(3,4,5-trimethoxyphenyl)methanone;
Compound 380
(2-(3-hydroxypropylamino)-5-(pyridin-2-yl)phenyl 3,4,5-trimethoxyphenyl)methanone;
Compound 381
(5-(pyridin-2-yl)-2-(1H-1,2,3,-triazol-1-yl)phenyl)(3,4,5-trimethoxyphenyl)methanone;
Compound 382
(5-(furan-2-yl)-2-(4-hydroxybutylamino)phenyl)(3,4,5-trimethoxyphenyl)methanone;
Compound 383
(5-(furan-2-yl)-2-(pyridin-3-yl)phenyl)(3,4,5-trimethoxyphenyl)methanone;
Compound 384
(S)-(2-(3-(dimethylamino)pyrrolidin-1-yl)-5-(furan-2-yl)phenyl)(3,4,5-trimethoxyphenyl)methanone;
Compound 385
(R)-(2-(3-(dimethylamino)pyrrolidin-1-yl)-5-(furan-2-yl)phenyl)(3,4,5-trimethoxyphenyl)methanone;
Compound 386
(S)-N-(1-(4-(furan-2-yl)-2-(3,4,5,-trimethoxybenzoyl)phenyl)pyrrolidin-3-yl)acetamide;
Compound 387
(R)-N-(1-(4-(furan-2-yl)-2-(3,4,5,-trimethoxybenzoyl)phenyl)pyrrolidin-3-yl)acetamide;
Compound 388
(S)-(2-(3-aminopyrrolidin-1-yl)-5-(furan-2-yl)phenyl)(3,4,5-trimethoxyphenyl)methanone;
Compound 389
(R)-(2-(3-aminopyrrolidin-1-yl)-5-(furan-2-yl)phenyl)(3,4,5-trimethoxyphenyl)methanone;
Compound 390
(5-(furan-2-yl)-2-morpholinophenyl)(3,4,5-trimethoxyphenyl)methanone;
Compound 391
(5-(thiophen-2-yl)-2-(1H-1,2,4,-triazol-1-yl)phenyl)(3,4,5-trimethoxyphenyl)methanone;
Compound 392
(2-(pyridin-4-yl)-5-(thiazol-2-yl)phenyl)(3,4,5-trimethoxyphenyl)methanone;
Compound 393
(4'-methoxy-4-(thiazol-2-yl)biphenyl-2-yl)(3,4,5-trimethoxyphenyl)methanone;
Compound 394
(2-(2-methoxypyridin-3-yl)-5-(thiazol-2-yl)phenyl)(3,4,5-trimethoxyphenyl)methanone;
Compound 395
(5-(thiazol-2-yl)-2-(thiophen-3-yl)phenyl)(3,4,5-trimethoxyphenyl)methanone;
Compound 396
4-(thiazol-2-yl)-2-(3,4,5-trimethoxybenzoyl)benzoic acid methoxymethyl ester;
Compound 397
2-(4-(thiazol-2-yl)-2-(3,4,5-trimethoxybenzoyl)benzamido)acetic acid methyl ester;
Compound 400
(5-(1H-imidazol-2-yl)-2-(1H-1,2,4-triazol-1-yl)phenyl)(3,4,5-trimethoxyphenyl)methanone;
Compound 401
(2-(1H-tetrazol-1-yl)-5-(thiazol-2-yl)phenyl)(3,4,5-trimethoxyphenyl)methanone;
Compound 402
(2-(3-aminophenoxy)-5-(thiophen-2-yl)phenyl)(3,4,5-trimethoxyphenyl)methanone;
Compound 403
(2-(3-aminophenoxy)-5-(pyridin-2-yl)phenyl)(3,4,5-trimethoxyphenyl)methanone;
Compound 408
4-(thiazol-2-yl)-2-(3,4,5-trimethoxybenzoyl)benzamide;
Compound 409
(5-(1H-pyrrol-2-yl)-2-(1H-1,2,4-triazol-1-yl)phenyl)(3,4,5-trimethoxyphenyl)methanone;

Compound 410
(5-(thiazol-2-yl)-2-(1H-1,2,4-triazol-1-yl)pyridin-3-yl)(3,4,5-trimethoxyphenyl)methanone;
Compound 411
(2-methoxy-5-(thiazol-2-yl)pyridin-3-yl)(3,4,5-trimethoxyphenyl)methanone;
Compound 420
(2-(4-hydroxyphenylamino)-5-(thiazol-2-yl)pyridin-3-yl)(3,4,5-trimethoxyphenyl)methanone;
Compound 421
(2-(3-hydroxypropylamino)-5-(thiazol-2-yl)pyridin-3-yl)(3,4,5-trimethoxyphenyl)methanone;
Compound 422
(2-(benzylamino)-5-(thiazol-2-yl)pyridin-3-yl)(3,4,5-trimethoxyphenyl)methanone;
Compound 425
(5-(furan-2-yl)-2-methoxyphenyl)(pentafluorophenyl)methanone;
Compound 426
(2-amino-5-(thiazol-2-yl)pyridin-3-yl)(3,4,5-trimethoxyphenyl)methanone;
Compound 427
N-(5-(thiazol-2-yl)-3-(3,4,5-trimethoxybenzoyl)pyridin-2-yl)acetamide;
Compound 429
(2-methoxy-5-(thiazol-2-yl)phenyl)(pentafluorophenyl)methanone;
Compound 434
(3-((dimethylamino)methyl)-5-(furan-2-yl)-2-hydroxyphenyl)(3,4,5-trimethoxyphenyl)methanone;
Compound 437
(2-fluoro-4-(furan-2-yl)phenyl)(pentafluorophenyl)methanone;
Compound 443
(4-(furan-2-yl)-2-(1H-1,2,4-triazol-1-yl)phenyl)(3,4,5-trimethoxyphenyl)methanone;
Compound 446
(4-(furan-2-yl)-2-(1H-1,2,4,-triazol-1-yl)phenyl)(pentafluorophenyl)methanone;
Compound 455
(4-(pyrimidin-5-yl)-2-(1H-1,2,4,-triazol-1-yl)phenyl)(3,4,5-trimethoxyphenyl)methanone;
Compound 456
(2'-hydroxy-3-(1H-1,2,4-triazol-1-yl)biphenyl-4-yl)(3,4,5-trimethoxyphenyl)methanone;
Compound 457
(2'-hydroxy-3-(fluoro)biphenyl-4-yl)(3,4,5-trimethoxyphenyl)methanone;
Compound 458
(2-fluoro-4-(thiophen-3-yl)phenyl)(3,4,5-trimethoxyphenyl)methanone;
Compound 462
(4-(thiophen-3-yl)-2-(1H-1,2,4,-triazol-1-yl)phenyl)(3,4,5-trimethoxyphenyl)methanone;
Compound 463
(2-fluoro-4-(thiazol-2-yl)phenyl)(3,4,5-trimethoxyphenyl)methanone;
Compound 464
(4=(thiazol-2-yl)-2-(1H-1,2,4-triazol-1-yl)phenyl)(3,4,5-trimethoxyphenyl)methanone;
Compound 469
(2-(3-hydroxypropylamino)-4-(thiazol-2-yl)phenyl)(3,4,5-trimethoxyphenyl)methanone;
Compound 474
(4'-methoxy-4-[1,2,4]triazol-1-yl-biphenyl-3-yl)(3,4,5-trimethoxyphenyl)methanone;
Compound 475
(4-(3,5-dimethyl-isoxazol-4-yl)-2-[1,2,4]triazol-1-yl-phenyl)(3,4,5-trimethoxyphenyl)methanone;
Compound 476
N-(3'-[1,2,4]triazol-1-yl-4'-(3,4,5-trimethoxybenzoyl)biphenyl-3-yl)methanesulfonamide;
Compound 477
(3'-hydroxy-3-[1,2,4]triazol-1-yl-biphenyl-4-yl)(3,4,5-trimethoxyphenyl)methanone;
Compound 479
(3'-ethanesulfonyl-3-[1,2,4]triazol-1-yl-biphenyl-4-yl)(3,4,5-trimethoxyphenyl)methanone;
Compound 480
3'-[1,2,4]triazol-1-yl-4'-(3,4,5-trimethoxybenzoyl)-biphenyl-3-carboxylic acid methyl ester;
Compound 482
(4'-methanesulfonyl-3-[1,2,4]triazol-1-yl-biphenyl-4-yl)(3,4,5-trimethoxyphenyl)methanone;
Compound 483
N-(3'-[1,2,4]triazol-1-yl-4-(3,4,5-trimethoxybenzoyl)-biphenyl-3-yl)acetamide;
Compound 484
methanesulfonic acid 5-(thiazol-2-yl)-2-(3,4,5-trimethoxybenzoyl)phenyl ester;
Compound 485
(4-hydroxy-3,5-dimethoxyphenyl)(5-thiazol-2-yl-2-[1,2,4]thiazol-1-yl-phenyl)methanone;
Compound 486
N-[4'-fluoro-3'-(3,4,5-trimethoxybenzoyl)-biphenyl-3-yl]-methanesulfonamide;
Compound 492
(2-amino-4-thiophen-3-yl phenyl)(3,4,5-trimethoxyphenyl)methanone;
Compound 493
(2-amino-4-furan-2-yl-phenyl)(3,4,5-trimethoxyphenyl)methanone;
Compound 494
N-(3'-amino-4'-(3,4,5-trimethoxybenzoyl)-biphenyl-3-yl)methanesulfonamide;
Compound 495
pentafluorophenyl-(4-thiazol-2-yl-2-[1,2,4]thiazol-1-yl-phenyl)methanone;
Compound 497
(2-amino-4-thiazol-2-yl-phenyl)(3,4,5-trimethoxyphenyl)methanone;
Compound 499
(2-(4-methoxy-benzylamino)-4-(thiazol-2-yl)-phenyl)(3,4,5-trimethoxyphenyl)methanone;
Compound 500
(3,4-dimethoxy-5-((methoxymethoxy)methyl)phenyl)(4-(thiazol-2-yl)-2-(1H-1,2,4-triazol-1-yl)phenyl)methanone;
Compound 501
(3-hydroxymethyl-4,5-dimethoxyphenyl)(4-thiazol-2-yl-2-[1,2,4]triazol-1-yl-phenyl)methanone;
Compound 502
(2-(2-hydroxyethylamino)-4-(thiazol-2-yl)phenyl)(3-hydroxymethyl-4,5-dimethoxyphenyl)methanone;
Compound 503
(2-amino-4-thiazol-2-yl-phenyl)(3-hydroxymethyl-4,5-dimethoxyphenyl)methanone;
Compound 505
(4-(2-amino-thiazol-4-yl)-2-fluoro-phenyl)(3,4,5-trimethoxyphenyl)methanone;
Compound 506
3'-[1,2,4]triazol-1-yl-4'-(3,4,5-trimethoxybenzoyl)-biphenyl-3-carbonitrile;

Compound 507
(3',5'-dimethyl-3-[1,2,4]thiazol-1-yl-biphenyl-4-yl)(3,4,5-trimethoxyphenyl)methanone;
Compound 508
(3'-nitro-3-[1,2,4]thiazol-1-yl-biphenyl-4-yl)(3,4,5-trimethoxyphenyl)methanone;
Compound 509
(3-hydroxymethyl-4,5-dimethoxy-phenyl)(5-thiazol-2-yl-2-[1,2,4]thiazol-1-yl-phenyl)methanone;
Compound 510
(4-thiazol-2-yl-2-[1,2,3]thiazol-1-yl-phenyl)(3,4,5-trimethoxyphenyl)methanone;
Compound 511
(4-pyridin-3-yl-2-[1,2,4]thiazol-1-yl-phenyl)(3,4,5-trimethoxyphenyl)methanone;
Compound 512
(4-(4-methoxypyridin-3-yl)-2-(1H-1,2,4-triazol-1-yl)phenyl)(3,4,5-trimethoxyphenyl)methanone;
Compound 513
(3',5'-difluoro-3-[1,2,4]triazol-1-yl-biphenyl-4-yl)(3,4,5-trimethoxyphenyl)methanone;
Compound 514
(3-bromo-4,5-dimethoxyphenyl)(2-fluoro-4-(thiazol-2-yl)phenyl)methanone;
Compound 515
(3-bromo-4,5-dimethoxyphenyl)(4-(thiazol-2-yl)-2-(1,2,4-triazol-1-yl)phenyl)methanone;
Compound 516
(4-(2-aminothiazol-4-yl)-2-(1H-1,2,4-triazol-1-yl)phenyl)(3,4,5-trimethoxyphenyl)methanone;
Compound 517
(4-(2-methylthiazol-4-yl)-2-(1H-1,2,4-triazol-1-yl)phenyl)(3,4,5-trimethoxyphenyl)methanone;
Compound 518
(4-(2-aminothiazol-4-yl)-2-(1H-1,2,4-triazol-1-yl)phenyl)(pentafluorophenyl)methanone;
Compound 525
(3'-amino-3-(1H-1,2,4-triazol-1-yl)biphenyl-4-yl)(3,4,5-trimethoxyphenyl)methanone;
Compound 531
N-(4-(3-(1H-1,2,4-triazol-1-yl)-4-(3,4,5-trimethoxybenzoyl)phenyl)-1H-imidazol-2-yl)acetamide;
Compound 534
(4-(thiazol-5-yl)-2-(1H-1,2,4-triazol-1-yl)phenyl)(3,4,5-trimethoxyphenyl)methanone;
Compound 538
(4-(difluoromethoxy)-3,5-dimethoxyphenyl)(4-(thiazol-2-yl)-2-(1H-1,2,4-triazol-1-yl)phenyl)methanone;
Compound 547
(4-(2-aminothiazol-4-yl)-2-(1H-1,2,4-triazol-1-yl)phenyl)(4-(difluoromethoxy)-3,5-dimethoxyphenyl)methanone;
Compound 550
(5'-(1H-1,2,4-triazol-1-yl)-4'-(3,4,5-trimethoxybenzoyl)biphenyl-3-sulfonamide;
Compound 554
((4-(4-hydroxymethyl)thiazol-2-yl)-2-(1H-1,2,4-triazol-1-yl)phenyl)(3,4,5-trimethoxyphenyl)methanone;
Compound 560
N-(4-(3-(1H-1,2,4-triazol-1-yl)-4-(3,4,5-trimethoxybenzoyl)phenyl)thiazol-2-yl)acetamide;
Compound 561
methyl 4-(3-(1H-1,2,4-triazol-1-yl)-4-(3,4,5-trimethoxybenzoyl)phenyl)thiazol-2-yl carbamate;
Compound 562
(4-(thiazol-4-yl)-2-(1H-1,2,4-triazol-1-yl)phenyl)(3,4,5-trimethoxyphenyl)methanone;
Compound 563
(4-(2-(2-hydroxypropan-2-yl)thiazol-4-yl)-2-(1H-1,2,4-triazol-1-yl)phenyl)(3,4,5-trimethoxyphenyl)methanone;
Compound 564
(4-(2-(hydroxymethyl)thiazol-4-yl)-2-(1H-1,2,4-triazol-1-yl)phenyl)(3,4,5-trimethoxyphenyl)methanone;
Compound 583
(2-methoxy-5-(thiazol-2-yl)phenyl)(3,4,5-trimethoxyphenyl)methanone;
Compound 588
(2-methoxy-5-(thiophen-3-yl)phenyl)(3,4,5-trimethoxyphenyl)methanone;
Compound 590
(2-methoxy-5-(oxazol-2-yl)phenyl)(3,4,5-trimethoxyphenyl)methanone;
Compound 594
(2-methoxy-5-(thiophen-2-yl)phenyl)(3,4,5-trimethoxyphenyl)methanone;
Compound 595
(2-methoxy-5-(methylthiazol-4-yl)phenyl)(3,4,5-trimethoxyphenyl)methanone;
Compound 596
(5-(2-methylthiazol-4-yl)-2-(1H-1,2,4-triazol-1-yl)phenyl)(3,4,5-trimethoxyphenyl)methanone;
Compound 597
(2-amino-5-(1H-pyrrol-2-yl)phenyl)(3,4,5-trimethoxyphenyl)methanone;
Compound 598
(2-methoxy-5-(1H-pyrazol-5-yl)phenyl)(3,4,5-trimethoxyphenyl)methanone;
Compound 599
(4-(1H-pyrrol-2-yl)-2-(1H-1,2,4-triazol-1-yl)phenyl)(3,4,5-trimethoxyphenyl)methanone;
Compound 601
(2-hydroxy-5-(thiazol-2-yl)phenyl)(3,4,5-trimethoxyphenyl)methanone; and
Compound 602
(4-(oxazol-2-yl)-2-(1H-1,2,4-triazol-1-yl)phenyl)(3,4,5-trimethoxyphenyl)methanone.

15. The compound according to claim 1, wherein the compound is selected from the following compounds, a pharmaceutically acceptable salt thereof:
Compound 200
(2-methoxy-5-(pyridin-3-yl)phenyl)(3,4,5-trimethoxyphenyl)methanone;
Compound 203
(5-(furan-2-yl)-2-methoxyphenyl)(3,4,5-trimethoxyphenyl)methanone;
Compound 206
(5-(furan-2-yl)-2,3-dimethoxyphenyl)(3,4,5-trimethoxyphenyl)methanone;
Compound 213
(4,4'-dimethoxybiphenyl-3-yl)(3,4,5-trimethoxyphenyl)methanone;
Compound 249
(5-(furan-2-yl)-2-methoxyphenyl)(3-(hydroxymethyl)-4,5-dimethoxyphenyl)methanone;
Compound 264
(5-(furan-2-yl)-2-methoxyphenyl)(4-methoxy-3,5-dimethylphenyl)methanone;
Compound 265
(5-(furan-2-yl)-2-methoxyphenyl)(4-(methoxymethoxy)-3,5-dimethylphenyl)methanone;
Compound 269
(3-allyl-4-hydroxy-5-methoxyphenyl)(5-(furan-2-yl)-2-methoxyphenyl)methanone;

Compound 583
(2-methoxy-5-(thiazol-2-yl)phenyl)(3,4,5-trimethoxyphenyl)methanone;
Compound 588
(2-methoxy-5-(thiophen-3-yl)phenyl)(3,4,5-trimethoxyphenyl)methanone;
Compound 590
(2-methoxy-5-(oxazol-2-yl)phenyl)(3,4,5-trimethoxyphenyl)methanone;
Compound 594
(2-methoxy-5-(thiophen-2-yl)phenyl)(3,4,5-trimethoxyphenyl)methanone;
Compound 595
(2-methoxy-5-(methylthiazol-4-yl)phenyl)(3,4,5-trimethoxyphenyl)methanone; and
Compound 598
(2-methoxy-5-(1H-pyrazol-5-yl)phenyl)(3,4,5-trimethoxyphenyl)methanone.

16. The compound according to claim 1, wherein the compound is selected from the following compounds, a pharmaceutically acceptable salt thereof:
Compound 224
(5-(furan 2-yl)-2-nitrophenyl)(3,4,5-trimethoxyphenyl)methanone;
Compound 225
(2-amino-5-(furan-2-yl)phenyl)(3,4,5-trimethoxyphenyl)methanone;
Compound 226
(4-amino-4'-methoxybiphenyl-3-yl)(3,4,5-trimethoxyphenyl)methanone;
Compound 231
N-(4-(furan-2-yl)-2-(3,4,5-trimethoxybenzoyl)phenyl)acetamide;
Compound 235
N-(4-(furan-2-yl)-2-(3,4,5-trimethoxybenzoyl)phenyl)methanesulfonamide;
Compound 237
2-amino-N-(4-(furan-2-yl)-2-(3,4,5-trimethoxybenzoyl)phenyl)acetamide;
Compound 238
(2-(allylamino)-5-(furan-2-yl)phenyl)(3,4,5-trimethoxyphenyl)methanone;
Compound 272
(2-amino-4-(1H-1,2,4-thiazol-1-yl)phenyl)(3,4,5-trimethoxyphenyl)methanone;
Compound 277
N-(4-(thiazol-2-yl)-2-(3,4,5-trimethoxybenzoyl)phenyl)acetamide;
Compound 278
(2-amino-5-(thiazol-2-yl)phenyl)(3,4,5-trimethoxyphenyl)methanone;
Compound 279
N-(4-(thiophen-2-yl)-2-(3,4,5-trimethoxybenzoyl)phenyl)acetamide;
Compound 282
(5-(furan-2-yl)-2-(methylamino)phenyl)(3,4,5-trimethoxyphenyl)methanone;
Compound 283
(2-amino-5-(thiophen-2-yl)phenyl)(3,4,5-trimethoxyphenyl)methanone;
Compound 286
(2-amino-5-(thiazol-2-yl)phenyl)(3-(hydroxymethyl)-4,5-dimethoxyphenyl)methanone;
Compound 289
(2-amino-5-(oxazol-2-yl)phenyl)(3,4,5-trimethoxyphenyl)methanone;
Compound 293
(2-amino-5-(pyridin-2-yl)phenyl)(3,4,5-trimethoxyphenyl)methanone;
Compound 294
N-(4-(2-aminothiazol-5-yl)-2-(3,4,5-trimethoxybenzoyl)phenyl)acetamide;
Compound 296
N-(4-(oxazol-2-yl)-2-(3,4,5-trimethoxybenzoyl)phenyl)acetamide;
Compound 297
(2-amino-5-(2-aminothiazol-4-yl)phenyl)(3,4,5-trimethoxyphenyl)methanone;
Compound 298
(2-amino-5-(2-methylthiazol-4-yl)phenyl)(3,4,5-trimethoxyphenyl)methanone;
Compound 300
N-(4-(thiophen-3-yl)-2-(3,4,5-trimethoxybenzoyl)phenyl)acetamide;
Compound 301
(2-amino-5-(thiophen-3-yl)phenyl)(3,4,5-trimethoxyphenyl)methanone;
Compound 308
N-(4-(thiazol-2-yl)-2-(3,4,5-trimethoxybenzoyl)phenyl)methanesulfonamide;
Compound 316
N-(4-(thiazol-2-yl)-2-(3,4,5-trimethoxybenzoyl)phenyl)formamide;
Compound 323
(5-(furan-2-yl)-2-(2-hydroxyethylamino)phenyl)(3,4,5-trimethoxyphenyl)methanone;
Compound 335
N-(4-(pyridin-2-yl)-2-(3,4,5-trimethoxybenzoyl)phenyl)methanesulfonamide;
Compound 337
(4,5'-diaminophenyl-3-yl)(3,4,5-trimethoxyphenyl)methanone;
Compound 341
(5-(furan-2-yl)-2-(3-hydroxypropylamino)phenyl)(3,4,5-trimethoxyphenyl)methanone;
Compound 348
(2-(3-hydroxypropylamino)-5-(thiazol-2-yl)phenyl)(3,4,5-trimethoxyphenyl)methanone;
Compound 354
(5-(furan-2-yl)-2-(1H-imidazol-1-yl)phenyl)(3,4,5-trimethoxyphenyl)methanone;
Compound 363
(2-(3-hydroxypropylamino)-5-(1H-pyrrol-2-yl)phenyl)(3,4,5-trimethoxyphenyl)methanone;
Compound 379
(5-(furan-2-yl)-2-(1H-1,2,3,-triazol-1-yl)phenyl)(3,4,5-trimethoxyphenyl)methanone;
Compound 380
(2-(3-hydroxypropylamino)-5-(pyridin-2-yl)phenyl)(3,4,5-trimethoxyphenyl)methanone;
Compound 401
(2-(1H-tetrazol-1-yl)-5-(thiazol-2-yl)phenyl)(3,4,5-trimethoxyphenyl)methanone;
Compound 469
(2-(3-hydroxypropylamino)-4-(thiazol-2-yl)phenyl)(3,4,5-trimethoxyphenyl)methanone;
Compound 494
N-(3'-amino-4'-(3,4,5-trimethoxybenzoyl)-biphenyl-3-yl)methanesulfonamide;
Compound 516
(4-(2-aminothiazol-4-yl)-2-(1H-1,2,4-triazol-1-yl)phenyl)(3,4,5-trimethoxyphenyl)methanone; and Compound 597
(2-amino-5-(1H-pyrrol-2-yl)phenyl)(3,4,5-trimethoxyphenyl)methanone.

17. The compound according to claim 1, wherein the compound is selected from the following compounds, a pharmaceutically acceptable salt thereof:

Compound 322
(5-(furan-2-yl)-2-(1H-1,2,4-triazol-1-yl)phenyl)(3,4,5-trimethoxyphenyl)methanone;
Compound 346
(5-(pyridin-2-yl)-2-(1H-1,2,4-triazol-1-yl)phenyl)(3,4,5-trimethoxyphenyl)methanone;
Compound 347
(5-(thiazol-2-yl)-2-(1H-1,2,4-thiazol-1-yl)phenyl)(3,4,5-trimethoxyphenyl)methanone;
Compound 359
(5-(oxazol-2-yl)-2-(1H-1,2,4-triazol-1-yl)phenyl)(3,4,5-trimethoxyphenyl)methanone;
Compound 391
(5-(thiophen-2-yl)-2-(1H-1,2,4,-triazol-1-yl)phenyl)(3,4,5-trimethoxyphenyl)methanone;
Compound 400
(5-(1H-imidazol-2-yl)-2-(1H-1,2,4-triazol-1-yl)phenyl)(3,4,5-trimethoxyphenyl)methanone;
Compound 409
(5-(1H-pyrrol-2-yl)-2-(1H-1,2,4-triazol-1-yl)phenyl)(3,4,5-trimethoxyphenyl)methanone;
Compound 443
(4-(furan-2-yl)-2-(1H-1,2,4-triazol-1-yl)phenyl)(3,4,5-trimethoxyphenyl)methanone;
Compound 446
(4-(furan-2-yl)-2-(1H-1,2,4,-triazol-1-yl)phenyl)(pentafluorophenyl)methanone;
Compound 455
(4-(pyrimidin-5-yl)-2-(1H-1,2,4,-triazol-1-yl)phenyl)(3,4,5-trimethoxyphenyl)methanone;
Compound 462
(4-(thiophen-3-yl)-2-(1H-1,2,4,-triazol-1-yl)phenyl)(3,4,5-trimethoxyphenyl)methanone;
Compound 464
(4-(thiazol-2-yl)-2-(1H-1,2,4-triazol-1-yl)phenyl)(3,4,5-trimethoxyphenyl)methanone;
Compound 474
(4'-methoxy-4-[1,2,4]triazol-1-yl-biphenyl-3-yl)(3,4,5-trimethoxyphenyl)methanone;
Compound 475
(4-(3,5-dimethyl-isoxazol-4-yl)-2-[1,2,4]triazol-1-yl-phenyl)(3,4,5-trimethoxyphenyl)methanone;
Compound 476
N-(3'-[1,2,4]triazol-1-yl-4'-(3,4,5-trimethoxybenzoyl)biphenyl-3-yl)methanesulfonamide;
Compound 479
(3'-ethanesulfonyl-3-[1,2,4]triazol-1-yl-biphenyl-4-yl)(3,4,5-trimethoxyphenyl)methanone;
Compound 506
3'-[1,2,4]triazol-1-yl-4'-(3,4,5-trimethoxybenzoyl)-biphenyl-3-carbonitrile;
Compound 511
(4-pyridin-3-yl-2-[1,2,4]thiazol-1-yl-phenyl)(3,4,5-trimethoxyphenyl)methanone;
Compound 516
(4-(2-aminothiazol-4-yl)-2-(1H-1,2,4-triazol-1-yl)phenyl)3,4,5-trimethoxyphenyl)methanone;
Compound 525
(3'-amino-3-(1H-1,2,4-triazol-1-yl)biphenyl-4-yl)(3,4,5-trimethoxyphenyl)methanone;
Compound 531
N-(4-(3-(1H-1,2,4-triazol-1-yl)-4-(3,4,5-trimethoxybenzoyl)phenyl)-1H-imidazol-2-yl)acetamide;
Compound 534
(4-(thiazol-5-yl)-2-(1H-1,2,4-triazol-1-yl)phenyl)(3,4,5-trimethoxyphenyl)methanone;
Compound 538
(4-(difluoromethoxy)-3,5-dimethoxyphenyl)(4-(thiazol-2-yl)-2-(1H-1,2,4-triazol-1-yl)phenyl)methanone;
Compound 547
(4-(2-aminothiazol-4-yl)-2-(1H-1,2,4-triazol-1-yl)phenyl)(4-(difluoromethoxy)-3,5-dimethoxyphenyl)methanone;
Compound 550
(5'-(1H-1,2,4-triazol-1-yl)-4'-(3,4,5-trimethoxybenzoyl)biphenyl-3-sulfonamide;
Compound 554
((4-(4-hydroxymethyl)thiazol-2-yl)-2-(1H-1,2,4-triazol-1-yl)phenyl)(3,4,5-trimethoxyphenyl)methanone;
Compound 560
N-(4-(3-(1H-1,2,4-triazol-1-yl)-4-(3,4,5-trimethoxybenzoyl)phenyl)thiazol-2-yl)acetamide;
Compound 561
methyl 4-(3-(1H-1,2,4-triazol-1-yl)-4-(3,4,5-trimethoxybenzoyl)phenyl)thiazol-2-yl carbamate;
Compound 562
(4-(thiazol-4-yl)-2-(1H-1,2,4-triazol-1-yl)phenyl)(3,4,5-trimethoxyphenyl)methanone;
Compound 563
(4-(2-(2-hydroxypropan-2-yl)thiazol-4-yl)-2-(1H-1,2,4-triazol-1-yl)phenyl)(3,4,5-trimethoxyphenyl)methanone;
Compound 564
(4-(2-(hydroxymethyl)thiazol-4-yl)-2-(1H-1,2,4-triazol-1-yl)phenyl)(3,4,5-trimethoxyphenyl)methanone;
Compound 596
(5-(2-methylthiazol-4-yl)-2-(1H-1,2,4-triazol-1-yl)phenyl)(3,4,5-trimethoxyphenyl)methanone;
Compound 599
(4-(1H-pyrrol-2-yl)-2-(1H-1,2,4-triazol-1-yl)phenyl)(3,4,5-trimethoxyphenyl)methanone; and
Compound 602
(4-(oxazol-2-yl)-2-(1H-1,2,4-triazol-1-yl)phenyl)(3,4,5-trimethoxyphenyl)methanone.

18. A pharmacological composition having a function of inhibiting a microtubule formation, comprising the compound according to claim 1, a pharmaceutically acceptable salt thereof as an effective component, and a pharmaceutically acceptable carrier or excipient.

* * * * *